United States Patent
Bernardelli et al.

(10) Patent No.: US 7,456,164 B2
(45) Date of Patent: Nov. 25, 2008

(54) 3- OR 4-MONOSUBTITUTED PHENOL AND THIOPHENOL DERIVATIVES USEFUL AS H3 LIGANDS

(75) Inventors: Patrick Bernardelli, Sandwich (GB); Andrew Michael Cronin, Sandwich (GB); Alexis Denis, Sandwich (GB); Stephen Martin Denton, Sandwich (GB); Henry Jacobelli, Sandwich (GB); Mark Ian Kemp, Sandwich (GB); Edwige Lorthiois, Sandwich (GB); Fiona Rousseau, Sandwich (GB); Delphine Serradeil-Civit, Sandwich (GB); Fabrice Vergne, Sandwich (GB)

(73) Assignee: Pfizer, Inc, New York, NY (US)

( * ) Notice: Subject to any disclaimer, the term of this patent is extended or adjusted under 35 U.S.C. 154(b) by 17 days.

(21) Appl. No.: 11/124,876

(22) Filed: May 9, 2005

(65) Prior Publication Data
US 2005/0267095 A1 Dec. 1, 2005

Related U.S. Application Data

(60) Provisional application No. 60/665,613, filed on Mar. 24, 2005, provisional application No. 60/585,307, filed on Jul. 1, 2004.

(30) Foreign Application Priority Data

May 7, 2004 (EP) .................................. 04291187
Mar. 4, 2005 (GB) .................................. 0504564.6

(51) Int. Cl.
*A61K 31/397* (2006.01)
*A61K 31/4025* (2006.01)
*A61K 31/4427* (2006.01)
*A61K 31/4439* (2006.01)
*A61K 31/443* (2006.01)
*A61K 31/4523* (2006.01)
*A61K 31/4525* (2006.01)
*A61K 31/453* (2006.01)
*A61K 31/4535* (2006.01)
*A61K 31/454* (2006.01)
*A61K 31/4545* (2006.01)
*C07D 205/04* (2006.01)
*C07D 405/12* (2006.01)
*C07D 401/12* (2006.01)
*C07D 403/12* (2006.01)
*C07D 413/12* (2006.01)

(52) U.S. Cl. .................. 514/210.19; 514/422; 514/318; 514/326; 514/336; 514/252.01; 514/256; 514/231.5; 546/207; 546/210; 546/208; 546/209; 546/268.4; 548/950; 548/517

(58) Field of Classification Search .................. None
See application file for complete search history.

(56) References Cited

U.S. PATENT DOCUMENTS

| 5,646,162 A | 7/1997 | Muller et al. ............ 514/311 |
| 5,856,354 A * | 1/1999 | Horwell et al. ........... 514/476 |
| 2002/0040024 A1 | 4/2002 | Apodaca et al. .......... 514/235.5 |

FOREIGN PATENT DOCUMENTS

| DE | 3024836 | 1/1982 |
| EP | 269363 A2 * | 6/1988 |
| WO | WO9111172 | 8/1991 |
| WO | WO9402518 | 2/1994 |
| WO | WO 9530668 A1 * | 11/1995 |
| WO | WO9855148 | 12/1998 |
| WO | WO0006254 | 2/2000 |
| WO | WO0035298 | 6/2000 |
| WO | WO0206223 | 1/2002 |
| WO | WO0212190 | 2/2002 |
| WO | WO0212214 | 2/2002 |
| WO | WO02076925 | 10/2002 |
| WO | WO 03048130 | 6/2003 |
| WO | WO 03074050 | 9/2003 |

OTHER PUBLICATIONS

Doepke, W. "Structure of the Alkaloid Amisine", Zeitschrift fuer Chemie, vol. 20(8), pp. 298-299 (1980).*
Haleblian, J. Pharm. Sci., 64(8), pp. 1269-1288 (1975).
Liang and Chen, Expert Opinion in Therapeutic Patents, 11(6), pp. 981-986 (2001).
Verma et al., Pharm. Technology On-line, 25(2), pp. 1-14 (2001).
Finnin and Morgan, J. Pharm. Sci. 88(10), pp. 955-958 (1999).

* cited by examiner

Primary Examiner—Rebecca L Anderson
Assistant Examiner—Micahel P Barker
(74) Attorney, Agent, or Firm—Steve T. Zelson; Pamela G. Salkeld

(57) ABSTRACT

The invention relates to 3- or 4-monosubstituted phenol and thiophenol derivatives of formula (I) and to processes for the preparation of, intermediates used in the preparation of, compositions containing and the uses of, such derivatives. Said 3- or 4-monosubstituted phenol and thiophenol derivatives are $H_3$ ligands and are useful in numerous diseases, disorders and conditions, in particular inflammatory, allergic and respiratory diseases, disorders and conditions.

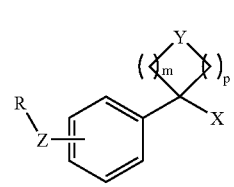

(1)

23 Claims, No Drawings

3- OR 4-MONOSUBTITUTED PHENOL AND THIOPHENOL DERIVATIVES USEFUL AS H3 LIGANDS

CROSS-REFERENCE TO RELATED APPLICATION

This patent application claims the benefit of U.S. Provisional Application Ser. No. 60/665,613, filed on Mar. 24, 2005, European Patent Application No. 0504564.6, filed on Mar. 4, 2005, U.S. Provisional Patent Application Ser. No. 60/585,307, filed on Jul. 1, 2004, and United Kingdom Patent Application No. 04291187.5, filed on May 7, 2004, all of which are herein incorporated by reference in their entirety.

FIELD OF THE INVENTION

The present invention relates to 3- or 4-monosubstituted phenol and thiophenol derivatives of general formula:

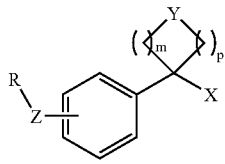

(1)

in which R, X, Y, Z, m and p have the meanings indicated below, and to processes for the preparation of, intermediates used in the preparation of, compositions containing and the uses of, such derivatives.

BACKGROUND OF THE INVENTION

Histamine $H_3$ receptors are found inter alia on presynaptic terminals of peripheral nerves, where they modulate autonomic neurotransmission and modulate a variety of end organ responses under control of the autonomic nervous system. They are also heteroreceptors, modulating the release of numerous other neurotransmitters such as dopamine, glutamate, noradrenaline, serotonin, GABA, acetylcholine, some peptides and co-transmitters.

Recently numerous histamine $H_3$ receptor ligands have been developed. An overview of the current advance in $H_3$ ligand research and patenting is given in *Expert Opin. Ther. Patents* (2003) 13(6). Examples of Histamine $H_3$ receptor ligands can be found in WO02/76925, WO00/06254, WO02/12190, WO02/12214 and WO02/06223.

$H_3$ receptor ligands are believed to be suitable for the treatment of various diseases including both disorders of the central nervous system and inflammatory disorders. Examples of diseases where treatment with $H_3$ ligands is believed to be useful are inflammatory bowel disease, Crohn's disease, colitis ulcerosa, sleep disorders, migraine, dyskinesia, stress-induced anxiety, psychotic disorders, epilepsy, Cognition deficiency diseases such as Alzheimer's disease or mild coginitive impairment, depression, mood disorders, schizophrenia, anxiety disorders, attention-deficit hyperactivity disorder (ADHD), psychotic disorders, obesity, dizziness, epilepsy, motion sickness, vertigo, respiratory diseases such as adult respiratory distress syndrome, acute respiratory distress syndrome, bronchitis, chronic bronchitis, chronic obstructive pulmonary disease, cystic fibrosis, asthma, emphysema, rhinitis, chronic sinusitis, allergy, allergy-induced airway responses, allergic rhinitis, viral rhinitis, non-allergic rhinitis, perennial and seasonal rhinitis, nasal congestion and allergic congestion.

Although $H_3$ ligands are known there is still a need to provide new $H_3$ ligands that are good drug candidates. In particular, preferred compounds should bind potently to the histamine $H_3$ receptor whilst showing little affinity for other receptors. They should be well absorbed from the gastrointestinal tract, be metabolically stable and possess favourable pharmacokinetic properties. They should be non-toxic and demonstrate few side-effects.

SUMMARY OF THE INVENTION

The present invention provides compounds of formula (I):

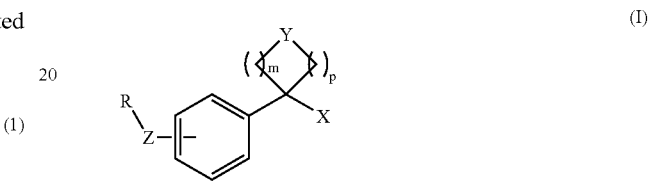

(I)

a stereoisomer thereof, or a pharmaceutically acceptable salt of said compound or stereoisomer, wherein:

-Z-R is in the meta or para position of the phenyl group;

X is —CN, —CH$_2$OH, —CH$_2$—O—(C$_1$-C$_4$)alkyl, —C(O)OH, —C(O)O(C$_1$-C$_4$)alkyl, —CH$_2$—NR$^1$R$^2$, —C(O)NR$^3$R$^4$, —CH$_2$—O-het$^2$, —CH$_2$-het$^1$ or het$^1$, wherein the group het$^1$ in both —CH$_2$-het$^1$ and het$^1$ is optionally and independently substituted with one to two halo, cyano, (C$_1$-C$_4$)alkyl, —S—(C$_1$-C$_4$)alkyl or (C$_1$-C$_4$)alkoxy;

R$^1$ is hydrogen or (C$_1$-C$_4$)alkyl optionally substituted with (C$_3$-C$_6$)cycloalkyl;

R$^2$ is: (i) hydrogen; (ii) (C$_1$-C$_6$)alkyl optionally and independently substituted with one to two (C$_3$-C$_6$)cycloalkyl, hydroxy, —S—(C$_1$-C$_4$)alkyl, —O—(C$_1$-C$_4$)alkyl, —SO$_2$—(C$_1$-C$_4$)alkyl, —SO—(C$_1$-C$_4$)alkyl, halo, het$^1$, amino, (C$_1$-C$_4$)alkylamino, [(C$_1$-C$_4$)alkyl]$_2$amino or phenyl, wherein said phenyl is optionally and independently substituted with one to two halo, hydroxy, cyano, (C$_1$-C$_4$)alkyl or (C$_1$-C$_4$)alkoxy; (iii) (C$_3$-C$_6$)cycloalkyl; (iv) het$^2$, optionally and independently substituted with one to two halo, cyano, (C$_1$-C$_4$)alkyl, NH$_2$ or (C$_1$-C$_4$)alkoxy; (v) —SO$_2$—R$^5$ wherein R$^5$ is (C$_1$-C$_4$)alkyl, amino, (C$_1$-C$_4$)alkylamino, [(C$_1$-C$_4$)alkyl]$_2$amino, phenyl or —(C$_1$-C$_4$)alkyl-phenyl, wherein said phenyl and phenyl of the group —(C$_1$-C$_4$)alkyl-phenyl is optionally and independently substituted with one to two halo, cyano, (C$_1$-C$_4$)alkyl or (C$_1$-C$_4$)alkoxy; or (vi) —C(O)—R$^6$ wherein R$^6$ is (C$_1$-C$_4$)alkyl, amino, (C$_1$-C$_4$)alkylamino, [(C$_1$-C$_4$)alkyl]$_2$amino, phenyl or —(C$_1$-C$_4$)alkyl-phenyl, wherein said phenyl and phenyl of the group —(C$_1$-C$_4$)alkyl-phenyl is optionally and independently substituted with one to two halo, cyano, (C$_1$-C$_4$)alkyl or (C$_1$-C$_4$)alkoxy; or R$^1$ and R$^2$, taken together with the N atom to which they are attached, form a 3-, 4-, 5-, 6- or 7-membered saturated heterocycle wherein one C atom is optionally replaced with N, O, S, SO or SO$_2$ and wherein said saturated heterocycle is optionally and independently substituted with one to two hydroxy, halo, =O, (C$_1$-C$_4$)alkyl, —(C$_1$-C$_4$)alkyl(C$_3$-C$_6$)cycloalkyl, (C$_1$-C$_4$)alkoxy, hydroxy(C$_1$-C$_4$)alkyl, (C$_1$-C$_4$)alkoxy(C$_1$-C$_4$)alkyl, —SO$_2$(C$_1$-C$_4$)alkyl, —C(O)(C$_1$-C$_4$)alkyl, [(C$_1$-C$_4$)alkyl]$_2$amino, amino, (C$_1$-C$_4$)alkylamino, —C(O)NH$_2$, C(O)O(C$_1$-C$_4$)alkyl or pyrrolidinone;

R[3] and R[4] are independently hydrogen, $(C_3-C_6)$cycloalkyl, or $(C_1-C_4)$alkyl, said $(C_3-C_6)$cycloalkyl and $(C_1-C_4)$alkyl are optionally and independently substituted with amino, $(C_1-C_4)$alkylamino, $[(C_1-C_4)$alkyl$]_2$amino or $(C_3-C_6)$cycloalkyl, or R[3] and R[4], taken together with the N atom to which they are attached, form a 4-, 5-, 6- or 7-membered saturated heterocycle wherein one C atom may be replaced by N or O and wherein said saturated heterocycle is optionally substituted with $(C_1-C_4)$alkyl, $[(C_1-C_4)$alkyl$]_2$amino, amino, $(C_1-C_4)$alkylamino, or $—C(O)(C_1-C_4)$alkyl, wherein said $—C(O)(C_1-C_4)$alkyl is optionally substituted with methoxy or ethoxy, Y is $CH_2$, $CH(OH)$, O, $C=O$ or N, wherein said N is substituted by H, $(C_1-C_4)$alkyl, $C(O)(C_1-C_4)$alkyl or $(C_1-C_4)$alkoxy$(C_1-C_4)$alkyl;

Z is O, S, SO or $SO_2$;

m and p are both integers which are independently 1, 2 or 3, with the condition that m+p is equal to or less than 4 so that the ring formed by:

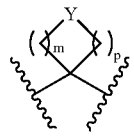

is a 4-, 5- or 6-membered ring;

and R is either a group of formula:

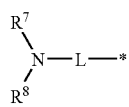

wherein * represents the attachment point to Z, L is a straight chain or branched $(C_2-C_6)$alkylene and R[7] and R[8] are each independently hydrogen, $(C_1-C_6)$alkyl, $(C_3-C_6)$cycloalkyl, or hydroxy$(C_1-C_6)$alkyl, or R[7] and R[8], taken together with the N atom to which they are attached, form a 4-, 5-, 6- or 7-membered saturated heterocycle wherein one C atom is optionally replaced by N, O, S, SO or $SO_2$ and wherein said saturated heterocycle is optionally and independently substituted with one to two $(C_1-C_4)$alkyl, $(C_1-C_4)$alkoxy, $(C_1-C_4)$alkoxy$(C_1-C_4)$alkyl, hydroxy$(C_1-C_4)$alkyl, hydroxy, $C(O)O(C_1-C_4)$alkyl, $—C(O)—(C_1-C_4)$alkyl-$NH_2$, $—C(O)NH_2$, halo, amino, $(C_1-C_4)$alkylamino or $[(C_1-C_4)$alkyl$]_2$amino;

or R is a group of formula:

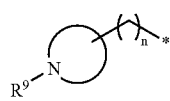

wherein * represents the attachment point to Z, the N-containing ring is a 4- to 7-membered saturated heterocycle, n is an integer equal to 0, 1 or 2, and R[9] is hydrogen, $(C_1-C_4)$alkyl, hydroxy$(C_1-C_6$ alkyl) or $(C_3-C_6)$cycloalkyl;

het[1] is a monocyclic or bicyclic heteroaromatic group comprising a 5- to 10-membered ring containing 1, 2, 3 or 4 heteroatom(s) selected from N, O, and S; and het[2] is a monocyclic or bicyclic heteroaromatic group comprising a 5- to 10-membered ring containing 1, 2, 3 or 4 heteroatom(s) selected from N, O and S.

DETAILED DESCRIPTION

It has been found that these compounds are H3 ligands and are thus particularly useful for the treatment of H3-related diseases such as neurologic disorders, or inflammatory, respiratory and allergic diseases, disorders and conditions.

In the present description the following definitions are used, unless otherwise specified. "halo" denotes a halogen atom selected from the group consisting of fluoro, chloro, bromo and iodo. "$(C_1-C_x)$alkyl" denotes a saturated, straight-chain or branched hydrocarbon group having from 1 to x carbon atoms and includes for example (when x=4) methyl, ethyl, propyl, i-propyl, n-butyl, i-butyl, sec-butyl and t-butyl and further (when x=6) pentyl, 1-pentyl, n-pentyl and hexyl. This also applies if the alkyl group carries substituents or is a substituent for another group, e.g. in $—S—(C_1-C_4)$alkyl, $—O—(C_1-C_4)$alkyl, $—SO_2—(C_1-C_4)$alkyl, $—SO—(C_1-C_4)$alkyl, $—CH_2—O—(C_1-C_4)$alkyl, $—C(O)O(C_1-C_4)$alkyl, $(C_1-C_4)$alkylamino, $[(C_1-C_4)$alkyl$]_2$amino, $—(C_1-C_4)$alkyl-phenyl, $—(C_1-C_4)$alkyl$(C_3-C_6)$cycloalkyl, hydroxy$(C_1-C_4)$alkyl, $(C_1-C_4)$alkoxy$(C_1-C_4)$alkyl, $—C(O)(C_1-C_4)$alkyl.

"$(C_1-C_4)$alkoxy" denotes straight-chain and branched alkoxy groups and includes for example methoxy, ethoxy, n-propoxy, i-propoxy, n-butoxy, i-butoxy, sec-butoxy and t-butoxy. "$(C_2-C_6)$alkylene" denotes a divalent radical derived from straight-chain or branched alkane containing from 2 to 6 carbon atoms. Examples of $(C_2-C_6)$alkylene radicals are methylene, ethylene (1,2-ethylene or 1,1-ethylene), trimethylene (1,3-propylene), tetramethylene (1,4-butylene), pentamethylene and hexamethylene.

"hydroxy$(C_1-C_4)$alkyl" radicals are alkyl radicals substituted by hydroxy. They can contain 1 or several hydroxy substituents, if not stated otherwise. Examples of suitable hydroxy$(C_1-C_4)$alkyl radicals are hydroxymethyl, 1-hydroxyethyl or 2-hydroxyethyl.

"$(C_3-C_6)$cycloalkyl" denotes a saturated monocyclic carbocyclic group having 3 to 6 carbon atoms and includes for example cyclopropyl, cyclobutyl, cyclopentyl and cyclohexyl. In the case where the $(C_1-C_x)$alkyl radicals are substituted by halo, such radical can contain 1 or several halogen atoms, if not stated otherwise. Said halo is preferably a fluoro, a chloro, a bromo or a iodo, in particular fluoro or chloro. For example in a fluoro-substituted alkyl radical, a methyl group can be present as a difluoromethyl or a trifluoromethyl group.

"saturated heterocycle" denotes a saturated monocyclic group having 4 to 7 ring members, which contains 1 nitrogen atom and optionally a further heteroatom selected from nitrogen, oxygen and sulphur. Examples of saturated heterocycles are azetidinyl, pyrrolidinyl, piperidinyl, morpholinyl, piperazinyl, oxazepanyl and azepanyl.

het[1] and het[2] are monocyclic or bicyclic heteroaromatic groups having 5 to 10 ring members, which contain 1, 2, 3 or 4 heteroatom(s) selected from nitrogen, oxygen and sulphur. In particular the heteroaromatic group contains either (a) 1 to 4 nitrogen atoms, (b) one oxygen atom or one sulfur atom or (c) 1 oxygen atom or 1 sulfur atom and 1 or 2 nitrogen atoms. het[2] is preferably C-linked, which means that the group is linked to the adjacent atom by a ring carbon atom. het[1] can be C-linked or N-linked. The heteroaryl group can be unsubstituted, monosubstituted or disubstituted, as indicated in the definition of X and R[2] hereabove for general formula (I) according to the present invention. Examples of heteroaryl groups include, but are not limited to thiophenyl, furanyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyranyl, pyridinyl, pyrazinyl, pyrimidinyl, pyridazinyl, triazinyl, thiadiazinyl, isobenzofuranyl, benzofuranyl, chromenyl, indolizinyl, isoindolyl, indolyl, indazolyl, purinyl, quinolinyl, isoquinolyl, cinnolinyl, phthalazinyl, naphthyridinyl, quinazolinyl, quinoxalinyl, benzoxazolyl, benzothiazolyl, benzimidazolyl, benzofuranyl, benzothiophenyl, pyrrolopyrazinyl, pyrrolopyridinyl, and imidazopyridinyl. Preferred definitions for het¹ and het² will follow hereafter.

In the general formula (I) according to the present invention, when a radical is mono- or poly-substituted, said substituent(s) can be located at any desired position(s), unless otherwise stated. Also, when a radical is polysubstituted, said substituents can be identical or different, unless otherwise stated.

According to a preferred aspect of the invention, X is selected from —CN, —CH₂OH, —C(O)OH, —CH₂—NR¹R², —C(O)NR³R⁴, —CH₂-het¹ and het¹, het¹ in both —CH₂-het¹ and het¹ being optionally substituted once or twice by (C₁-C₄)alkyl, more preferably X is selected from —CH₂—NR¹R², —CONR³R⁴, —CH₂-het¹ and het¹ het¹ in both —CH₂-het¹ and het¹ being optionally substituted once or twice by (C₁-C₄)alkyl, wherein R¹, R², R³, R⁴ and het¹ are as previously defined.

het¹ is preferably selected from a 5 or 6 membered monocyclic heteroaromatic group, or a 9 membered bicyclic heteroaromatic group, each heteroaromatic group containing 1 to 3 nitrogen atoms, or 1 to 2 nitrogen atoms and 1 oxygen atom, or 1 nitrogen atom and 1 sulphur atom, and each heteroaromatic group being optionally substituted once or twice by (C₁-C₄)alkyl, and preferably, optionally substituted once or twice by (C₁-C₂)alkyl.

More preferably, X is thiazolyl, benzimidazolylmethyl-, pyridinyl, oxazolyl, imidazopyridinylmethyl-, pyrimidinyl, imidazolyl, imidazolylmethyl- or triazolylmethyl-, said thiazolyl, benzimidazolylmethyl-, pyridinyl, oxazolyl, imidazopyridinylmethyl-, pyrimidinyl, imidazolyl, imidazolylmethyl- and triazolylmethyl- each being optionally substituted with one methyl group.

R¹ is preferably hydrogen, methyl or ethyl.

R² is preferably selected from the group consisting of hydrogen, (C₁-C₆)alkyl optionally substituted by one or two substituents independently selected from —S—(C₁-C₄)alkyl, —O—(C₁-C₄)alkyl, —SO₂—(C₁-C₄)alkyl, and phenyl, said phenyl being optionally substituted by one or two substituents independently selected from halo, hydroxy, cyano, (C₁-C₄)alkyl and (C₁-C₄)alkoxy, (C₃-C₆)cycloalkyl, het² optionally substituted by one or two substituents independently selected from halo, cyano, (C₁-C₄)alkyl and (C₁-C₄)alkoxy, wherein het² is defined as above, —SO₂—R⁵ wherein R⁵ is selected from the group consisting of (C₁-C₄)alkyl, [(C₁-C₄)alkyl]₂amino, phenyl, and —(C₁-C₄)alkyl-phenyl, wherein said phenyl is optionally substituted by 1 substituent independently selected from halo and cyano and —C(O)—R⁶ wherein R⁶ is selected from the group consisting of (C₁-C₄)alkyl, ((C₁-C₄)alkyl]₂amino, amino, and —(C₁-C₄)alkyl-phenyl, said phenyl being optionally substituted by one or two substituents independently selected from halo, cyano, (C₁-C₄)alkyl and (C₁-C₄)alkoxy.

More preferably R² is selected from the group consisting of (C₁-C₃)alkyl optionally substituted by —O—(C₁-C₃)alkyl, preferably methoxy, (C₃-C₅)cycloalkyl, het², wherein het² is preferably selected from the group consisting of 5 or 6 membered monocyclic heteroaromatic ring systems containing 1 to 2 nitrogen atoms or 1 nitrogen atom and 1 oxygen atom or 1 nitrogen atom and 1 sulphur atom, said het² being optionally substituted by one or two substituents independently selected from halo, cyano, (C¹-C₄)alkyl and (C₁-C₄)alkoxy, preferably (C₁-C₄)alkyl, SO₂—R⁵ wherein R⁵ is selected from the group consisting of (C₁-C₄)alkyl, [(C₁-C₄)alkyl]₂amino, phenyl, and —(C₁-C₄)alkyl-phenyl, wherein said phenyl is optionally substituted by 1 substituent independently selected from halo and cyano and wherein R⁵ is preferably (C₁-C₄)alkyl, C(O)—R⁶ wherein R⁶ is selected from the group consisting of (C₁-C₄)alkyl, ((C₁-C₄)alkyl]₂amino, amino, and —(C₁-C₄)alkyl-phenyl, said phenyl being optionally substituted by one or two substituents independently selected from halo, cyano, (C₁-C₄)alkyl and (C₁-C₄)alkoxy, and wherein R6 is preferably (C₁-C₄)alkyl.

In another aspect of the invention, R² is preferably (C₁-C₃) alkyl optionally substituted by methoxy.

het² is preferably selected from the group consisting of 5 or 6 membered monocyclic heteroaromatic ring systems containing 1 or 2 nitrogen atoms.

In another aspect of the invention, R² is preferably a pyridazinyl group.

According to a further preferred aspect of the invention R¹ and R² form together with the N atom to which they are attached a 4-, 5-, 6- or 7-membered saturated heterocycle wherein one C atom may be replaced by N, O, S, SO or SO₂ and wherein said saturated heterocycle is optionally substituted by one or two groups independently selected from hydroxy, halo, =O, (C₁-C₄)alkyl, —(C₁-C₄)alkyl(C₃-C₆)cycloalkyl, (C₁-C₄)alkoxy, hydroxy(C₁-C₄)alkyl, (C₁-C₄)alkoxy(C₁-C₄)alkyl, —SO₂(C₁-C₄)alkyl, —C(O)(C₁-C₄)alkyl, [(C₁-C₄)alkyl]₂amino, —C(O)NH₂, C(O)O(C₁-C₄)alkyl and pyrrolidinone, more preferably R¹ and R² form together with the N atom to which they are attached a 5- or 6-membered saturated heterocycle selected from

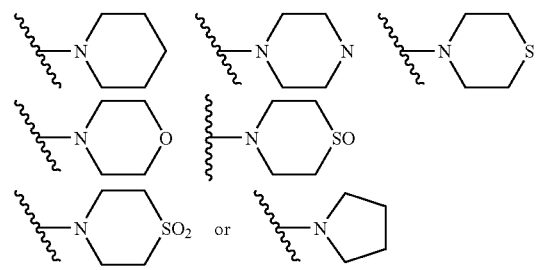

optionally substituted by one or two groups independently selected from hydroxy, fluoro, hydroxymethyl, methoxymethyl, SO₂(C₁-C₄)alkyl, —C(O)(C₁-C₄)alkyl, —CONH₂, and pyrrolidinone.

Even more preferably, R¹ and R² form together with the N atom to which they are attached a morpholinyl group.

Preferably R³ and R⁴ are each independently selected from hydrogen and (C₁-C₄)alkyl or R³ and R⁴ form together with the N atom to which they are attached a 4, 5 or 6 membered saturated heterocycle wherein one C atom may be replaced by N or O and wherein said saturated heterocycle is optionally substituted by (C₁-C₄)alkyl.

More preferably, R³ and R⁴ are selected independently from hydrogen, methyl and ethyl, or R³ and R⁴ form together with the N atom to which they are attached a pyrrolidinyl, piperidinyl, piperazinyl or azetidinyl ring, (each pyrrolidinyl, piperidinyl, piperazinyl and azetidinyl ring being optionally methyl substituted).

Preferably, Y is selected from $CH_2$, CH(OH), O and C=O, more preferably Y is O.

Preferably, Z is O

Preferably m is equal to 1 or 2 and p is equal to 2, more preferably m and p are both 2.

In one preferred aspect of the invention R is a group of formula:

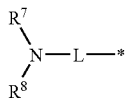

wherein * represents the attachment point to Z, L is a $(C_2-C_5)$ alkylene and $R^7$ and $R^8$ are each independently selected from hydrogen, $(C_1-C_6)$alkyl, $(C_3-C_6)$cycloalkyl, hydroxy$(C_1-C_6)$ alkyl or $R^7$ and $R^8$ form together with the N atom to which they are attached a 4-, 5-, 6- or 7-membered saturated heterocycle wherein one C atom is optionally replaced by N, O, S, SO or $SO_2$ and wherein said saturated heterocycle is optionally substituted by one or two groups independently selected from $(C_1-C_4)$alkyl, $(C_1-C_4)$alkoxy, $(C_1-C_4)$alkoxy$(C_1-C_4)$ alkyl, hydroxy$(C_1-C_4)$alkyl, hydroxy, $C(O)O(C_1-C_4)$alkyl, —C(O)—$(C_1-C_4)$alkyl-$NH_2$, —C(O)$NH_2$ and halo. Examples of the 4-, 5-, 6- or 7-membered saturated heterocycle are:

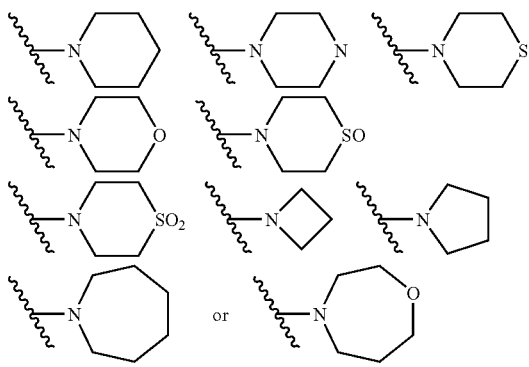

Even more preferably, $R^7$ and $R^8$ form together with the N atom to which they are attached a morpholinyl or oxazepanyl group.

In another preferred aspect, $R^7$ and $R^8$ form together with the N atom to which they are attached a 4-, 5- or 6-membered saturated heterocycle, optionally substituted by one or two $(C_1-C_4)$alkyl, preferably methyl. In another more preferred aspect, the saturated heterocycle is a pyrrolidinyl group, optionally substituted by one or two methyl groups.

Preferably, L is propylene.

According to another preferred aspect of the invention R is a group of formula:

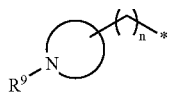

wherein * represents the attachment point to Z, the N-containing ring is a 4- or 6-membered saturated heterocycle, n is an integer equal to 0 or 1, and $R^9$ represents a substituent selected from hydrogen, $(C_1-C_4)$alkyl and $(C_3-C_6)$cycloalkyl.

Preferably, $R^9$ is isopropyl or cyclobutyl.

When one of the groups in the compound of formula (I) is substituted by halo, generally fluoro or chloro, in particular fluoro is preferred.

Particularly preferred compounds of the invention include those in which each variable in formula (I) is selected from the suitable and/or preferred groups for each variable. Even more preferable compounds of the invention include those where each variable in formula (I) is selected from the more preferred or most preferred groups for each variable.

According to a particular aspect of the invention the following compounds are excluded from the invention: compounds of formula (I), wherein Y is O, Z is O, R is a group of formula:

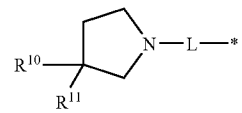

wherein $R^{10}$ is hydrogen or $(C_1-C_4)$alkyl, $R^{11}$ is $(C_1-C_4)$ alkoxy, hydroxy or $N((C_1-C_4)alkyl)_2$ and X is —CN, —$CH_2OH$, —$CH_2$—O—$(C_1-C_4)$alkyl, —C(O)OH, —C(O) O$(C_1-C_4)$alkyl, —$CONR^3R^4$ or $CH_2NR^1R^2$ wherein $R^1$ is hydrogen or a $(C_1-C_4)$alkyl group and $R^2$ is either hydrogen, $(C_1-C_4)$alkyl (optionally substituted by phenyl) or —C(O) $(C_1-C_4)$alkyl.

In another embodiment of the present invention, there is provided a compound of formula (I) selected from:

3-(4-{4-[(dimethylamino)methyl]tetrahydro-2H-pyran-4-yl}phenoxy)-N,N-dimethylpropan-1-amine;

1-isopropyl-4-{4-[4-(4-methyl-1,3-thiazol-2-yl)tetrahydro-2H-pyran-4-yl]phenoxy}piperidine;

4-methyl-2-{4-[4-(4-pyrrolidin-1-ylbutoxy)phenyl]tetrahydro-2H-pyran-4-yl}-1,3-thiazole;

2-{4-[4-(4-pyrrolidin-1-ylbutoxy)phenyl]tetrahydro-2H-pyran-4-yl}-1,3-thiazole;

4-(4-{3-[ethyl(methyl)amino]propoxy}phenyl)tetrahydro-2H-pyran-4-carbonitrile;

4-[4-(4-pyrrolidin-1-ylbutoxy)phenyl]tetrahydro-2H-pyran-4-carboxamide;

1-({4-[4-(4-pyrrolidin-1-ylbutoxy)phenyl]tetrahydro-2H-pyran-4-yl}carbonyl)pyrrolidine;

N-ethyl-N',N'-dimethyl-N-({4-[4-(3-pyrrolidin-1-ylpropoxy)phenyl]tetrahydro-2H-pyran-4-yl}methyl)ethane-1,2-diamine;

1-(4-{4-[4-(azetidin-1-ylcarbonyl)tetrahydro-2H-pyran-4-yl]phenoxy}butyl)pyrrolidine;

N,N-dimethyl-4-[4-(4-pyrrolidin-1-ylbutoxy)phenyl]tetrahydro-2H-pyran-4-carboxamide;

N-methyl-1-pyridin-2-yl-N-({4-[4-(3-pyrrolidin-1-ylpropoxy)phenyl]tetrahydro-2H-pyran-4-yl}methyl)methanamine;

1-cyclohexyl-N-methyl-N-({4-[4-(3-pyrrolidin-1-ylpropoxy)phenyl]tetrahydro-2H-pyran-4-yl}methyl)methanamine;

N,N-dimethyl-1-({4-[4-(3-pyrrolidin-1-ylpropoxy)phenyl] tetrahydro-2H-pyran-4-yl}carbonyl)azetidin-3-amine;

N,N,N'-trimethyl-N'-({4-[4-(3-pyrrolidin-1-ylpropoxy)phenyl]tetrahydro-2H-pyran-4-yl}methyl)ethane-1,2-diamine;

N,N-dimethyl-1-({4-[4-(3-pyrrolidin-1-ylpropoxy)phenyl] tetrahydro-2H-pyran-4-yl}methyl)azetidin-3-amine;

N-(3-{4-[4-(aminomethyl)tetrahydro-2H-pyran-4-yl]
phenoxy}propyl)cyclobutanamine;
3-{4-[4-(aminomethyl)tetrahydro-2H-pyran-4-yl]phenoxy}-N-ethyl-N-methylpropan-1-amine;
N-cyclobutyl-4-[4-(3-pyrrolidin-1-ylpropoxy)phenyl]tetrahydro-2H-pyran-4-carboxamide;
N-cyclopentyl-4-[4-(3-pyrrolidin-1-ylpropoxy)phenyl]tetrahydro-2H-pyran-4-carboxamide;
N-(cyclopropylmethyl)-4-[4-(3-pyrrolidin-1-ylpropoxy)phenyl]tetrahydro-2H-pyran-4-carboxamide;
N-cyclohexyl-4-[4-(3-pyrrolidin-1-ylpropoxy)phenyl]tetrahydro-2H-pyran-4-carboxamide;
1-(4-{4-[(2-pyrrolidin-1-ylethyl)thio]phenyl}tetrahydro-2H-pyran-4-yl)methanamine;
N,N-dimethyl-1-(4-{4-[(2-pyrrolidin-1-ylethyl)thio]phenyl}tetrahydro-2H-pyran-4-yl)methanamine;
1-[3-(4-{4-[(dimethylamino)methyl]tetrahydro-2H-pyran-4-yl}phenoxy)propyl]pyrrolidin-3-ol;
1-[4-(4-{3-[(2R,6S)-2,6-dimethylmorpholin-4-yl]propoxy}phenyl)tetrahydro-2H-pyran-4-yl]-N,N-dimethylmethanamine;
1-[(4-{4-[(3-pyrrolidin-1-ylpropyl)thio]phenyl}tetrahydro-2H-pyran-4-yl)carbonyl]piperidine;
1-[3-({4-[4-(pyrrolidin-1-ylcarbonyl)tetrahydro-2H-pyran-4-yl]phenyl}thio)propyl]pyrrolidine;
(4-{4-[(3-pyrrolidin-1-ylpropyl)thio]phenyl}tetrahydro-2H-pyran-4-yl)methanol;
N-ethyl-N-({4-[4-(3-thiomorpholin-4-ylpropoxy)phenyl]tetrahydro-2H-pyran-4-yl}methyl)acetamide;
N,N-dimethyl-1-[4-(4-{3-[(3R)-3-methylmorpholin-4-yl]propoxy}phenyl)tetrahydro-2H-pyran-4-yl]methanamine;
N-[(4-{4-[(3-pyrrolidin-1-ylpropyl)thio]phenyl}tetrahydro-2H-pyran-4-yl)methyl]acetamide;
N-[(4-{4-[(3-pyrrolidin-1-ylpropyl)thio]phenyl}tetrahydro-2H-pyran-4-yl)methyl]ethanamine;
N-methyl-N-[(4-{4-[(3-pyrrolidin-1-ylpropyl)thio]phenyl}tetrahydro-2H-pyran-4-yl)methyl]ethanamine;
N-ethyl-N-[(4-{4-[(3-pyrrolidin-1-ylpropyl)thio]phenyl}tetrahydro-2H-pyran-4-yl)methyl]acetamide;
N-methyl-N-({4-[4-(3-thiomorpholin-4-ylpropoxy)phenyl]tetrahydro-2H-pyran-4-yl}methyl)ethanamine;
N-ethyl-N-({4-[4-(3-thiomorpholin-4-ylpropoxy)phenyl]tetrahydro-2H-pyran-4-yl}methyl)ethanamine;
4-(3-{4-[4-(pyrrolidin-1-ylcarbonyl)tetrahydro-2H-pyran-4-yl]phenoxy}propyl)thiomorpholine;
N-ethyl-N-[(4-{4-[(3-pyrrolidin-1-ylpropyl)thio]phenyl}tetrahydro-2H-pyran-4-yl)methyl]ethanamine;
N-({4-[4-(3-thiomorpholin-4-ylpropoxy)phenyl]tetrahydro-2H-pyran-4-yl}methyl)pyridin-2-amine;
4-[(4-{4-[(1-isopropylpiperidin-4-yl)oxy]phenyl}tetrahydro-2H-pyran-4-yl)methoxy]pyridine;
4-[3-(4-{1-[(4-methylpiperazin-1-yl)carbonyl]cyclohexyl}phenoxy)propyl]morpholine;
4-(3-{4-[1-(piperazin-1-ylcarbonyl)cyclohexyl]phenoxy}propyl)morpholine;
(4-{4-[(1-isopropylazetidin-3-yl)methoxy]phenyl}tetrahydro-2H-pyran-4-yl)methanol;
4-[3-(4-{4-[(4-methylpiperazin-1-yl)carbonyl]tetrahydro-2H-pyran-4-yl}phenoxy)propyl]morpholine;
4-(3-{4-[4-(piperazin-1-ylcarbonyl)tetrahydro-2H-pyran-4-yl]phenoxy}propyl)morpholine;
4-[(4-{4-[(1-isopropylazetidin-3-yl)methoxy]phenyl}tetrahydro-2H-pyran-4-yl)methoxy]pyridine;
4-[(4-{4-[(1-isopropylazetidin-3-yl)methoxy]phenyl}tetrahydro-2H-pyran-4-yl)carbonyl]morpholine;
4-{4-[4-(1H-imidazol-1-ylmethyl)tetrahydro-2H-pyran-4-yl]phenoxy}-1-isopropylpiperidine;
4-[4-(1-methyl-3-pyrrolidin-1-ylpropoxy)phenyl]tetrahydro-2H-pyran-4-carbonitrile;
4-(4-{3-[(3R)-3-hydroxypyrrolidin-1-yl]propoxy}phenyl)tetrahydro-2H-pyran-4-carbonitrile;
4-{4-[(1-ethylpiperidin-4-yl)oxy]phenyl}tetrahydro-2H-pyran-4-carbonitrile;
4-{4-[(1-propylpiperidin-4-yl)oxy]phenyl}tetrahydro-2H-pyran-4-carbonitrile;
(3R)-N,N-dimethyl-1-[3-(4-{4-[(methylamino)methyl]tetrahydro-2H-pyran-4-yl}phenoxy)propyl]pyrrolidin-3-amine;
N-{[4-(4-{3-[(3R)-3-(dimethylamino)pyrrolidin-1-yl]propoxy}phenyl)tetrahydro-2H-pyran-4-yl]methyl}-N-methylmethanesulfonamide;
(3R)-1-{3-[4-(4-{[(2-methoxyethyl)(methyl)amino]methyl}tetrahydro-2H-pyran-4-yl)phenoxy]propyl}-N,N-dimethylpyrrolidin-3-amine;
N-{[4-(4-{3-[(3R)-3-(dimethylamino)pyrrolidin-1-yl]propoxy}phenyl)tetrahydro-2H-pyran-4-yl]methyl}-N,N',N'-trimethylurea;
(3R)-N,N-dimethyl-1-(3-{4-[4-(1,3-thiazol-2-yl)tetrahydro-2H-pyran-4-yl]phenoxy}propyl)pyrrolidin-3-amine;
(3R)-N,N-dimethyl-1-(3-{4-[4-(morpholin-4-ylcarbonyl)tetrahydro-2H-pyran-4-yl]phenoxy}propyl)pyrrolidin-3-amine;
N-{[4-(4-{3-[(3R)-3-(dimethylamino)pyrrolidin-1-yl]propoxy}phenyl)tetrahydro-2H-pyran-4-yl]methyl}-N-methylpyrimidin-2-amine;
(3R)-N,N-dimethyl-1-(3-{4-[4-(morpholin-4-ylmethyl)tetrahydro-2H-pyran-4-yl]phenoxy}propyl)pyrrolidin-3-amine;
1-isopropyl-4-{4-[4-(piperidin-1-ylcarbonyl)tetrahydro-2H-pyran-4-yl]phenoxy}piperidine;
4-[(4-{4-[(1-isopropylpiperidin-4-yl)oxy]phenyl}tetrahydro-2H-pyran-4-yl)carbonyl]morpholine;
N-isopropyl-4-{4-[(1-isopropylpiperidin-4-yl)oxy]phenyl}-N-methyltetrahydro-2H-pyran-4-carboxamide;
N*4*-{4-[4-(3-Pyrrolidin-1-yl-propoxy)-phenyl]-tetrahydro-pyran-4-ylmethyl}-pyridine-3,4-diamine;
N*2*-{4-[4-(3-Pyrrolidin-1-yl-propoxy)-phenyl]-tetrahydro-pyran-4-ylmethyl}-pyridine-2,3-diamine;
Particularly preferred compounds of formula (I) are as described in the Examples section hereafter. Where the salt form is obtained in the Examples, a compound of the present invention includes the free base thereof, for example:
{4-[4-(3-Pyrrolidin-1-ylpropoxy)phenyl]tetrahydropyran-4-yl}methylamine;
{4-[4-(3-Piperidin-1-ylpropoxy)phenyl]tetrahydropyran-4-yl}methylamine; and
Dimethyl-{4-[4-(3-piperidin-1-ylpropoxy)phenyl]tetrahydro-pyran-4-ylmethyl}amine.
In another embodiment of the invention, particularly preferred examples are:
{4-[4-(1-Isopropylpiperidin-4-yloxy)phenyl]tetrahydropyran-4-ylmethyl}dimethyl-amine;
Dimethyl-{4-[4-(4-pyrrolidin-1-ylbutoxy)phenyl]tetrahydro-pyran-4-ylmethyl}amine;
{4-[4-(3-Pyrrolidin-1-ylpropoxy)phenyl]tetrahydropyran-4-yl}methylamine;
Dimethyl-{4-[4-(3-pyrrolidin-1-ylpropoxy)phenyl]-tetrahydropyran-4-ylmethyl}amine;
{4-[4-(3-Piperidin-1-ylpropoxy)phenyl]tetrahydropyran-4-yl}methylamine;
Dimethyl-{4-[4-(3-piperidin-1-ylpropoxy)phenyl]tetra-hydropyran-4-ylmethyl}amine;

1-Methyl-4-{4-[4-(3-pyrrolidin-1-yl-propoxy)-phenyl]-tetrahydro-pyran-4-ylmethyl}-piperazine;
(R)-2-Methoxymethyl-1-{4-[4-(3-pyrrolidin-1-yl-propoxy)-phenyl]-tetrahydro-pyran-4-yl}-pyrrolidine;
(S)-2-Methoxymethyl-1-{4-[4-(3-pyrrolidin-1-ylpropoxy)-phenyl]tetrahydropyran-4-ylmethyl}pyrrolidine;
1-{4-[4-(3-Pyrrolidin-1-ylpropoxy)phenyl]tetrahydropyran-4-ylmethyl}piperidine;
methyl-{4-[4-(3-pyrrolidin-1-ylpropoxy)phenyl]-tetrahydropyran-4-ylmethyl}amine;
isopropyl-methyl-{4-[4-(3-pyrrolidin-1-ylpropoxy)phenyl]-tetrahydropyran-4-ylmethyl}amine;
1-{4-[4-(3-Pyrrolidin-1-ylpropoxy)phenyl]tetrahydropyran-4-ylmethyl}pyrrolidine;
4-{4-[4-(3-Pyrrolidin-1-ylpropoxy)phenyl]tetrahydropyran-4-ylmethyl}-morpholine;
(2-methoxyethyl)-methyl-{4-[4-(3-pyrrolidin-1-ylpropoxy)-phenyl]tetrahydropyran-4-ylmethyl}amine;
4-[4-(1-Isopropylpiperidin-4-yloxy)phenyl]tetrahydropyran-4-carbonitrile;
4-[4-(3-Pyrrolidin-1-ylpropoxy)phenyl]tetrahydro-2H-pyran-4-carboxylic acid amide;
N-methyl-1-{1-[4-(3-pyrrolidin-1-ylpropoxy)phenyl]-cyclohexyl}methanamine;
N-ethyl-N-({4-[4-(3-pyrrolidin-1-ylpropoxy)phenyl]tetrahydro-2H-pyran-4-yl}methyl)ethanamine;
N-({4-[4-(3-pyrrolidin-1-ylpropoxy)phenyl]tetrahydro-2H-pyran-4-yl}methyl)ethanamine;
N-methyl-N-({4-[4-(3-pyrrolidin-1-ylpropoxy)phenyl]-tetrahydro-2H-pyran-4-yl}methyl)ethanamine;
4-{4-[(1-cyclobutyl-4-piperidinyl)oxy]phenyl}tetrahydro-2H-pyran-4-carbonitrile;
4-{4-[(1-isopropylpiperidin-4-yl)oxy]phenyl}tetrahydro-2H-pyran-4-carboxamide;
4-{4-[(1-isopropylpiperidin-4-yl)oxy]phenyl]-N,N-dimethyltetrahydro-2H-pyran-4-carboxamide;
4-{4-[(1-isopropylpiperidin-4-yl)oxy]phenyl]-N,N-diethyltetra-hydro-2H-pyran-4-carboxamide;
4-{4-[(1-isopropylpiperidin-4-yl)oxy]phenyl)tetrahydro-2H-pyran-4-yl]carbonyl}pyrrolidine;
4-methyl-2-[4-(4-(3-pyrrolidin-1-ylpropoxy)phenyl)tetrahydro-2H-pyran-4-yl]-1,3-thiazole;
2-[4-(4-(3-pyrrolidin-1-ylpropoxy)phenyl)tetrahydro-2H-pyran-4-yl]-1,3-thiazole;
N-[(4-{4-[(1-isopropylpiperidin-4-yl)oxy]phenyl}tetrahydro-2H-pyran-4-yl)methyl]-N-methylamine;
N-[(4-{4-[(1-isopropylpiperidin-4-yl)oxy]phenyl}tetrahydro-2H-pyran-4-yl)methyl]-N-ethylamine;
N-{[4-(4-[(1-isopropylpiperidin-4-yl)oxy]phenyl)tetrahydro-2H-pyran-4-yl]methyl}pyrimidin-2-amine;
N-{[4-(4-(3-Pyrrolidin-1-ylpropoxy)phenyl)tetrahydro-2H-pyran-4-yl]methyl}pyrimidin-2-amine;
1-(4-{4-[(1-cyclopentylazetidin-3-yl)methoxy]phenyl}tetrahydro-2H-pyran-4-yl)-N,N-dimethylmethanamine;
3-({4-[4-(3-pyrrolidin-1-ylpropoxy)phenyl]tetrahydro-2H-pyran-4-yl}methyl)-3H-imidazo[4,5-b]pyridine;
2-{[methyl({4-[4-(3-pyrrolidin-1-ylpropoxy)phenyl]tetrahydro-2H-pyran-4-yl}methyl)amino]methyl}phenol;
N-methyl-N-({4-[4-(3-pyrrolidin-1-ylpropoxy)phenyl]tetrahydro-2H-pyran-4-yl}methyl)cyclopentanamine;
2-[methyl({4-[4-(3-pyrrolidin-1-ylpropoxy)phenyl]tetrahydro-2H-pyran-4-yl}methyl)amino]ethanol;
N-methyl-N-({4-[4-(3-pyrrolidin-1-ylpropoxy)phenyl]tetrahydro-2H-pyran-4-yl}methyl)cyclopropanamine;
1-(3-{4-[4-(aziridin-1-ylmethyl)tetrahydro-2H-pyran-4-yl]phenoxy}propyl)pyrrolidine;
N-({4-[4-(3-thiomorpholin-4-ylpropoxy)phenyl]tetrahydro-2H-pyran-4-yl}methyl)ethanamine;
1-(4-{4-[(1-cyclobutylpiperidin-4-yl)oxy]phenyl}tetrahydro-2H-pyran-4-yl)-N,N-dimethylmethanamine;
N,N-dimethyl-1-(4-{4-[(3-pyrrolidin-1-ylpropyl)thio]phenyl}tetrahydro-2H-pyran-4-yl)methanamine;
N-methyl-N-({4-[4-(3-pyrrolidin-1-ylpropoxy)phenyl]tetrahydro-2H-pyran-4-yl}methyl)cyclohexanamine;
1-[3-({4-[4-(pyrrolidin-1-ylmethyl)tetrahydro-2H-pyran-4-yl]phenyl}thio)propyl]pyrrolidine;
1-({1-[4-(3-pyrrolidin-1-ylpropoxy)phenyl]cyclohexyl}methyl)piperidin-4-ol;
1-({4-[4-(3-pyrrolidin-1-ylpropoxy)phenyl]tetrahydro-2H-pyran-4-yl}methyl)-1H-benzimidazole;
4-{4-[(1-cyclobutylpiperidin-4-yl)oxy]phenyl}tetrahydro-2H-pyran-4-carboxamide;
N-methyl-N-({4-[4-(3-pyrrolidin-1-ylpropoxy)phenyl]tetrahydro-2H-pyran-4-yl}methyl)hexan-1-amine;
1-cyclopropyl-N-(cyclopropylmethyl)-N-({4-[4-(3-pyrrolidin-1-ylpropoxy)phenyl]tetrahydro-2H-pyran-4-yl}methyl)methanamine;
N-[2-(dimethylamino)ethyl]-N-ethyl-4-[4-(3-pyrrolidin-1-ylpropoxy)phenyl]tetrahydro-2H-pyran-4-carboxamide;
N-methyl-N-({4-[4-(3-pyrrolidin-1-ylpropoxy)phenyl]tetrahydro-2H-pyran-4-yl}methyl)butan-1-amine;
4-{4-[4-(4,5-dimethyl-1H-imidazol-2-yl)tetrahydro-2H-pyran-4-yl]phenoxy}-1-isopropylpiperidine;
3-{[methyl({4-[4-(3-pyrrolidin-1-ylpropoxy)phenyl]tetrahydro-2H-pyran-4-yl}methyl)amino]methyl}phenol;
4-[(4-{4-[(1-cyclopentylazetidin-3-yl)methoxy]phenyl}tetrahydro-2H-pyran-4-yl)methyl]morpholine;
N-methyl-N-({4-[4-(3-pyrrolidin-1-ylpropoxy)phenyl]tetrahydro-2H-pyran-4-yl}methyl)pentan-1-amine;
4-{4-[(1-cyclobutylpiperidin-4-yl)oxy]phenyl}-N,N-dimethyltetrahydro-2H-pyran-4-carboxamide;
N,N-dimethyl-1-(4-{4-[3-(1,4-oxazepan-4-yl)propoxy]phenyl}tetrahydro-2H-pyran-4-yl)methanamine;
N,3,3-trimethyl-N-({4-[4-(3-pyrrolidin-1-ylpropoxy)phenyl]tetrahydro-2H-pyran-4-yl}methyl)butan-1-amine;
4-{4-[(1-cyclobutylpiperidin-4-yl)oxy]phenyl}-N-isopropyltetrahydro-2H-pyran-4-carboxamide;
1-methyl-4-({4-[4-(3-pyrrolidin-1-ylpropoxy)phenyl]tetrahydro-2H-pyran-4-yl}methyl)-1,4-diazepane;
1-cyclobutyl-4-{4-[4-(1,3-thiazol-2-yl)tetrahydro-2H-pyran-4-yl]phenoxy}piperidine;
N-[(4-{4-[(1-cyclobutylpiperidin-4-yl)oxy]phenyl}tetrahydro-2H-pyran-4-yl)methyl]pyridin-2-amine;
N-methyl-1-{4-[4-(3-morpholin-4-ylpropoxy)phenyl]tetrahydro-2H-pyran-4-yl}methanamine;
1-[(4-{4-[(1-isopropylpiperidin-4-yl)oxy]phenyl}tetrahydro-2H-pyran-4-yl)carbonyl]-4-methylpiperazine;
1-cyclopentyl-N-methyl-N-({4-[4-(3-pyrrolidin-1-ylpropoxy)phenyl]tetrahydro-2H-pyran-4-yl}methyl)methanamine;
4-{4-[(1-cyclobutylpiperidin-4-yl)oxy]phenyl}-N-ethyltetrahydro-2H-pyran-4-carboxamide;
N-[(4-{4-[(1-cyclobutylpiperidin-4-yl)oxy]phenyl}tetrahydro-2H-pyran-4-yl)methyl]pyrimidin-2-amine;
N,N-diethyl-4-[4-(3-pyrrolidin-1-ylpropoxy)phenyl]tetrahydro-2H-pyran-4-carboxamide;

4-[(4-{4-[(1-cyclobutylazetidin-3-yl)methoxy]
  phenyl}tetrahydro-2H-pyran-4-yl)methyl]morpholine;
4-{4-[(1-cyclobutylpiperidin-4-yl)oxy]phenyl}-N-methyltetrahydro-2H-pyran-4-carboxamide;
1-cyclobutyl-4-{4-[4-(4-methyl-1,3-thiazol-2-yl)tetrahydro-2H-pyran-4-yl]phenoxy}piperidine;
4-[(4-{4-[(1-isopropylazetidin-3-yl)methoxy]
  phenyl}tetrahydro-2H-pyran-4-yl)methyl]morpholine;
1-isopropyl-4-{4-[4-(1,3-thiazol-2-yl)tetrahydro-2H-pyran-4-yl]phenoxy}piperidine;
1-(4-{4-[(1-cyclobutylazetidin-3-yl)methoxy]
  phenyl}tetrahydro-2H-pyran-4-yl)methanamine;
1-ethyl-4-({4-[4-(3-pyrrolidin-1-ylpropoxy)phenyl]tetrahydro-2H-pyran-4-yl}carbonyl)piperazine;
N-ethyl-N-methyl-4-[4-(3-pyrrolidin-1-ylpropoxy)phenyl]
  tetrahydro-2H-pyran-4-carboxamide;
1-(4-{4-[(1-isopropylazetidin-3-yl)methoxy]
  phenyl}tetrahydro-2H-pyran-4-yl)methanamine;
1-[(4-{4-[(1-isopropylpiperidin-4-yl)oxy]
  phenyl}tetrahydro-2H-pyran-4-yl)methyl]4-methylpiperazine;
1-(cyclopropylmethyl)-4-({4-[4-(3-pyrrolidin-1-ylpropoxy)
  phenyl]tetrahydro-2H-pyran-4-;yl}methyl)piperazine
N,N-dimethyl-1-{4-[4-(3-morpholin-4-ylpropoxy)phenyl]
  tetrahydro-2H-pyran-4-yl}methanamine;
N-[2-(dimethylamino)ethyl]-N-methyl-4-[4-(3-pyrrolidin-1-ylpropoxy)phenyl]tetrahydro-2H-pyran-4-carboxamide;
1-({4-[4-(3-pyrrolidin-1-ylpropoxy)phenyl]tetrahydro-2H-pyran-4-yl}carbonyl)piperazine;
1-ethyl-4-({4-[4-(3-pyrrolidin-1-ylpropoxy)phenyl]tetrahydro-2H-pyran-4-yl}methyl)piperazine;
4-[(4-{4-[(1-cyclobutylpiperidin-4-yl)oxy]
  phenyl}tetrahydro-2H-pyran-4-yl)carbonyl]morpholine;
N-[(4-{4-[(1-cyclobutylpiperidin-4-yl)oxy]
  phenyl}tetrahydro-2H-pyran-4-yl)methyl]pyridin-3-amine;
1-methyl-4-({1-[4-(3-pyrrolidin-1-ylpropoxy)phenyl]
  cyclohexyl}carbonyl)piperazine;
1-({4-[4-(3-pyrrolidin-1-ylpropoxy)phenyl]tetrahydro-2H-pyran-4-yl}methyl)-1H-imidazole;
N-[(4-{4-[(1-isopropylpiperidin-4-yl)oxy]
  phenyl}tetrahydro-2H-pyran-4-yl)methyl]pyridin-2-amine;
1-isopropyl-4-({4-[4-(3-pyrrolidin-1-ylpropoxy)phenyl]tetrahydro-2H-pyran-4-yl}methyl)piperazine;
1-({4-[4-(3-pyrrolidin-1-ylpropoxy)phenyl]tetrahydro-2H-pyran-4-yl}methyl)-1H-imidazo[4,5-c]pyridine;
N-({4-[4-(3-piperidin-1-ylpropoxy)phenyl]tetrahydro-2H-pyran-4-yl}methyl)pyridin-2-amine;
1-propyl-4-({4-[4-(3-pyrrolidin-1-ylpropoxy)phenyl]tetrahydro-2H-pyran-4-yl}carbonyl)piperazine;
N-({4-[4-(3-pyrrolidin-1-ylpropoxy)phenyl]tetrahydro-2H-pyran-4-yl}methyl)pyridazin-4-amine;
N-ethyl-4-{4-[(1-isopropylpiperidin-4-yl)oxy]phenyl}-N-methyltetrahydro-2H-pyran-4-carboxamide;
1-methyl-4-({4-[4-(3-pyrrolidin-1-ylpropoxy)phenyl]tetrahydro-2H-pyran-4-yl}carbonyl)piperazine;
1-propyl-4-({4-[4-(3-pyrrolidin-1-ylpropoxy)phenyl]tetrahydro-2H-pyran-4-yl}methyl)piperazine;
N-({4-[4-(3-pyrrolidin-1-ylpropoxy)phenyl]tetrahydro-2H-pyran-4-yl}methyl)pyridin-2-amine;
4-{4-[(azetidin-1-ylcarbonyl)tetrahydro-2H-pyran-4-yl]
  phenoxy}-1-isopropylpiperidine;
1-(2-methoxyethyl)-4-({4-[4-(3-pyrrolidin-1-ylpropoxy)
  phenyl]tetrahydro-2H-pyran-4-yl}methyl)piperazine;
2-{4-[4-(3-pyrrolidin-1-ylpropoxy)phenyl]tetrahydro-2H-pyran-4-yl}pyridine;
N-[(4-{4-[(1-isopropylpiperidin-4-yl)oxy]
  phenyl}tetrahydro-2H-pyran-4-yl)methyl]pyridazin-4-amine;
N-[(4-{4-[(1-isopropylazetidin-3-yl)methoxy]
  phenyl}tetrahydro-2H-pyran-4-yl)methyl]pyridin-2-amine;
4-[(4-{4-[(1-isopropylpiperidin-4-yl)oxy]
  phenyl}tetrahydro-2H-pyran-4-yl)methyl]morpholine;
1-methyl-4-({4-[4-(3-pyrrolidin-1-ylpropoxy)phenyl]tetrahydro-2H-pyran-4-yl}carbonyl)-1,4-diazepane;
4-(3-{4-[4-(morpholin-4-ylmethyl)tetrahydro-2H-pyran-4-yl]phenoxy}propyl)-1,4-oxazepane;
1-({4-[4-(3-pyrrolidin-1-ylpropoxy)phenyl]tetrahydro-2H-pyran-4-yl}carbonyl)piperidine;
1-methyl-4-[4-(3-pyrrolidin-1-ylpropoxy)phenyl]piperidine-4-carbonitrile;
1-(3-{4-[4-(pyrrolidin-1-ylcarbonyl)tetrahydro-2H-pyran-4-yl]phenoxy}propyl)pyrrolidine;
2-(methylthio)-1-({4-[4-(3-pyrrolidin-1-ylpropoxy)phenyl]
  tetrahydro-2H-pyran-4-yl}methyl)-1H-imidazole;
4-[4-(3-pyrrolidin-1-ylpropoxy)phenyl]piperidine-4-carbonitrile;
N-[(4-(4-[(1-isopropylpiperidin-4-yl)oxy]phenyl-tetrahydro-2H-pyran-4-yl)methyl]pyridin-3-amine;
6-methyl-N-({4-[4-(3-pyrrolidin-1-ylpropoxy)phenyl]tetrahydro-2H-pyran-4-yl}methyl)pyridin-3-amine;
N-[(4-(4-[(1-ethylpiperidin-4-yl)oxy]phenyl(tetrahydro-2H-pyran-4-yl)methyl]pyridin-2-amine;
N,N-dimethyl-4-[4-(3-pyrrolidin-1-ylpropoxy)phenyl]tetrahydro-2H-pyran-4-carboxamide;
4-({4-[4-(3-pyrrolidin-1-ylpropoxy)phenyl]tetrahydro-2H-pyran-4-yl}methyl)-4H-1,2,4-triazole;
1-({1-[4-(3-pyrrolidin-1-ylpropoxy)phenyl]
  cyclohexyl}methyl)piperazine;
1-isopropyl-4-[4-(3-pyrrolidin-1-ylpropoxy)phenyl]piperidine-4-carbonitrile;
5-{4-[4-(3-pyrrolidin-1-ylpropoxy)phenyl]tetrahydro-2H-pyran-4-yl}-1,3-oxazole;
1-acetyl-4-({1-[4-(3-pyrrolidin-1-ylpropoxy)phenyl]
  cyclohexyl}methyl)piperazine;
4-({4-[4-(3-pyrrolidin-1-ylpropoxy)phenyl]tetrahydro-2H-pyran-4-yl}methoxy)pyridine;
1-acetyl-4-({4-[4-(3-pyrrolidin-1-ylpropoxy)phenyl]tetrahydro-2H-pyran-4-yl}methyl)piperazine;
N-({4-[4-(4-pyrrolidin-1-ylbutoxy)phenyl]tetrahydro-2H-pyran-4-yl}methyl)pyridin-2-amine;
1-[3-(4-{4-[(dimethylamino)methyl]tetrahydro-2H-pyran-4-yl}phenoxy)propyl]-N,N-dimethylazetidin-3-amine;
1-(3-{4-[4-(azetidin-1-ylcarbonyl)tetrahydro-2H-pyran-4-yl]phenoxy}propyl)pyrrolidine;
N-[(4-{4-[(1-cyclobutylazetidin-3-yl)methoxy]
  phenyl}tetrahydro-2H-pyran-4-yl)methyl]pyridin-2-amine;
N-{[4-(4-{3-[cyclobutyl(methyl)amino]propoxy}phenyl)
  tetrahydro-2H-pyran-4-yl]methyl}pyridin-2-amine;
N-({4-[4-(3-pyrrolidin-1-ylpropoxy)phenyl]tetrahydro-2H-pyran-4-yl}methyl)pyridin-3-amine;
4-(3-{4-[4-(morpholin-4-ylmethyl)tetrahydro-2H-pyran-4-yl]phenoxy}propyl)morpholine;
N,N-dimethyl-1-(4-{4-[3-(4-methyl-1,4-diazepan-1-yl)propoxy]phenyl}tetrahydro-2H-pyran-4-yl)methanamine;
1-({4-[4-(3-pyrrolidin-1-ylpropoxy)phenyl]tetrahydro-2H-pyran-4-yl}methyl)-1H-imidazo[4,5-b]pyridine;
4-({4-[4-(3-azetidin-1-ylpropoxy)phenyl]tetrahydro-2H-pyran-4-yl}methyl)morpholine;

2-{4-[4-(3-pyrrolidin-1-ylpropoxy)phenyl]tetrahydro-2H-pyran-4-yl}-1H-imidazole;
4-(3-{4-[4-(piperazin-1-ylcarbonyl)tetrahydro-2H-pyran-4-yl]phenoxy}propyl)-1,4-oxazepane;
4-[3-(4-{4-[(4-methylpiperazin-1-yl)carbonyl]tetrahydro-2H-pyran-4-yl}phenoxy)propyl]-1,4-oxazepane;
4-{4-[4-(3-pyrrolidin-1-ylpropoxy)phenyl]tetrahydro-2H-pyran-4-yl}pyrimidine;
4-methyl-1-({4-[4-(3-pyrrolidin-1-ylpropoxy)phenyl]tetrahydro-2H-pyran-4-yl}methyl)-1H-imidazole;
4-{4-[4-(3-pyrrolidin-1-ylpropoxy)phenyl]tetrahydro-2H-pyran-4-yl}-1H-imidazole;
4-[4-(4-{3-[ethyl(methyl)amino]propoxy}phenyl)tetrahydro-2H-pyran-4-ylmethyl]-morpholine;

Another embodiment of the invention is an intermediate as described herein

Pharmaceutically acceptable salts of the compounds of formula (I) include the acid addition and base salts thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) or by ring-opening a suitable cyclic precursor, for example, a lactone or lactam, using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts.

Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

In accordance with the present invention, compounds of formula (I) include all salts, solvates and complexes thereof.

The compounds of the invention include compounds of formula (I) as hereinbefore defined, including all polymorphs and crystal habits thereof, prodrugs and isomers thereof (including optical, geometric and tautomeric isomers) as hereinafter defined and isotopically-labeled compounds of formula (I).

As indicated, so-called 'pro-drugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T. Higuchi and W. Stella) and 'Bioreversible Carriers in Drug Design', Pergamon Press, 1987 (ed. E. B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H. Bundgaard (Elsevier, 1985).

Some examples of prodrugs in accordance with the invention include:
(i) where the compound of formula (I) contains a carboxylic acid functionality (—C(O)OH), an ester thereof, for example, a compound wherein the hydrogen of the carboxylic acid functionality of the compound of formula (I) is replaced by $(C_1-C_8)$alkyl;
(ii) where the compound of formula (I) contains an alcohol functionality (—OH), an ether thereof, for example, a compound wherein the hydrogen of the alcohol functionality of the compound of formula (I) is replaced by $(C_1-C_6)$alkanoyloxymethyl; and
(iii) where the compound of formula (I) contains a primary or secondary amino functionality (—$NH_2$ or —NHR where R≠H), an amide thereof, for example, a compound wherein, as the case may be, one or both hydrogens of the amino functionality of the compound of formula (I) is/are replaced by $(C_1-C_{10})$alkanoyl.

Further examples of replacement groups in accordance with the foregoing examples and examples of other prodrug types may be found in the aforementioned references.

Moreover, certain compounds of formula (I) may themselves act as prodrugs of other compounds of formula (I).

Also included within the scope of the invention are metabolites of compounds of formula (I), that is, compounds formed in vivo upon administration of the drug. Some examples of metabolites in accordance with the invention include:
(i) where the compound of formula (I) contains a methyl group, an hydroxymethyl derivative thereof (—$CH_3$→—$CH_2OH$):
(ii) where the compound of formula (I) contains an alkoxy group, an hydroxy derivative thereof (—OR→—OH);

(iii) where the compound of formula (I) contains a tertiary amino group, a secondary amino derivative thereof (—NR$^a$R$^b$→—NHR$^a$ or —NHR$^b$);
(iv) where the compound of formula (I) contains a secondary amino group, a primary derivative thereof (—NHR$^a$→—NH$_2$);
(v) where the compound of formula (I) contains a phenyl moiety, a phenol derivative thereof (-Ph→-PhOH); and
(vi) where the compound of formula (I) contains an amide group, a carboxylic acid derivative thereof (—CONR$^c$R$^d$→COOH).

Compounds of formula (I) containing one or more asymmetric carbon atoms can exist as two or more stereoisomers. Where structural isomers are interconvertible via a low energy barrier, tautomeric isomerism ('tautomerism') can occur. This can take the form of proton tautomerism in compounds of formula (I) containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the elutate affords the enriched mixture.

Stereoisomeric conglomerates may be separated by conventional techniques known to those skilled in the art—see, for example, "Stereochemistry of Organic Compounds" by E. L. Eliel (Wiley, New York, 1994).

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labelled reagent previously employed.

Pharmaceutically acceptable solvates in accordance with the invention include those wherein the solvent of crystallization may be isotopically substituted, e.g. D$_2$O, d$_6$-acetone, d$_6$-DMSO.

The phenol and thiophenol derivatives of formula (I) can be prepared using conventional procedures such as by the following illustrative methods in which R, X, Y, Z, m, p, R$^1$, R$^2$, R$^3$, R$^4$, R$^5$, R$^6$, R$^7$, R$^8$ and R$^9$ are as previously defined unless otherwise stated.

The compounds of formula (I), wherein X is —CH$_2$NR$^1$R$^2$, may be prepared from compounds of formula (2):

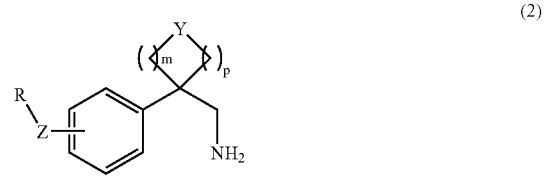

(2)

using standard techniques for functional group interconversion known to those skilled in the art, for example as described in *Comprehensive Organic Transformations*, R. C. Larock, 1$^{st}$ Edition, 1989 VCH Publishers Inc.

These techniques include:
1) Reductive alkylation with aldehydes or ketones with a reducing agent (e.g. formic acid or NaHB(OAc)$_3$) in a suitable solvent (e.g. dichloromethane, tetrahydrofuran), optionally with the addition of acetic acid, at between room temperature (about 20° C.) and reflux;
2) Alkylations with alkyl halides and a base (e.g. potassium carbonate, potassium tert-butoxide) in a suitable solvent (e.g. acetonitrile, tetrahydrofuran) at between room temperature (about 20° C.) and reflux;
3) Sulphonylation with a sulphonyl chloride and a base (e.g. triethylamine, N-ethyldiisopropylamine) in a suitable solvent (e.g. dichloromethane) at between room temperature and reflux;
4) Heteroarylation with a haloheteroaromatic or heteroaromatic sulphonic acid compound and a base (e.g. potassium carbonate) in a suitable solvent (e.g. acetonitrile) at between room temperature (about 20° C.) and reflux. Alternatively this reaction may be performed under microwave radiation, alternatively using N-ethyldiisopropylamine as base, optionally in a suitable solvent (e.g. N-methylpyrrolidinone, acetonitrile).

5) Urea formation with a dialkylcarbamoyl chloride or a cyanate salt, optionally in the presence of a base (e.g. triethylamine) or an acid (e.g. acetic acid) in a suitable solvent (e.g. dichloromethane or water) at between room temperature and reflux;

6) Sulphonyl urea formation with a dialkylsulphamoyl chloride and a base (e.g. triethylamine) in a suitable solvent (e.g. dichloromethane) at between room temperature and reflux;

7) Acylation with an activated acid (e.g. an acyl chloride or anhydride) and a base (e.g. triethylamine) in a suitable solvent (e.g. dichloromethane) at between room temperature and reflux.

8) By palladium catalysed cross-coupling with a haloheteroaromatic compound, using a suitable palladium source (e.g. tris(dibenzylideneacetone)palladium (0)), optionally in the presence of a chelating ligand (e.g. BINAP) and in the presence of a suitable base (e.g. sodium tert-butoxide) in a solvent (e.g. toluene), at between room temperature and reflux.

These transformations can be performed sequentially to prepare compounds in which $R^1$ and $R^2$ are as here above defined.

The compounds of formula (2) may be prepared by reduction of the corresponding cyano derivatives of formula (3):

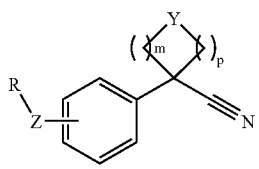

(3)

with a suitable reducing agent (e.g. LiAlH$_4$ or hydrogen gas in the presence of a catalyst such as PtO$_2$) in a suitable solvent (e.g. Et$_2$O/dichloromethane, tetrahydrofuran or isopropanol) at between room temperature and reflux.

The compounds of formula (3) above correspond actually to the compounds of formula (I) wherein X is a CN group.

The compounds of formula (3) wherein Z is O may be prepared by alkylation of the corresponding hydroxy derivatives of formula (4):

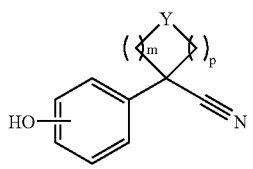

(4)

with a derivative of formula R—$R^{LG}$ wherein $R^{LG}$ is a leaving group such as halo, mesylate or tosylate, in the presence of a base (e.g. potassium carbonate) and optionally in the presence of an additive (e.g. potassium iodide) in a suitable solvent (e.g. dimethylformamide) at between room temperature and reflux.

When R is a group of formula:

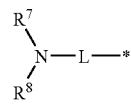

as previously defined, then the derivative of formula R—$R^{LG}$ may be prepared by alkylation of the corresponding amino derivative of formula NHR$^7$R$^8$ with a derivative of formula $R^{LG}$-L-$R^{LG}$ and a base (e.g. NaOH, Na$_2$CO$_3$, K$_2$CO$_3$, Cs$_2$CO$_3$), optionally in the presence of an additive (e.g. potassium iodide) in a suitable solvent (e.g. N,N-dimethylformamide, acetonitrile, acetone/H$_2$O) at between room temperature and reflux. The amino derivative of formula NHR$^7$R$^8$ is either commercial or made using procedures known to the skilled person.

When R is a group of formula:

as previously defined, then the derivative of formula R—$R^{LG}$ is either commercial or may be prepared using literature procedures well-known to the skilled person.

The compounds of formula (4) may be prepared by deprotection of the corresponding derivatives of formula (5) wherein Z is O:

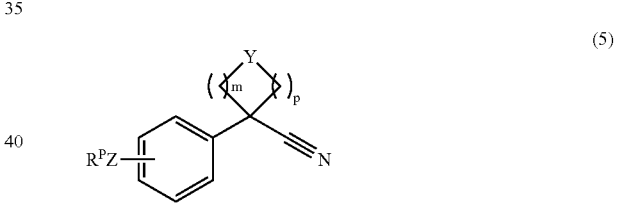

(5)

herein $R^P$ is a protecting group (e.g. methyl, deprotected with BBr$_3$ in dichloromethane at between 0° C. and room temperature).

The compounds of formula (5) are either commercial or may be prepared by double alkylation of the compounds of formula (6):

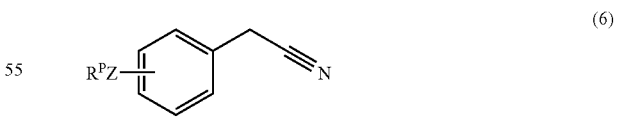

(6)

wherein $R^P$ is as previously defined, with the compounds of formula (7):

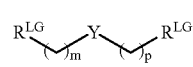

(7)

wherein $R^{LG}$ is as previously defined, and a base (e.g. NaOH), optionally in the presence of an additive (e.g. potassium iodide) in a suitable solvent (e.g. N,N-dimethylformamide, N-methylpyrrolidinone) at between room temperature and reflux.

The compounds of formula (6) and (7) are each either commercially available or made using literature procedures well-known to the skilled person.

Compounds of formula (3), wherein Z represents S may be prepared from compounds of formula (5) wherein Z represents S and $R^P$ is Me by a Pummerer rearrangement, followed by alkylation of the resulting intermediate with a derivative of formula R—$R^{LG}$. The reaction is achieved by treatment of the compound of formula (5) with a suitable oxidant (e.g. m-CPBA) in a suitable solvent (e.g. dichloromethane) at 0° C. to provide the corresponding sulphide. Treatment of this intermediate with trifluoroacetic anhydride in the presence of a suitable base (e.g. 2,6-lutidine) in a suitable solvent (e.g. acetonitrile) at about −15° C., followed by reaction with R—$R^{LG}$, in the presence of a base (e.g. triethylamine, potassium carbonate) in a suitable solvent (e.g. N,N-dimethylformamide) at between 0° C. and room temperature provides the compound of formula (3).

Alternatively, the compounds of formula (3) wherein Z is O may be prepared by alkylation of the compounds of formula (4) with the alcohol derivative of formula ROH, which is either commercial or made using literature procedures well-known to the skilled person, using Mitsunobu reagents such as PPh$_3$ and DIAD in a suitable solvent (e.g. THF) at between 0° C. and reflux.

Persons skilled in the art will appreciate that, in order to obtain compounds of formula (I) in an alternative or more convenient manner, the individual process steps mentioned in this section may be performed in a different order. For example compounds of formula (I) wherein Z is O and X is —CH$_2$NR$^1$R$^2$, may be prepared by alkylation of the compounds of formula (8):

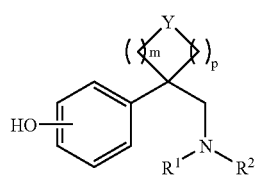

(8)

with a derivative of formula R—$R^{LG}$ or ROH as previously defined, using conditions analogous to those described for the preparation of compounds of formula (3).

The compounds of formula (8) may be prepared by deprotection of the compounds of formula (9):

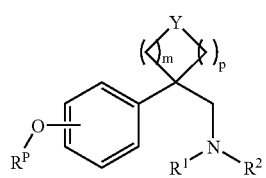

(9)

wherein $R^P$ is as previously defined, using conditions appropriate for the protecting group and the nature of R$^1$ and R$^2$ (e.g. using NaSMe in dimethylformamide at 130° C. wherein $R^P$ is methyl and R$^1$ and R$^2$ are (C$_1$-C$_4$)alkyl).

The compounds of formula (9) may be prepared from the corresponding amino derivatives of formula (10):

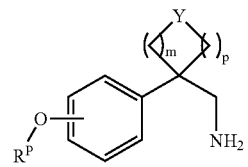

(10)

using analogous conditions to those described for the preparation of compounds of formula (I) from compounds of formula (2).

The compounds of formula (10) may be prepared from compounds of formula (5) wherein Z is O using analogous reduction conditions to those described for the preparation of compounds of formula (2) from compounds of formula (3).

A further example of performing the individual process steps described in this section in a different order to obtain compounds of formula (I) in an alternative or more convenient manner, is the preparation of compounds of formula (I) wherein Z is O by double alkylation of the compounds of formula (11):

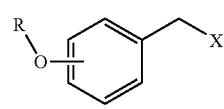

(11)

with the compounds of formula (7) as previously defined, using analogous conditions described for the preparation of compounds of formula (5) from compounds of formula (6).

The compounds of formula (11) may be prepared from the corresponding hydroxy derivatives of formula (12):

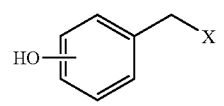

(12)

using analogous conditions described for the preparation of compounds of formula (3) from compounds of formula (4).

The compounds of formula (12) are either commercial or made using literature procedures well-known to the skilled person.

An example of performing the individual process steps described in this section in a different order to obtain compounds of formula (I) wherein Z is O and R is a group of formula:

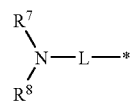

is the preparation of these compounds by reaction of the compounds of formula (13):

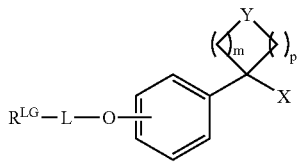

wherein $R^{LG}$ is as previously defined, with the amino derivatives of formula $NHR^7R^8$ using analogous conditions to those previously described for the preparation of $R\text{---}R^{LG}$.

Alternatively, the same transformation can be achieved by heating the compounds of formula (13) with the amino derivatives of formula $NHR^7R^8$ and a base (e.g. diisopropylethylamine) in a suitable solvent (e.g. N-methylpyrrolidinone) at 150-200° C. for 5-10 min using a microwave oven.

Alternatively, the compounds of formula (I) wherein Z is O, X is —$CH_2NR^1R^2$ and $R^1$ and $R^2$ are hydrogen or an optionally substituted $(C_1$-$C_4)$alkyl or together with the N atom to which they are attached form an optionally substituted 4-, 5- or 6-membered saturated heterocycle wherein a C atom may be replaced by N, O, S, SO or $SO_2$, may be prepared by reductive amination of the compounds of formula (14):

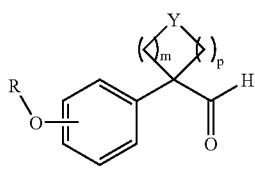

with the amino derivative of formula $HNR^1R^2$ and a reducing agent (e.g. $NaHB(OAc)_3$), optionally in the presence of a Lewis acid (e.g. $Ti(O^iPr)_4$) in a suitable solvent (e.g. EtOH) at between 0° C. and reflux.

The compounds of formula (14) may be prepared by reduction of the compounds of formula (3) wherein Z is O with a reducing agent (e.g. diisobutylaluminium hydride) in a suitable solvent (e.g. toluene) at between -78° C. and room temperature (about 20° C.).

Alternatively, the compounds of formula (14) may be prepared by oxidation of the compounds of formula (I) wherein Z is O and X is —$CH_2OH$, using an oxidant (e.g. pyridinium chlorochromate) in a suitable solvent (e.g. dichloromethane) at between 0° C. and reflux.

The compounds of formula (I) wherein X is —$CH_2OH$, may be prepared by reduction of the compounds of formula (I) wherein X is —$C(O)O(C_1$-$C_4)$alkyl, with a reducing agent (e.g. $LiAlH_4$) in a suitable solvent (e.g. tetrahydrofuran) at between -78° C. and reflux.

The compounds of formula (I) wherein X is —$C(O)O(C_1$-$C_4)$alkyl, may be prepared by esterification of the compounds of formula (I) wherein X is COOH, using the standard procedures well-known to the skilled person. For example, the esterification can be achieved by using a reagent capable of activating a carboxylic acid (e.g. thionyl chloride) and $HO(C_1$-$C_4)$alkyl, optionally in the presence of an additional solvent (e.g. dichloromethane) at between 0° C. and reflux.

The compounds of formula (I) wherein X is C(O)OH, may be prepared by hydrolysis of the compounds of formula (3) as previously defined with a mineral acid (e.g. concentrated aqueous HCl), optionally in the presence of a suitable co-solvent (e.g. dioxane), at between 0° C. and reflux.

The compounds of formula (I) wherein m and p are both equal to 2, Z is O and Y is CH(OH), may be prepared by reduction of the compounds of formula (I) wherein m and p are both equal to 2 and Y is C=O, with a reducing agent (e.g. $LiAlH_4$) in a suitable solvent (e.g. $Et_2O$) at between 0° C. and reflux.

The compounds of formula (I) wherein m and p are both equal to 2, Z is O and Y is C=O, may be prepared by treatment of the compounds of formula (15):

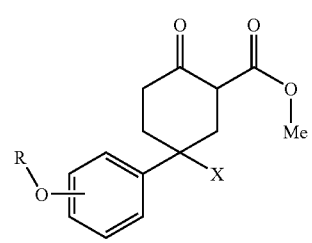

with sodium chloride in a suitable solvent (e.g. dimethylsulphoxide/water) at between 100° C. and reflux.

The compounds of formula (15) may be prepared by treatment of the compounds of formula (16):

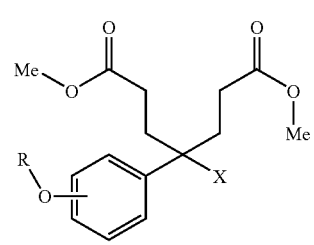

with a base (e.g. NaOH) in a suitable solvent (e.g. 1,2-dimethoxyethane) at between room temperature and reflux.

The compounds of formula (16) may be prepared by alkylation of the compounds of formula (11) as previously defined with methyl acrylate and a base (e.g. benzyltrimethylammonium hydroxide) in a suitable solvent (e.g. methanol/acetonitrile) at between room temperature and reflux.

The compounds of formula (I) wherein X is —$CONH_2$, may be prepared by treatment of the compounds of formula (3) as previously defined with polyphosphoric acid or boron trifluoride-acetic acid complex at between room temperature and 100° C.

The compounds of formula (I) wherein X is —$CONR^3R^4$, may be prepared by reaction of the compounds of formula (I) wherein X is COOH, sequentially with a reagent capable of activating a carboxylic acid (e.g. thionyl chloride) and then with the amino derivative of formula $HNR^3R^4$, in a suitable solvent (e.g. dichloromethane) at between 0° C. and reflux. Alternatively the acid may be treated with the amine of formula $HNR^3R^4$, in the presence of a coupling agent (e.g. TBTU, O-benzotriazol-1-yl-N,N,N',N'-tetramethyluronium hexafluorophosphate, 1-(3-dimethylaminopropyl)-3-ethyl-carbodiimide hydrochloride), optionally in the presence of a suitable additive (e.g. 1-hydroxybenzotriazole) and base (e.g.

triethylamine) in a suitable solvent (e.g. dichloromethane, N,N-dimethylformamide) at room temperature.

Compounds of formula (I) wherein X is $CH_2NR^1R^2$ may be prepared by reduction of compounds of formula (I) wherein X is —$CONR^3R^4$ and $NR^1R^2$ equals $NR^3R^4$, with a reducing agent (e.g. lithium aluminium hydride) in a suitable solvent (e.g. tetrahydrofuran, ether) at between room temperature and 50° C.

The compounds of formula (I) wherein X is —$CH_2$—O—($C_1$-$C_4$)alkyl may be prepared by alkylation of the compounds of formula (I) wherein X is —$CH_2$—OH, with a derivative of formula $R^{LG}$($C_1$-$C_4$)alkyl, wherein $R^{LG}$ is as previously defined, and a base (e.g. NaH) in a suitable solvent (e.g. dimethylformamide) at between room temperature and reflux.

The compounds of formula (I) wherein X is —$CH_2$—O-$het^2$ may be prepared by alkylation of the compounds of formula (I) wherein X is —$CH_2$—OH, with a derivative of formula $R^{LG}Het^2$, by palladium catalysed cross-coupling with a haloheteroaromatic compound, using a suitable palladium source (e.g. tris(dibenzylideneacetone)palladium (0)), optionally in the presence of a chelating ligand (e.g. BINAP) and in the presence of a suitable base (e.g. sodium tert-butoxide) in a solvent (e.g. toluene), at between room temperature and reflux.

Compounds of formula (I) wherein X is $het^1$, may be prepared from compounds of formula (I) wherein X is COOH, or alternatively from compounds of formula (3) or (14) using methods known to those skilled in the art, such as those described in general heterocyclic texts such as *Heterocyclic Chemistry*, J. A. Joule and K. Mills, 4th Edition, Blackwell publishing, 2000 or Comprehensive Heterocyclic chemistry I and II, Pergamon Press.

For example, compounds of formula (I) where X is optionally substituted 2-thiazolyl and Z is O may be prepared by treating compounds of formula (17):

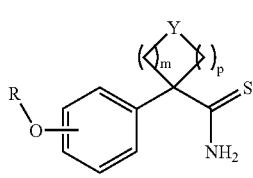

(17)

with a suitable reagent (e.g. bromoacetaldehyde dimethyl acetal, chloroacetone) and HCl in a suitable solvent (e.g. EtOH) at reflux.

Compounds of formula (17) may be prepared by reacting compounds of formula (3) wherein Z is O with diethyldithiophosphate and water at 60° C.

Compounds of formula (I) wherein X is —$CH_2$-$het^1$, and where said $het^1$ is N-linked, may be prepared from compounds of formula (I) wherein X is —$CH_2$—$NH_2$ using methods known to those skilled in the art, such as those described in general heterocyclic texts such as *Heterocyclic Chemistry*, J. A. Joule and K. Mills, 4th Edition, Blackwell publishing, 2000 or Comprehensive Heterocyclic chemistry I and II, Pergamon Press.

Compounds of formula (I) wherein X is —$CH_2$-$het^1$, and where said $het^1$ is C-linked, may be prepared from compounds of formula (I) wherein X is —COOH by a two step process of $CH_2$ homologation using the Arndt-Eistert synthesis (*Advanced Organic Chemistry*, J. March, 4th edition, Wiley-Interscience publication, 1992) followed by standard techniques for heterocycle construction from a carboxylic acid known to those skilled in the art.

The compounds of formula (I) and their precursors which contain a sulphide group can be oxidised to the corresponding sulphoxides or sulphones using standard techniques well-known to those skilled in the art, for example as described in *Comprehensive Organic Transformations*, R. C. Larock, 1st Edition, 1989 VCH Publishers Inc.

It will be appreciated by those skilled in the art that, certain compounds of formula (I) may be converted to alternative compounds of formula (I) using standard chemical transformations. Examples of these include, acylation and sulphonation of amine functions (e.g. see examples 166, 229, 230), reductive amination reactions (e.g. see examples 167, 168), alkylation (e.g. see example 228) or hydrogenation of halo atoms (e.g. see examples 202, 203).

It will be appreciated by those skilled in the art that, in the course of carrying out the processes described above, the functional groups of intermediate compounds may need to be protected by protecting groups.

These functional groups include hydroxyl, amino and carboxylic acid. Suitable protecting groups for hydroxyl include trialkylsilyl and diarylalkylsilyl (e.g. tert-butyldimethylsilyl, tert-butyldiphenylsilyl or trimethylsilyl), alkyl (e.g. methyl or methoxyethyl) and tetrahydropyranyl. Suitable protecting groups for amino include tert-butyloxycarbonyl, 9-fluorenyl-methoxycarbonyl or benzyloxycarbonyl. Suitable [protecting groups for carboxylic acid include ($C_1$-$C_4$)alkyl or benzyl esters.

The protection and deprotection of functional groups may take place before or after any of the reaction steps described hereinbefore.

The introduction and removal of protecting groups is fully described in *Protective Groups in Organic Chemistry*, edited by J. W. F. McOmie, Plenum Press (1973), *Protective Groups in Organic Synthesis*, 2nd edition, T. W. Greene & P. G. M. Wutz, Wiley-Interscience Publication, 1991) and *Protecting Groups*, P. J. Kocienski, Thieme, 1994.

Also, the compounds of formula (I) as well as intermediates for the preparation thereof, can be purified according to various well-known methods such as recrystallisation and chromatography.

The compounds of formula (I), their pharmaceutically acceptable salts and/or derived forms, are valuable pharmaceutically active compounds, which are suitable for the therapy and prophylaxis of numerous disorders in which the histamine $H_3$ receptor is involved or in which agonism or antagonism of this receptor may induce benefit.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

According to another aspect of the invention, there is provided a pharmaceutical composition including a compound of the formula (I) or a pharmaceutically acceptable salt and/or solvate thereof, as defined in any one of the preceding claims, together with a pharmaceutically acceptable excipient.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences,* 19th Edition (Mack Publishing Company, 1995).

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets,* Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function.

The compound of formula (I) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (I) may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line,* 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 µg to 4000 µg of the compound of formula (I). The overall daily dose will typically be in the range 1 µg to 20 mg which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the 0.001 mg to 2000 mg depending, of course, on the mode of administration. For example, oral administration may require a total daily dose of from 1 mg to 2000 mg, while an intravenous dose may only require from 0.01 mg to 100 mg. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

For the avoidance of doubt, references herein to "treatment" include references to curative, palliative and prophylactic treatment.

According to another embodiment of the present invention, the compounds of the formula (I), or pharmaceutically acceptable salts, derived forms or compositions thereof, can also be used as a combination with one or more additional therapeutic agents to be co-administered to a patient to obtain some particularly desired therapeutic end result. The second and more additional therapeutic agents may also be a compound of the formula (I), or a pharmaceutically acceptable salt, derived forms or compositions thereof, or one or more histamine $H_3$ receptor ligands known in the art. More typically, the second and more therapeutic agents will be selected from a different class of therapeutic agents.

As used herein, the terms "co-administration", "co-administered" and "in combination with", referring to the compounds of formula (I) and one or more other therapeutic agents, is intended to mean, and does refer to and include the following:

simultaneous administration of such combination of compound(s) of formula (I) and therapeutic agent(s) to a patient in need of treatment, when such components are formulated together into a single dosage form which releases said components at substantially the same time to said patient, substantially simultaneous administration of such combination of compound(s) of formula (I) and therapeutic agent(s) to a patient in need of treatment, when such components are formulated apart from each other into separate dosage forms which are taken at substantially the same time by said patient, whereupon said components are released at substantially the same time to said patient, sequential administration of such combination compound(s) of formula (I) and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of compound(s) of formula (I) and therapeutic agent(s) to a patient in need of treatment, when such components are formulated together into a single dosage form which releases said components in a controlled manner whereupon they are concurrently, consecutively, and/or overlapingly administered at the same and/or different times by said patient, where each part may be administered by either the same or different route.

Suitable examples of other therapeutic agents which may be used in combination with the compound(s) of formula (I), or pharmaceutically acceptable salts, derived forms or compositions thereof, include, but are by no means limited to:

Histamine $H_1$ receptor antagonists, for instance loratidine, desloratidine, fexofenadine and cetirizine Histamine $H_4$ receptor antagonists Histamine $H_2$ receptor antagonists Leukotriene antagonists, including antagonists of $LTB_4$, $LTC_4$, $LTD_4$, and $LTE_4$, in particular Montelukast Phosphodiesterase inhibitors such as PDE4 inhibitors or PDE5 inhibitors, neurotransmitter re-uptake inhibitors, for instance fluoxetine, sertraline, paroxetine, ziprasidone 5-Lipoxygenase (5-LO) inhibitors or 5-lipoxygenase activating protein (FLAP) antagonists, $\alpha_1$- and $\alpha_2$-adrenoceptor agonist vasoconstrictor sympathomimetic agents for decongestant use, Muscarinic M3 receptor antagonists or anticholinergic agents, $\beta_2$-adrenoceptor agonists, Theophylline, Sodium cromoglycate, COX-1 inhibitors (NSAIDs) and COX-2 selective inhibitors, Oral or inhaled Glucocorticosteroids, Monoclonal antibodies active against endogenous inflammatory entities, Anti-tumor necrosis factor (anti-TNF-α) agents,
Adhesion molecule inhibitors including VLA4 antagonists,
Kinin-$B_1$- and $B_2$-receptor antagonists,
Immunosuppressive agents,
Inhibitors of matrix metalloproteases (MMPs),
Tachykinin $NK_1$, $NK_2$ and $NK_3$ receptor antagonists,
Elastase inhibitors,
Adenosine A2a receptor agonists,
Inhibitors of urokinase,
Compounds that act on dopamine receptors, e.g. D2 agonists,
Modulators of the NFκβ pathway, e.g. IKK inhibitors,
Agents that can be classed as mucolytics or anti-tussive,
antibiotics,
modulators of cytokine signalling pathways such as p38 MAP kinase, syk kinase or JAK kinase inhibitors,
HDAC (histone deacetylase) inhibitors and
PI3 kinase inhibitors
According to the present invention, combination of the compounds of formula (I) with:
Histamine $H_1$ receptor antagonists, for instance loratidine, desloratidine, fexofenadine and cetirizine
Histamine $H_4$ receptor antagonists
Histamine $H_2$ receptor antagonists
Leukotriene antagonists, including antagonists of $LTB_4$, $LTC_4$, $LTD_4$, and $LTE_4$, in particular Montelukast
Phosphodiesterase PDE4 inhibitors
neurotransmitter re-uptake inhibitors, for instance fluoxetine, sertraline, paroxetine, ziprasidone are preferred.

The compounds of formula (I) have the ability to interact with the $H_3$ receptor and thereby have a wide range of therapeutic applications, as described further below, because of the essential role which the $H_3$ receptor plays in the physiology of all mammals. According to this invention $H_3$ ligands are meant to include $H_3$ receptor antagonists, agonists and inverse agonists. For the preferred indications to be treated according to the invention, $H_3$ antagonists are believed to be most suitable.

In another aspect of the invention there is provided a compound of the formula (I) as defined in herein, or a pharmaceutically acceptable salt and/or solvate thereof, for use as a medicament.

A further aspect of the present invention relates to the compounds of formula (I), or pharmaceutically acceptable salts, derived forms or compositions thereof, for use in the treatment of diseases, disorders, and conditions in which the $H_3$ receptor is involved. More specifically, the present invention also concerns the compounds of formula (I), or pharmaceutically acceptable salts, derived forms or compositions thereof, for use in the treatment of diseases, disorders, and conditions selected from the group consisting of:

diseases of the central nervous system: sleep disorders, migraine, dyskinesia, stress-induced anxiety, psychotic disorders, epilepsy, Cognition deficiency diseases such as Alzheimer's disease or mild cognitive impairment, depression, mood disorders, schizophrenia, anxiety disorders, attention-deficit hyperactivity disorder (ADHD), psychotic disorders, obesity, dizziness, vertigo, epilepsy, motion sickness
inflammatory diseases
respiratory diseases (adult respiratory distress syndrome, acute respiratory distress syndrome, bronchitis, chronic bronchitis, chronic obstructive pulmonary disease, cystic fibrosis, asthma, emphysema, rhinitis, chronic sinusitis), allergy, allergy-induced airway responses, allergic rhinitis, viral rhinitis, non-allergic rhinitis, perennial and seasonal rhinitis, nasal congestion, allergic congestion
Female sexual dysfunction including hypoactive sexual desire disorder, sexual arousal disorder, orgasmic disorder and sexual pain disorder
Male sexual dysfunction including male desire disorders, male erectile dysfunction, male orgasmic disorders such as premature ejaculation
cardiac dysfunctions such as myocardial ischaemia and arrythmia
diseases of the gastrointestinal tract such as inflammatory bowel disease, Crohn's disease and colitis ulcerosa
cancer
hypotension
pain and
overactive bladder conditions The compounds of formula (I) of the invention are particularly suitable for the treatment of allergy, allergy-induced airway responses, allergic rhinitis, viral rhinitis, non-allergic rhinitis, perennial and seasonal rhinitis, nasal congestion, allergic congestion.

A still further aspect of the present invention also relates to the use of the compounds of formula (I), or pharmaceutically acceptable salts, derived forms or compositions thereof, for the manufacture of a drug being a $H_3$ ligand. In particular, the present inventions concerns the use of the compounds of formula (I), or pharmaceutically acceptable salts, derived forms or compositions thereof, for the manufacture of a drug for the treatment of H3-mediated diseases and/or conditions, in particular the diseases and/or conditions listed above.

Another aspect of the invention relates to the use of a compound of formula (I), or a pharmaceutically acceptable salt, derived form or composition thereof, for the manufacture of a medicament for the treatment of female sexual dysfunction, including hypoactive sexual desire disorder, sexual arousal disorder, orgasmic disorder and sexual pain disorder, or for the treatment of male sexual dysfunction including male desire disorders, male erectile dysfunction or male orgasmic disorders such as premature ejaculation.

As a consequence, the present invention provides a particularly interesting method to treat a mammal, including a human being, with an effective amount of a compound of formula (I), or a pharmaceutically acceptable salt, derived form or composition thereof. More precisely, the present invention provides a particularly interesting method for the treatment of a H3-mediated diseases and/or conditions in a mammal, including a human being, in particular the diseases and/or conditions listed above, comprising administering to said mammal an effective amount of a compound of formula (I), its pharmaceutically acceptable salts and/or derived forms.

EXAMPLES

The following examples illustrate the preparation of phenol and thiophenol derivatives of the formula (I):

Glossary
APCI atmospheric pressure chemical ionisation
Arbocel® filter agent
BINAP 2,2'-Bis(diphenylphosphino)-1,1'-binaphthyl
BOC tert-butoxycarbonyl
Br broad
CDI carbonyldiimidazole
δ chemical shift
D doublet
Δ heat DCM dichloromethane
DIAD diisopropyl azodicarboxylate
DMF N,N-dimethylformamide
DMSO dimethylsulfoxide
EDCI see WSCDI
ESI+ electrospray ionisation positive scan
ESI- electrospray ionisation negative scan
H hours
HBTU O-(1H-benzotriazol-1-yl)-N,N,N',N'-tetramethyluronium hexafluorophosphate
HOAT 1-hydroxy-7-azabenzotriazole
HOBT 1-hydroxybenzotriazole
HPLC high pressure liquid chromatography
Hunig's base Diisopropylethylamine
m/z mass charge ratio
Min Minutes
MS mass spectrum
$NH_3$ 0.88 ammonia aqueous solution
NMM N-methyl morpholine
NMR nuclear magnetic resonance
Q Quartet
S Singlet
STAB sodium triacetoxyborohydride
T Triplet
TBME tert-butyl methyl ether
TBUT 2-(1H-benzotriazol-1-yl)-1,1,3,3-tetramethyluronium tetrafluoroborate
Tf Trifluoromethanesulfonyl
TFA trifluoroacetic acid
THF Tetrahydrofuran
TLC thin layer chromatography
TosMIC Tosylmethyl isocyanide
WSCDI 1-(3-dimethylaminopropyl)-3-ethylcarbodiimide hydrochloride Intermediate 1: 4-(4-methoxyphenyl)-tetrahydro-2H-pyran-4-carbonitrile 4-Methoxyphenylacetonitrile (10 g, 67.9 mmol) in DMF (50 ml) was added slowly to a suspension of NaH (5.04 g, 150 mmol) in DMF (50 ml) at 0° C. under $N_2$. The reaction was allowed to warm up to room temperature and stirred for 30 min. The reaction was cooled to 0° C. and bis(2-chloroethyl) ether (10.7 g, 74.7 mmol) in DMF (100 ml) was added dropwise over 80 min. The reaction was allowed to warm up to room temperature and stirred for 1 hour. The reaction was quenched with water (200 ml) and extracted with ethyl acetate (3×300 ml). The combined organic extracts were washed with water (2×200 ml), brine (200 ml), dried over $MgSO_4$, filtered, washed with ethyl acetate and concentrated in vacuo to give the title compound (17.2 g, 100%).

Intermediate 2: 4-(4-Hydroxy-phenyl)-tetrahydro-pyran-4-carbonitrile

Boron tribromide (1M in DCM, 262 ml) was added to a solution of 4-(4-methoxyphenyl)-tetrahydro-2H-pyran-4-carbonitrile (14.7 g, 67.9 mmol) in DCM (294 ml) at 0° C. under $N_2$ keeping the temperature below 5° C. The reaction was allowed to warm to room temperature and stirred for 48 hours. The mixture was cooled to −10-0° C. with dry ice acetone and quenched with saturated aqueous sodium bicarbonate (294 ml). The mixture was allowed to warm to room temperature and stirred for 1 hour. The mixture was separated and the aqueous extracted with DCM (3×250 ml). The combined organic extracts were dried over $MgSO_4$, filtered, washed with DCM and concentrated in vacuo to give the title compound (10.8 g, 78%).

Intermediate 3: 4-(4-Dimethylaminomethyl-tetrahydro-pyran-4-yl)-phenol

Step 1: To a stirred suspension of $LiAlH_4$ (79 g, 2.08 mol, 5 eq) in THF (900 ml) at 0 to 5° C. under an atmosphere of nitrogen was added 4-(4-methoxyphenyl)-tetrahydro-2H-pyran-4-carbonitrile (90 g, 0.414 mol) in THF (900 ml) over a 25 minutes maintaining the temperature at 5 to 10° C. The reaction mixture was allowed to warm to ambient temperature and stirred until complete. Sodium hydroxide (2N, 850 ml) was added dropwise, the resulting solids filtered and washed with THF (2×800 ml), the organics concentrated in vacuo at 40° C. The residue was dissolved in EtOAc (300 ml) and dried over $MgSO_4$, filtered and concentrated in vacuo at 40° C. to provide {[4-(4-methoxyphenyl)-tetrahydro-2H-pyran-4-yl]methyl}amine as a light yellow oil (92 g, quantitative).

Step 2: To a solution of {[4-(4-methoxyphenyl)-tetrahydro-2H-pyran-4-yl]methyl}amine (60 g, 0.271 mol) in $H_2O$ (444 mL) and AcOH (213 ml) was charged formaldehyde (37% ww solution in $H_2O$, 408 mL) and the mixture cooled to 0 to 5° C. Sodium triacetoxyborohydride (345 g, 1.626 mol, 6 eq) was added portion wise while maintaining the temperature below 12° C. The mixture was stirred at ambient temperature until complete. Sodium hydroxide (2M, 1000 ml) was added slowly and the mixture extracted with DCM (4×250 ml). The organic extracts were dried over $MgSO_4$, filtered and concentrated in vacuo at 30° C. to provide {[4-(4-methoxyphenyl)-tetrahydro-2H-pyran-4-yl]methyl}dimethylamine as a yellow oil (53.5 g, 80%).

Step 3: To a suspension of Sodium thiomethoxide (49.2 g, 0.702 mol, 5 eq) in DMF (140 ml) was added {[4-(4-methoxyphenyl)-tetrahydro-2H-pyran-4-yl]methyl}dimethylamine (35 g, 0.140 mol) and the resulting mixture was heated to 130° C. Once complete, allowed to cool to ambient temperature and saturated aqueous $NH_4Cl$ (525 ml) was added. The resultant was extracted with EtOAc (3×500 ml), dried over $MgSO_4$, filtered and concentrated in vacuo at 35° C. to provide 4-(4-dimethylaminomethyl-tetrahydro-pyran-4-yl)-phenol (intermediate 3) as a yellow solid (35.7 g, 108%) containing residual DMF and EtOAc.

Intermediate 4: 3-{4-[(dimethylamino)methyl]tetrahydro-pyran-4-yl}phenol

Step 1: 3-Methoxyphenylacetonitrile (10 g, 67.9 mmol) in DMF (50 ml) was added slowly to a suspension of NaH (5.04 g, 150 mmol) in DMF (50 ml) at 0° C. under $N_2$. The reaction was allowed to warm to room temperature and stirred for 30 nms. The reaction was cooled to 0° C. and bis(2-chloroethyl) ether (10.7 g, 74.7 mmol) in DMF (100 ml) was added dropwise over 80 min. The reaction was allowed to warm to room temperature and stirred for 1 hour. The reaction was quenched with water (500 ml) and extracted with ethyl acetate (3×100 ml). The combined organic extracts were washed with brine (3×50 ml), dried over $MgSO_4$, filtered, washed with ethyl acetate and concentrated in vacuo. The crude mixture was purified by column chromatography, eluting with heptane increasing the polarity to heptane:ethyl acetate (90:10), to give 4-(3-methoxyphenyl)tetrahydro-pyran-4-carbonitrile (4.1 g, 28%).

Step 2: To a stirred suspension of $LiAlH_4$ (3.7 g, 96.7 mmol) in diethyl ether (100 mL) cooled at 0° C. was added dropwise a solution of 4-(3-methoxyphenyl)-tetrahydro-pyran-4-carbonitrile (4.2 g, 19.3 mmol) in diethyl ether (100 mL). After being stirred at room temperature for 30 min, the reaction mixture was refluxed for another 15 min. The mixture was cooled to 10° C. and water, sodium hydroxide (15% w/v in water, 0.48 mL) and water again were successively added dropwise. After being stirred for 15 min at room temperature, the mixture was filtered over diatomaceous earth and concentrated. The residue was purified with flash chromatography (DCM/MeOH: 95/5) to provide (4-(3-methoxyphenyl)tetrahydro-pyran-4-yl]methylamine (4 g, 94%).

Step 3: A mixture of [4-(3-methoxyphenyl)tetrahydro-pyran-4-yl]methylamine (0.51 g, 2.3 mmol), acetic acid (0.535 mL, 9.2 mmol), sodium triacetoxyborohydride (0.974 g, 4.6 mmol), 37% solution of formaldehyde in water (0.55 mL) and DCM (40 mL) was stirred 72 h at ambient temperature. The organic phase was washed twice with water. Concentrated NaOH was added to the aqueous phase (pH 12) and the mixture was extracted twice with dichloromethane. The organic extracts were dried over Na$_2$SO$_4$, filtered and concentrated in vacuo to provide N-{[4-(3-methoxyphenyl)tetrahydro-pyran-4-yl]methyl}-N,N-dimethylamine as an oil (0.35 g, 61%).

Step 4: To a suspension of Sodium thiomethoxide (0.42 g, 6 mmol) in DMF (1.2 mL) was added N-{[4-(3-methoxyphenyl)tetrahydro-pyran-4-yl]methyl}-N,N-dimethylamine (0.3 g, 1.2 mmol) and the resulting mixture was heated to 65° C. for 7 h, allowed to cool to ambient temperature and quenched with saturated aqueous NH$_4$Cl (6 mL). The mixture was extracted with DCM, dried over Na$_2$SO$_4$, filtered and concentrated in vacuo to provide 0.25 g of crude product. A mixture of the crude and HBr (3 mL) was heated to reflux for 1 h. After cooling, water was added to quench the reaction and the mixture was basified with NaHCO$_3$ and extracted with DCM. The organic extracts were dried over Na$_2$SO$_4$, filtered and concentrated. The residue was purified by flash chromatography (DCM/MeOH (10% NH$_3$)) to provide 3-{4-[(dimethylamino)methyl]tetrahydro-pyran-4-yl}phenol (0.100 g, 35.5%).

General Procedure A for the Synthesis of Chlorides (R—R$^{LG}$ Wherein R$^{LG}$ is Chloride):

Amine (1 eq.) was charged to a reaction flask followed by acetone (3 vol or 20 vol), 5M NaOH solution (1.2 eq.) and 1-bromo-3-chloropropane (1.5 eq. or 3 eq.). The reaction was stirred overnight at room temperature. The phases were separated and the acetone layer concentrated in vacuo. The aqueous was acidified with 2M HCl solution to pH 1 (~10 vol). The concentrate was diluted with TBME (30 vol) and washed with water (15 vol). The aqueous was extracted with TBME (2×15 ml). The combined TBME was washed with 2M HCl solution (15 ml) and combined with the first acidic phase. The combined acidic layers were washed with TBME (15 vol) and basified to pH 14 with 4M NaOH solution (~40 ml). The aqueous was extracted with TBME (3×30 ml). The combined organic layers were dried over MgSO$_4$, filtered, washed with TBME (5 vol) and concentrated in vacuo to give the required chloride.

General procedure B:

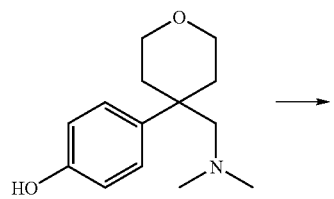

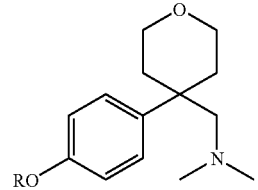

4-(4-Dimethylaminomethyl-tetrahydro-pyran-4-yl)-phenol (500 mg, 2.13 mmol), chloride (378 mg, 2,13 mmol), DMF (10 ml), water (17 ml) and K$_2$CO$_3$ (1.18 g, 8.52 mmol) was heated to 130° C. Cooled to ambient temperature, water (40 ml) added, extracted with EtOAc (3×25 ml) and the combined organic extracts washed with water (2×25 ml). The organics were dried over MgSO$_4$, filtered and concentrated in vacuo at 35° C. Purification of the crude material by chromatography on silica, eluant (4% MeOH, 1% NH$_3$, in DCM) provided the title compounds.

Intermediate 5: 1-(3-Chloro-propyl)-pyrrolidine

Pyrrolidine (10 g, 0.14 mol), acetone (28 ml), 5M NaOH solution (21 ml) and 1-bromo-3-chloropropane (24.4 g, 0.15 mol) were stirred together under N$_2$ for 8 hours. The organic layer was separated and concentrated in vacuo. The crude product was purified by vacuum distillation (b.p. 90° C./30 mbar) to give the title compound (11.7 g, 57%) as a colourless oil.

Example 1

Dimethyl-{4-[3-(3-pyrrolidin-1-ylpropoxy)phenyl]tetrahydro-pyran-4-ylmethyl}amine

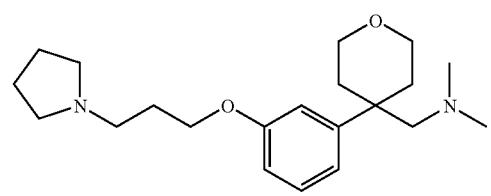

Alkylation of 3-[4-(dimethylamino)methyltetrahydro-2H-pyran-4-yl]phenol (0.1 g, 0.425 mmol) with 1-(3-chloropropyl)pyrrolidine (0.125 g, 0.85 mmol) according to general procedure B gave the desired compound after purification by flash chromatography (0.030 g, 20%). $^1$H NMR (400 MHz, CDCl$_3$) δ7.27-7.18 (m, 1H), 6.92-6.84 (m, 2H), 6.75 (dd, 1H), 4.05 (t, 2H), 3.8-3.7 (m, 2H), 3.55 (t, 2H), 2.65 (t, 2H), 2.6-2.5 (m, 4H), 2.4 (s, 2H), 2.15-1.85 (m, 6H), 2.0 (s, 6H), 1.85-1.75 (m, 4H).

Intermediate 6: 1-(3-Chloro-propyl)-2(R),5(R)-trans-dimethyl-pyrrolidine

2(R),5(R)-trans-Dimethyl-pyrrolidine (0.75 g, 7.56 mmol), acetone (15 ml, 20 vol), 5M NaOH solution (1.8 ml, 1.2 eq.) and 1-bromo-3-chloropropane (3.57 g, 22.7 mmol, 3 eq.) were reacted together according to general procedure A to give the title compound (0.5 g, 38%) as a yellow oil.

Example 2

(4-{4-[3-(2,5-Dimethylpyrrolidin-1-yl)propoxy]phenyl}tetra-hydro-pyran-4-ylmethyl)dimethylamine

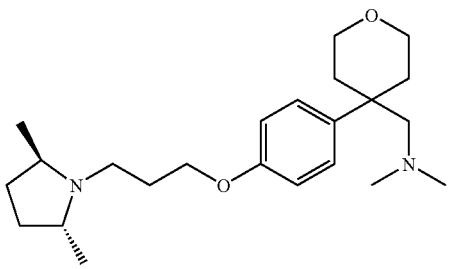

4-(4-Dimethylaminomethyl-tetrahydro-pyran-4-yl)-phenol (330 mg, 1.43 mmol), 1-(3-chloro-propyl)-2,5-trans-dimethyl-pyrrolidine (221 mg, 1.26 mmol), DMF (7.6 ml) and K$_2$CO$_3$ (790 mg, 5.72 mmol) were reacted together according to general procedure B. The isolated material was subjected to chromatography on silica, eluant 95:4:1 (DCM, MeOH, NH$_3$) to give the title compound as a yellow oil (180 mg, 34%). $^1$H NMR (400 MHz, CDCl$_3$) δ7.20 (d, 2H), 6.87 (d, 2H), 4.08-3.95 (m, 2H), 3.79-3.70 (m, 2H), 3.59-3.49 (m, 2H), 3.11-3.00 (m, 2H), 2.77 (m, 1H), 2.54 (m, 1H), 2.40 (s, 2H), 2.14-1.81 (m, 8H), 1.96 (s, 6H), 1.44-1.31 (m, 2H), 0.97 (d, 6H).

Intermediate 7: 1-(3-Chloro-propyl)-2-methyl-pyrrolidine

2-Methylpyrrolidine (0.9 g, 10.6 mmol), acetone (18 ml, 20 vol), 5M NaOH solution (2.50 ml) and 1-bromo-3-chloropropane (5 g, 31.8 mmol, 3 eq) were reacted together according to general procedure A to give the title compound (1 g, 59%) as a pale yellow oil.

Example 3

Dimethyl-(4-{4-[3-(2-methyl-pyrrolidin-1-yl)-propoxy]-phenyl}-tetrahydro-pyran-4-ylmethyl)-amine

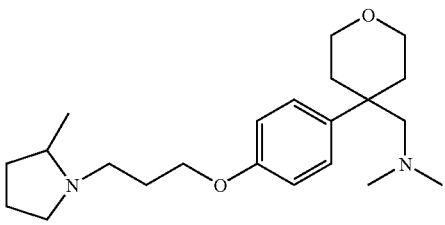

4-(4-Dimethylaminomethyl-tetrahydro-pyran-4-yl)-phenol (500 mg, 2.13 mmol), 1-(3-chloro-propyl)-2-methyl-pyrrolidine (344 mg, 2,13 mmol), DMF (10 ml) and K$_2$CO$_3$ (1.18 g, 8.52 mmol) were reacted together according to general procedure B. The isolated material was subjected to chromatography on silica, eluant 95:4:1 (DCM, MeOH, NH$_3$) to give the title compound as a yellow oil (120 mg, 16%). $^1$H NMR (400 MHz, CDCl$_3$) δ7.20 (d, 2H), 6.87 (d, 2H), 4.08-3.96 (m, 2H), 3.75 (dt, 2H), 3.55 (td, 2H), 3.18 (td, 1H), 2.98 (m, 1H), 2.40 (s, 2H), 2.29 (m, 1H), 2.20 (m, 1H), 2.16-1.62 (m, 10H), 1.96 (s, 6H), 1.42 (m, 1H), 1.09 (d, 3H).

Intermediate 8: 1-(3-Chloro-propyl)-2,6-cis-dimethyl-piperidine

Step 1: 2,6-cis-Dimethyl-piperidine (1.0 g, 8.83 mmol), K$_2$CO$_3$ (1.52 g, 1.25 eq.) and 3-bromopropanol (6.14 g, 44.2 mmol, 4 vol) were reacted together at 100° C. for 2 hours. The reaction was allowed to cool to room temperature, diluted with DCM (20 ml) and quenched with 2M HCl solution (20 ml). The aqueous was extracted with DCM (2×20 ml) and basified to pH 14 with 2M NaOH solution (~15 ml). The aqueous was extracted with DCM (3×20 ml). The combined DCM layers were dried over MgSO$_4$, filtered washed with DCM and concentrated in vacuo to give 1-(propan-1'-ol)-2,6-cis-dimethyl-piperidine (1.22 g, 81%) as a pale yellow oil.

Step 2: 1-(Propan-1'-ol)-2,6-cis-dimethyl-piperidine (1.22 g, 7.12 mmol) was dissolved in DCM (24 ml) and cooled to 0-5° C. under N$_2$. Thionyl chloride (1.04 ml, 14.25 mmol) was added dropwise. The reaction was allowed to warm to room temperature and stirred for 30 mins. The reaction was quenched with 2M HCl solution (25 ml). The aqueous was extracted with DCM (25 ml) and basified to pH 14 with 5M NaOH solution (~25 ml). The aqueous was extracted with TBME (3×25 ml). The combined organic layers were dried over MgSO$_4$, filtered washed with TBME and concentrated in vacuo to give the title compound (1.26 g, 93%) as a yellow oil.

Example 4

(4-{4-[3-(2,6-Dimethylpiperidin-1-yl)propoxy]phenyl}tetra-hydro-pyran-4-ylmethyl)dimethylamine

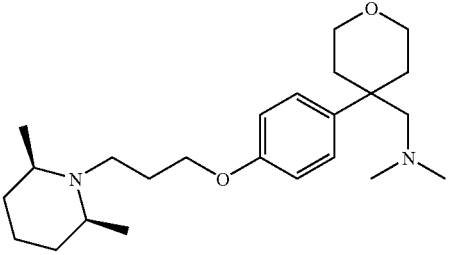

4-(4-Dimethylaminomethyl-tetrahydro-pyran-4-yl)-phenol (500 mg, 2.13 mmol), 1-(3-chloro-propyl)-2,6-cis-dimethyl-piperidine (410 mg, 2,13 mmol), DMF (10 ml) and K$_2$CO$_3$ (1.18 g, 8.52 mmol) were reacted together according to general procedure B. The isolated material was subjected to chromatography on silica, eluant 95:4:1 (DCM, MeOH, NH$_3$) to give the title compound as a yellow oil (280 mg, 33.9%). $^1$H NMR (400 MHz, CDCl$_3$) δ7.20 (d, 2H), 6.85 (d, 2H), 3.93 (t, 2H), 3.75 (dt, 2H), 3.55 (td, 2H), 2.95 (t, 2H), 2.51-2.36 (m, 2H), 2.40 (s, 2H), 2.14-2.04 (m, 2H), 1.96 (s, 6H), 1.93-1.82 (m, 4H), 1.74-1.51 (m, 3H), 1.41-1.21 (m, 3H), 1.13 (d, 6H).

Intermediate 9: 4-(3-Chloro-propyl)-thiomorpholine

Thiomorpholine (5 g, 49 mmol), acetone (15 ml, 3 vol), 5M NaOH solution (11.8 ml) and 1-bromo-3-chloropropane (11.6 g, 73.5 mmol, 1.5 eq.) were reacted together according to general procedure A to give the title compound (8.5 g, 96%) as a pale yellow oil.

Example 5

Dimethyl-{4-[4-(3-thiomorpholin-4-ylpropoxy)phenyl]tetra-hydro-pyran-4-ylmethyl}amine

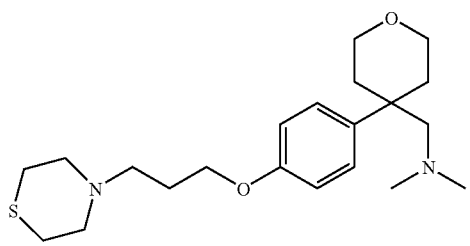

4-(4-Dimethylaminomethyl-tetrahydro-pyran-4-yl)-phenol (1000 mg, 4.25 mmol), 4-(3-chloro-propyl)-thiomorpholine (764 mg, 2,13 mmol), DMF (20 ml), and $K_2CO_3$ (2.34 g, 17 mmol) were reacted together according to general procedure B. The isolated material was subjected to chromatography on silica, eluant DCM:MeOH:$NH_3$ (95:5:1) to give the title compound (320 mg, 20%). $^1$H NMR (400 MHz, $CDCl_3$) δ 7.20 (d, 2H), 6.86 (d, 2H), 3.99 (t, 2H), 3.75 (dt, 2H), 3.55 (td, 2H), 2.79-2.64 (m, 8H), 2.55 (t, 2H), 2.40 (s, 2H), 2.16-2.04 (m, 2H), 2.01-1.82 (m, 4H), 1.97 (s, 6H).

Example 6

Dimethyl-(4-{4-[3-(1-oxothiomorpholin-4-yl)propoxy]phenyl}-tetrahydropyran-4-ylmethyl)amine

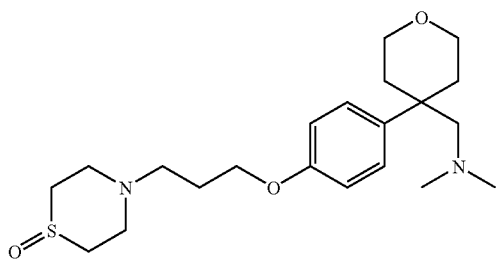

Dimethyl-{4-[4-(3-thiomorpholin-4-ylpropoxy)phenyl]tetrahydro-pyran-4-ylmethyl}amine (300 mg, 0.792 mmol) and TFA (0.99 ml) were cooled to 0 to 5° C. and trifluoroperacetic acid (4M, 0.77 ml) [4M solution prepared by the addition of 27.5% $H_2O_2$ (0.94 ml) to TFA (1.56 ml)] was added and the reaction stirred for six hours at 0 to 5° C. The mixture was diluted with DCM (6 ml), basified with NaOH (2M, 8 ml) and extracted with DCM (2×20 ml). The DCM extracts were dried over $MgSO_4$, filtered and concentrated in vacuo at 35° C. Purification by chromatography on silica, eluant DCM:MeOH:$NH_3$ (96:4:1) provided the title compound (200 mg, 61%) as a white solid. $^1$H NMR (400 MHz, $CDCl_3$) δ7.21 (d, 2H), 6.86 (d, 2H), 4.01 (t, 2H), 3.75 (dt, 2H), 3.55 (td, 2H), 3.15-3.02 (m, 2H), 2.93-2.79 (m, 4H), 2.72 (dt, 2H), 2.64 (t, 2H), 2.40 (s, 2H), 2.16-1.82 (m, 6H), 1.97 (s, 6H).

Example 7

(4-{4-[3-(1,1-Dioxo-thiomorpholin-4-yl)propoxy]phenyl}tetra-hydro-pyran-4-ylmethyl)dimethylamine

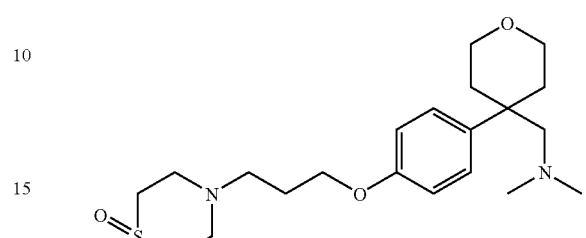

Dimethyl-{4-[4-(3-thiomorpholin-4-ylpropoxy)phenyl]tetrahydro-pyran-4-ylmethyl}amine (300 mg, 0.792 mmol) and TFA (0.99 ml) were cooled to 0 to 5° C. and trifluoroperacetic acid (4M, 0.77 ml) was added and the reaction allowed to warm to ambient temperature overnight. The mixture was diluted with DCM (6 ml), basified with NaOH (2M, 8 ml) and extracted with DCM (2×20 ml). The DCM extracts were dried over $MgSO_4$, filtered and concentrated in vacuo at 35° C. Purification by chromatography on silica, eluant DCM:MeOH:$NH_3$ (96:4:1) provided the title compound (151 mg, 46%) as a white solid. $^1$H NMR (400 MHz, $CDCl_3$) δ7.22 (d, 2H), 6.85 (d, 2H), 4.01 (t, 2H), 3.75 (dt, 2H), 3.55 (td, 2H), 3.10-2.97 (m, 8H), 2.72 (t, 2H), 2.40 (s, 2H), 2.14-1.82 (m, 6H), 1.97 (s, 6H).

Intermediate 10: 1-(3-Chloro-propyl)-piperidin-4-ol

4-Hydroxypiperidine (3 g, 30 mmol), acetone (60 ml, 20 vol), 5M NaOH solution (7.2 ml) and 1-bromo-3-chloropropane (14.2 g, 90 mmol, 3 eq.) were reacted together according to general procedure A to give the title compound (1.5 g, 28%) as a pale yellow oil.

Example 8

1-{3-[4-(4-Dimethylaminomethyl-tetrahydro-pyran-4-yl)-phenoxy]-propyl}-piperidin-4-ol

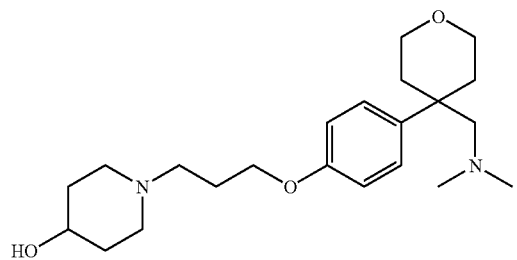

4-(4-Dimethylaminomethyl-tetrahydro-pyran-4-yl)-phenol (500 mg, 2.13 mmol), 1-(3-chloro-propyl)-piperidin-4-ol (378 mg, 2,13 mmol), DMF (10 ml) and $K_2CO_3$ (1.18 g, 8.52 mmol) were reacted together according to general procedure B. The isolated material was dissolved in EtOAc (30 ml), washed with NaOH (2M, 2×20 ml) and water (25 ml), dried over $MgSO_4$ filtered and concentrated in vacuo at 35° C. to give the title compound (411 mg, 51%). $^1$H NMR (400 MHz, CDCl$_3$) δ7.20 (d, 2H), 6.86 (d, 2H), 4.00 (t, 2H), 3.80-3.65 (m, 3H), 3.55 (td, 2H), 2.85-2.73 (m, 2H), 2.52 (t, 2H), 2.40 (s, 2H), 2.22-1.82 (m, 10H), 1.97 (s, 6H), 1.66-1.54 (m, 2H), 1.52 (br s, 1H).

Intermediate 11: 1-(3-Chloro-propyl)-4-methoxy-piperidine

4-Methoxy-piperidine (1.5 g, 13 mmol), acetone (30 ml, 20 vol), 5M NaOH solution (3.13 ml) and 1-bromo-3-chloropropane (6.14 g, 39 mmol, 3 eq.) were reacted together according to general procedure A to give the title compound (1.5 g, 60%) as a pale yellow oil.

Example 9

(4-{4-[3-(4-Methoxy-piperidin-1-yl)-propoxy]-phenyl}-tetrahydro-pyran-4-ylmethyl)-dimethyl-amine

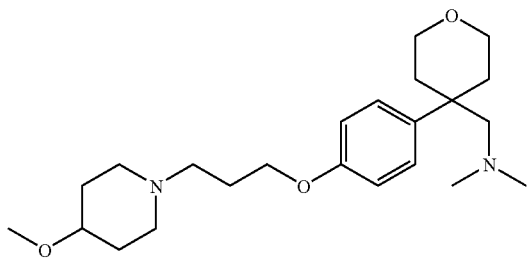

4-(4-Dimethylaminomethyl-tetrahydro-pyran-4-yl)-phenol (500 mg, 2.13 mmol), 1-(3-chloro-propyl)-4-methoxy-piperidine (410 mg, 2,13 mmol), DMF (10 ml) and K$_2$CO$_3$ (1.18 g, 8.52 mmol) were reacted together according to general procedure B. The isolated material was subjected to chromatography on silica, eluant 95:4:1 (DCM:MeOH:NH$_3$) to give the title compound as a yellow oil (415 mg, 50%). $^1$H NMR (400 MHz, CDCl$_3$) δ7.20 (d, 2H), 6.86 (d, 2H), 4.00 (t, 2H), 3.75 (dt, 2H), 3.55 (td, 2H), 3.34 (s, 3H), 3.22 (m, 1H), 2.83-2.71 (m, 2H), 2.51 (t, 2H), 2.40 (s, 2H), 2.23-1.81 (m, 10H), 1.97 (s, 6H), 1.67-1.53 (m, 2H).

Intermediate 12: 2-[1-(3-Chloro-propyl)-piperidin-4-yl]-ethanol

4-Piperidine ethanol (0.9 g, 7.5 mmol), acetone (18 ml, 20 vol), 5M NaOH solution (1.8 ml) and 1-bromo-3-chloropropane (3.54 g, 22.5 mmol, 3 eq.) were reacted together according to general procedure A to give the title compound (0.6 g, 37%) as an orange oil.

Example 10

2-(1-{3-[4-(4-Dimethylaminomethyltetrahydropyran-4-yl)phenoxy]propyl}piperidin-4-yl)ethanol

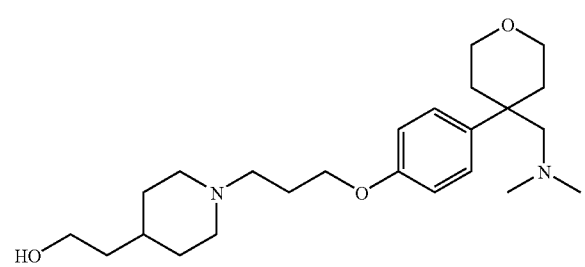

4-(4-Dimethylaminomethyl-tetrahydro-pyran-4-yl)-phenol (288 mg, 1.22 mmol), 2-[1-(3-chloro-propyl)-piperidin-4-yl]-ethanol (252 mg, 1.22 mmol), DMF (8 ml) and K$_2$CO$_3$ (674 mg, 4.88 mmol) were reacted together according to general procedure B. Purification by chromatography on silica, eluant DCM:MeOH:NH$_3$ (96:4:1) provided the title compound (180 mg, 36%) as an off white solid. $^1$H NMR (400 MHz, CDCl$_3$) δ7.20 (d, 2H), 6.86 (d, 2H), 3.99 (t, 2H), 3.75 (dt, 2H), 3.70 (t, 2H), 3.55 (td, 2H), 2.98-2.88 (m, 2H), 2.49 (t, 2H), 2.40 (s, 2H), 2.14-1.82 (m, 6H), 1.97 (s, 6H), 1.75-1.15 (m, 10H).

Intermediate 13: 1-(3-Chloro-propyl)-4-(2-methoxy-ethyl)-piperidine

Step 1: N-Boc-4-(2-hydroxy-ethyl)-piperidine (5 g, 21.8 mmol) in THF (25 ml) was added to a suspension of NaH (1.47 g, 43.7 mmol) in THF (75 ml) at 0° C. under N$_2$. The reaction was stirred for 1 hour at 0° C. and MeI (2.72 ml, 43.7 mmol) added slowly. The reaction was allowed to warm to room temperature and stirred overnight. The reaction was quenched with water (100 ml) and extracted with DCM (3×100 ml). The combined DCM layers were dried over MgSO$_4$, filtered, washed with DCM and concentrated in vacuo. The crude reaction (7.5 g) was treated with 3M HCl solution in EtOH (150 ml) for 12 hours. The reaction was concentrated in vacuo and azeotroped with toluene (2×150 ml) to give 4-(2-methoxy-ethyl)-piperidine hydrochloride (3.5 g, 89%) as a pale yellow solid.

Step 2: 4-(2-Methoxy-ethyl)-piperidine hydrochloride (1.5 g, 8.4 mmol), acetone (30 ml, 20 vol), 5M NaOH solution (6.03 ml, 3.6 eq.) and 1-bromo-3-chloropropane (3.96 g, 25.1 mmol, 3 eq.) were reacted together according to general procedure A to give the title compound (1.6 g, 88%) as a pale yellow oil.

Example 11

[4-(4-{3-[4-(2-Methoxy-ethyl)-piperidin-1-yl]-propoxy}-phenyl)-tetrahydro-pyran-4-ylmethyl]-dimethyl-amine

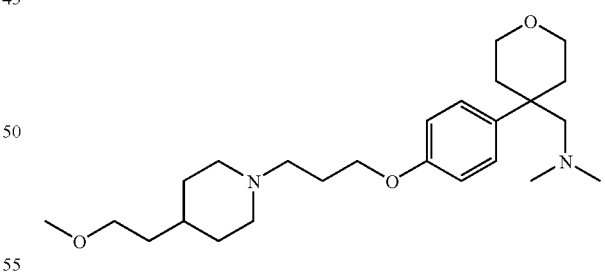

4-(4-Dimethylaminomethyl-tetrahydro-pyran-4-yl)-phenol (500 mg, 2.13 mmol), 1-(3-chloro-propyl)-4-(2-methoxy-ethyl)-piperidine (466 mg, 2,13 mmol), DMF (10 ml) and K$_2$CO$_3$ (1.18 g, 8.52 mmol) were reacted together according to general procedure B. Purification by chromatography on silica, eluant DCM:MeOH:NH$_3$ (96:4:1) provided the title compound (409 mg, 46%) as a yellow oil. $^1$H NMR (400 MHz, CDCl$_3$) δ7.20 (d, 2H), 6.86 (d, 2H), 3.99 (t, 2H), 3.75 (dt, 2H), 3.55 (td, 2H), 3.41 (t, 2H), 3.33 (s, 3H), 2.97-2.86 (m, 2H), 2.49 (t, 2H), 2.40 (s, 2H), 2.15-1.78 (m, 8H), 1.97 (s, 6H), 1.74-1.17 (m, 7H).

Intermediate 14: 1-(3-Chloro-propyl)-piperidine-4-carboxylic acid amide

Piperidine-4-carboxylic acid amide (0.5 g, 3.90 mmol), acetone (1.5 ml, 3 vol), 5M NaOH solution (1.20 ml, 1.2 eq.) and 1-bromo-3-chloropropane (0.50 ml, 5.04 mmol, 1 eq.) were reacted together according to general procedure A to give the title compound (0.16 g, 20%) as a pale yellow oil.

Example 12

1-{3-[4-(4-Dimethylaminomethyl-tetrahydro-pyran-4-yl)-phenoxy]-propyl}-piperidine-4-carboxylic acid amide

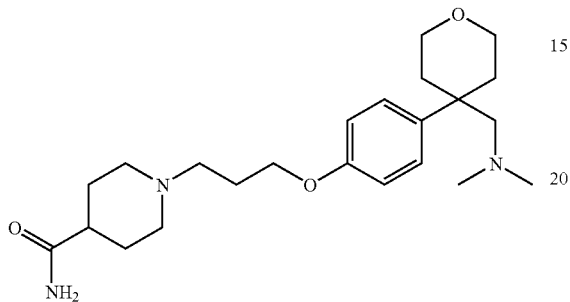

4-(4-Dimethylaminomethyl-tetrahydro-pyran-4-yl)-phenol (500 mg, 2.13 mmol), 1-(3-chloro-propyl)-piperidine-4-carboxylic acid amide (436 mg, 2,13 mmol), DMF (10 ml) and K₂CO₃ (1.18 g, 8.52 mmol) were reacted together according to general procedure B. The isolated material was subjected to chromatography on silica, eluant 95:4:1 (DCM:MeOH:NH₃) to give the title compound as a white solid (175 mg, 20%). ¹H NMR (400 MHz, CDCl₃) δ7.21 (d, 2H), 6.86 (d, 2H), 5.44 (br s, 1H), 5.25 (br s, 1H), 4.00 (t, 2H), 3.75 (dt, 2H), 3.55 (td, 2H), 3.03-2.93 (m, 2H), 2.51 (t, 2H), 2.40 (s, 2H), 2.22-1.66 (m, 13H), 1.97 (s, 6H).

Intermediate 15: 4-(3-Chloro-Propyl)-piperazine-1-carboxylic acid ethyl ester

Piperazine-1-carboxylic acid ethyl ester (3.0 g, 18.9 mmol), K₂CO₃ (2.8 g, 1.1 eq.), DMF (30 ml, 10 vol) and 1-bromo-3-chloropropane (1.8 ml, 18.9 mmol, 1 eq.) were reacted together at room temperature overnight. The reaction was quenched with water (100 ml) and extracted with DCM (3×50 ml). The combined DCM extracts were dried over MgSO₄, filtered washed with DCM and concentrated in vacuo to give the title compound (3.1 g, 70%) as a pale yellow oil.

Example 13

{3-[4-(4-Dimethylaminomethyltetrahydropyran-4-yl)phenoxy]-propyl}piperazine-1-carboxylic acid ethyl ester

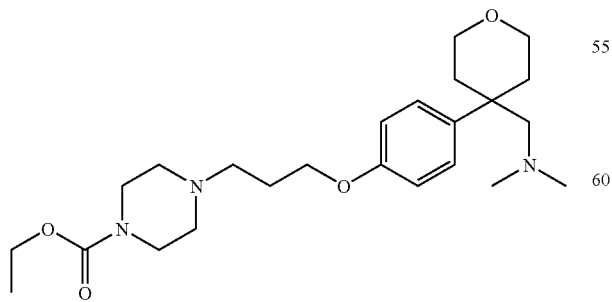

4-(4-Dimethylaminomethyl-tetrahydro-pyran-4-yl)-phenol (500 mg, 2.13 mmol), 4-(3-chloro-propyl)-piperazine-1-carboxylic acid ethyl ester (499 mg, 2,13 mmol), DMF (10 ml) and K₂CO₃ (1.189, 8.52 mmol) were reacted together according to general procedure B. Purification by chromatography on silica, eluant (10% MeOH in DCM) the title compound (276 mg, 26%). ¹H NMR (400 MHz, CDCl₃) δ7.21 (d, 2H), 6.86 (d, 2H), 4.14 (q, 2H), 4.01 (t, 2H), 3.75 (dt, 2H), 3.60-3.42 (m, 6H), 2.54 (t, 2H), 2.47-2.36 (m, 4H), 2.40 (s, 2H), 2.16-1.82 (m, 6H), 1.97 (s, 6H), 1.26 (t, 3H).

Intermediate 16: (3-Chloro-propyl)-diethyl-amine

Diethyl-amine (7.27 ml, 70 mmol), acetone (15 ml, 3 vol), 5M NaOH solution (16.8 ml, 1.2 eq.) and 1-bromo-3-chloropropane (16.5 g, 105 mmol, 1.5 eq.) were reacted together according to general procedure A to give the title compound (6.2 g, 59%) as a colourless oil.

Example 14

{3-[4-(4-Dimethylaminomethyltetrahydropyran-4-yl)phenoxy]-propyl}diethyl-amine

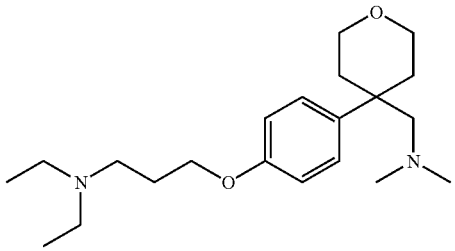

4-(4-Dimethylaminomethyl-tetrahydro-pyran-4-yl)-phenol (500 mg, 2.13 mmol), (3-chloro-propyl)-diethyl-amine (319 mg, 2,13 mmol), DMF (10 ml) and K₂CO₃ (1.18 g, 8.52 mmol) were reacted together according to general procedure B. Purification by chromatography on silica, eluant (36% EtOH: 1% NH₃ in DCM) gave the title compound as a pale yellow clear oil (160 mg, 22%). ¹H NMR (400 MHz, CDCl₃) δ7.20 (d, 2H), 6.86 (d, 2H), 4.00 (t, 2H), 3.75 (dt, 2H), 3.55 (td, 2H), 2.61 (t, 2H), 2.54 (q, 4H), 2.40 (s, 2H), 2.15-1.82 (m, 6H), 1.97 (s, 6H), 1.02 (t, 6H).

Intermediate 17: 2-[(3-Chloro-propyl)-ethyl-amino]-ethanol

2-Ethylamino ethanol (6.2 g, 70 mmol), acetone (18 ml, 3 vol), 5M NaOH solution (16.8 ml, 1.2 eq.) and 1-bromo-3-chloropropane (16.5 g, 105 mmol, 1.5 eq.) were reacted together according to general procedure A to give the title compound (4.5 g, 39%) as a colourless oil.

Example 15

2-({3-[4-(4-Dimethylaminomethyltetrahydropyran-4-yl)-phenoxy]propyl}ethylamino) ethanol

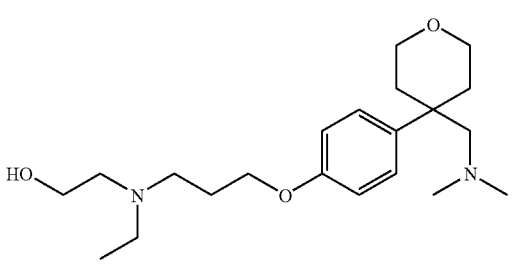

4-(4-Dimethylaminomethyl-tetrahydro-pyran-4-yl)-phenol (500 mg, 2.13 mmol), 2-[(3-chloro-propyl)-ethylamino]-ethanol (353 mg, 2,13 mmol), DMF (10 ml) and K$_2$CO$_3$ (1.18 g, 8.52 mmol) were reacted together according to general procedure B. The isolated material was subjected to chromatography on silica, eluant 95:4:1 (DCM:MeOH:NH$_3$) to give the title compound as a white solid (150 mg, 19%). $^1$H NMR (400 MHz, CDCl$_3$) δ7.21 (d, 2H), 6.86 (d, 2H), 4.00 (t, 2H), 3.75 (dt, 2H), 3.60-3.49 (m, 4H), 2.68 (t, 2H), 2.62 (t, 2H), 2.59 (q, 2H), 2.40 (s, 2H), 2.14-1.82 (m, 6H), 1.97 (s, 6H), 1.62 (br s, 1H), 1.03 (t, 3H).

Intermediate 18: (3-Chloro-propyl)-isopropyl-methyl-amine

Isopropylmethylamine (4 g, 56 mmol), acetone (12 ml, 3 vol), 5M NaOH solution (13.44 ml, 1.2 eq.) and 1-bromo-3-chloropropane (13.22 g, 84 mmol, 1.5 eq.) were reacted together according to general procedure A to give the title compound (4.8 g, 66%) as a colourless oil.

Example 16

{3-[4-(4-Dimethylaminomethyltetrahydropyran-4-yl)phenoxy]-propyl}isopropylmethylamine

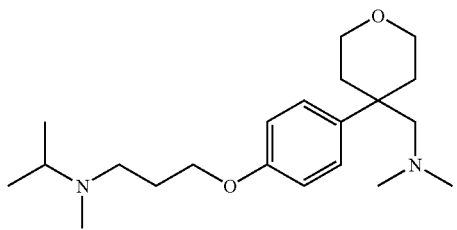

4-(4-Dimethylaminomethyl-tetrahydro-pyran-4-yl)-phenol (500 mg, 2.13 mmol), (3-chloro-propyl)-isopropyl-methyl-amine (318 mg, 2,13 mmol), DMF (10 ml) and K$_2$CO$_3$ (1.18 g, 8.52 mmol) were reacted together according to general procedure B. Purification by chromatography on silica, eluant DCM:MeOH:NH$_3$ (96:3:1) provided the title compound (200 mg, 43%) as a white solid. $^1$H NMR (400 MHz, CDCl$_3$) δ7.20 (d, 2H), 6.87 (d, 2H), 4.00 (t, 2H), 3.75 (dt, 2H), 3.55 (td, 2H), 2.83 (sep, 1H), 2.55 (t, 2H), 2.40 (s, 2H), 2.22 (s, 3H), 2.14-2.05 (m, 2H), 1.96 (s, 6H), 2.00-1.82 (m, 4H), 1.00 (d, 6H).

Intermediate 19: 1-(2-chloro-ethyl)-pyrrolidine

Pyrrolidine (10.4 g, 0.15 mol), acetone (200 ml), 5M NaOH solution (35 ml) and 1-bromo-2-chloroethane (62.9 g, 0.44 mol) were reacted according to general procedure A. The crude mixture was purified by column chromatography eluting with ethyl acetate to give the title compound (2.0 g, 10%) as a pale yellow oil.

Example 17

Dimethyl-{4-[4-(2-pyrrolidin-1-ylethoxy)phenyl]tetrahydro-pyran-4-ylmethyl}amine

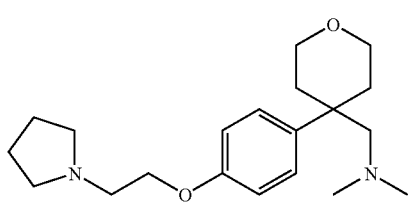

4-(4-Dimethylaminomethyl-tetrahydro-pyran-4-yl)-phenol (389 mg, 1.65 mmol), 1-(2-chloro-ethyl)-pyrrolidine (210 mg, 1.57 mmol), DMF (4.5 ml) and K$_2$CO$_3$ (885 g, 6.40 mmol) was heated to 130° C. for 30 minutes. The mixture was cooled to ambient temperature; water (9 ml) was added and the mixture was extracted with EtOAc (3×4.5 ml). The organic phase was washed with brine (10 ml), NaOH solution (2M, 10 ml) and water (10 ml). The organic layer was dried over MgSO$_4$, filtered and concentrated in vacuo at 35° C. and the residue subjected to chromatography on silica eluting with DCM:MeOH:NH3 (98:1:1) to give the title compound as a white solid (150 mg, 27%). $^1$H NMR (400 MHz, CDCl$_3$) δ7.21 (d, 2H), 6.89 (d, 2H), 4.10 (t, 2H), 3.75 (dt, 2H), 3.55 (td, 2H), 2.89 (t, 2H), 2.67-2.58 (m, 4H), 2.40 (s, 2H), 2.13-2.05 (m, 2H), 1.97 (s, 6H), 1.88 (ddd, 2H), 1.84-1.77 (m, 4H).

Intermediate 20: 1-(3-Chloro-2-methyl-propyl)-pyrrolidine

Pyrrolidine (3.0 g, 42 mmol), acetone (60 ml), 5M NaOH solution (10 ml) and 1-bromo-3-chloro-2-methyl-propane (21.7 g, 0.13 mol) were reacted together according to general procedure A to give the title compound (3.9 g, 58%) as a pale yellow oil.

Example 18

Dimethyl-{4-[4-(2-methyl-3-pyrrolidin-yl-propoxy)-phenyl]-tetrahydro-pyran-4-ylmethyl}-amine

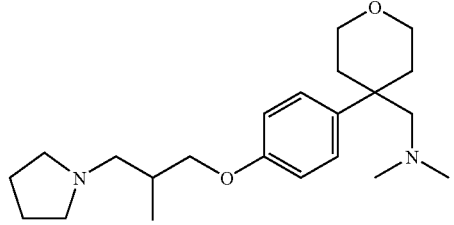

4-(4-Dimethylaminomethyl-tetrahydro-pyran-4-yl)-phenol (0.91 g, 3.87 mmol), 1-(3-chloro-2-methyl-propyl)-pyrrolidine (500 mg, 3.10 mmol), DMF (5 ml) and K$_2$CO$_3$ (2.14 g, 15.50 mmol) were reacted according to general procedure B. The organic phase was washed with 2M NaOH (3×20 ml), water (2×20 ml), dried over MgSO$_4$, fitered and concentrated in vacuo at 35° C. The crude material was subjected to chromatography on silica eluting with DCM:MeOH:NH$_3$ (97:2:1) to provide the title compound (464 mg, 42%) as a pale yellow oil. $^1$H NMR (400 MHz, CDCl$_3$) δ7.20 (d, 2H), 6.88 (d, 2H), 4.00 (dd, 1H), 3.80-3.70 (m, 3H), 3.55 (td, 2H), 2.59-2.43 (m, 5H), 2.40 (s, 2H), 2.33 (dd, 1H), 2.21-2.04 (m, 3H), 1.97 (s, 6H), 1.88 (ddd, 2H), 1.82-1.70 (m, 4H), 1.08 (d, 3H).

Intermediate 21: Methanesulfonic acid 1-isopropyl-piperidin-4-yl ester

Step 1: 4-Hydroxypiperidine (2.13 g, 21.1 mmol), K$_2$CO$_3$ (5.83 g, 2 eq.), 2-bromopropane (11.2 g, 91 mmol, 4.3 eq.) and MeOH (21.3 ml) were refluxed together overnight. The reaction was allowed to cool to room temperature and quenched with 2M HCl solution (40 ml) and extracted with TBME (40 ml). The aqueous phase was basified to pH 14 with 2M NaOH solution and extracted with DCM (9×50 ml). The combined organic extracts were dried over MgSO$_4$, filtered, washed with DCM and concentrated in vacuo to give 1-isopropyl-4-hydroxypiperidine (2.41 g, 80%) as a pale yellow oil.

Step 2: 1-Isopropyl-4-hydroxypiperidine (1 g, 6.98 mmol), DCM (10 ml) and triethylamine (1.08 ml, 7.68 mmol) were cooled to 0-5° C. and mesyl chloride (0.54 ml, 6.98 mmol) was added dropwise under N₂. The reaction was allowed to warm to room temperature and stirred for 1 hour. The reaction was quenched with sat. NaHCO₃ (20 ml) and the aqueous phase extracted with DCM (2×5 ml). The combined organic extracts were dried over MgSO₄, filtered, washed with DCM and concentrated in vacuo to give the title compound (1.55 g, 100%) as a pale yellow oil.

Example 19

{4-[4-(1-Isopropylpiperidin-4-yloxy)phenyl]tetrahydropyran-4-ylmethyl}dimethyl-amine

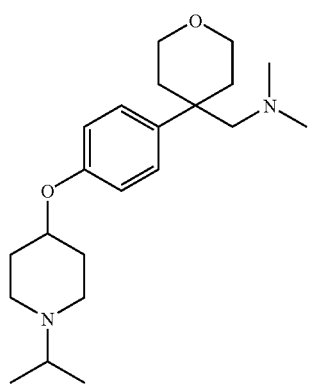

4-(4-Dimethylaminomethyl-tetrahydro-pyran-4-yl)-phenol (532 mg, 2.26 mmol) in DMF (2 ml) was added to a solution of NaH (100 mg, 2.5 mmol) in DMF (2 ml) at room temperature under N₂. The reaction was stirred for 1 hr and a solution of methanesulfonic acid 1-isopropyl-piperidin-4-yl ester (400 mg, 1.81 mmol) in DMF (1.3 ml) was slowly added. The reaction was heated to 75° C. and stirred for 6 hrs. The reaction was allowed to cool to room temperature and diluted with TBME (20 ml), water (10 ml) and 5M NaOH solution (10 ml). The organic layer was washed with 2.5M NaOH (2×20 ml), brine (2×20 ml), dried over MgSO₄, filtered and concentrated in vacuo. The crude reaction was purified by column chromatography, eluting with DCM:MeOH:NH₃ (98:1:1) to give the title compound as a white crystalline solid (113 mg, 17%). ¹H NMR (400 MHz, CDCl₃) δ7.20 (d, 2H), 6.87 (d, 2H), 4.27 (m, 1H), 3.75 (dt, 2H), 3.55 (td, 2H), 2.85-2.68 (m, 3H), 2.45-2.32 (m, 2H), 2.40 (s, 2H), 2.14-1.94 (m, 4H), 1.96 (s, 6H), 1.93-1.75 (m, 4H), 1.06 (d, 6H).

Intermediate 22: Methanesulfonic acid 1-cyclopentyl-piperidin-4-yl ester

Step 1: 4-Hydroxypiperidine (2.08 g, 21.2 mmol), K₂CO₃ (5.86 g, 2 eq.), cylopentylbromide (11.51 g, 77.6 mmol, 3.7 eq.) and MeOH (20.8 ml) were refluxed together overnight. The reaction was allowed to cool to room temperature and quenched with 2M HCl solution (40 ml) and extracted with TBME (40 ml). The aqueous phase was basified to pH 14 with a 2M NaOH solution and extracted with DCM (4×50 ml). The combined organic extracts were dried over MgSO₄, filtered, washed with DCM and concentrated in vacuo to give 1-cyclopentyl-4-hydroxypiperidine (2.55 g, 71%) as a pale yellow oil.

Step 2: 1-Cyclopentyl-4-hydroxypiperidine (1 g, 5.91 mmol), DCM (10 ml) and triethylamine (0.91 ml, 6.5 mmol) were cooled to 0-5° C. and mesyl chloride (0.46 ml, 5.91 mmol) was added dropwise under N₂. The reaction was allowed to warm to room temperature and stirred for 1 hour. The reaction was quenched with sat. NaHCO₃ (20 ml) and the aqueous phase extracted with DCM (2×5 ml). The combined organic extracts were dried over MgSO₄, filtered, washed with DCM and concentrated in vacuo to give the title compound (1.38 g, 95%) as a pale yellow oil.

Example 20

{4-[4-(1-Cyclopentylpiperidin-4-yloxy)phenyl]tetrahydropyran-4-ylmethyl}dimethylamine

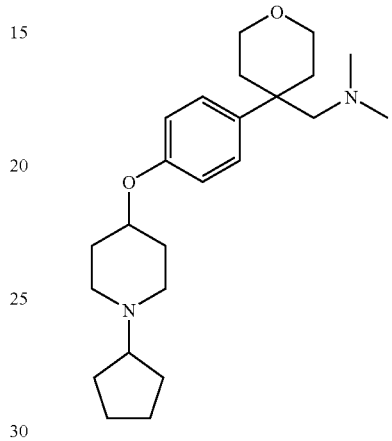

4-(4-Dimethylaminomethyl-tetrahydro-pyran-4-yl)-phenol (487 mg, 2.07 mmol) in DMF (2 ml) was added to a solution of NaH (100 mg, 2.5 mmol) in DMF (2 ml) at room temperature under N₂. The reaction was stirred for 1 hr and a solution of methanesulfonic acid 1-cyclopentyl-piperidin-4-yl ester (409 mg, 1.65 mmol) in DMF (1.5 ml) was slowly added. The reaction was heated to 75° C. and stirred for 6 hrs. The reaction was allowed to cool to room temperature and diluted with TBME (20 ml), water (10 ml) and 5M NaOH solution (10 ml). The organic layer was washed with 2.5M NaOH (2×20 ml), brine (2×20 ml), dried over MgSO₄, filtered and concentrated in vacuo. The crude reaction was purified by column chromatography, eluting with DCM:MeOH:NH₃ (98:1:1) to give the title compound as a white solid (78 mg, 12%). ¹H NMR (400 MHz, CDCl₃) δ7.20 (d, 2H), 6.87 (d, 2H), 4.28 (m, 1H), 3.75 (dt, 2H), 3.55 (td, 2H), 2.89-2.76 (m, 2H), 2.52 (p, 1H), 2.40 (s, 2H), 2.37-2.25 (m, 2H), 2.14-1.94 (m, 4H), 1.96 (s, 6H), 1.93-1.77 (m, 6H), 1.76-1.34 (m, 6H).

Example 21

{3-[4-(4-Dimethylaminomethyl-tetrahydro-pyran-4-yl)-phenoxy]-propyl}-isopropyl-amine

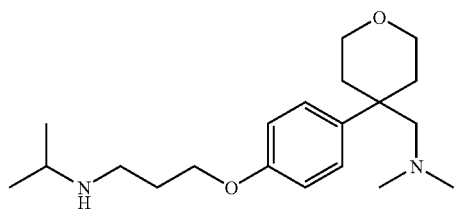

4-(4-Dimethylaminomethyl-tetrahydro-pyran-4-yl)-phenol (730 mg, 3.10 mmol), 3-chloro-1-bromopropane (980 mg, 6.20 mmol), DMF (10 ml) and $K_2CO_3$ (1.72 g, 12.40 mmol) were reacted together according to general procedure B. Purification by chromatography on silica, eluant DCM:MeOH (20:1) provided a mixture of bromo and chloro phenoxy ether (250 mg) which was used in the next stage. The mixture (250 mg) was refluxed with isopropyl amine (34° C.) (10 ml, 40 vol) for 7 days. The reaction was concentrated in vacuo and partitioned between 2M NaOH (10 ml) and DCM (10 ml). The aqueous phase was extracted with DCM (3×10 mL). The combined DCM layers were dried over $MgSO_4$, filtered, washed with DCM and concentrated in vacuo. Purification by chromatography on silica, eluant DCM:MeOH:$NH_3$ (95:5:0) increasing gradually to DCM:MeOH:$NH_3$ (90:9:1) gave the title compound as a pale yellow solid (180 mg, 17% over the 2 steps). $^1$H NMR (400 MHz, $CDCl_3$) δ7.20 (d, 2H), 6.88 (d, 2H), 4.03 (t, 2H), 3.75 (dt, 2H), 3.59-3.50 (m, 2H), 2.89-2.76 (m, 3H), 2.40 (s, 2H), 2.15-2.05 (m, 2H), 2.03-1.93 (m, 2H), 1.96 (s, 6H), 1.88 (ddd, 2H), 1.49 (br s, 1H), 1.07 (d, 6H).

Example 22

Dimethyl-{4-[4-(4-pyrrolidin-1-ylbutoxy)phenyl]tetrahydro-pyran-4-ylmethyl}amine

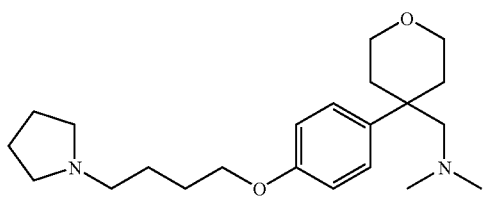

4-(4-Dimethylaminomethyl-tetrahydro-pyran-4-yl)-phenol (1.5 g, 6.38 mmol), 1-bromo-4-chlorobutane (1.5 ml, 12.77 mmol), DMF (20 ml) and $K_2CO_3$ (3.5 g, 25.53 mmol) were reacted together according to general procedure B. Purification of a fraction of the crude (900 mg) by chromatography on alumina, eluant ethyl acetate:heptanes (12:88) provided a mixture of bromo and chloro phenoxy ether (220 mg) which was used in the next stage. The purified mixture (220 mg, 0.68 mmol) and pyrrolidine (0.17 ml, 2.03 mmol) were refluxed in EtOH (3 ml, 15 vol) overnight. The reaction was concentrated in vacuo and partitioned between 2M NaOH (10 ml) and ethyl acetate (10 ml). The aqueous was extracted with ethyl acetate (3×5 mL). The combined ethyl acetate layers were washed with brine (3×5 ml), dired over $MgSO_4$, filtered, washed with ethyl acetate and concentrated in vacuo. Purification by chromatography on silica, eluant 95:3:2 (DCM:MeOH:$NH_3$) followed by a second column eluting with DCM:MeOH:$NH_3$ (96.5:3:0.5), gave the title compound as a colourless oil (134 mg, 55%). $^1$H NMR (400 MHz, $CDCl_3$) δ7.21 (d, 2H), 6.86 (d, 2H), 3.97 (t, 2H), 3.75 (dt, 2H), 3.59-3.50 (m, 2H), 2.57-2.45 (m, 6H), 2.40 (s, 2H), 2.14-2.05 (m, 2H), 1.96 (s, 6H), 1.92-1.65 (m, 10H).

General procedure C:

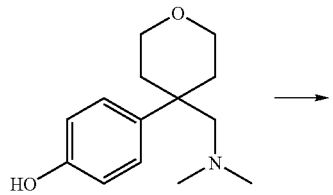

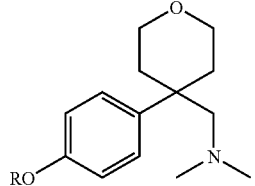

4-(4-Dimethylaminomethyl-tetrahydro-pyran-4-yl)-phenol (1 eq.), alcohol (R—OH) (0.8 eq.) and $PPh_3$ (1 eq.) were mixed together in THF (10 vol) and cooled to 0° C. under $N_2$. DIAD (1 eq.) in THF (10 vol) was added slowly to the reaction and allowed to warm to room temperature overnight. The reaction was quenched with 2M HCl solution (10 vol) and extracted with ethyl acetate (3×10 vol). The aqueous phase was basified to pH 14 with NaOH (~30 vol) and extracted with ethyl acetate (3×10 vol). The organic phase was dried over $MgSO_4$, filtered and concentrated in vacuo at 35° C. Purification of the crude material by chromatography on silica, eluant (10% MeOH in DCM) provided the title compounds.

Intermediate 23: 2,2-Dimethyl-3-pyrrolidin-1-yl-propan-1-ol

Pyrrolidine (1.82 g, 25 mmol), $K_2CO_3$ (3.0 g, 1.04 eq.), 3-bromo-2,2-dimethyl-propan-1-ol (8.45 g, 50 mmol, 2 eq.) were heated together at 90° C. overnight. The reaction was allowed to cool to room temperature and quenched with 2M HCl solution (50 ml) and extracted with TBME (3×50 ml). The aqueous phase was basified to pH 14 with 2M NaOH solution and extracted with DCM (3×50 ml). The combined organic extracts were dried over $MgSO_4$, filtered, washed with DCM and concentrated in vacuo to give the title compound (1.03 g, 26%) as a pale yellow oil.

Example 23

{4-[4-2,2-Dimethyl-3-pyrrolidin-1-yl-propoxy)-phenyl]-tetra-hydropyran-4-ylmethyl}-dimethyl-amine

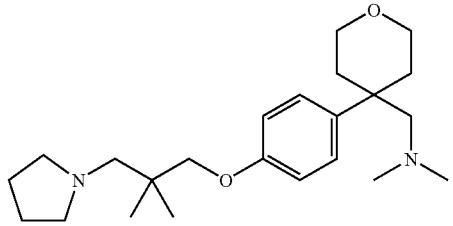

4-(4-Dimethylaminomethyl-tetrahydro-pyran-4-yl)-phenol (0.28 g, 1.19 mmol), 2,2-dimethyl-3-pyrrolidin-1-yl-propan-1-ol (0.15 g, 0.96 mmol), $PPh_3$ (0.31 g, 1.19 mmol), THF (3 ml) and DIAD (0.24 ml, 1.19 mmol) were reacted together according to general procedure C. The crude material was subjected to chromatography on silica eluting with DCM:MeOH:$NH_3$ (97:2:1) to provide the title compound (85 mg, 24%) as an off-white solid. $^1$H NMR (400 MHz, $CDCl_3$) δ7.23 (d, 2H), 6.91 (d, 2H), 3.84-3.69 (m, 4H), 3.69-3.54 (m, 2H), 2.67-2.56 (m, 4H), 2.50 (s, 2H), 2.44 (s, 2H), 2.18-2.08 (m, 2H), 2.01 (s, 6H), 1.92 (ddd, 2H), 1.79-1.67 (m, 4H), 1.04 (s, 6H).

Intermediate 24: 4-Pyrrolidin-1-yl-butan-2-ol

Pyrrolidine (2 ml, 24 mmol), THF (20 ml) and methyl vinylketone (2.5 ml, 31 mmol) were mixed together and stirred overnight. NaBH$_4$ (1.17 g, 31 mmol) was added to the reaction mixture and stirred for 3 hours. The reaction was quenched with water (20 ml) and extracted with TBME (2×20 ml). The combined organic extracts were dried over MgSO$_4$, filtered, washed with TBME and concentrated in vacuo. The crude product was purified by column chromatography, eluting with DCM:MeOH:NH$_3$ (94:5:1), to give the title compound as a pale yellow oil (1.3 g, 38%).

Example 24

Dimethyl-{4-[4-(1-methyl-3-pyrrolidin-1-ylpropoxy)phenyl]-tetrahydropyran-4-ylmethyl}amine

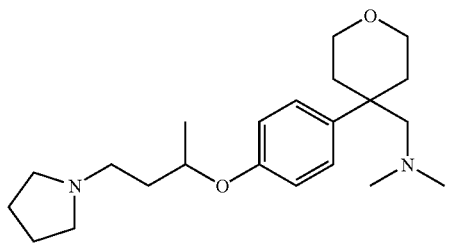

4-(4-Dimethylaminomethyl-tetrahydro-pyran-4-yl)-phenol (1.03 g, 4.40 mmol), 4-pyrrolidin-1-yl-butan-2-ol (0.5 g, 3.50 mmol), PPh$_3$ (1.15 g, 4.40 mmol), THF (10 ml) and DIAD (0.86 ml, 4.40 mmol) were reacted together according to general procedure C. The crude product was purified by preparative HPLC, eluting with acetonitrile/water/0.1% TFA as a gradient, to give the title compound as a yellow oil (125 mg, 10%). $^1$H NMR (400 MHz, CDCl$_3$) δ7.19 (d, 2H), 6.86 (d, 2H), 4.43 (m, 1H), 3.75 (dt, 2H), 3.60-3.51 (m, 2H), 2.67-2.46 (m, 6H), 2.40 (s, 2H), 2.14-2.04 (m, 2H), 1.97 (s, 6H), 1.93-1.73 (m, 8H), 1.31 (d, 3H).

Intermediate 25: 3-Pyrrolidin-1-yl-butan-1-ol

Pyrrolidine (28.159, 0.4 mol), toluene (200 ml), catalytic p-TsOH (200 mg) and ethyl acetoacetate (20 g, 0.15 mol) were refluxed together in a Dean-Stark apparatus under N$_2$ for 3 hours. The reaction was cooled to room temperature and concentrated in vacuo. NaBH$_4$ (3.1 g, 82 mmol) was dissolved in MeOH (50 ml) and cooled to 0-5° C. A portion of the previous crude reaction (5 g, 27 mmol) in MeOH (25 ml) was added to the reaction mixture and stirred for 72 hours. The reaction was quenched with an aqueous solution of NaOH (1% w/w, 50 ml) and concentrated in vacuo. The aqueous phase was extracted with TBME (3×50 ml). The combined organic extracts were dried over MgSO$_4$, filtered, washed with TBME and concentrated in vacuo to give a mixture of the title compound, 3-pyrrolidin-1-yl-butanoic acid ethyl ester and residual TBME (3.5 g). The mixture (3.5 g) in THF (20 ml) was added to a solution of LiALH$_4$ (1M in THF, 33.5 ml, 33.5 mmol) at 0-5° C. under N$_2$. The reaction was allowed to warm to room temperature and stirred for 3 hours. The reaction was quenched with an aqueous solution of NaOH (1% w/w, 50 ml) at 0-5° C., filtered and washed with THF (3×20 ml). The combined organic layers were dried over MgSO$_4$, filtered, washed with THF and concentrated in vacuo to give the title compound as a yellow oil (2 g, 73%).

Example 25

Dimethyl-{4-[4-(3-pyrrolidin-1-yl-butoxy)-phenyl]-tetrahydro-pyran-4-ylmethyl}-amine

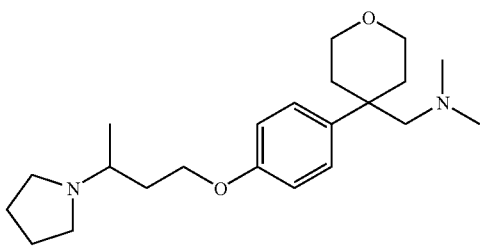

4-(4-Dimethylaminomethyl-tetrahydro-pyran-4-yl)-phenol (925 mg, 3.93 mmol), 3-pyrrolidin-1-yl-butan-1-ol (450 mg, 3.14 mmol), PPh$_3$ (1.03 g, 3.93 mmol), THF (9 ml) and DIAD (0.77 ml, 3.93 mmol) were reacted together according to general procedure C. The crude material was subjected to chromatography on silica eluting with DCM:MeOH (99.5:0.5) to provide the title compound (268 mg, 24%) as a colourless oil. $^1$H NMR (400 MHz, CDCl$_3$) δ7.21 (d, 2H), 6.88 (d, 2H), 4.11-3.97 (m, 2H), 3.75 (dt, 2H), 3.55 (td, 2H), 2.66-2.52 (m, 5H), 2.40 (s, 2H), 2.19-2.05 (m, 3H), 1.96 (s, 6H), 1.93-1.70 (m, 7H), 1.16 (d, 3H).

Example 26

Dimethyl-(4-{4-[2-(1-methylpyrrolidin-2-yl)ethoxy]phenyl}-tetrahydropyran-4-ylmethyl)amine

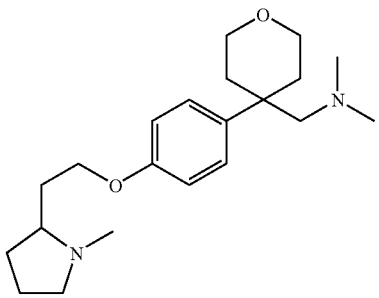

4-(4-Dimethylaminomethyl-tetrahydro-pyran-4-yl)-phenol (405 mg, 1.72 mmol), 2-(1-methyl-pyrrolidin-2-yl)-ethanol (178 mg, 1.38 mmol), PPh$_3$ (451 mg, 1.72 mmol), THF (8 ml) and DIAD (348 mg, 1.72 mmol) were reacted together according to general procedure C. The crude product was subjected to chromatography on alumina eluting with ethyl acetate:heptane (50:50) to provide the title compound (130 mg, 27%) as a colourless oil. $^1$H NMR (400 MHz, CDCl$_3$) δ7.21 (d, 2H), 6.87 (d, 2H), 4.09-3.95 (m, 2H), 3.75 (dt, 2H), 3.55 (td, 2H), 3.09 (m, 1H), 2.40 (s, 2H), 2.35 (s, 3H), 2.30-1.99 (m, 6H), 1.96 (s, 6H), 1.93-1.63 (m, 6H).

Example 27

4-[4-(3-Pyrrolidin-1-yl-propoxy)-phenyl]-tetrahydro-pyran-4-carbonitrile

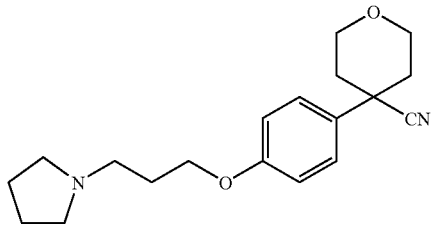

4-(4-Hydroxy-phenyl)-tetrahydro-pyran-4-carbonitrile (2 g, 9.86 mmol), 1-(3-chloro-propyl)-pyrrolidine (2.33 g, 15.78 mmol), DMF (40 ml) and $K_2CO_3$ (5.45 g, 39.44 mmol) were reacted together according to general procedure E. The crude reaction product was diluted with 2M HCl solution (200 ml) and washed with ethyl acetate (3×50 ml). The aqueous phase was basified to pH 14 with 2M NaOH (200 ml) and extracted with ethyl acetate (4×50 ml). The combined organic extracts were dried over $MgSO_4$, filtered, washed with ethyl acetate and concentrated in vacuo to give a white solid. The solid was slurried in TBME (15 ml) and heptane (15 ml), filtered, washed with heptane (8 ml) and dried on the filter for 2 hours to give the title compound as a white solid (1.6 g, 53%). $^1$H NMR (400 MHz, DMSO-$d_6$) δ7.43 (d, 2H), 6.99 (d, 2H), 4.08-3.94 (m, 4H), 3.64 (dt, 2H), 2.57-2.47 (m, 2H), 2.46-2.36 (m, 4H), 2.12-1.94 (m, 4H), 1.87 (p, 2H), 1.73-1.62 (m, 4H).

Alternatively, 4-[4-(3-Pyrrolidin-1-yl-propoxy)-phenyl]-tetrahydro-pyran-4-carbonitrile can be prepared by the following steps:

Step 1: 4-Hydroxybenzylcyanide (20 g, 0.15 mol) was dissolved in DMF (500 mL) and then $K_2CO_3$ (41.4 g, 0.3 mol) and NaI (7.8 g, 0.052 mol) were added followed by dropwise addition of 3-(1-pyrrolidine)-propylchloride (26.5 g, 0.18 mol) at 60° C. Heating was continued at 90° C. for 3 h and then the mixture was heated overnight at 60° C. 3-(1-Pyrrolidine)-propylchloride (10 g, 0.067 mol) was again added as the reaction was not complete and heating was continued for a further 6 h. The reaction mixture was concentrated and taken up in EtOAc. The organic layer was washed with water, finally with brine. Crude [4-(3-pyrrolidin-1-ylpropoxy)phenyl]acetonitrile was purified by DCM/MeOH 9.5/0.5 over a silica gel column. Yield: 25.5 g (70%). $^1$H-NMR (400 MHz, CDCl$_3$) δ1.77 (m, 4H); 1.98 (m, 2H); 2.50 (m, 4H); 2.59 (t, 2H); 3.66 (s, 2H); 4.00 (t, 2H); 6.87 (d, 2H); 7.19 (d, 2H).

Step 2: NaH (14.6 g, 0.61 mol) was suspended in DMF (100 mL). [4-(3-Pyrrolidin-1-ylpropoxy)phenyl]acetonitrile (25.5 g, 0.10 mol) was dissolved in DMF (100 mL) and added dropwise to the ice-cooled suspension of NaH. The reaction mixture was stirred at room temperature for 30 min followed by dropwise addition of 2-bromoethylether (36.2 g, 0.16 mol) in DMF (200 mL) in ice-cold condition. The reaction mixture was poured into ice-cold water. The solid was filtered, washed with water, dried and the resulting solid was washed with 5% EtOAc in hexane to give the title compound (22 g, 67%).

Example 28

{4-[4-(3-Pyrrolidin-1-ylpropoxy)phenyl]tetrahydro-pyran-4-yl}methylamine dihydrochloride

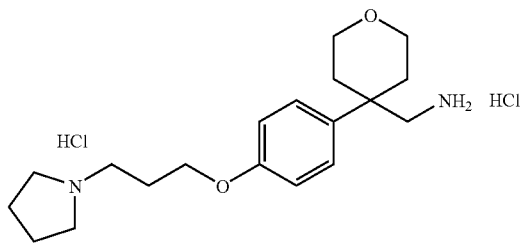

To a stirred suspension of LiAlH$_4$ (1.81 g, 47.7 mmol, 5 eq) in Et$_2$O/DCM (1:1, 30 mL) at 0 to 5° C. under a nitrogen atmosphere was added 4-[4-(3-pyrrolidin-1-yl-propoxy)-phenyl]-tetrahydro-pyran-4-carbonitrile (3 g, 9.55 mmol) in Et$_2$O/DCM (1:1, 30 mL) over 15 minutes maintaining the temperature at 5 to 10° C. The reaction mixture was allowed to warm up to ambient temperature and stirred until complete. Sodium hydroxide (2N, 15 mL) was added dropwise and the resulting solids were filtered, washed with Et$_2$O/DCM (1:1, 6×50 mL) and concentrated in vacuo at 40° C. A portion of the crude product from the above reaction (0.5 g, 1.57 mmol) was dissolved in dioxane (5 mL) and 4M HCl in dioxane (1.18 mL) added under N$_2$. The reaction was stirred for 3 hours and filtered under a blanket of N$_2$ (hygroscopic), washed with TBME and dried in the oven at 40° C. to give the title compound as a white solid (0.5 g, 81%). $^1$H NMR (400 MHz, DMSO-d$_6$) δ11.24 (br s, 1H), 8.00 (br s, 3H), 7.33 (d, 2H), 6.98 (d, 2H), 4.08 (t, 2H), 3.76-3.63 (m, 2H), 3.60-3.46 (m, 2H), 3.45-3.18 (m, 4H), 3.07-2.87 (m, 4H), 2.25-1.77 (m, 10H).

Example 29

Dimethyl-{4-[4-(3-pyrrolidin-1-ylpropoxy)phenyl]-tetrahydro-pyran-4-ylmethyl}amine

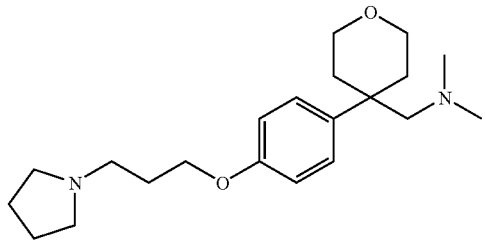

To a mixture of {4-[4-(3-pyrrolidin-1-ylpropoxy)phenyl]tetrahydropyran-4-yl}methylamine (2.5 g, 7.86 mmol), acetic acid (6 ml), and water (12.5 ml) was added formaldehyde (11.5 ml) and stirred for 15 minutes. STAB (10 g, 4.72 mmol) was added portionwise and stirred for one hour. Sodium hydroxide (2M, 100 ml) was added slowly to attain a pH of 9. The resulting mixture was extracted with DCM (3×100 ml) and the combined organic phases were dried over MgSO$_4$, filtered and concentrated in vacuo at 35° C. The crude mixture was purified by column chromatography on silica eluting with DCM:MeOH:NH$_3$ (95:4:1) to give the title compound as a white solid (1.09 g, 40%). ¹H NMR (400 MHz, CDCl₃) 97.21 (d, 2H), 6.87 (d, 2H), 4.02 (t, 2H), 3.75 (dt, 2H), 3.55 (td, 2H), 2.65 (t, 2H), 2.56 (br s, 4H), 2.40 (s, 2H), 2.15-1.74 (m, 10H), 1.97 (s, 6H).

Example 30

4-[4-(3-Piperidin-1-yl-propoxy)-phenyl-tetrahydro-pyran-4-carbonitrile

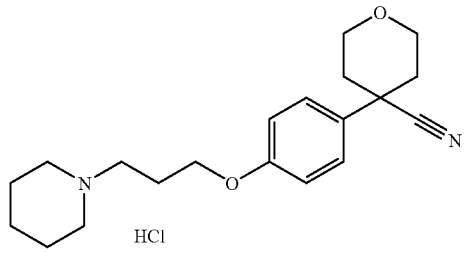

A mixture of 4-(4-hydroxyphenyl)tetrahydro-2H-pyran-4-carbonitrile (1.0 g, 5 mmol), 1-(3-chloropropyl)piperidine (1.2 g, 7.5 mmol) obtained following the procedure described in the Patent DD 60557, cesium carbonate (2.4 g, 7.5 mmol), KI (1.2 g, 7.5 mmol) in DMF (50 mL) was heated to 70° C. overnight. After DMF removal under reduced pressure, the residue was quenched with water and extracted with DCM. The organic phases were dried over Na₂SO₄ filtered and concentrated. The residue was purified by flash chromatography (50 g silica gel, DCM/MeOH) to provide the title compound (1.45 g, 88%). The hydrochloride salt as analytical sample was prepared with ether/HCl 2M in dichloromethane and crystallization in ether. ¹H NMR (500 MHz, CDCl₃) δ12.14 (bs, 1H), 7.32 (d, 2H), 6.83 (d, 2H), 4.07-3.97 (m, 4H), 3.85-3.78 (m, 2H), 3.57-3.48 (m, 2H), 3.14-3.07 (m, 2H), 2.67-2.56 (m, 2H), 2.45-2.36 (m, 2H), 2.32-2.19 (m, 2H), 2.06-1.92 (m, 4H), 1.90-1.75 (m, 4H), 1.43-1.32 (m, 1H).

Example 31

{4-[4-(3-Piperidin-1-ylpropoxy)phenyl]tetrahydro-pyran-4-yl}methylamine dihydrochloride

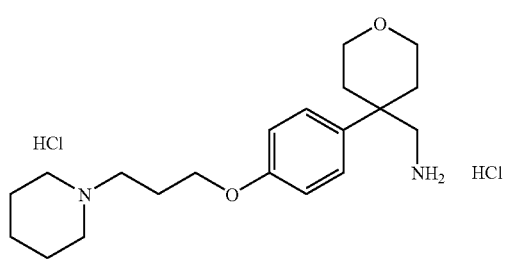

A mixture of 4-[4-(3-piperidin-1-yl-propoxy)-phenyl]-tetrahydro-pyran-4-carbonitrile (1.45 g, 4.4 mmol), isopropanol (12 mL), concentrated HCl (350 μL), and PtO₂ (115 mg) was stirred and hydrogenated to 50° C. overnight at atmospheric pressure. The mixture was filtrated over diatomaceous earth and concentrated. The residue was dissolved in DCM/MeOH mixture and washed with NaOH (1M). The organic layers were dried over Na₂SO₄, filtered and concentrated, purified by flash chromatography (10 g silica gel, DCM/MeOH (10% NH₃)) to provide the title compound as free base (0.650 g, 44.5%). This was then converted to the dihydrochloride salt. ¹H NMR (400 MHz, DMSO-D6) δ 10.66 (bs, 1H), 7.74 (bs, 3H), 7.32 (d, 2H), 6.97 (d, 2H), 4.07 (t, 2H), 3.73-3.65 (m, 2H), 3.47-3.28 (m, 4H), 3.18-3.10 (m, 2H), 2.98-2.81 (m, 4H), 2.25-2.16 (m, 2H), 2.14-2.06 (m, 2H), 1.90-1.67 (m, 7H), 1.44-1.31 (m, 1H).

Example 32

Dimethyl-{4-[4-(3-piperidin-1-ylpropoxy)phenyl] tetrahydro-pyran-4-ylmethyl}amine dihydrochloride

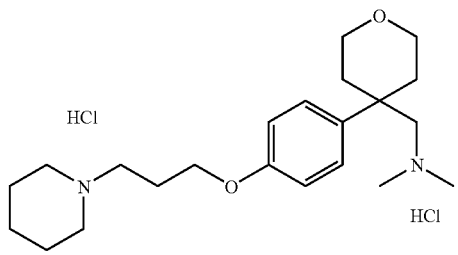

To (0.50 g, 1.5 mmol) of {4-[4-(3-Piperidin-1-ylpropoxy) phenyl]tetrahydropyran-4-yl}methylamine dihydrochloride was added 1.5 mL of formaldehyde (37% W/W solution in H₂O). 1.9 mL of formic acid was added and the mixture was heated to 100° C. for 1.5 h. After cooling, water was added and the mixture extracted with ether. NaOH was added to the aqueous phase and the mixture extracted 3 times with ether. The organic extracts were washed with brine, dried over Na₂SO₄ filtered and concentrated in vacuo. The residue was purified by flash chromatography (25 g silica gel, DCM/MeOH/10% NH₃). This was then converted to the dihydrochloride salt. ¹H NMR (400 MHz, DMSO-D6) δ10.63 (bs, 1H), 9.73 (bs, 1H), 7.43 (d, 2H), 6.99 (d, 2H), 4.11-4.03 (t, 2H), 3.76-3.67 (m, 2H), 3.47-3.29 (m, 7H), 3.19-3.11 (m, 2H), 2.92-2.81 (m, 2H), 2.41-2.35 (m, 5H), 2.32-2.16 (m, 4H), 1.95-1.66 (m, 7H), 1.45-1.32 (m, 1H).

Intermediate 26: 1-(4-hydroxyphenyl)cyclohexanecarbonitrile

To a solution of 1-(4-methoxyphenyl)cyclohexanecarbonitrile (2 g, 9.29 mmol) in DCM (40 mL) at 0° C. under N₂ was added dropwise BBr₃ (2.63 mL, 27.87 mmol). The reaction was allowed to warm to room temperature and stirred for 48 hours. The mixture was stirred for 3 hours at 0° C. and quenched with water (30 mL). The mixture was separated and the organic layer was washed with a saturated aqueous solution of NaHCO₃ then water. The combined organic extracts were dried over Na₂SO₄, filtered, concentrated in vacuo and purified by column chromatography on silica gel eluting with DCM:acetone (97:3) to give the title compound (1.71 g, 91%).

Example 33

1-[4-(3-pyrrolidin-1-ylpropoxy)phenyl]cyclohexanecarbonitrile

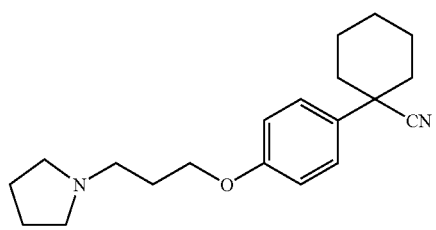

1-(4-Hydroxyphenyl)cyclohexanecarbonitrile (1.70 g, 8.45 mmol), 1-(3-chloro-propyl)-pyrrolidine (1.87 g, 12.67 mmol), acetone (50 mL), sodium iodide (0.444 g, 2.96 mmol) and $K_2CO_3$ (5.45 g, 39.44 mmol) were heated to 50° C. overnight. The solvent was evaporated and the crude product was taken into DCM, washed with 0.5N NaOH, extracted with 0.5N HCl solution and washed with DCM. The aqueous layer was basified with 0.5N NaOH and extracted with DCM. The combined organic extracts were dried over $Na_2SO_4$, filtered, washed with DCM and concentrated in vacuo to give a yellowish solid. The solid was slurried in ether, filtered, washed with ether to give the title compound as a white solid (1.34 g, 51%). $^1$H NMR (400 MHz, $CDCl_3$) δ7.30 (d, 2H), 6.83 (d, 2H), 3.95 (t, 2H), 2.54 (t, 2H), 2.44 (m, 4H), 2.06 (m, 2H), 1.92 (m, 2H), 1.84-1.58 (m, 12H).

Example 34

N-({1-[4-(3-pyrrolidin-1-ylpropoxy)phenyl]cyclohexyl}methyl)-N,N-dimethylamine

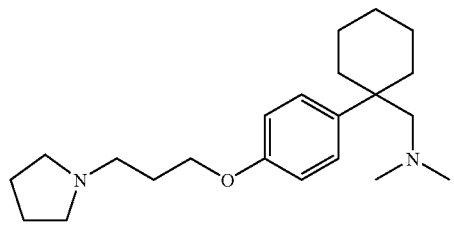

Step 1: To a stirred suspension of $LiAlH_4$ (0.607 g, 16 mmol) in diethyl ether (15 mL) cooled at 0° C. was added dropwise a solution of 1-[4-(3-pyrrolidin-1-ylpropoxy)phenyl]cyclohexanecarbonitrile (1 g, 3.2 mmol) in diethyl ether (10 mL). After being stirred at room temperature for 30 min, the reaction mixture was refluxed for another 30 min. The mixture was cooled to 0° C. and water (1.38 mL), a 5N aqueous solution of sodium hydroxide (1.38 mL) and water (5.52 mL) again were successively added dropwise. After being stirred for 15 min at room temperature, the mixture was filtered over diatomaceous earth and concentrated. The crude {1-[4-(3-pyrrolidin-1-ylpropoxy)phenyl]cyclohexyl}methylamine (0.961 g, 95%) was used in the next step without further purification.

Step 2: To {1-[4-(3-pyrrolidin-1-ylpropoxy)phenyl]cyclohexyl}methylamine (0.96 g, 3 mmol) was added formic acid (5 mL) followed by formaldehyde (37% w/w solution in $H_2O$, 0.915 mL, 33 mmol). The mixture was refluxed for 3 h and allowed to stir overnight at room temperature. It was then diluted with DCM, basified to pH 12 with an aqueous solution of NaOH and the mixture was extracted with DCM. The organic extracts were dried over $Na_2SO_4$, filtered, concentrated in vacuo and purified by column chromatography on silica gel eluting with a gradient of DCM:MeOH:$NH_3$ (from 99:0:1 to 90:10:1) to provide the title compound (0.447 g, 43%) as an oil. $^1$H NMR (400 MHz, $CDCl_3$) δ7.18 (d, 2H), 6.78 (d, 2H), 3.94 (t, 2H), 2.55 (t, 2H), 2.45 (m, 4H), 2.22 (m, 2H), 2.06-1.86 (m, 10H), 1.72 (m, 4H), 1.58-1.19 (m, 8H).

Intermediate 27: 4-[4-(3-pyrrolidin-1-ylpropoxy)phenyl]tetrahydro-2H-pyran-4-carbaldehyde Step 1: A solution of 4-[4-(3-pyrrolidin-1-ylpropoxy)phenyl]tetrahydro-2H-pyran-4-carbonitrile (20 g, 0.0636 mol) in concentrated hydrochloric acid (200 ml, 10 vol) was heated and stirred at reflux for 16 h after which time LC/LCMS analysis showed the reaction had stalled at 85-90% conversion. The solution was evaporated to dryness in vacuo, azeotroped with methanol (200 ml, 20 vol) and toluene (2×200 ml, 2×20 vol) to yield 4-[4-(3-pyrrolidin-1-ylpropoxy)phenyl]tetrahydro-2H-pyran-4-carboxylic acid as a beige solid which was used directly (no NMR data recorded).

Step 2: A suspension of 4-[4-(3-pyrrolidin-1-ylpropoxy)phenyl]tetrahydro-2H-pyran-4-carboxylic acid (23.5 g, 0.0636 mol) in methanol (235 ml, 10 vol) was stirred and cooled to 0 to −5° C. under nitrogen. Thionyl chloride (9.3 ml, 0.1272 mol, 0.40 vol) was charged dropwise over 20 minutes, maintaining the temperature at −5 to +5° C. The resulting slurry was then heated and stirred at reflux under nitrogen for 16 h after which time LC analysis showed 1.4% by area of acid remaining. The solution was evaporated to dryness in vacuo at 40° C. to give a brown sludge. The sludge was dissolved in ethyl acetate (118 ml, 5 vol) and water (235 ml, 10 vol) and the layers separated. The aqueous layer was washed with ethyl acetate (118 ml, 5 vol) and basified to pH 11 with saturated aqueous potassium carbonate (118 ml, 5 vol). The product was extracted into dichloromethane (3×118 ml, 3×5 vol) and the combined extracts dried over magnesium sulfate (23 g) and concentrated in vacuo at 40° C. to yield methyl 4-[4-(3-pyrrolidin-1-ylpropoxy)phenyl]tetrahydro-2H-pyran-4-carboxylate (21.7 g, 98% from the nitrile) as a cream solid.

Step 3: Anhydrous tetrahydrofuran (141 ml, 10 vol) was charged rapidly onto stirred and cooled (0-5° C.) lithium aluminium hydride (6.2 g, 0.1634 mol, 0.44 wt) under nitrogen. The resulting slurry was cooled to 0-5° C. and then a solution of methyl 4-[4-(3-pyrrolidin-1-ylpropoxy)phenyl]tetrahydro-2H-pyran-4-carboxylate (14.1 g, 0.04058 mol) in tetrahydrofuran (99 ml, 7 vol) was added dropwise over 30 minutes maintaining 0-5° C. On complete addition the reaction was allowed to warm to room temperature over 30 minutes and stirred at 18-25° C. for 30 minutes, LC analysis showed the reaction to be complete. The mixture was cooled to 0 to 5° C., a 1:1 mixture of tetrahydrofuran and water (18.6 ml, 1.32 vol) was added very slowly. The mixture was further quenched with 20% w/v sodium hydroxide solution (6.2 ml, 0.44 vol) and water (18.6 ml, 1.32 vol) and the resulting white suspension stirred vigorously for 30 minutes at 18-25° C. The salts were removed by filtration and rinsed with tetrahydrofuran (3×150 ml). The combined filtrates were evaporated to dryness at 40° C. to yield {4-[4-(3-pyrrolidin-1-ylpropoxy)phenyl]tetrahydro-2H-pyran-4-yl}methanol (12.1 g, 94%) as a white solid.

Step 4: Pyridinium chlorochromate (20.3 g, 0.09415 mol), 1.69 wt) was charged to a stirred suspension of celite (24 g, 2 wt) and {4-[4-(3-pyrrolidin-1-ylpropoxy)phenyl]tetrahydro-2H-pyran-4-yl}methanol (12.03 g, 0.03766 mol) in dichloromethane (120 ml, 10 vol) with stirring. The mixture was stirred at 18-25° C. for 3.5 hours after which time LC analysis showed the reaction to be 70% complete. Magnesium sulphate (12 g, 1 wt) was added and the resulting slurry filtered through a pad of aluminium oxide (activated, basic, Brockmann I, standard grade, ~150 mesh) (481 g, 40 wt) eluting with 1% methanol/dichloromethane. Clean fractions were combined and evaporated to dryness at 40° C. The resulting brown solid was stirred in tertbutylmethylether (120 ml, 10 vol). Undissolved residue was removed by filtration and rinsed with tertbutylmethylether (3×120 ml, 3×10 vol). The combined filtrates were evaporated at 40° C. to yield 4-[4-(3-pyrrolidin-1-ylpropoxy)phenyl]tetrahydro-2H-pyran-4-carbaldehyde (6.0 g, 50.2%) as a beige waxy solid.

Alternatively, 4-[4-(3-pyrrolidin-1-ylpropoxy)phenyl]tetrahydro-2H-pyran-4-carbaldehyde can be prepared as follows. To a solution of 4-[4-(3-pyrrolidin-1-ylpropoxy)phenyl]tetrahydro-2H-pyran-4-carbonitrile (250 mg, 0.79 mmol) in anhydrous toluene (2 mL) at −78° C. was added dropwise a 1.5M solution of diisobutyl aluminium hydride in toluene (1.59 mL, 2.38 mmol, 3 equiv). The reaction mixture was stirred for 2 h at −78° C. Ethyl acetate was then added followed by a saturated solution of sodium potassium tartrate and dichloromethane. After stirring at room temperature for 1 h, the organic layer was separated. The aqueous layer was extracted three times with dichloromethane. The combined organic extracts were dried over sodium sulfate, filtered and concentrated under reduced pressure to give an 8:2 mixture of the desired aldehyde and starting nitrile as an orange oil.

General procedure D:

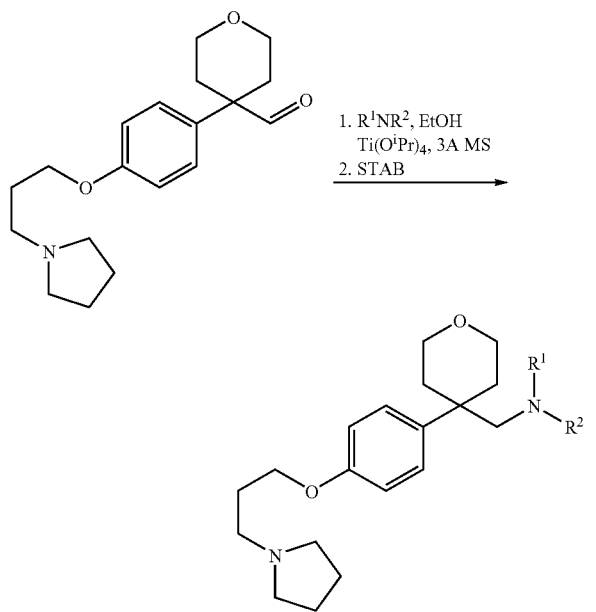

A solution of the 4-[4-(3-pyrrolidin-1-ylpropoxy)phenyl]tetrahydro-2H-pyran-4-carbaldehyde (700 mg, 2.205 mmol, 1 wt) and secondary amine ($NR^1R^2$) (4.21 mmol) in absolute ethanol (28 ml, 40 vol) was stirred 18 to 25° C. under nitrogen over activated 3 Å molecular sieves (700 mg, 1 wt). Titanium (IV) isopropoxide (3.25 ml, 11.025 mmol, 4.62 vol) was added dropwise over 2 minutes. The resulting solution was stirred at 18 to 25° C. under nitrogen for 20 to 24 h, over which time precipitation was observed. Sodium triacetoxyborohydride (3.97 g, 0.0187 mol, 5.67 wt) was then added in one portion (Note: not exothermic, but gentle gas evolution was observed) and the reaction was stirred for 1 to 8 h until LC analysis showed the reaction to be either complete or stalled at 1-10% aldehyde by area). The reaction mixture was decanted from the sieves and evaporated to dryness in vacuo at 40° C. tert-Butylmethyl ether (28 ml, 40 vol), 50% w/v Rochelle's solution (28 ml, 40 vol) and sat. aqueous potassium carbonate solution (28 ml, 40 vol) were added and the mixture stirred vigorously for 1 to 2 h until two layers were visible (the organic layer was clear, the aqueous cloudy). The layers were separated and the aqueous layer re-extracted with tert-butylmethyl ether (28 ml, 40 vol). The extracts were combined, washed with sat. aqueous sodium chloride solution (28 ml, 40 vol), dried over magnesium sulfate (700 mg, 1 wt) and evaporated in vacuo at 40° C. to yield a viscous oil. The oil was purified by column chromatography on silica (20 g, 28.6 wt) eluting with DCM(95):MeOH(4):$NH_3$(1) to remove unreacted aldehyde, alcohol by-product (typically 1-10% by area) and the excess secondary amine to yield the pure product as a viscous oil contaminated by dichloromethane after evaporation. The oil was dissolved in ethanol (5 ml, 7.1 vol) and evaporated to dryness in vacuo at 40° C., then in a vacuum oven at 40° C. for 12 to 24 h to yield the required tertiary amine product as a viscous oil or waxy solid.

Example 35

(1-{4-[4-(3-Pyrrolidin-1-ylpropoxy)phenyl]tetrahydropyran-4-ylmethyl}piperidin-4-yl)-methanol 4-[4-(3-Pyrrolidin-1-ylpropoxy)phenyl]tetrahydro-2H-pyran-4-carbaldehyde (700 mg, 2.205 mmol, 1 wt), 4-piperidinemethanol (485 mg, 4.21 mmol), absolute ethanol (28 ml, 40 vol), activated 3 Å molecular sieves (700 mg), titanium (IV) isopropoxide (3.25 ml, 11.03 mmol) and STAB (3.97 g, 18.7 mmol) was reacted in accordance with the general procedure D. The isolated waxy solid was purified by column chromatography on silica eluting with DCM:MeOH:$NH_3$ 95:4:1 to give the title compound as a colorless oil (820 mg, 72%). $^1$H NMR (400 MHz, $CDCl_3$) δ7.20 (d, 2H), 6.85 (d, 2H), 4.02 (t, 2H), 3.75 (dt, 2H), 3.59-3.46 (m, 2H), 3.42 (d, 2H), 2.63 (t, 2H), 2.53 (br s, 4H), 2.39-2.26 (m, 4H), 2.15-1.03 (m, 18H).

Example 36

1-{4-[4-(3-Pyrrolidin-1-ylpropoxy)phenyl]tetrahydropyran-4-ylmethyl}piperidin-4-ol 4-[4-(3-Pyrrolidin-1-ylpropoxy)phenyl]tetrahydro-2H-pyran-4-carbaldehyde (420 mg, 1.30 mmol, 1 wt), 4-hydroxypiperidine (268 mg, 2.60 mmol), absolute ethanol (17 ml, 40 vol), activated 3 Å molecular sieves (420 mg), titanium (IV) isopropoxide (1.94 ml, 4.62 vol) and STAB (2.34 g, 11.1 mmol) was reacted in accordance with the general procedure D. The isolated waxy solid was purified by preparative HPLC, eluting with acetonitrile/water/0.1% TFA as a gradient, to give the title compound as a white solid (380 mg, 73%). $^1$H NMR (400 MHz, CDCl$_3$) δ7.21 (d, 2H), 6.86 (d, 2H), 4.02 (t, 2H), 3.75 (dt, 2H), 3.59-3.47 (m, 2H), 2.63 (t, 2H), 2.53 (br s, 4H), 2.35 (s, 2H), 2.33-2.25 (m, 2H), 2.13-1.96 (m, 6H), 1.93-1.83 (m, 2H), 1.82-1.76 (m, 4H), 1.72-1.59 (m, 3H), 1.47-1.29 (m, 3H).

Example 37

1-{4-[4-(3-Pyrrolidin-1-yl-propoxy)-phenyl]-tetrahydro-pyran-4-ylmethyl}-piperidine-4-carboxylic acid amide

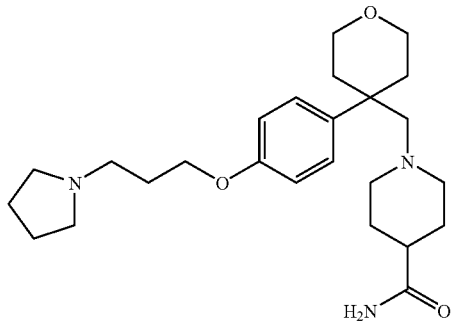

4-[4-(3-Pyrrolidin-1-ylpropoxy)phenyl]tetrahydro-2H-pyran-4-carbaldehyde (500 mg, 1.58 mmol), isonipecotamide (434 mg, 3.03 mmol), absolute ethanol (20 ml), activated 3 Å molecular sieves (500 mg), titanium (IV) isopropoxide (2.31 ml, 7.88 mmol) and STAB (2.84 g, 13.6 mmol) were reacted in accordance with the general procedure D. The isolated crude product was purified by column chromatography on silica eluting with DCM:MeOH:NH$_3$ (97:2:1) to give the title compound as a colorless solid (400 mg, 59%). $^1$H NMR (400 MHz, CDCl$_3$) δ7.20 (d, 2H), 6.85 (d, 2H), 5.45 (br s, 2H), 4.01 (t, 2H), 3.79-3.69 (m, 2H), 3.57-3.46 (m, 2H), 2.63 (t, 2H), 2.53 (br s, 4H), 2.35 (s, 2H), 2.31 (br s, 1H), 2.14-1.72 (m, 14H), 1.67-1.51 (m, 4H).

Example 38

1-Methyl-4-{4-[4-(3-pyrrolidin-1-yl-propoxy)-phenyl]-tetrahydro-pyran-4-ylmethyl}-piperazine

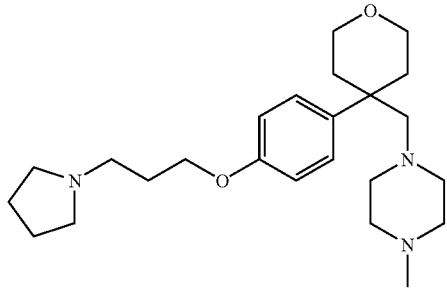

A solution of 4-[4-(3-pyrrolidin-1-ylpropoxy)phenyl]tetrahydro-2H-pyran-4-carbaldehyde (500 mg, 1.58 mmol, 1 wt), 1-methylpiperazine (300 mg, 2.99 mmol), absolute ethanol (20 ml, 40 vol), activated 3 Å molecular sieves (500 mg), titanium (IV) isopropoxide (2.32 ml, 7.83 mmol) and STAB (1.43 g, 6.73 mmol) were reacted in accordance with the general procedure D. The isolated oil was purified by column chromatography on silica (20 g, 28.6 wt) eluting with DCM (95):MeOH(4):NH$_3$(I) to give the title compound as a clear viscous oil (360 mg, 56%). $^1$H NMR (400 MHz, CDCl$_3$) δ7.21 (d, 2H), 6.86 (d, 2H), 4.02 (t, 2H), 3.75 (dt 2H), 3.60-3.47 (m, 2H), 2.63 (t, 2H), 2.53 (br s, 4H), 2.38 (s, 2H), 2.34-2.14 (m, 11H), 2.13-1.73 (m, 10H).

Example 39

1-{4-[4-(3-Pyrrolidin-1-ylpropoxy)phenyl]tetrahydropyran-4-ylmethyl}piperazine

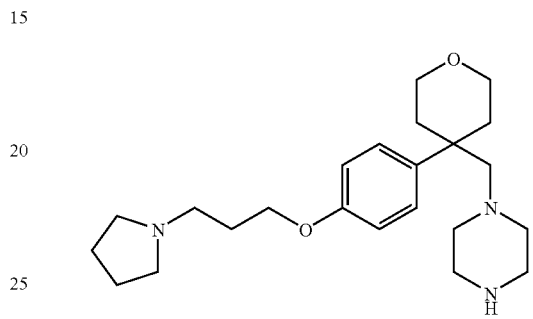

4-[4-(3-Pyrrolidin-1-ylpropoxy)phenyl]tetrahydro-2H-pyran-4-carbaldehyde (350 mg, 1.103 mmol), 4-piperazine-1-carboxylic acid tert-butyl ester (372 mg, 1.98 mmol), absolute ethanol (40 ml), activated 3 Å molecular sieves (350 mg), titanium (IV) isopropoxide (1.62 ml, 5.48 mmol) and STAB (2.0 g, 9.74 mmol) were reacted in accordance with the general procedure D. The isolated crude product was purified by column chromatography on silica eluting with DCM:MeOH:NH$_3$ (98:1:1) to give a white solid (295 mg, 69%). This was re-dissolved in methanol (3.2 ml) and 1,4-dioxane (8 ml), HCl in dioxane (4M, 1.95 ml) was added. The mixture was stirred overnight and concentrated in vacuo at 40° C. TBME (13 ml) and NaOH (2M aqueous) were added to attain a pH of 12-14. The organic phase was separated and dried over MgSO$_4$ and concentrated in vacuo at 35° C. The crude product was subjected to chromatography on silica eluting with DCM:MeOH:NH$_3$ (94:4:2) to give the title compound as a yellow oil (100 mg, 23%). $^1$H NMR (400 MHz, CDCl$_3$) δ7.21 (d, 2H), 6.85 (d, 2H), 4.02 (t, 2H), 3.80-3.70 (m, 2H), 3.58-3.46 (m, 2H), 2.73-2.66 (m, 4H), 2.63 (t, 2H), 2.53 (br s, 4H), 2.34 (s, 2H), 2.17-1.48 (m, 15H).

Example 40

1-{4-[4-(3-Pyrrolidin-1-ylpropoxy)phenyl]tetrahydropyran-4-ylmethyl)pyrrolidin-3-ol

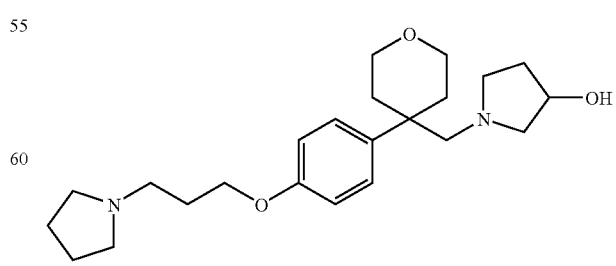

4-[4-(3-Pyrrolidin-1-ylpropoxy)phenyl]tetrahydro-2H-pyran-4-carbaldehyde (350 mg, 1.103 mmol), 3-pyrrolidinol (200 mg, 2.02 mmol), absolute ethanol (40 ml), activated 3 Å molecular sieves (350 mg), titanium (IV) isopropoxide (1.62 ml, 5.48 mmol) and STAB (2.0 g, 9.74 mmol) were reacted in accordance with the general procedure D. The isolated crude product was purified by column chromatography on silica eluting with DCM:MeOH:NH₃ (97:2:1) to give the title compound as a white solid (390 mg, 91%). ¹H NMR (400 MHz, CDCl₃) δ 7.20 (d, 2H), 6.87 (d, 2H), 4.10-4.01 (m, 3H), 3.81-3.68 (m, 3H), 3.55 (t, 2H), 2.67-2.48 (m, 9H), 2.28-1.61 (m, 15H).

Example 41

(R)-2-Methoxymethyl-1-{4-[4-(3-pyrrolidin-1-yl-propoxy)-phenyl]-tetrahydro-pyran-4-ylmethyl}-pyrrolidine

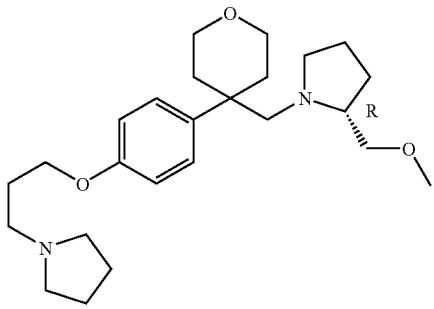

4-[4-(3-Pyrrolidin-1-ylpropoxy)phenyl]tetrahydro-2H-pyran-4-carbaldehyde (500 mg, 1.575 mmol), (R)-2-(methoxymethyl)pyrrolidine (347 mg, 4.21 mmol), absolute ethanol (20 ml), activated 3 Å molecular sieves (500 mg), titanium (IV) isopropoxide (2.33 ml, 7.88 mmol) and STAB (2.84 g, 13.4 mmol) were reacted in accordance with the general procedure D. The isolated waxy solid was purified by column chromatography on silica eluting with DCM:MeOH:NH₃ 95:14:1 to give the title compound as a viscous pale yellow oil (390 mg, 59%). ¹H NMR (400 MHz, CDCl₃) δ7.18 (d, 2H), 6.86 (d, 2H), 4.02 (t, 2H), 3.85-3.69 (m, 2H), 3.59 (td, 1H), 3.45 (td, 1H), 3.27 (s, 3H), 3.10 (dd, 1H), 3.02 (dd, 1H), 2.94 (d, 1H), 2.63 (t, 2H), 2.58-2.45 (m, 6H), 2.39 (m, 1H), 2.21 (m, 1H), 2.07-1.67 (m, 11H), 1.57-1.33 (m, 3H).

Example 42

(S)-2-Methoxymethyl-1-{4-[4-(3-pyrrolidin-1-ylpropoxy)-phenyl]tetrahydropyran-4-ylmethyl}pyrrolidine

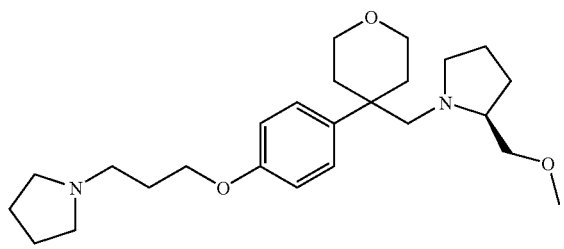

4-[4-(3-Pyrrolidin-1-ylpropoxy)phenyl]tetrahydro-2H-pyran-4-carbaldehyde (350 mg, 1.103 mmol), (s)-(+)-2-(methoxymethyl)pyrrolidine (230 mg, 2.00 mmol), absolute ethanol (40 ml), activated 3 Å molecular sieves (350 mg), titanium (IV) isopropoxide (1.62 ml, 5.48 mmol) and STAB (2.09, 9.74 mmol) were reacted in accordance with the general procedure D. The isolated crude product was purified by column chromatography on silica eluting with DCM:MeOH:NH₃ (98:1:1) to give the title compound as a white solid (330 mg, 72%). ¹H NMR (400 MHz, CDCl₃) δ7.18 (d, 2H), 6.86 (d, 2H), 4.02 (t, 2H), 3.84-3.70 (m, 2H), 3.59 (td, 1H), 3.45 (td, 1H), 3.27 (s, 3H), 3.10 (dd, 1H), 3.02 (dd, 1H), 2.94 (d, 1H), 2.63 (t, 2H), 2.59-2.45 (m, 5H), 2.39 (m, 1H), 2.21 (m, 1H), 2.06-1.34 (m, 15H).

Example 43

1-(1-{4-[4-(3-Pyrrolidin-1-ylpropoxy)phenyl]tetrahydropyran-4-ylmethyl}piperidin-4-yl)pyrrolidin-2-one

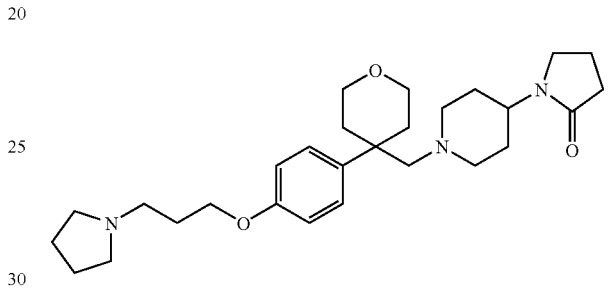

4-[4-(3-Pyrrolidin-1-ylpropoxy)phenyl]tetrahydro-2H-pyran-4-carbaldehyde (400 mg, 1.260 mmol), 4-(N-2-pyrrolidinone)piperidine hydrochloride (493 mg, 4.407 mmol), absolute ethanol (16 ml), activated 3 Å molecular sieves (400 mg), titanium (IV) isopropoxide (1.86 ml, 6.30 mmol) and STAB (2.27 g, 10.71 mmol) were reacted in accordance with the general procedure D. The isolated waxy solid was purified by column chromatography on silica eluting with DCM(95):MeOH(4):NH₃(1) to give the title compound as a pale yellow oil (133 mg, 22%). ¹H NMR (400 MHz, CDCl₃) δ7.20 (d, 2H), 6.86 (d, 2H), 4.02 (t, 2H), 3.83-3.71 (m, 3H), 3.52 (dt, 2H), 3.32 (t, 2H), 2.63 (t, 2H), 2.53 (br s, 4H), 2.41-2.30 (m, 6H), 2.18 (dt, 2H), 2.12-1.36 (m, 16H).

Example 44

4-{4-[4-(3-Pyrrolidin-1-yl-propoxy)-phenyl]-tetrahydro-pyran-4-ylmethyl}-thiomorpholine

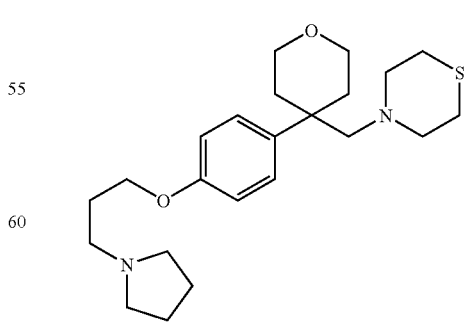

4-[4-(3-Pyrrolidin-1-ylpropoxy)phenyl]tetrahydro-2H-pyran-4-carbaldehyde (1.5 g, 4.726 mmol, 1 wt), thiomorpholine (930 mg, 9.027 mmol), absolute ethanol (60 ml), activated 3 Å molecular sieves (1.5 g), titanium (IV) isopropoxide (6.97 ml, 23.630 mmol) and STAB (8.51 g, 40.15 mmol) were reacted in accordance with the general procedure D. The isolated waxy solid was purified by column chromatography on silica eluting with DCM(95):MeOH(4):NH$_3$(I) to give the title compound as a pale yellow oil (1.06 g, 55%). $^1$H NMR (400 MHz, CDCl$_3$) δ7.20 (d, 2H), 6.86 (d, 2H), 4.02 (t, 2H), 3.75 (dt, 2H), 3.57-3.45 (m, 2H), 2.63 (t, 2H), 2.59-2.39 (m, 12H), 2.36 (s, 2H), 2.14-1.95 (m, 4H), 1.92-1.73 (m, 6H).

Example 45

4-{4-[4-(3-Pyrrolidin-1-ylpropoxy)phenyl]tetrahydropyran-4-ylmethyl}thiomorpholine-1-oxide

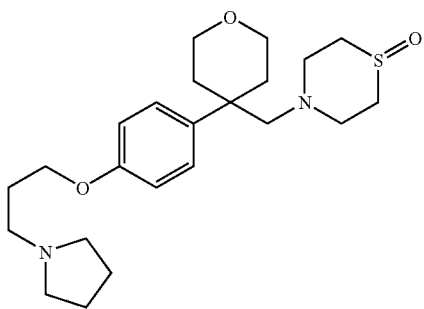

To a solution of 4-{4-[4-(3-pyrrolidin-1-yl-propoxy)-phenyl]-tetrahydro-pyran-4-ylmethyl}-thiomorpholine (200 mg, 0.494 mmol) in TFA (0.67 ml) at 5 to 10° C. was added dropwise a solution of trifluoro-peracetic acid [4M solution prepared by the addition of 27.5% H$_2$O$_2$ (0.94 ml) to TFA (1.56 ml)] and stirred at 5 to 10° C. for 1 hour. The reaction mixture was diluted with DCM (5 ml) and NaOH (5M solution, 4 ml) was added to attain pH14. The mixture was extracted with DCM ((2×5 ml), the combined DCM extracts were washed with saturated aqueous brine (10 ml), dried over MgSO$_4$, filtered and concentrated in vacuo. The isolated yellow oil was purified by column chromatography on silica eluting with DCM(95):MeOH(4):NH$_3$(I) to give the title compound as a yellow oil (165 mg, 79%). $^1$H NMR (400 MHz, CDCl$_3$) δ 7.20 (d, 2H), 6.87 (d, 2H), 4.02 (t, 2H), 3.81-3.69 (m, 2H), 3.59-3.43 (m, 2H), 2.99-2.82 (m, 2H), 2.76-2.2.59 (m, 6H), 2.53 (br s, 4H), 2.46 (s, 2H), 2.31-1.73 (m, 12H).

Example 46

4-{4-[4-(3-Pyrrolidin-1-yl-propoxy)-phenyl]-tetrahydro-pyran-4-ylmethyl}-thiomorpholine 1,1-dioxide

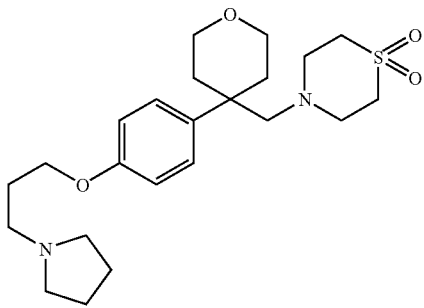

To a solution of 4-{4-[4-(3-Pyrrolidin-1-yl-propoxy)-phenyl]-tetrahydro-pyran-4-ylmethyl}-thiomorpholine (230 mg, 0.56 mmol) in TFA (0.77 ml) at 0 to 5° C. was added dropwise a solution of trifluoro-peracetic acid [4M solution prepared by the addition of 27.5% H$_2$O$_2$ (0.94 ml) to TFA (1.56 ml)]. The reaction was allowed to warm to room temperature and stirred overnight. The reaction mixture was cooled to 0 to 5° C., diluted with DCM (5 ml) and quenched with NaOH (5M solution, 5 ml) to attain pH14. The mixture was extracted with DCM (4×5 ml), the combined DCM extracts were dried over MgSO$_4$, filtered and concentrated in vacuo. The isolated yellow oil was purified by column chromatography on silica eluting with DCM(95):MeOH(4):NH$_3$(I) to give the title compound as a colourless oil (96.6 mg, 39%). $^1$H NMR (400 MHz, CDCl$_3$) δ 7.20 (d, 2H), 6.88 (d, 2H), 4.02 (t, 2H), 3.75 (dt, J=11 and 4 Hz, 2H), 3.57-3.45 (m, 2H), 2.89-2.79 (m, 4H), 2.73-2.65 (m, 4H), 2.63 (t, 2H), 2.55 (br s, 4H), 2.53 (s, 2H), 2.22-2.11 (m, 2H), 2.01 (m, 2H), 1.87-1.73 (m, 6H).

Example 47

4-{4-[4-(3-Pyrrolidin-1-yl-propoxy)phenyl]tetrahydropyran-4-ylmethyl}piperazine-1-carboxylic acid ethyl ester

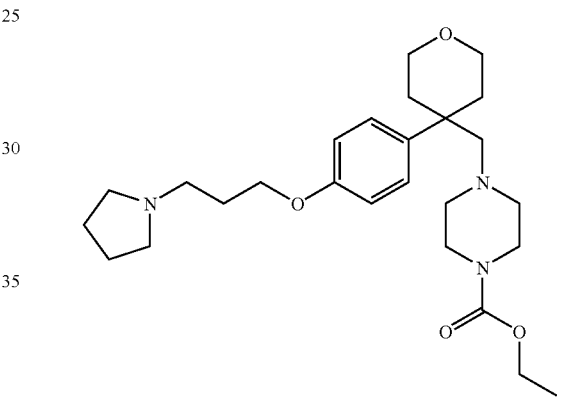

4-[4-(3-Pyrrolidin-1-ylpropoxy)phenyl]tetrahydro-2H-pyran-4-carbaldehyde (500 mg, 1.58 mmol), ethyl piperazine-1-carboxylate (471 mg, 3.00 mmol), absolute ethanol (20 ml), activated 3 Å molecular sieves (500 mg), titanium (IV) isopropoxide (2.31 ml, 7.88 mmol) and STAB (2.84 g, 13.6 mmol) were reacted in accordance with the general procedure D. The isolated crude product was purified by column chromatography on silica eluting with DCM:MeOH: NH$_3$ (97:2:1) to give the title compound as a white solid containing residual 4-[4-(3-pyrrolidin-1-ylpropoxy)phenyl] tetrahydro-2H-pyran-4-carbaldehyde (350 mg). The material was dissolved in DCM (14 ml) and PS-AMPS (loading 2.04 mmol-1 g, 23 mg) was added and shaken for 24 hours. The resin was filtered and the solution concentrated in vacuo at 30° C., the crude material was subjected to chromatography on silica eluting with DCM:MeOH:NH$_3$ (97:2:1) to give the title compound as a white solid (130 mg, 18%). $^1$H NMR (400 MHz, CDCl$_3$) δ 7.20 (d, 2H), 6.86 (d, 2H), 4.08 (q, 2H), 4.02 (t, 2H), 3.79-3.70 (m, 2H), 3.57-3.47 (m, 2H), 3.27 (br s, 4H), 2.63 (t, 2H), 2.53 (br s, 4H), 2.38 (s, 2H), 2.21-1.73 (m, 14H), 1.21 (t, 3H).

Intermediate 28: Piperazine-1-carboxylic acid amide hydrochloride

4-Piperazine-1-carboxylic acid tert-butyl ester (1.0 g, 5.4 mmol), acetic acid (3 ml) and water (5 ml) were mixed together. Potassium cyanate (2.25 g, 27.7 mmol) was added portionwise as a solution in water (5 ml) and stirred for 4 hours, during which time a solid precipitated. The solid was filtered, re-dissolved in DCM (20 ml), dried over MgSO$_4$, filtered, the filter cake washed with DCM (5 vol) and concentrated in vacuo to give a white solid (0.38 g). The white solid (0.38 g) was dissolved in methanol (3.8 ml) and 1,4-dioxane (0.7 ml), 4M HCl in 1,4-dioxane (2.5 ml, 10 mmol) was added to the reaction and stirred overnight. The reaction was concentrated in vacuo to give the title compound (0.28 g, 31% over 2 steps) as a white solid.

Example 48

4-{4-[4-(3-Pyrrolidin-1-yl propoxy)phenyl]tetrahydropyran-4-ylmethyl}piperazine-1-carboxylic acid amide

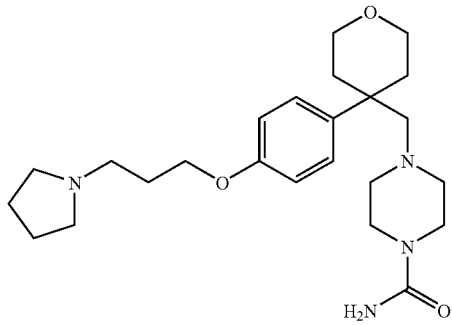

4-[4-(3-Pyrrolidin-1-ylpropoxy)phenyl]tetrahydro-2H-pyran-4-carbaldehyde (317 mg, 1 mmol), piperazine-1-carboxylic acid amide hydrochloride (273 mg, 1.65 mmol), absolute ethanol (12.7 ml), activated 3 Å molecular sieves (320 mg), Et$_3$N (0.278 ml), titanium (IV) isopropoxide (1.46 ml, 5.20 mmol) and STAB (1.8 g, 8.5 mmol) were reacted in accordance with the general procedure D. The isolated crude product was purified by column chromatography on silica eluting with DCM:MeOH:NH$_3$ (98:1:1) to give the title compound as a off white solid (70 mg, 16%). $^1$H NMR (400 MHz, CDCl$_3$) δ 7.21 (d, 2H), 6.86 (d, 2H), 4.30 (br s, 2H), 4.02 (t, 2H), 3.80-3.71 (m, 2H), 3.58-3.48 (m, 2H), 3.23-3.15 (m, 4H), 2.63 (t, 2H), 2.53 (br s, 4H), 2.40 (s, 2H), 2.19-1.73 (m, 14H).

Example 49

1-{4-[4-(3-Pyrrolidin-1-ylpropoxy)phenyl]tetrahydropyran-4-ylmethyl}piperidine

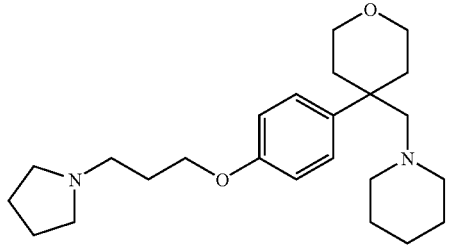

4-[4-(3-Pyrrolidin-1-ylpropoxy)phenyl]tetrahydro-2H-pyran-4-carbaldehyde (272 mg, 0.86 mmol), piperidine (0.161 mL, 1.63 mmol), absolute ethanol (11 mL), activated 4 Å molecular sieves, titanium (IV) isopropoxide (1.205 mL, 4.28 mmol) and STAB (1.54 g, 7.28 mmol) were reacted in accordance with the general procedure D. The isolated waxy solid was purified by column chromatography on silica eluting with a gradient of DCM:MeOH:NH$_3$ (from 99:0:1 to 90:9:1) to give the title compound (97.4 mg, 25%). $^1$H NMR (400 MHz, CDCl$_3$) δ 7.21 (d, 2H), 6.85 (d, 2H), 4.02 (t, 2H), 3.77-3.72 (m, 2H), 3.54-3.48 (t, 2H), 2.63 (t, 2H), 2.53 (m, 4H), 2.29 (s, 2H), 2.13-1.87 (m, 10H), 1.79 (quint, 4H), 1.41-1.36 (m, 4H), 1.30-1.26 (m, 2H).

Example 50

4,4-difluoro-1-{4-[4-(3-Pyrrolidin-1-ylpropoxy)phenyl]tetra-hydropyran-4-ylmethyl}piperidine

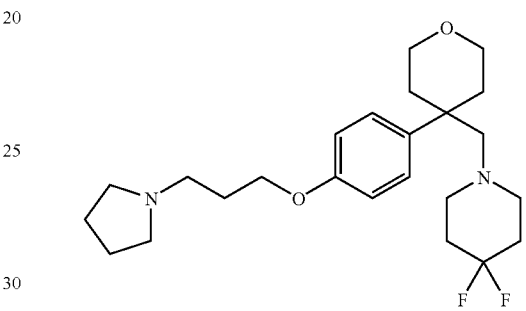

4-[4-(3-Pyrrolidin-1-ylpropoxy)phenyl]tetrahydro-2H-pyran-4-carbaldehyde (260 mg, 0.82 mmol), 4,4-difluoropiperidine hydrochloride (323 mg, 2.05 mmol), absolute ethanol (11 mL), activated 4 Å molecular sieves, titanium (IV) isopropoxide (1.209 mL, 4.09 mmol) and STAB (1.475 g, 6.96 mmol) were reacted in accordance with the general procedure D. The isolated waxy solid was purified by reverse phase preparative HPLC on a Xterra column eluting with a gradient of MeCN:H$_2$O:Et$_3$N (from 29.9:70:0.1 to 94.9:5:0.1 in 13 min) to give the title compound (26 mg, 6%). $^1$H NMR (400 MHz, CDCl$_3$) δ 7.21 (d, 2H), 6.88 (d, 2H), 4.02 (t, 2H), 3.77-3.73 (m, 2H), 3.53-3.47 (t, 2H), 2.64 (t, 2H), 2.54 (m, 4H), 2.39 (s, 2H), 2.30-2.24 (m, 6H), 2.13 (d, 2H), 2.02 (m, 2H), 1.90-1.71 (m, 6H).

Example 51 methyl-{4-[4-(3-pyrrolidin-1-ylpropoxy)phenyl]-tetrahydropyran-4-ylmethyl}amine

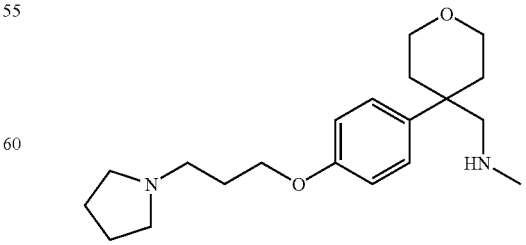

Step 1: To a stirred solution of {4-[4-(3-pyrrolidin-1-ylpropoxy)phenyl]tetrahydropyran-4-yl}methylamine (10.83 g, 34.05 mmol) and triethylamine (10.31 g, 102.16 mmol) in dry dichloromethane at 0° C. was added dropwise a solution of di-tert-butyldicarbonate (9.65 g, 44.27 mmol) in dry dichloromethane. Stirring was continued for another hour at 0° C. and then overnight at room temperature. The reaction mixture was then diluted with dichloromethane, washed with water and brine, dried over Na$_2$SO$_4$ and concentrated under reduced pressure to provide a crude product. The crude product was purified by column chromatography on silica gel (EtOAc-MeOH-Et$_3$N) to give methyl-{4-[4-(3-pyrrolidin-1-ylpropoxy)phenyl]tetrahydro-pyran-4-ylmethyl}carbamic acid tert-butyl ester (9.80 g, 69% yield). $^1$H NMR (400 MHz, CDCl$_3$) δ 1.37 (s, 9H); 1.75-1.88 (m, 6H); 1.96-2.07 (m, 4H); 2.48-2.55 (m, 4H); 2.61 (t, 2H); 3.28 (d, 2H); 3.51-3.59 (m, 2H); 3.76-3.80 (m, 2H); 4.01 (t, 2H); 4.15 (brm, 1H); 6.89 (d, 2H); 7.16 (d, 2H).

Step 2: To a stirred solution of LiAlH$_4$ (2.59 g, 68.18 mmol) in dry THF at 0° C. was added dropwise a solution of methyl-{4-[4-(3-pyrrolidin-1-ylpropoxy)phenyl]tetrahydro-pyran-4-ylmethyl}carbamic acid tert-butyl ester (9.50 g, 22.72 mmol). The reaction mixture was then brought to room temperature and finally heated to reflux for 3 h. The reaction mixture was quenched with aqueous NaOH solution and filtered over a short pad of celite, dried over Na$_2$SO$_4$ and concentrated under reduced pressure to provide the title compound (7.1 g, 94% yield). $^1$H NMR (400 MHz, CDCl$_3$) δ 1.71-1.78 (m, 4H); 1.80-1.90 (m, 2H); 1.88-2.02 (m, 2H); 2.06-2.14 (m, 2H); 2.23 (s, 3H); 2.46-2.53 (m, 4H); 2.51-2.63 (m, 4H); 3.47-3.56 (m, 2H); 3.70-3.77 (m, 2H); 3.99 (t, 2H); 6.86 (d, 2H); 7.17 (d, 2H).

Example 52 methyl-(3-methylsulfanyl-propyl)-{4-[4-(3-pyrrolidin-1-ylpropoxy)phenyl]tetrahydropyran-4-ylmethyl}amine

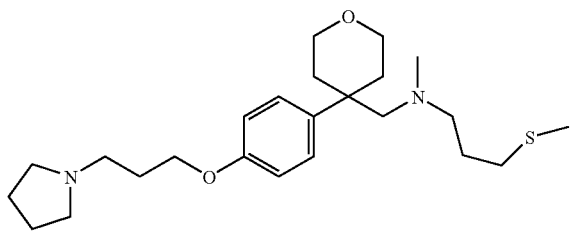

To a solution of methyl-4-[4-(3-pyrrolidin-1-ylpropoxy)phenyl]tetrahydropyran-4-ylmethyl}amine (200 mg, 0.629 mmol) in dichloroethane (5 mL) under nitrogen atmosphere was added acetic acid (45 mg, 1.258 mmol), triethylamine (76 mg, 1.258 mmol) and 3-(methylthio)propanal (108 mg, 1.04 mmol). The mixture was stirred for 30 min and a solution of NaHB(OAc)$_3$ (236 mg, 1.15 mmol) in dichloroethane (5 mL) was added. After stirring at room temperature overnight, the reaction mixture was filtered over celite, concentrated in vacuo and purified by column chromatography on silica gel eluting with DCM:MeOH:NH$_3$ (94.9:5:0.1) to give the title compound (29 mg, 7%). $^1$H NMR (400 MHz, CDCl$_3$) δ 7.19 (d, 2H), 6.86H), 4.02 (t, 2H), 3.78-3.73 (m, 2H), 3.54-3.49 (m, 2H), 2.67 (t, 2H), 2.59 (m, 4H), 2.42 (s, 2H), 2.35 (t, 2H), 2.22 (t, 2H), 2.11-2.00 (m, 7H), 1.91-1.86 (m, 5H), 1.85-1.82 (m, 4H), 1.56 (q, 2H).

Example 53

(3-methanesulfonyl-propyl)-methyl-{4-[4-(3-pyrrolidin-1-yl-propoxy)phenyl]tetrahydropyran-4-ylmethyl}amine

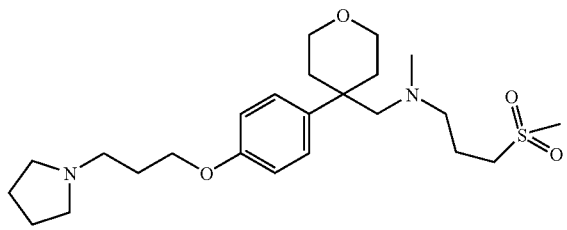

To a solution of methyl-(3-methylsulfanyl-propyl)-{4-[4-(3-pyrrolidin-1-ylpropoxy)phenyl]tetrahydropyran-4-ylmethyl}amine (170 mg, 0.404 mmol) in DCM (10 mL) under nitrogen atmosphere at 0° C. was added TFA (0.240 mL, 3.2 mmol) followed by meta-chloroperbenzoic acid (70% pure, 199 mg, 0.808 mmol). The reaction mixture was stirred overnight allowing it to warm up to room temperature. It was quenched with an aqueous solution of Na$_2$S2O$_3$. The organic layer was separated and washed with an aqueous solution of NaHCO$_3$. The organic layer was then dried over sodium sulphate, filtered, concentrated and purified by column chromatography on silica gel eluting with DCM:MeOH:NH$_3$ (89.9:10:0.1) to give the title compound. $^1$H NMR (400 MHz, CDCl$_3$) δ 7.18 (d, 2H), 6.88 (d, 2H), 4.03 (t, 2H), 3.78-3.73 (m, 2H), 3.53-3.48 (m, 2H), 2.82 (s, 3H), 2.69-2.73 (m, 2H), 2.65 (m, 2H), 2.55 (m, 4H), 2.47 (s, 2H), 2.22 (t, 2H), 2.12-2.09 (m, 2H), 1.89-2.05 (m, 5H), 1.68-1.85 (m, 8H).

Example 54 isopropyl-{4-[4-(3-pyrrolidin-1-ylpropoxy)phenyl]-tetrahydro-pyran-4-ylmethyl}amine

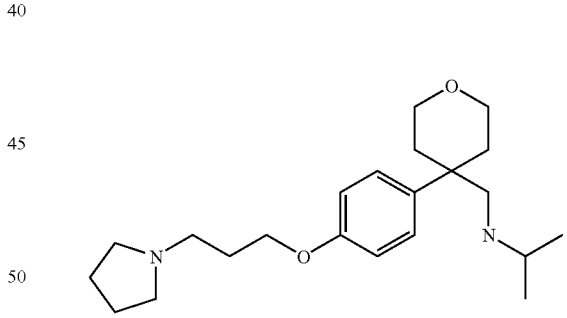

To a solution of {4-[4-(3-pyrrolidin-1-ylpropoxy)phenyl]tetrahydropyran-4-yl}methylamine (400 mg, 1.256 mmol) in dichloroethane (10 mL) under nitrogen atmosphere was added acetic acid (180.5 mg, 2.76 mmol), triethylamine (306.4 mg, 2.76 mmol) and acetone (80.2 mg, 1.38 mmol). The mixture was stirred for 1 h at ambient temperature and NaHB(OAc)$_3$ (601 mg, 2.76 mmol) was added. After stirring overnight, the reaction mixture was filtered over celite, concentrated in vacuo and purified by column chromatography on silica gel eluting with DCM:MeOH:NH$_3$ (89:10:1) to give the title compound as an oil (282 mg, 60%). $^1$H NMR (400 MHz, CDCl3) δ 7.13 (d, 2H), 6.82 (d, 2H), 3.96 (t, 2H), 3.68 (m, 2H), 3.49 (m, 2H), 2.61 (s, 2H), 2.56 (t, 2H), 2.46 (m, 5H), 2.04 (m, 2H), 1.94 (m, 2H), 1.84 (m, 2H), 1.72 (m, 4H), 1.19 (s, 1H), 0.83 (d, 6H).

Example 55 isopropyl-methyl-{4-[4-(3-pyrrolidin-1-ylpropoxy)phenyl]-tetrahydropyran-4-ylmethyl}amine

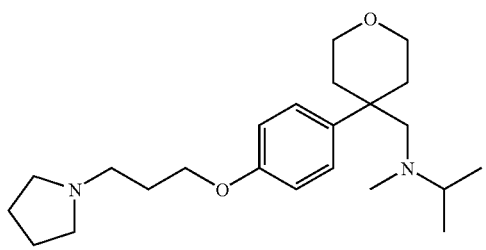

To isopropyl-{4-[4-(3-pyrrolidin-1-ylpropoxy)phenyl]tetrahydropyran-4-ylmethyl}-amine (258 mg, 0.71 mmol) was added formaldehyde (37% w/w solution in H$_2$O, 1 mL) and formic acid (1.5 mL). The resulting mixture was heated to 60° C. overnight. After cooling, H$_2$O and ethyl acetate were added. The aqueous layer was separated, basified with 30% NaOH and extracted 3 times with ethyl acetate. The combined organic extracts were dried over Na$_2$SO$_4$, filtered and concentrated in vacuo to give the title compound as an oil (170 mg, 65%). $^1$H NMR (400 MHz, CDCl$_3$) δ 7.19 (d, 2H), 6.86 (d, 2H), 4.02 (t, 2H), 3.76 (m, 2H), 3.50 (m, 2H), 2.63 (t, 2H), 2.53 (m, 4H), 2.44 (m, 1H), 2.38 (s, 2H), 2.08 (m, 2H), 2.01 (m, 2H), 1.89 (m, 2H), 1.85 (s, 3H), 1.79 (m, 4H), 0.84 (d, 6H).

Example 56 cyclopentyl-{4-[4-(3-pyrrolidin-1-ylpropoxy)phenyl]tetra-hydropyran-4-ylmethyl}amine

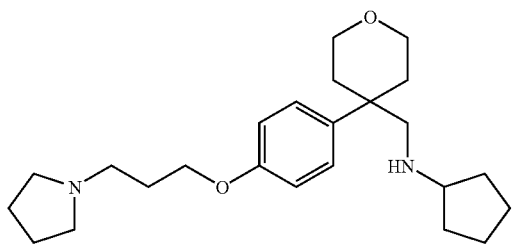

To a solution of (4-[4-(3-pyrrolidin-1-ylpropoxy)phenyl]tetrahydropyran-4-yl}methylamine (254 mg, 0.798 mmol) in dichloroethane (5 mL) under nitrogen atmosphere were added acetic acid (37 mg, 1.6 mmol), triethylamine (97 mg, 1.6 mmol) and cyclopentanone (10 mg, 1.19 mmol). The mixture was stirred for 30 min at ambient temperature and NaHB(OAc)$_3$ (204 mg, 1.6 mmol) was added at 0° C. After stirring overnight, the reaction mixture was filtered over celite, concentrated in vacuo and purified by column chromatography on silica gel eluting with DCM:MeOH:NH$_3$ (89:10:1) to give the title compound (226 mg, 58%). $^1$H NMR (400 MHz, CDCl$_3$) δ 7.20 (d, 2H), 6.88H), 4.03 (t, 2H), 3.78-3.73 (m, 2H), 3.59-3.53 (m, 2H), 2.84 (q, 1H), 2.73 (t, 2H), 2.65- 2.68 (m, 6H), 2.03-2.12 (m, 4H), 1.84-1.94 (m, 6H), 1.65-1.72 (m, 2H), 1.51-1.58 (m, 2H), 1.41-1.46 (m, 2H), 1.07-1.16 (m, 2H).

Example 57

1-{4-[4-(3-Pyrrolidin-1-ylpropoxy)phenyl]tetrahydropyran-4-ylmethyl}pyrrolidine

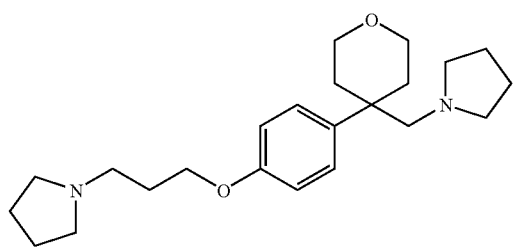

To a stirred solution of {4-[4-(3-pyrrolidin-1-ylpropoxy)phenyl]tetrahydropyran-4-yl}methylamine (150 mg, 0.47 mmol) and 1-bromo-4-chloroethane (54.2 µL, 0.47 mmol) in anhydrous acetonitrile (5 mL) was added potassium carbonate (65 mg, 0.47 mmol). The mixture was heated to 60° C. overnight then concentrated under reduced pressure. The crude product was purified by column chromatography on silica gel eluting with DCM:MeOH:NH$_3$ (94:5:1) to give the title compound (40 mg, 23% yield). $^1$H NMR (400 MHz, CDCl$_3$) δ 7.20 (d, 2H), 6.86 (d, 2H), 4.02 (t, 2H), 3.73-3.78 (m, 2H), 3.57-3.53 (m, 2H), 2.65-2.61 (m, 4H), 2.53 (m, 4H), 2.20 (m, 4H), 2.10-1.88 (m, 6H), 1.56 (m, 4H).

Example 58

4-{4-[4-(3-Pyrrolidin-1-ylpropoxy)phenyl]tetrahydropyran-4-ylmethyl}-morpholine

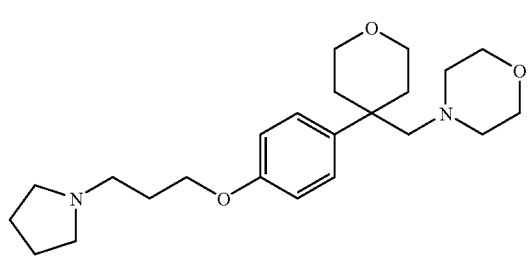

To a stirred solution of {4-[4-(3-pyrrolidin-1-ylpropoxy)phenyl]tetrahydropyran-4-yl}methylamine (207 mg, 0.65 mmol) and bis(2-bromoethyl)ether (82 µL, 1.3 mmol) in anhydrous acetonitrile (10 mL) was added potassium carbonate (180 mg, 1.3 mmol). The mixture was heated to 60° C. overnight then concentrated under reduced pressure. The crude product was purified by column chromatography on silica gel eluting with DCM:MeOH (97:3) with 10% NH$_3$ to give the title compound (90 mg, 23% yield).

Example 59 methyl-phenethyl-{4-[4-(3-pyrrolidin-1-ylpropoxy)phenyl]tetra-hydropyran-4-ylmethyl}amine

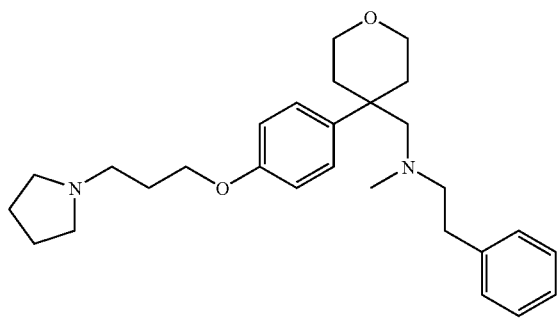

Methyl-{4-[4-(3-pyrrolidin-1-ylpropoxy)phenyl]tetrahydropyran-4-ylmethyl}amine (150 mg, 0.45 mmol) was treated with (2-bromoethyl)benzene (100 mg, 0.54 mmol) and potassium carbonate (187 mg, 1.35 mmol) in a sealed tube under microwave (Smith Personal Synthesiser) (55° C.) for 80 min. The reaction mixture was taken in DCM (10 mL) and water (5 mL). The organic layer was separated and washed twice with water and brine. The combined organic extracts were dried over $Na_2SO_4$, filtered, concentrated in vacuo and purified by column chromatography on silica gel eluting with DCM:MeOH (90:10) with 10% $NH_3$ to give the title compound as a colorless oil (41.4 mg, 20%). $^1H$ NMR (400 MHz, $CDCl_3$) δ 7.23 (m, 7H), 6.87 (d, 2H), 4.00 (t, 2H), 3.66 (m, 2H), 3.51 (m, 2H), 3.29 (t, 2H), 3.20 (t, 2H), 2.62 (t, 2H), 2.51 (m, 6H), 2.10 (m, 2H), 1.99 (m, 2H), 1.90 (m, 2H), 1.86 (s, 3H), 1.78 (m, 4H).

Example 60 methyl-benzyl-{4-[4-(3-pyrrolidin-1-ylpropoxy)phenyl]tetra-hydropyran-4-ylmethyl}amine

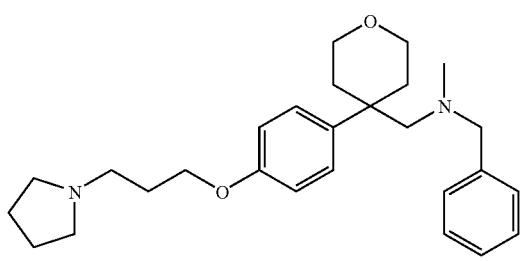

This example was prepared from methyl-{4-[4-(3-pyrrolidin-1-ylpropoxy)phenyl]tetrahydropyran-4-ylmethyl}amine similarly to the procedure used for example 59. $^1H$ NMR (400 MHz, $CDCl_3$) δ 7.28-7.19 (m, 7H), 6.87 (d, 2H), 4.00 (t, 2H), 3.69-3.65 (m, 2H), 3.53-3.48 (t, 2H), 3.29 (s, 2H), 2.61 (t, 2H), 2.54-2.50 (m, 6H), 2.10-2.07 (m, 2H), 2.01-1.97 (m, 2H), 1.93-1.88 (m, 2H), 1.86 (s, 3H), 1.78-1.76 (m, 4H).

Example 61

(2-methoxyethyl)-methyl-{4-[4-(4-(3-pyrrolidin-1-ylpropoxy)-phenyl]tetrahydropyran-4-ylmethyl}amine

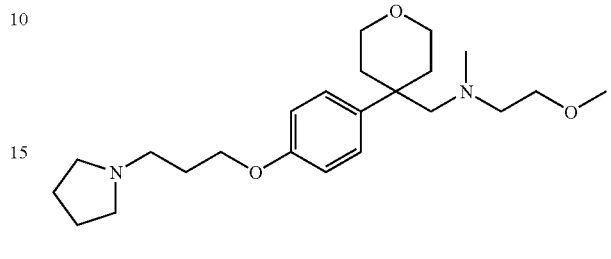

To a stirred solution of methyl-{4-[4-(3-pyrrolidin-1-ylpropoxy)phenyl]tetra-hydropyran-4-ylmethyl}amine (150 mg, 0.45 mmol) and 2-bromoethylmethylether (43 μL, 0.45 mmol) in anhydrous acetonitrile (5 mL) was added potassium carbonate (62.4 mg, 0.45 mmol). The mixture was heated to 60° C. overnight then to 80° C. for a day and concentrated under reduced pressure. The crude product was purified by column chromatography on silica gel eluting with DCM:MeOH (95:5) with 10% $NH_3$ to give the title compound as an oil (69 mg, 18% yield). $^1H$ NMR (400 MHz, $CDCl_3$) δ 7.20 (d, 2H), 6.86 (d, 2H), 4.02 (t, 2H), 3.78-3.48 (m, 4H), 3.29 (t, 2H), 3.27 (s, 3H), 2.67 (t, 2H), 2.59 (m, 4H), 2.48 (s, 2H), 2.39 (t, 2H), 2.11-2.00 (m, 4H), 1.98 (s, 3H), 1.92-1.85 (m, 2H), 1.84-1.80 (m, 4H).

Example 62 methyl-pyrymidin-2-{4-[4-(3-pyrrolidin-1-ylpropoxy)-phenyl]-tetrahydropyran-4-ylmethyl}amine

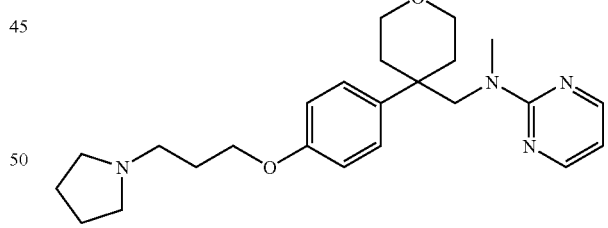

To a solution of methyl-{4-[4-(3-pyrrolidin-1-ylpropoxy)phenyl]tetrahydropyran-4-ylmethyl}amine (150 mg, 0.45 mmol) and 2-chloropyrymidine (52 mg, 0.45 mmol) in anhydrous acetonitrile (5 mL) was added potassium carbonate (62 mg, 0.45 mmol). The mixture was heated to 60° C. overnight then refluxed for 2 days, filtered and concentrated under reduced pressure. The crude product was purified by column chromatography on silica gel eluting with DCM:MeOH (97:3) with 10% $NH_3$ to give the title compound (40 mg, 22% yield). $^1H$ NMR (400 MHz, $CDCl_3$) δ 8.24 (m, 2H), 7.20 (d, 2H), 6.88 (d, 2H), 6.42 (m, 1H), 4.02 (m, 2H), 3.80 (m, 4H), 3.52 (t, 2H), 2.59 (m, 9H), 2.01 (m, 8H), 1.79 (s, 3H).

Example 63

N-{4-[4-(3-Pyrrolidin-1-yl-propoxy)-phenyl]-tetrahydro-pyran-4-ylmethyl}-methanesulfonamide

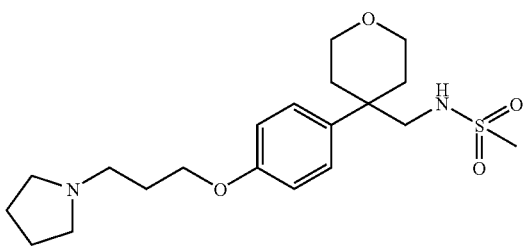

To a stirred solution of {4-[4-(3-pyrrolidin-1-ylpropoxy)phenyl]tetrahydropyran-4-yl}methylamine (200 mg, 0.628 mmol) and triethylamine (106 μL, 0.754 mmol) in anhydrous dichloromethane (8 mL) under nitrogen atmosphere was added dropwise a solution of mesyl chloride (58 μL, 0.754 mmol) in anhydrous dichloromethane (2 mL). After stirring overnight, the reaction mixture was quenched with a saturated aqueous solution of NaHCO$_3$. The organic layer was separated and washed with a saturated aqueous solution of NaHCO$_3$ and water then dried over magnesium sulphate, filtered and concentrated under reduced pressure to give the title compound (140 mg, 56%). $^1$H NMR (400 MHz, CDCl$_3$) δ 7.19 (d, 2H), 6.94 (d, 2H), 4.04 (t, 2H), 3.79 (m, 2H), 3.57 (m, 2H), 3.24 (d, 2H), 2.75 (s, 3H), 2.63 (t, 2H), 2.54 (m, 4H), 2.12 (m, 2H), 2.01 (m, 2H), 1.88 (m, 2H), 1.80 (m, 4H).

Example 64

C-Phenyl-N-{4-[4-(3-pyrrolidin-1-yl-propoxy)-phenyl]-tetra-hydropyran-4-ylmethyl}-methanesulfonamide

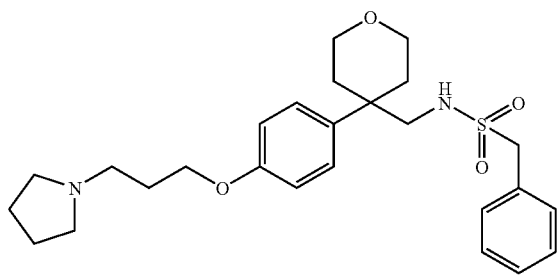

To a stirred solution of {4-[4-(3-pyrrolidin-1-ylpropoxy)phenyl]tetrahydropyran-4-yl}methylamine (200 mg, 0.628 mmol) and triethylamine (106 μL, 0.754 mmol) in anhydrous dichloromethane (8 mL) under nitrogen atmosphere was added dropwise a solution of α-toluenesulfonylchloride (143 mg, 0.754 mmol) in anhydrous dichloromethane (2 mL). After stirring overnight, the reaction mixture was quenched with a saturated aqueous solution of NaHCO$_3$. The organic layer was separated and washed with water, dried over magnesium sulphate, filtered and concentrated under reduced pressure to give the title compound (207 mg, 69%). $^1$H NMR (400 MHz, CDCl$_3$) δ 7.27-7.22 (m, 3H), 7.16-7.14 (m, 2H), 7.07 (d, 2H), 6.83 (d, 2H), 4.05 (s, 2H), 3.95 (t, 2H), 3.68-3.63 (m, 2H), 3.55 (t, 1H), 3.49-3.44 (m, 2H), 3.01 (d, 2H), 2.57 (t, 2H), 2.47 (s, 4H), 2.02-1.93 (m, 4H), 1.78-1.72 (m, 6H).

Example 65

3-Cyano-N-{4-[4-(3-pyrrolidin-1-yl-propoxy)-phenyl]-tetrahydro-pyran-4-ylmethyl}-benzenesulfonamide

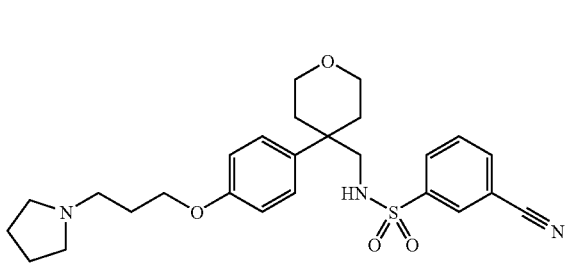

To a stirred solution of {4-[4-(3-pyrrolidin-1-ylpropoxy)phenyl]tetrahydropyran-4-yl}methylamine (100 mg, 0.314 mmol) and triethylamine (0.1 mL, 0.63 mmol) in anhydrous dichloromethane (3 mL) under nitrogen atmosphere at 0° C. was added 3-cyanobenzenesulfonylchloride (100 mg, 0.47 mmol). The reaction mixture was stirred for 2 h allowing it to warm up to room temperature. It was then diluted with dichloromethane and quenched with water. The organic layer was separated and washed with water, dried over sodium sulfate, filtered and concentrated under reduced pressure. The crude product was purified by column chromatography on silica gel eluting with DCM:MeOH (95:5 to 90:10) to give the title compound. $^1$H NMR (400 MHz, CDCl$_3$) δ 7.97 (s, 1H), 7.93-7.91 (d, 1H), 7.83-7.81 (d, 1H), 7.62-7.58 (m, 1H), 7.11-7.09 (d, 2H), 6.89-6.86 (d, 2H), 4.06-4.03 (m, 3H), 3.77-3.72 (m, 2H), 3.56-3.51 (m, 2H), 3.08 (br s, 2H), 2.70-2.67 (m, 2H), 3.08 (br s, 4H), 2.08-2.01 (m, 4H), 1.85-1.82 (m, 6H).

Example 66

2-Fluoro-N-{4-[4-(3-pyrrolidin-1-yl-propoxy)-phenyl]-tetrahydro-pyran-4-ylmethyl}-benzenesulfonamide

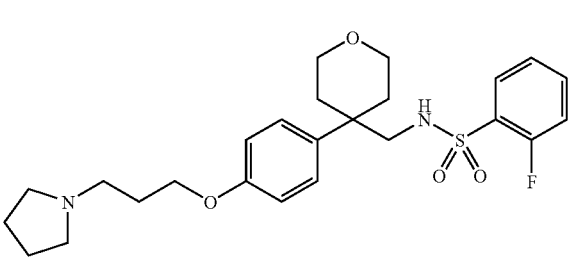

To a stirred solution of {4-[4-(3-pyrrolidin-1-ylpropoxy)phenyl]tetrahydropyran-4-yl}methylamine (100 mg, 0.314 mmol) and triethylamine (0.1 mL, 0.63 mmol) in anhydrous dichloromethane (3 mL) under nitrogen atmosphere at 0° C. was added 2-fluorobenzenesulfonylchloride (91 mg, 0.47 mmol). The reaction mixture was stirred for 2 h allowing it to warm up to room temperature. It was then diluted with dichloromethane and quenched with a saturated aqueous solution of NaHCO$_3$. The organic layer was separated and washed with water, dried over sodium sulfate, filtered and concentrated under reduced pressure to give the title compound (120 mg, 80%). ¹H NMR (400 MHz, CDCl₃) δ7.86-7.82 (t, 1H), 7.58-7.52 (m, 1H), 7.28-7.24 (m, 1H), 7.13-7.12 (m, 3H), 6.90-6.88 (m, 2H), 4.19 (m, 1H), 4.05-4.02 (t, 2H), 3.73-3.70 (m, 2H), 3.56-3.51 (t, 2H), 3.10-3.08 (d, 2H), 2.66-2.62 (t, 2H), 2.54 (m, 4H), 2.06-1.99 (m, 4H), 1.85-1.8 (m, 6H).

Example 67

N-methyl-N-{4-[4-(3-Pyrrolidin-1-yl-propoxy)-phenyl]-tetra-hydropyran-4-ylmethyl}-methanesulfonamide

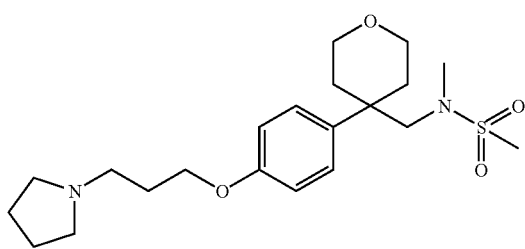

To a stirred solution of methyl-{4-[4-(3-pyrrolidin-1-yl-propoxy)phenyl]tetrahydropyran-4-ylmethyl}amine (200 mg, 0.60 mmol) and triethylamine (102 μL, 0.72 mmol) in anhydrous dichloromethane (8 mL) under nitrogen atmosphere was added dropwise a solution of mesyl chloride (56 μL, 0.72 mmol) in anhydrous dichloromethane (2 mL). After stirring overnight, the reaction mixture was quenched with a saturated aqueous solution of NaHCO₃. The organic layer was separated, washed with water then dried over magnesium sulfate, filtered and concentrated under reduced pressure to give the title compound (175 mg, 71%). ¹H NMR (400 MHz, CDCl₃) δ 7.22 (d, 2H), 6.92-6.90 (d, 2H), 4.03 (t, 2H), 3.83-3.78 (m, 2H), 3.52 (t, 2H), 3.16 (s, 2H), 2.68 (s, 3H), 2.64 (t, 2H), 2.54 (m, 4H), 2.19-2.15 (m, 5H), 2.05-1.91 (m, 4H), 1.81-1.78 (m, 4H).

Example 68

N'-{[4-(4-(3-Pyrrolidin-1-yl-propoxy)-phenyl)tetrahydro-2H-pyran-4-yl]methyl}-N,N-dimethylsulfamide

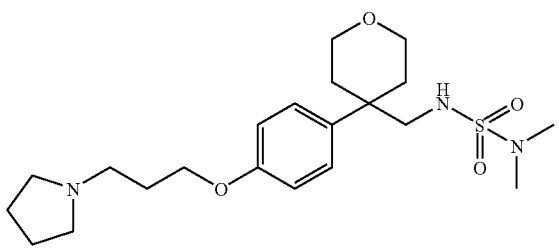

To a stirred solution of {4-[4-(3-pyrrolidin-1-ylpropoxy)phenyl]tetrahydropyran-4-yl}methylamine (200 mg, 0.628 mmol) and triethylamine (106 μL, 0.754 mmol) in anhydrous dichloromethane (8 mL) under nitrogen atmosphere was added dropwise a solution of dimethylsulfamoyl chloride (81 μL, 0.754 mmol) in anhydrous dichloromethane (2 mL). After stirring overnight, the reaction mixture was quenched with a saturated aqueous solution of NaHCO₃. The organic layer was separated and washed with water then dried over magnesium sulfate, filtered and concentrated under reduced pressure to give the title compound (207 mg, 77%). ¹H NMR (400 MHz, CDCl₃) δ7.19 (D, 2H), 6.93-6.91 (D, 2H), 4.05 (T, 2H), 3.78-3.76 (M, 2H), 3.59-3.54 (M, 2H), 3.17-3.15 (D, 2H), 2.76-2.70 (M, 12H), 2.15-2.06 (M, 4H), 1.90-1.87 (M, 6H).

Example 69

N-{4-[4-(3-Pyrrolidin-1-yl-propoxy)-phenyl]-tetrahydro-pyran-4-ylmethyl}-acetamide

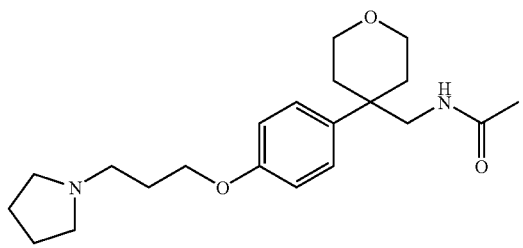

To a stirred solution of {4-[4-(3-pyrrolidin-1-ylpropoxy)phenyl]tetrahydropyran-4-yl}methylamine (200 mg, 0.628 mmol) and triethylamine (106 μL, 0.754 mmol) in anhydrous dichloromethane (8 mL) under nitrogen atmosphere was added dropwise a solution of acetyl chloride (54 μL, 0.754 mmol) in anhydrous dichloromethane (2 mL). After stirring overnight, the reaction mixture was quenched with a saturated aqueous solution of NaHCO₃. The organic layer was separated and washed with a saturated aqueous solution of NaHCO₃ and water then dried over magnesium sulfate, filtered and concentrated under reduced pressure to give the title compound (102 mg, 45%). ¹H NMR (400 MHz, CDCl₃) δ7.18 (d, 2H), 6.94 (d, 2H), 4.97 (s, 1H), 4.05 (t, 2H), 3.80 (m, 2H), 3.59 (m, 2H), 3.46 (d, 2H), 2.66 (t, 2H), 2.57 (m, 4H), 2.03 (m, 4H), 1.80 (m, 8H).

Example 70

N-methyl-N-{4-[4-(3-Pyrrolidin-1-yl-propoxy)-phenyl]-tetrahydro-pyran-4-ylmethyl}-acetamide

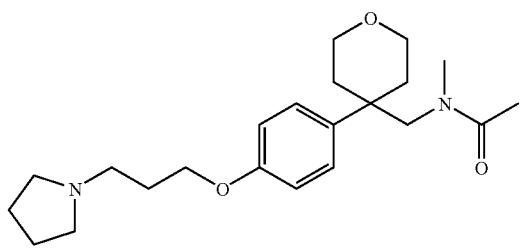

To a stirred solution of methyl-{4-[4-(3-pyrrolidin-1-yl-propoxy)phenyl]tetrahydropyran-4-ylmethyl}amine (200 mg, 0.60 mmol) and triethylamine (102 μL, 0.72 mmol) in anhydrous dichloromethane (8 mL) under nitrogen atmosphere was added dropwise a solution of acetyl chloride (52 μL, 0.72 mmol) in anhydrous dichloromethane (2 mL). After stirring overnight, the reaction mixture was quenched with a saturated aqueous solution of NaHCO₃. The organic layer was separated and washed with water then dried over magnesium sulfate, filtered, concentrated under reduced pressure and purified by column chromatography on silica gel eluting with DCM:MeOH (95:5 to 90:10) to give the title compound (86 mg, 36%). ¹H NMR (400 MHz, CDCl₃) δ Shows rotomers 7.19-7.13 (2d, 2H), 6.91-6.88 (d, 2H), 4.05-4.02 (m, 2H), 3.85-3.80 (m, 2H), 3.56-3.45 (m, 4H), 2.67-2.65 (m, 2H), 2.60-2.56 (m, 4H), 2.32-1.96 (several multiplets, 12H).

Example 71

2-Phenyl-N-{4-[4-(3-pyrrolidin-1-yl-propoxy)-phenyl]-tetrahydro-pyran-4-ylmethyl}-acetamide

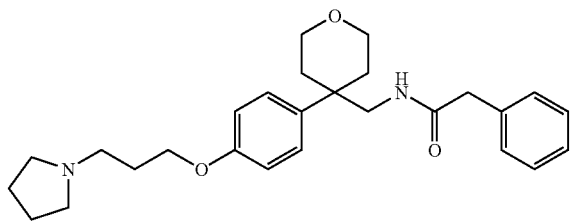

To a stirred solution of {4-[4-(3-pyrrolidin-1-ylpropoxy)phenyl]tetrahydropyran-4-yl}methylamine (200 mg, 0.63 mmol) and triethylamine (93 μL, 0.66 mmol) in anhydrous dichloromethane (8 mL) under nitrogen atmosphere at 0° C. was added dropwise a solution of phenylacetyl chloride (93 μL, 0.66 mmol) in anhydrous dichloromethane (2 mL). After stirring for 3 h at 0° C., the reaction mixture was quenched with a saturated aqueous solution of NaHCO₃. The organic layer was separated and washed with water then dried over magnesium sulfate, filtered, concentrated under reduced pressure and purified by column chromatography on silica gel eluting with DCM:MeOH (98:2) to give the title compound (34 mg, 12%). ¹H NMR (400 MHz, CDCl₃) δ7.32-7.31 (m, 3H), 7.12-7.10 (m, 2H), 6.89-6.87 (d, 2H), 6.76-6.74 (d, 2H), 4.91 (t, 1H), 4.02 (t, 2H), 3.79-3.74 (m, 2H), 3.53-3.51 (m, 2H), 3.47 (s, 2H), 3.37-3.35 (d, 2H), 2.62 (m, 6H), 2.08-2.06 (m, 2H), 1.93-1.85 (m, 6H), 1.76-1.74 (m, 2H).

Example 72

1,1-Dimethyl-3-{4-[4-(3-pyrrolidin-1-yl-propoxy)-phenyl]-tetrahydro-pyran-4-ylmethyl}-urea

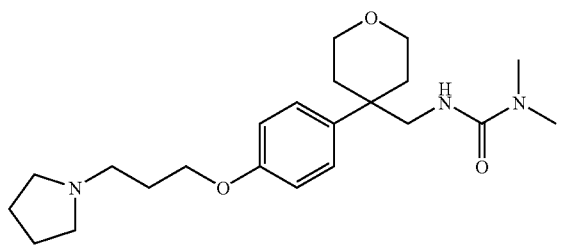

To a stirred solution of {4-[4-(3-pyrrolidin-1-ylpropoxy)phenyl]tetrahydropyran-4-yl}methylamine (200 mg, 0.63 mmol) and triethylamine (106 μL, 0.754 mmol) in anhydrous dichloromethane (9 mL) under nitrogen atmosphere was added dropwise a solution of dimethylcarbamoylchloride (69 μL, 0.754 mmol) in anhydrous dichloromethane (1 mL). After stirring for 3 h at 0° C., the reaction mixture was quenched with a saturated aqueous solution of NaHCO₃. The organic layer was separated and washed with water then dried over magnesium sulfate, filtered, concentrated under reduced pressure and purified by column chromatography on silica gel eluting with DCM:MeOH (95:5 to 90:10) to give the title compound (80 mg, 32%). ¹H NMR (400 MHz, CDCl₃) δ7.13 (d, 2H), 6.86 (d, 2H), 3.98 (t, 2H), 3.84 (t, 1H), 3.74 (m, 2H), 3.52 (m, 2H), 3.36 (d, 2H), 2.69 (s, 6H), 2.65 (m, 2H), 2.57 (m, 4H), 2.02-1.95 (m, 4H), 1.84-1.78 (m, 6H).

Example 73

1,1,3-Trimethyl-3-{4-[4-(3-pyrrolidin-1-yl-propoxy)-phenyl]-tetrahydro-pyran-4-ylmethyl]-urea

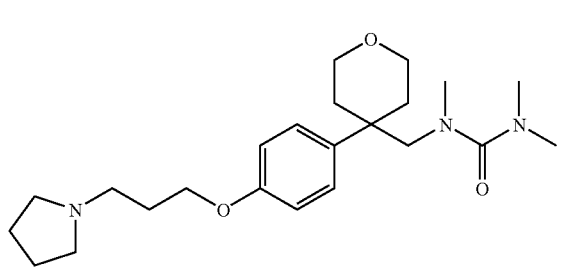

To a stirred solution of methyl-{4-[4-(3-pyrrolidin-1-yl-propoxy)phenyl]tetrahydropyran-4-ylmethyl}amine (200 mg, 0.60 mmol) and triethylamine (102 μL, 0.72 mmol) in anhydrous dichloromethane (8 mL) under nitrogen atmosphere was added dropwise a solution of dimethylcarbamoylchloride (67 μL, 0.72 mmol) in anhydrous dichloromethane (2 mL). After stirring overnight, the reaction mixture was quenched with a saturated aqueous solution of NaHCO₃. The organic layer was separated, washed with a saturated aqueous solution of NaHCO₃ and water then dried over magnesium sulfate, filtered, concentrated under reduced pressure and purified by column chromatography on silica gel eluting with DCM:MeOH (95:5) followed by DCM:MeOH:NH₃ (90:5:5) to give the title compound (84 mg, 39%). ¹H NMR (400 MHz, CDCl₃) δ7.19 (d, 2H), 6.90-6.88 (d, 2H), 4.03 (t, 2H), 3.81-3.78 (m, 2H), 3.56-3.52 (m, 4H), 2.70 (s, 6H), 2.66 (t, 2H), 2.29 (s, 3H), 2.05-2.01 (m, 4H), 1.86-1.81 (m, 6H).

Example 74

{4-[4-(3-Pyrrolidin-1-yl-propoxy)-phenyl]-tetrahydro-pyran-4-ylmethyl}-urea

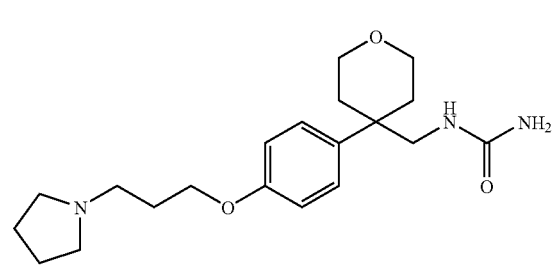

To a stirred solution of {4-[4-(3-pyrrolidin-1-ylpropoxy)phenyl]tetrahydropyran-4-yl}methylamine (200 mg, 0.63 mmol) and acetic acid (108 µL, 1.89 mmol) in water (12 mL) was added portionwise potassium cyanate (153 mg, 1.89 mmol). After stirring overnight, the reaction mixture was quenched with a 0.1N aqueous solution of NaOH. The organic layer was separated and the aqueous layer extracted twice with dichloromethane. The combined organic extracts were dried over magnesium sulfate, filtered, concentrated under reduced pressure and purified by column chromatography on silica gel eluting with DCM:MeOH (95:5) followed by DCM:MeOH (90:10) and DCM:MeOH:NH$_3$ (90:5:5) to give the title compound (25 mg, 11%). $^1$H NMR (400 MHz, CDCl$_3$) δ7.18 (d, 2H), 6.92-6.90 (d, 2H), 4.24 (s, 2H), 4.17 (t, 1H), 4.03 (t, 2H), 3.84-3.79 (m, 2H), 3.61-3.55 (m, 2H), 3.36-3.35 (d, 2H), 2.63 (t, 2H), 2.53 (m, 4H), 2.07-1.97 (m, 4H), 1.88-1.79 (m, 6H).

Intermediate 29: 4-aminomethyl-4-[4-(3-pyrrolidin-1-yl-propoxy)-phenyl]-cyclohexanol Step 1: A three-neck reaction vessel was charged with [4-(3-pyrrolidin-1-ylpropoxy)phenyl]acetonitrile (7 g, 28.6 mmol), benzyltrimethylammonium hydroxide (40% in methanol, 1.3 mL) in acetonitrile (185 mL). The solution was heated to reflux and methyl acrylate (25 mL, 286 mmol) was added dropwise. After refluxing for 5 hr, the mixture was concentrated to half, diethyl ether was added and the organics were washed with 1N HCl and brine, dried over Na$_2$SO$_4$, filtered and concentrated. The residue was purified by flash-chromatography to provide 4-cyano-4-[4-(3-pyrrolidin-1-yl-propoxy)-phenyl]-heptanedioic acid dimethyl ester (8.8 g, 74%).

Step 2: To a solution of 4-cyano-4-[4-(3-pyrrolidin-1-yl-propoxy)-phenyl]-heptanedioic acid dimethyl ester (8.8 g, 21.1 mmol) in 1,2-dimethoxyethane (176 mL) was charged portions of NaH (60% dispersion, 2.55 g, 63.4 mmol). The reaction mixture was heated to reflux. After 4.5 hr, the ¾ of solvent were evaporated and the mixture cooled to 20° C. with an ice bath and quenched with water (100 mL), HCl 1N (100 mL). The aqueous layer was extracted with ether (100 mL). After basification with NaOH the aqueous phases were extracted with dichloromethane. The combined organics were washed with water, dried over Na$_2$SO$_4$, filtered and concentrated to provide 5-cyano-2-oxo-5-[4-(3-pyrrolidin-1-ylpropoxy)-phenyl]-cyclohexane-carboxylic acid methyl ester (6.6 g, 81%) as an oil.

Step 3: To a solution of 5-cyano-2-oxo-5-[4-(3-pyrrolidin-1-ylpropoxy)-phenyl]-20 cyclohexanecarboxylic acid methyl ester (6.6 g, 17 mmol) and dimethylsulfoxide (128 mL) was added water (8.0 mL) and sodium chloride (6.4 g, 109 mmol). The reaction mixture was heated to 142-146° C. After 5 hr, the mixture was concentrated and the residue was dissolved in DCM (120 mL), washed with water (100 mL), and brine, dried over Na$_2$SO$_4$, filtered and concentrated. The residue was purified by flash chromatography (70 g silica gel, eluant:gradient of DCM/MeOH 95/5 to 90/10) providing 4-oxo-1-[4-(3-pyrrolidin-1-ylpropoxy)-phenyl]-cyclohexanecarbonitrile as a crystallizing oil (2.2 g 45.5%). After crystallization in ether, 0.2 g of analytical sample were obtained.

Step 4: To a stirred suspension of LiAlH$_4$ (0.59 g, 15 mmol, 10 eq) in diethyl ether (8 mL) was added dropwise at ambient temperature a solution of 4-oxo-1-[4-(3-pyrrolidin-1-ylpropoxy)-phenyl]-cyclohexanecarbonitrile (0.5 g, 1.5 mmol) in diethyl ether (25 mL). The reaction mixture was heated to reflux for 2 h. The reaction mixture was cooled to 0° C. and, successively, a solution of water, sodium hydroxide (15% w/v, 0.68 mL) and water again were carefully added dropwise. After being stirred for 15 min at room temperature, the mixture was filtered over diatomaceous earth and concentrated. The residue was purified by flash chromatography (10 g silica gel, DCM/MeOH (10% NH$_3$) to provide the title compound (0.27 g, 54%) as an oil.

Example 75

4-dimethylaminomethyl-4-[4-(3-pyrrolidin-1-yl-propoxy)-phenyl]-cyclohexanol

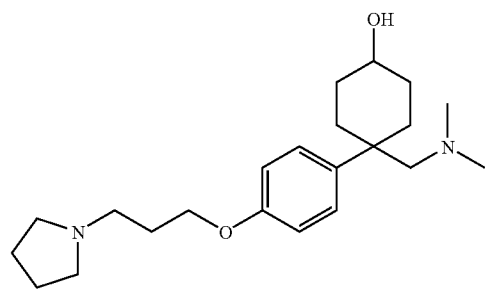

To 4-aminomethyl-4-[4-(3-pyrrolidin-1-yl-propoxy)-phenyl]-cyclohexanol (0.26 g, 0.78 mmol) was added 0.8 mL of formaldehyde (37% w/w solution in H$_2$O). 1 mL of formic acid was added and the mixture was heated to about 100° C. for 20 min. After cooling, water was added and the mixture extracted with ether. NaOH was added at the aqueous phase and the mixture extracted 3 times with ether. The organic extracts were washed with brine, dried over Na$_2$SO$_4$, filtered and concentrated in vacuo to provide 0.23 g of oil. The residue was purified by flash chromatography (25 g silica gel, DCM/MeOH (10% NH$_3$) to provide 0.18 g of product. After trituration with 10 mL hexanes (0.13 g, 46.4%) of title compound were obtained. $^1$H NMR (400 MHz, CDCl$_3$) δ7.25 (d, 2H), 6.85 (d, 2H), 4. (t, 2H), 3.8 (bs, 1H), 2.62 (t, 2H), 2.56-2.49 (m, 4H), 2.39 (s, 2H), 2.08-1.92 (m, 3H), 1.95 (s, 6H), 1.85-1.74 (m, 6H), 1.73-1.64 (m, 4H), 1.62-1.52 (m, 2H).

General procedure E:

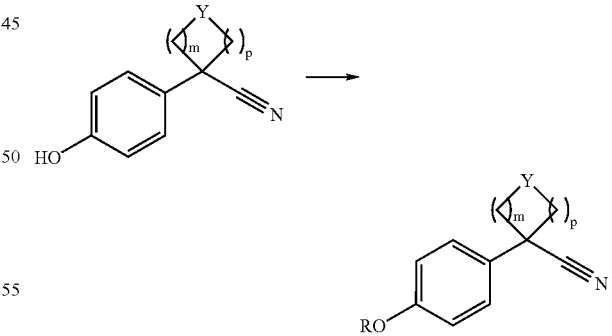

Starting phenol (3.69 mmol), chloride (5.90 mmol), DMF (15 ml) and K$_2$CO$_3$ (14.83 mmol) was heated to 130° C. until the reaction is complete (1 to 2 hrs). Cooled to ambient temperature, water (30 ml) was added, extracted with EtOAc (3×9 ml) and the combined organic extracts were washed with NaOH (2M, 2×25 ml). The organics were dried over MgSO$_4$, filtered and concentrated in vacuo at 35° C. Purification of the crude material by chromatography on silica, eluant (10% MeOH in DCM) provided the title compounds.

Example 76

4-[3-(3-Pyrrolidin-1-ylpropoxy)phenyl]tetrahydropyran-4-carbonitrile

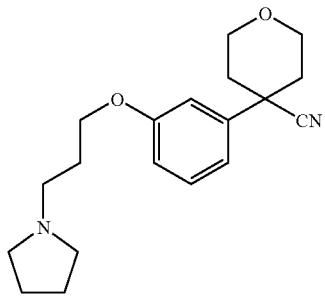

4-(3-Hydroxy-phenyl)-tetrahydro-2H-pyran-4-carbonitrile (1.03 g, 5.10 mmol), 1-(3-chloro-propyl)-pyrrolidine (600 mg, 4.08 mmol), DMF (6.8 ml) and K$_2$CO$_3$ (2.82 g, 20.4 mmol) were reacted together according to general procedure E. The organic phase was washed with 2M NaOH (3×50 ml), brine (3×50 ml), dried over MgSO$_4$, fitered and concentrated in vacuo at 35° C. The crude mixture was slurried in TBME:heptane (1:20, 10 ml). The solid was filtered, washed with heptane (10 ml) and dried on the filter for 2 hours to give the title compound (0.4 g, 31%). $^1$H NMR (400 MHz, CDCl$_3$) δ 7.32 (t, 1H), 7.07-6.99 (m, 2H), 6.87 (dd, 1H), 4.11-4.04 (m, 2H), 4.05 (t, 2H), 3.90 (td, 2H), 2.63 (t, 2H), 2.57-2.49 (m, 4H), 2.18-1.97 (m, 6H), 1.84-1.75 (m, 4H).

Example 77

4-{4-[3-(2,5-Dimethylpyrrolidin-1-yl)propoxy]phenyl}-tetra-hydropyran-4-carbonitrile

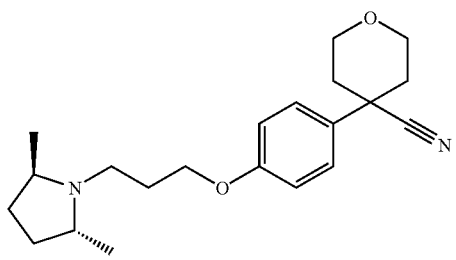

4-[4-(3-pyrrolidin-1-ylpropoxy)phenyl]tetrahydro-2H-pyran-4-carbonitrile (318 mg, 1.56 mmol), 1-(3-chloro-propyl)-2,5-trans-dimethyl-pyrrolidine (250 mg, 1.42 mmol), DMF (5 ml) and K$_2$CO$_3$ (785 mg, 5.70 mmol) were reacted together according to general procedure E. The crude was dissolved in ethyl acetate (20 ml), washed with brine (2×10 ml), dried over MgSO$_4$, filtered and concentrated in vacuo to give the title compound (200 mg, 56%) as a light brown solid. $^1$H NMR (400 MHz, CDCl$_3$), δ 7.37 (d, 2H), 6.93 (d, 2H), 4.13-3.97 (m, 4H), 3.89 (td, 2H), 3.14-2.98 (m, 2H), 2.76 (m, 1H), 2.55 (m, 1H), 2.16-1.88 (m, 8H), 1.46-1.30 (m, 2H), 0.97 (d, 6H).

Example 78

4-{4-[3-(2-Methylpyrrolidin-1-yl)-propoxy]-phenyl}tetra-hydropyran-4-carbonitrile

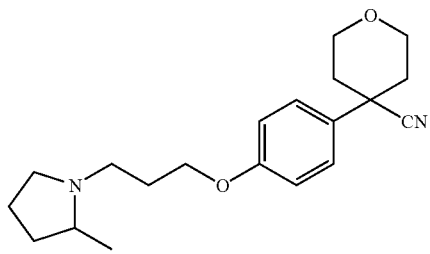

4-[4-(3-pyrrolidin-1-ylpropoxy)phenyl]tetrahydro-2H-pyran-4-carbonitrile (315 mg, 1.55 mmol), 1-(3-chloro-propyl)-2-methyl-pyrrolidine (400 mg, 2.48 mmol), DMF (6 ml) and K$_2$CO$_3$ (833 mg, 6.03 mmol) were reacted together according to general procedure E. Purification by chromatography on silica, eluant DCM:MeOH:NH$_3$ (92:6:2) provided the title compound (450 mg, 88%) as an orange oil. $^1$H NMR (400 MHz, CDCl$_3$), δ 7.37 (d, 2H), 6.93 (d, 2H), 4.12-3.99 (m, 4H), 3.89 (td, 2H), 2.35-1.62 (m, 14H), 1.42 (m, 1H), 1.09 (d, 3H).

Example 79

4-[4-(3-Thiomorpholin-4-ylpropoxy)phenyl]tetrahydropyran-4-carbonitrile

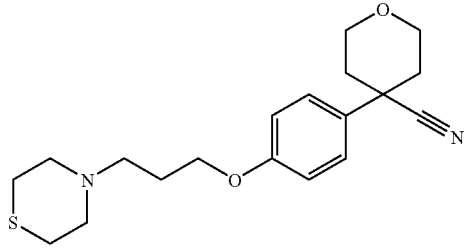

4-[4-(3-pyrrolidin-1-ylpropoxy)phenyl]tetrahydro-2H-pyran-4-carbonitrile (750 mg, 3.69 mmol), 4-(3-chloro-propyl)-thiomorpholine (1.06 g, 5.91 mmol), DMF (15 ml) and K$_2$CO$_3$ (2.05 g, 14.83 mmol) were reacted together according to general procedure E. Purification by chromatography on silica, eluant DCM:MeOH:NH$_3$ (96:3:1) provided the title compound (365 mg, 29%) as an off white solid. $^1$H NMR (400 MHz, CDCl$_3$), δ 7.37 (d, 2H), 6.93 (d, 2H), 4.12-4.04 (m, 2H), 4.01 (t, 2H), 3.89 (td, 2H), 2.77-2.64 (m, 8H), 2.54 (t, 2H), 2.16-1.99 (m, 4H), 1.95 (p, 2H).

Example 80

4-{4-[3-(1-Oxo-thiomorpholin-4-yl)-propoxy]-phenyl}-tetra-hydropyran-4-carbonitrile

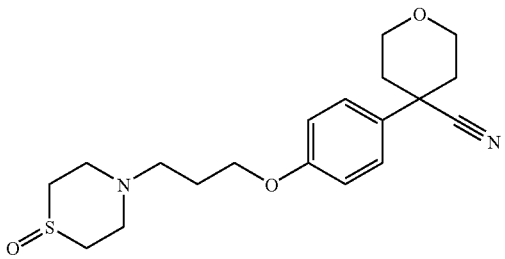

Sodium perborate tetrahydrate (221 mg, 1.43 mmol) and glacial acetic acid (5 ml) was heated to 50 to 60° C. and 4-[4-(3-Thiomorpholin-4-ylpropoxy)phenyl]tetrahydropyran-4-carbonitrile (500 mg, 1.43 mmol) was added in one portion and the heating was maintained for 3 hours. The reaction mixture was cooled to ambient temperature and filtered. The filtrate was added to ice water (15 ml) and extracted with EtOAc (3×5 ml), which was discarded. The aqueous phase was basified to pH 8-9 with 2M sodium hydroxide and extracted with DCM (3×25 ml), dried over $MgSO_4$, filtered and concentrated in vacuo at 35° C. The crude material was subjected to chromatography on silica eluting with DCM:MeOH:$NH_3$ (97:2:1 to 92:6:2) to provided the title compound (300 mg, 58%) as a white solid. $^1$H NMR (400 MHz, $CDCl_3$), δ 7.38 (d, 2H), 6.92 (d, 2H), 4.11-4.05 (m, 2H), 4.03 (t, 2H), 3.89 (td, 2H), 3.15-3.03 (m, 2H), 2.94-2.67 (m, 6H), 2.63 (t, 2H), 2.16-1.92 (m, 6H).

Example 81

4-{4-[3-(1,1-Dioxo-1λ6-thiomorpholin-4-yl)propoxy]-phenyl}tetrahydro-pyran-4-carbonitrile

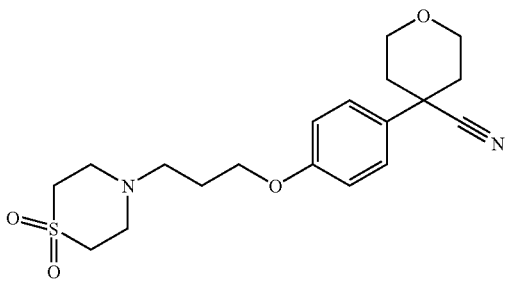

To a solution of 4-[4-(3-Thiomorpholin-4-ylpropoxy)phenyl]tetrahydropyran-4-carbonitrile (500 mg, 1.44 mmol) in TFA (1.65 ml) at 0 to 5° C. was added drop wise a solution of trifluoro-peracetic acid (4M in TFA, 0.72 ml). The reaction was allowed to warm to room temperature and stirred for 3 hours. A further portion of trifluoro-peracetic acid (4M in TFA, 0.097 ml) [4M solution prepared by the addition of 27.5% $H_2O_2$ (0.94 ml) to TFA (1.56 ml)] was added to the reaction and stirred overnight. The reaction mixture was cooled to 0 to 5° C., diluted with DCM (20 ml) and quenched with NaOH (5M solution, 12 ml) to attain pH10. The mixture was extracted with DCM (3×20 ml), the combined DCM extracts were dried over $MgSO_4$, filtered and concentrated in vacuo. The isolated yellow oil was purified by column chromatography on basic alumina eluting with DCM(95):MeOH(4):$NH_3$(1) to give the title compound as an off-white solid (230 mg, 42%). $^1$H NMR (400 MHz, $CDCl_3$), δ 7.39 (d, 2H), 6.92 (d, 2H), 4.12-4.05 (m, 2H), 4.03 (t, 2H), 3.89 (td, 2H), 3.11-2.96 (m, 8H), 2.71 (t, 2H), 2.15-1.99 (m, 4H), 1.96 (p, 2H).

Example 82

4-{4-[3-(4-Hydroxypiperidin-1-yl)propoxy]phenyl}tetrahydro-pyran-4-carbonitrile

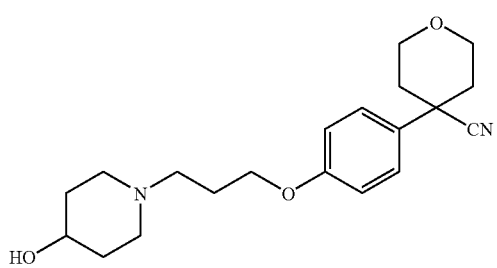

4-[4-(3-pyrrolidin-1-ylpropoxy)phenyl]tetrahydro-2H-pyran-4-carbonitrile (533 mg, 2.62 mmol), 1-(3-chloro-propyl)-piperidin-4-ol (750 mg, 4.22 mmol), DMF (10 ml) and $K_2CO_3$ (1.44 g, 10.42 mmol) were reacted together according to general procedure E. Purification by chromatography on silica, eluant DCM:MeOH:$NH_3$ (92:6:2) provided the title compound (550 mg, 61%) as an off white solid. $^1$H NMR (400 MHz, $CDCl_3$), δ 7.38 (d, 2H), 6.93 (d, 2H), 4.13-4.04 (m, 2H), 4.02 (t, 2H), 3.89 (td, 2H), 3.70 (m, 1H), 2.87-2.71 (m, 2H), 2.50 (t, 2H), 2.23-1.84 (m, 10H), 1.68-1.49 (m, 3H).

Example 83

4-(4-{3-[4-(2-Hydroxyethyl)-piperidin-1-yl]propoxy}phenyl)-tetrahydro-pyran-4-carbonitrile

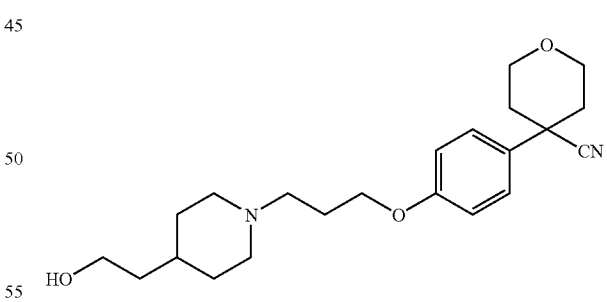

4-[4-(3-pyrrolidin-1-ylpropoxy)phenyl]tetrahydro-2H-pyran-4-carbonitrile (185 mg, 0.91 mmol), 2-[1-(3-chloropropyl)-piperidin-4-yl]-ethanol (300 mg, 1.46 mmol), DMF (4 ml) and $K_2CO_3$ (497 mg, 3.60 mmol) were reacted together according to general procedure E. Purification by chromatography on silica, eluant DCM:MeOH:$NH_3$ (92:6:2) provided the title compound (220 mg, 65%) as a pale pink solid. $^1$H NMR (400 MHz, $CDCl_3$) δ 7.37 (d, 2H), 6.93 (d, 2H), 4.11-4.04 (m, 2H), 4.01 (t, 2H), 3.89 (td, 2H), 3.70 (t, 2H), 2.97-2.87 (m, 2H), 2.48 (t, 2H), 2.15-1.88 (m, 8H), 1.77-1.57 (m, 3H), 1.57-1.38 (m, 3H), 1.35-1.21 (m, 2H).

Example 84

1-{3-[4-(4-Cyano-tetrahydro-pyran-4-yl)-phenoxy]-propyl}-piperidine-4-carboxylic acid amide

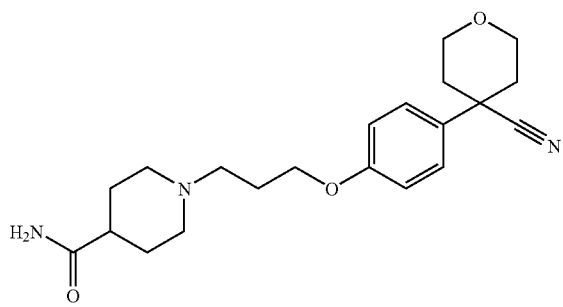

-[4-(3-pyrrolidin-1-ylpropoxy)phenyl]tetrahydro-2H-pyran-4-carbonitrile (200 mg, 0.98 mmol), 1-(3-chloro-propyl)-piperidine-4-carboxylic acid amide (200 mg, 0.98 mmol), DMF (4 ml) and $K_2CO_3$ (550 mg, 3.98 mmol) were reacted together according to general procedure E. The reaction mixture was poured onto water (30 ml), the resulting precipitate was filtered and redissolved in DCM (20 ml). The DCM solution was washed with NaOH solution (2M, 2×5 ml) and water (5 ml), dried over $MgSO_4$, filtered and concentrated in vacuo at 35° C., displacing residual DCM with EtOH to provide the title compound (210 mg, 58%) as an off white solid. $^1$H NMR (400 MHz, $CDCl_3$), δ 7.38 (d, 2H), 6.93 (d, 2H), 5.45 (br s, 1H), 5.35 (br s, 1H), 4.12-4.05 (m, 2H), 4.02 (t, 2H), 3.89 (td, 2H), 3.03-2.92 (m, 2H), 2.50 (t, 2H), 2.22-1.84 (m, 11H), 1.81-1.67 (m, 2H).

Example 85

4-{3-[4-(4-Cyanotetrahydropyran-4-yl)-phenoxy]propyl}-piperazine-1-carboxylic acid ethyl ester

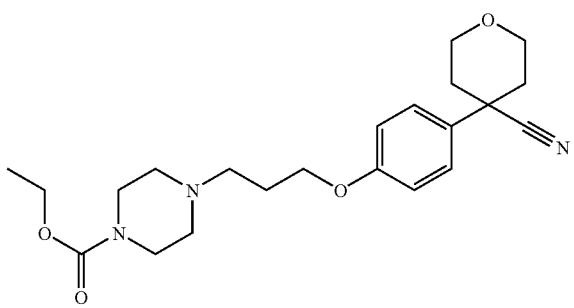

4-[4-(3-pyrrolidin-1-ylpropoxy)phenyl]tetrahydro-2H-pyran-4-carbonitrile (500 mg, 2.46 mmol), 4-(3-chloro-propyl)-piperazine-1-carboxylic acid ethyl ester (570 mg, 2.43 mmol), DMF (10 ml) and $K_2CO_3$ (1.36 g, 9.84 mmol) were reacted together according to general procedure E. The organic phase was washed with 2M NaOH (3.×20 ml), water (2×20 ml), dried over $MgSO_4$, fitered and concentrated in vacuo at 35° C. The crude product was subjected to chromatography on silica eluting with DCM:MeOH:$NH_3$ (97:2:1) to provide the title compound (280 mg, 28%) as an off white solid. $^1$H NMR (400 MHz, $CDCl_3$), δ 7.38 (d, 2H), 6.93 (d, 2H), 4.14 (q, 2H), 4.11-4.05 (m, 2H), 4.03 (t, 2H), 3.89 (td, 2H), 3.55-3.42 (m, 4H), 2.53 (t, 2H), 2.47-2.36 (m, 4H), 2.15-1.92 (m, 6H), 1.26 (t, 3H).

Intermediate 30: 4-(3-Chloro-propyl)-piperazine-1-carboxylic acid tert-butyl ester 4-piperazine-1-carboxylic acid tert-butyl ester (4.0 g, 21.5 mmol), acetone (80 ml, 20 vol), 5M NaOH solution (5.16 ml, 1.2 eq.) and 1-bromo-3-chloropropane (10.15 g, 64.5 mmol, 3 eq.) were reacted together according to general procedure A to give the title compound (2.78 g, 66%) as a colourless oil.

Example 86

4-{3-[4-(4-Cyano-tetrahydro-pyran-4-yl)-phenoxy]-propyl}-piperazine-1-carboxylic acid tert-butyl ester

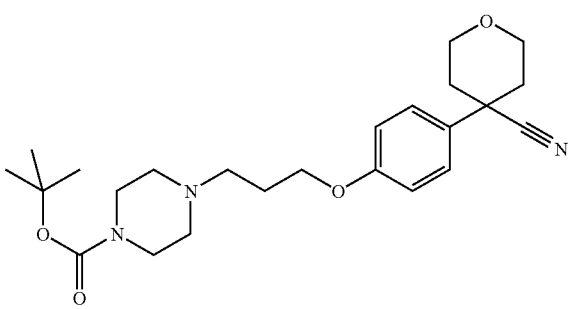

4-[4-(3-pyrrolidin-1-ylpropoxy)phenyl]tetrahydro-2H-pyran-4-carbonitrile (200 mg, 0.99 mmol), 4-(3-chloro-propyl)-piperazine-1-carboxylic acid tert-butyl ester (203 mg, 0.76 mmol), DMF (4 ml) and $K_2CO_3$ (553 g, 4.00 mmol) was heated to 70° C. and work up according to general procedure E. The organic phase was washed with 2M NaOH (3.×20 ml), water (2×20 ml), dried over $MgSO_4$, fitered and concentrate in vacuo at 35° C. to provided the title compound (272 mg, 64%) as an off white solid. $^1$H NMR (400 MHz, $CDCl_3$), δ 7.38 (d, 2H), 6.93 (d, 2H), 4.11-4.04 (m, 2H), 4.03 (t, 2H), 3.89 (td, 2H), 3.50-3.37 (m, 4H), 2.53 (t, 2H), 2.45-2.34 (m, 4H), 2.15-2.00 (m, 4H), 1.97 (p, 2H), 1.46 (s, 9H).

Example 87

4-[4-(3-Piperazin-1-ylpropoxy)phenyl]tetrahydropyran-4-carbonitrile

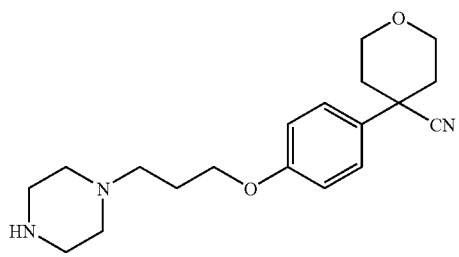

4-{3-[4-(4-Cyano-tetrahydro-pyran-4-yl)-phenoxy]-propyl}-piperazine-1-carboxylic acid tert-butyl ester (500 mg, 1.16 mmol), MeOH (5 ml), 1,4-dioxane (1 ml) and HCl in dioxane (4M, 1.8 ml) was stirred at ambient temperature overnight. The reaction mixture was concentrated in vacuo at 40° C., and diluted with TBME (5 ml). Aqueous NaOH (2M solution) was added to attain a pH of 14 and the mixture separated and extracted with TBME (2×5 ml). The combined organic extracts were dried over $MgSO_4$, filtered and concentrated in vacuo to provide title compound as a yellow oil (275 mg, 72%). ¹H NMR (400 MHz, CDCl₃), δ 7.38 (d, 2H), 6.93 (d, 2H), 4.11-4.05 (m, 2H), 4.03 (t, 2H), 3.89 (td, 2H), 2.90 (t, 4H), 2.51 (t, 2H), 2.44 (br s, 4H), 2.15-2.00 (m, 4H), 1.97 (m, 2H), 1.74 (br s, 1H).

Example 88

4-(4-{3-[4-(2-Aminopropionyl)piperazin-1-yl]propoxy}phenyl)-tetrahydropyran-4-carbonitrile

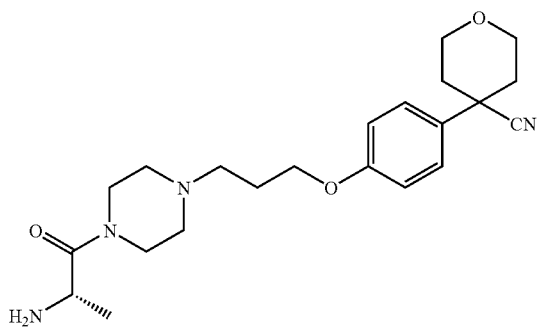

4-[4-(3-piperazin-1-ylpropoxy)phenyl]tetrahydropyran-4-carbonitrile (265 mg, 0.81 mmol), DCM (10.6 ml), HOBT (120 mg, 0.89 mmol), FMoc (L)-aniline (277 mg, 0.89 mmol) and EDCl.HCl (171 mg, 0.89 mmol) were stirred at ambient temperature overnight. Water (10 ml) was added and stirred for one hour, the mixture was filtered and the organic phase separated and washed with water (10 ml), the organic phase was dried over MgSO₄, filtered and concentrated in vacuo at 35° C. The residue was dissolved in DCM (9 ml) and piperidine (86 mg, 10 mmol) was added, the mixture was stirred at ambient temperature for one hour. To the reaction mixture, water (5 ml) was added and the organic phase separated, dried over MgSO₄, filtered and concentrated in vacuo at 35° C. The crude material was subjected to chromatography on silica eluting with 2% MeOH in DCM to provide title compound (136 mg, 42%). ¹H NMR (400 MHz, CDCl₃), δ 7.38 (d, 2H), 6.93 (d, 2H), 4.11-4.05 (m, 2H), 4.03 (t, 2H), 3.89 (td, 2H), 3.77 (q, 1H), 3.65 (br s, 2H), 3.49 (br s, 2H), 2.55 (t, 2H), 2.45 (br s, 4H), 2.14-2.00 (m, 4H), 1.97 (m, 2H), 1.58 (br s, 2H), 1.25 (d, 3H).

Intermediate 31: 2-[(3-Chloro-propyl)-methyl-amino]-ethanol 2-(Methylamino)-ethanol (1.0 g, 13.3 mmol), acetone (20 ml, 20 vol), 5M NaOH solution (3.19 ml, 1.2 eq.) and 1-bromo-3-chloropropane (6.28 g, 39.9 mmol, 3 eq.) were reacted together according to general procedure A to give the title compound (1.14 g, 55%) as a colourless oil.

Example 89

4-{4-[3-(2-Hydroxyethyl)methylamino]propoxy}-phenyl)tetra-hydropyran-4-carbonitrile

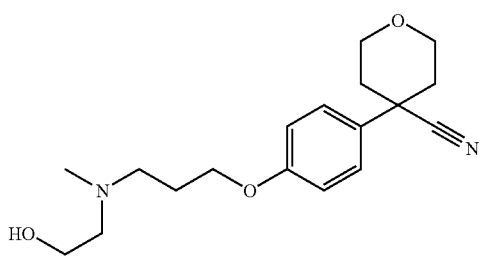

4-[4-(3-pyrrolidin-1-ylpropoxy)phenyl]tetrahydro-2H-pyran-4-carbonitrile (800 mg, 3.94 mmol), 2-[(3-chloro-propyl)-methyl-amino]-ethanol (595 mg, 3.94 mmol), DMF (8 ml) and K₂CO₃ (2.18 g, 15.76 mmol) were reacted together according to general procedure E. The organic phase was washed with 2M NaOH (3.×20 ml), water (2×20 ml), dried over MgSO₄, fitered and concentrated in vacuo at 35° C. to provided the title compound (550 mg, 44%) as a pale yellow oil. ¹H NMR (400 MHz, CDCl₃), δ 7.37 (d, 2H), 6.92 (d, 2H), 4.11-4.04 (m, 2H), 3.88 (dt, 2H), 3.60 (t, 2H), 2.61 (t, 2H), 2.56 (t, 2H), 2.37 (br s, 1H), 2.29 (s, 3H), 2.15-1.91 (m, 6H)

Example 90

4-[4-(2-Pyrrolidin-1-ylethoxy)phenyl]tetrahydropyran-4-carbonitrile

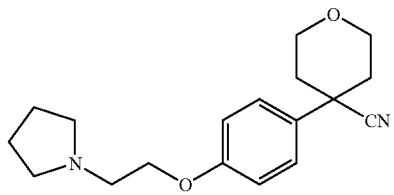

4-[4-(3-pyrrolidin-1-ylpropoxy)phenyl]tetrahydro-2H-pyran-4-carbonitrile (570 mg, 2.82 mmol), 1-(2-chloro-ethyl)-pyrrolidine (300 mg, 2.25 mmol), DMF (5.7 ml) and K₂CO₃ (1.56 g, 1.13 mmol) were reacted together according to general procedure E. The organic phase was washed with 2M NaOH (3.×20 ml), water (2×20 ml), dried over MgSO₄, fitered and concentrated in vacuo at 35° C. The crude material was subjected to chromatography on silica eluting with 5% MeOH in DCM and gradient to 10% MeOH in DCM to provided the title compound (400 mg, 47%) as an off white solid. ¹H NMR (400 MHz, CDCl₃), δ 7.38 (d, 2H), 6.95 (d, 2H), 4.13 (t, 2H), 4.10-4.03 (m, 2H), 3.89 (td, 2H), 2.92 (t, 2H), 2.64 (br s, 4H), 2.15-1.99 (m, 4H), 1.88-1.76 (m, 4H).

Example 91

4-[4-(2-Methyl-3-pyrrolidin-1-ylpropoxy)phenyl]-tetrahydro-pyran-4-carbonitrile

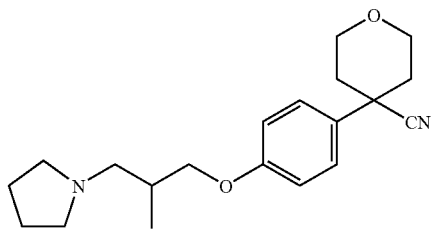

4-(4-Hydroxy-phenyl)-tetrahydro-pyran-4-carbonitrile (790 mg, 3.87 mmol), 1-(3-chloro-2-methyl-propyl)-pyrrolidine (500 mg, 3.10 mmol), DMF (5 ml) and K₂CO₃ (2.14 g, 15.50 mmol) were reacted together according to general procedure E. The organic phase was washed with 2M NaOH (3×20 ml), water (2×20 ml), dried over MgSO₄, fitered and concentrated in vacuo at 35° C. to provide the title compound (979 mg, 96%) as a yellow solid. ¹H NMR (400 MHz, CDCl₃), δ 7.37 (d, 2H), 6.95 (d, 2H), 4.11-4.03 (m, 2H), 4.02 (dd, 1H), 3.89 (td, 2H), 3.77 (dd, 1H), 2.60-2.42 (m, 5H), 2.32 (dd, 1H), 2.22-1.99 (m, 5H), 1.82-1.72 (m, 4H), 1.07 (d, 3H).

Intermediate 32: 1-(3-Chloro-1-methyl-propyl)-pyrrolidine hydrochloride

Step 1: Pyrrolidine (28.15 g, 0.4 mol), toluene (200 ml), catalytic p-TsOH (200 mg) and ethyl acetoacetate (20 g, 0.15 mol) were refluxed together with a Dean-Stark apparatus under N₂ for 3 hours. The reaction was cooled to room temperature and concentrated in vacuo. NaBH₄ (3.1 g, 82 mmol) was dissolved in MeOH (50 ml) and cooled to 0-5° C. A portion of the previous crude reaction (5 g, 27 mmol) in MeOH (25 ml) was added to the reaction mixture and stirred for 72 hours. The reaction was quenched with an aqueous solution of NaOH (1% w/w, 50 ml) and concentrated in vacuo. The aqueous was extracted with TBME (3×50 ml). The combined organic extracts were dried over MgSO₄, filtered, washed with TBME and concentrated in vacuo to give a mixture of the title compound, 3-pyrrolidin-1-yl-butanoic acid ethyl ester and residual TBME (3.5 g). The mixture (3.5 g) in THF (20 ml) was added to a solution of LiALH₄ (1M in THF, 33.5 ml, 33.5 mmol) at 0-5° C. under N₂. The reaction was allowed to warm to room temperature and stirred for 3 hours. The reaction was quenched with an aqueous solution of NaOH (1% w/w, 50 ml) at 0-5° C., filtered and washed with THF (3×20 ml). The combined organics were dried over MgSO₄, filtered, washed with THF and concentrated in vacuo to give 3-pyrrolidin-1-yl-butan-1-ol as a yellow oil (2 g, 73%).

Step 2: 3-Pyrrolidin-1-yl-butan-1-ol (1.0 g, 7 mmol) was dissolved in DCM (20 ml). The reaction was cooled to 0-5° C. and thionyl chloride (1.65 g, 14 mmol) was added slowly. The reaction was allowed to warm to room temperature and stirred overnight. The reaction was concentrated in vacuo and azeotroped with DCM (20 ml) to give the title compound (1.4 g, 100%) as a brown oil.

Example 92

4-[4-(3-Pyrrolidin-1-ylbutoxy)phenyl]tetrahydropyran-4-carbonitrile

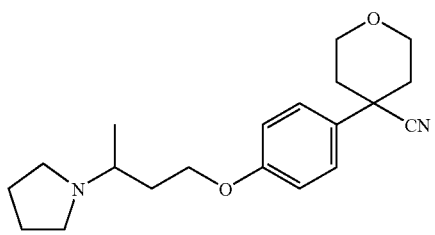

4-(4-Hydroxy-phenyl)-tetrahydro-pyran-4-carbonitrile (1.0 g, 4.9 mmol), 1-(3-chloro-1-methyl-propyl)-pyrrolidine (780 mg, 3.90 mmol), DMF (20 ml) and K₂CO₃ (2.71 g, 19.60 mmol) were reacted together according to general procedure E. The organic phase was washed with 2M NaOH (3×20 ml), water (2×20 ml), dried over MgSO₄, fitered and concentrated in vacuo at 35° C. and purified by preparative HPLC, eluting with acetonitrile/water/0.1% TFA as a gradient, to provide the title compound (120 mg, 9%) as a yellow oil. ¹H NMR (400 MHz, CDCl₃) δ 7.38 (d, 2H), 6.93 (d, 2H), 4.15-3.98 (m, 4H), 3.89 (td, 2H), 2.75-2.51 (m, 5H), 2.22-1.74 (m, 10H), 1.17 (d, 3H).

Example 93

4-{4-[2-(1-Methylpyrrolidin-2-yl)ethoxy]phenyl}tetrahydro-pyran-4-carbonitrile

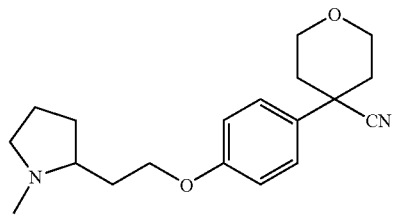

4-(4-Hydroxy-phenyl)-tetrahydro-pyran-4-carbonitrile (1.0 g, 4.9 mmol), 2-(2-chloro-ethyl)-1-methyl-pyrrolidine (722 mg, 3.90 mmol), DMF (20 ml) and K₂CO₃ (2.71 g, 19.60 mmol) were reacted together according to general procedure E. The organic phase was washed with 2M NaOH (3×20 ml), water (2×20 ml), dried over MgSO₄, fitered and concentrated in vacuo at 35° C. and purified by prep TLC, eluting with DCM:MeOH:NH₃ (95:5:3), to provide the title compound (180 mg, 15%) as a yellow oil. ¹H NMR (400 MHz, CDCl₃), δ 7.38 (d, 2H), 6.93 (d, 2H), 4.12-4.03 (m, 4H), 3.89 (td, 2H), 3.08 (m, 1H), 2.35 (s, 3H), 2.29-1.94 (m, 8H), 1.85-1.65 (m, 2H), 1.62-1.50 (m, 2H).

Example 94

4-[4-(1-Isopropylpiperidin-4-yloxy)phenyl]tetrahydropyran-4-carbonitrile

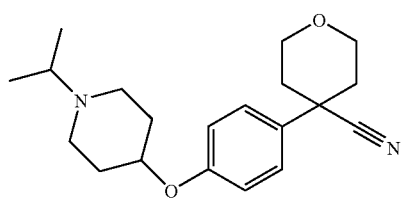

4-(4-Hydroxy-phenyl)-tetrahydro-pyran-4-carbonitrile (459 mg, 2.26 mmol) in DMF (2 ml) was added to a solution of NaH (100 mg, 2.5 mmol) in DMF (2 ml) at room temperature under N₂. The reaction was stirred for 1 hr and a solution of methanesulfonic acid 1-isopropyl-piperidin-4-yl ester (400 mg, 1.81 mmol) in DMF (1.3 ml) was slowly added. The reaction was heated to 75° C. and stirred for 6 hrs. The reaction was allowed to cool to room temperature and diluted with TBME (20 ml), water (10 ml) and 5M NaOH solution (10 ml). The organic layer was washed with 2.5M NaOH (2×20 ml), brine (2×20 ml), dried over MgSO₄, filtered and concentrated in vacuo. The crude reaction was purified by successive column chromatography, eluting with DCM:MeOH:NH₃ (98:1:1) to give the title compound as a pale yellow solid (116 mg, 19%). ¹H NMR (400 MHz, CDCl₃) δ 7.37 (d, 2H), 6.93 (d, 2H), 4.30 (m, 1H), 4.12-4.02 (m, 2H), 3.89 (td, 2H), 2.84-2.68 (m, 3H), 2.45-2.34 (m, 2H), 2.15-1.96 (m, 6H), 1.88-1.75 (m, 2H), 1.06 (d, 6H).

Example 95

4-[4-(1-Cyclopentylpiperidin-4-yloxy)phenyl]tetrahydropyran-4-carbonitrile

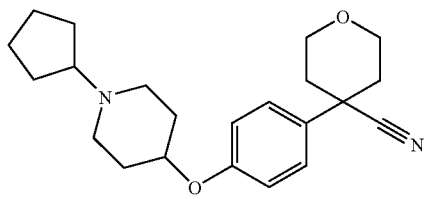

4-(4-Hydroxy-phenyl)-tetrahydro-pyran-4-carbonitrile (459 mg, 2.26 mmol) in DMF (2 ml) was added to a solution of NaH (100 mg, 2.5 mmol) in DMF (2 ml) at room temperature under $N_2$. The reaction was stirred for 1 hr and a solution of methanesulfonic acid 1-cyclopentyl-piperidin-4-yl ester (447 mg, 1.81 mmol) in DMF (1.3 ml) was slowly added. The reaction was heated to 75° C. and stirred for 6 hrs. The reaction was allowed to cool to room temperature and diluted with TBME (20 ml), water (10 ml) and 5M NaOH solution (10 ml). The organic layer was washed with 2.5M NaOH (2×20 ml), brine (2×20 ml), dried over $MgSO_4$, filtered and concentrated in vacuo. The crude reaction was purified by successive column chromatography, eluting with DCM: MeOH:$NH_3$ (98:1:1) to give the title compound as a pale yellow solid (81 mg, 13%). $^1$H NMR (400 MHz, $CDCl_3$) δ 7.37 (d, 2H), 6.93 (d, 2H), 4.36 (m, 1H), 4.11-4.04 (m, 2H), 3.89 (td, 2H), 2.91-2.77 (m, 2H), 2.67-2.25 (m, 2H), 2.15-1.99 (m, 7H), 1.95-1.81 (m, 4H), 1.78-1.64 (m, 2H), 1.62-1.39 (m, 4H).

Intermediates 33 and 34: 4-[4-(3-chloro-propoxy)-phenyl]-tetrahydropyran-4-carbonitrile and 4-[4-(3-bromo-propoxy)-phenyl]-tetrahydropyran-4-carbonitrile 4-(4-hydroxy-phenyl)-tetrahydro-pyran-4-carbonitrile (3.4 g, 16.73 mmol) was taken in DMF (75 ml) and then $Cs_2CO_3$ (4.84 g, 25.095 mmol) was added followed by dropwise addition of 1-bomo-3-chloroprorane (2.45 ml) at 60° C. The heating was continued at 60° C. overnight. First the reaction mixture was concentrated and quenched by adding water and extracted with ethyl acetate. The compound was purified by column chromatography (0-14%, ethyl acetate-hexane). Yield: 3.3 g (70% of a 10:3 mixture of chloro and bromo compound).

General procedure F:

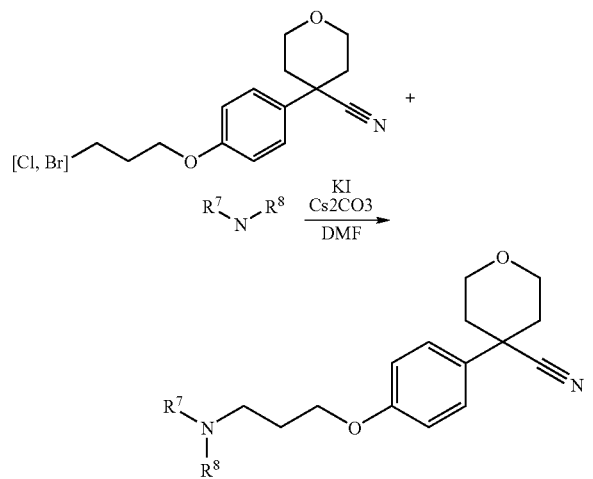

A mixture of halide (0.7 mmol), $Cs_2CO_3$ (0.350 g, 1.07 mmol), potassium iodide (0.180 g, 1.07 mmol) and amines (NR$^7$R$^8$) (1.07 mmol) in DMF (7 mL) was heated to 70° C. overnight. The mixture was cooled to ambient temperature, water was added, and the resulting mixture was extracted with dichloromethane and the organic extracts were dried over $Na_2SO_4$, filtered and concentrated in vacuo. Purification of the crude material was carried out with flash chromatography (20 g silica gel, DCM/MeOH gradient).

Example 96

4-[4-(3-morpholino-4-ylpropoxy)phenyl]tetrahydro-pyran-4-carbonitrile

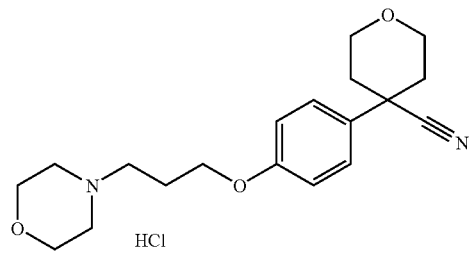

The compound was obtained according the general procedure F, using morpholine as amine. The hydrochloride salt as analytical sample was prepared with ether/HCl 2M in dichloromethane and crystallization in ether. Yield=34% $^1$H NMR (400 MHz, DMSO-D6) δ 1.95-2.12 (m, 4H); 2.16-2.25 (m, 2H); 3.01-3.12 (m, 2H); 3.19-3.27 (m, 2H); 3.40-3.48 (m, 2H); 3.60-3.69 (t, 2H); 3.80-3.89 (m, 2H); 3.91-4.03 (m, 4H); 4.08-4.13 (m, 2H); 7.20 (d, 2H); 7.46 (d, 2H); 11.33 (bs, 1H)

Example 97

4-{4-[3-(4-methyl-piperazin-1-yl)-propoxy]phenyl}tetrahydro-pyran-4-carbonitrile

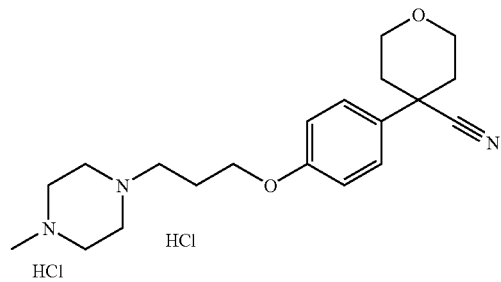

The compound was obtained according the general procedure F, using 1-methylpiperazine as amine. The hydrochloride salt as analytical sample was prepared with ether/HCl 1M in dichloromethane and triturated with pentane. Yield=57% $^1$H NMR (400 MHz, DMSO-D$_6$) δ11.85 (bs, 1H), 7.46 (d, 2H), 7.02 (d, 2H), 4.13-4.07 (m, 2H), 4.03-3.96 (m, 2H), 3.84-3.18 (m, 12H), 2.87-2.78 (m, 3H), 2.24-2.13 (m, 2H), 2.11-1.96 (m, 4H).

Example 98

4-{4-[3-(2-methyl-piperidin-1-yl)-propoxy]phenyl}-tetrahydro-pyran-4-carbonitrile

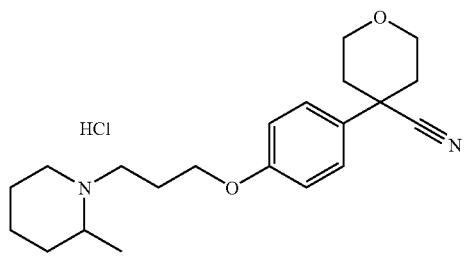

The compound was obtained according the general procedure F, using 2-methylpiperidine as amine. The hydrochloride salt as analytical sample was prepared with ether/HCl 1M in dichloromethane and trituration with pentane. Yield=28%
$^1$H NMR (400 MHz, DMSO-D6) δ10.22 (bs, 1H), 7.46 (d, 2H), 7.01 (d, 2H), 4.13-4.06 (m, 2H), 4.03-3.96 (dd, 2H), 3.69-3.60 (t, 2H), 3.48-3.38 (m, 1H), 3.25-3.06 (m, 3H), 3.01-2.90 (m, 1H), 2.21-1.95 (m, 7H), 1.88-1.57 (m, 5H), 1.56-1.39 (m, 1H), 1.32 (d, 2H), 1.24 (d, 1H).

Example 99

4-{4-[3-(3-methyl-piperidin-1-yl)-propoxy]phenyl}-tetrahydro-pyran-4-carbonitrile

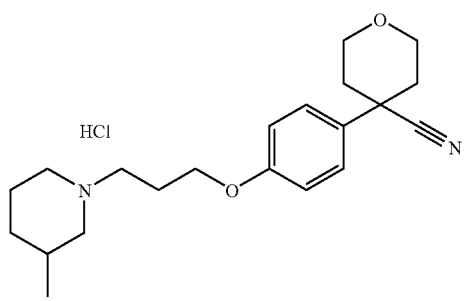

The compound was obtained according the general procedure F, using 3-methylpiperidine as amine. The hydrochloride salt as analytical sample was prepared with ether/HCl 1M in dichloromethane and trituration with pentane. Yield=52%
$^1$H NMR (400 MHz, DMSO-D6) δ10.32 (bs, 1H), 7.46 (d, 2H), 7.01 (d, 2H), 4.11-4.05 (t, 2H), 4.03-3.96 (dd, 2H), 3.69-3.60 (t, 2H), 3.48-3.35 (m, 2H), 3.19-3.11 (m, 2H), 2.82-2.72 (m, 1H), 2.58-2.45 (m, 1H), 2.24-2.16 (m, 2H), 2.12-1.90 (m, 5H), 1.85-1.70 (m, 3H), 1.12-1.02 (m, 1H), 0.89 (d, 3H).

Example 100

4-{4-[3-(4-methyl-piperidin-1-yl)-propoxy]phenyl}-tetrahydro-pyran-4-carbonitrile

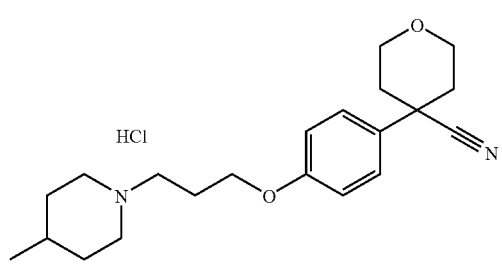

The compound was obtained according the general procedure F, using 4-methylpiperidine as amine. The hydrochloride salt as analytical sample was prepared with ether/HCl 1M in dichloromethane and trituration with pentane. Yield=60%
$^1$H NMR: (400 MHz, DMSO-D6) δ10.18 (bs, 1H), 7.46 (d, 2H), 7.01 (d, 2H), 4.11-4.05 (t, 2H), 4.03-3.96 (dd, 2H), 3.69-3.60 (t, 2H), 3.49-3.42 (m, 2H), 3.19-3.11 (m, 2H), 2.94-2.83 (m, 2H), 2.22-2.13 (m, 2H), 2.11-1.95 (m, 4H), 1.81-1.73 (m, 2H), 1.65-1.54 (m, 1H), 1.53-1.41 (m, 2H), 0.91 (d, 3H).

Example 101

4-[4-(3-azepan-1-ylpropoxy)phenyl]tetrahydropyran-4-carbonitrile

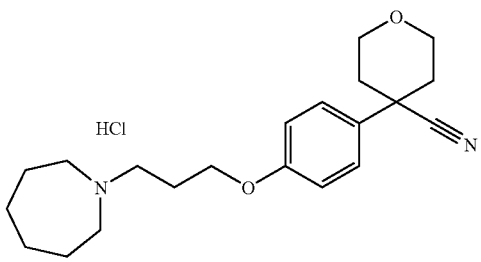

The compound was obtained according the general procedure F, using hexamethyleneimine as amine. The hydrochloride salt as analytical sample was prepared with ether/HCl 1M in dichloromethane and trituration with ether. Yield=9% $^1$H NMR (400 MHz, DMSO-D6) δ10.54 (bs, 1H), 7.41 (d, 2H), 7.01 (d, 2H), 4.11-4.05 (t, 2H), 4.03-3.96 (dd, 2H), 3.69-3.60 (dt, 2H), 3.41-3.30 (m, 2H), 3.24-3.17 (m, 2H), 3.16-3.06 (m, 2H), 2.24-2.16 (m, 2H), 2.12-1.95 (m, 4H), 1.92-1.76 (m, 4H), 1.72-1.52 (m, 4H).

Example 102

4-{4-[3-(4,4-difluoro-piperidin-1-yl)-propoxy]phenyl}-tetra-hydropyran-4-carbonitrile

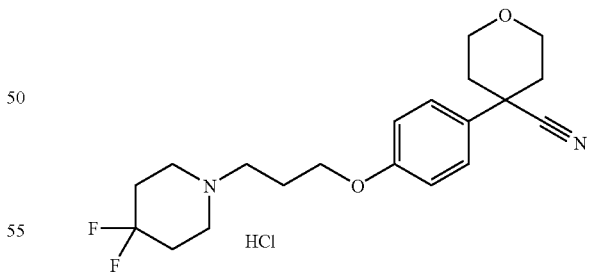

The compound was obtained according the general procedure F, using 4,4-difluoropiperidine hydrochloride as amine (add $(C_2H_5)_3N$ to obtain the free base). The hydrochloride salt as analytical sample was prepared with ether/HCl 1M in dichloromethane and trituration with ether. Yield=9% $^1$H NMR: (400 MHz, DMSO-D6) δ10.28 (bs, 1H), 7.46 (d, 2H), 7.01 (d, 2H), 4.12-4.07 (t, 2H), 4.03-3.96 (dd, 2H), 3.69-3.59 (dt, 4H), 3.33-3.25 (m, 2H), 3.21-3.11 (m, 2H), 2.39-2.27 (m, 2H), 2.27-2.17 (m, 2H), 2.12-1.95 (m, 4H).

Example 103

4-[4-(5-Pyrrolidin-1-ylpentyloxy)phenyl]tetrahydro-pyran-4-carbonitrile

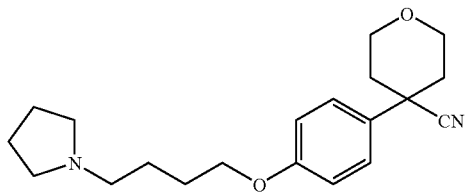

4-(4-Hydroxy-phenyl)-tetrahydro-pyran-4-carbonitrile (1.5 g, 7.39 mmol), 1-bromo-4-chlorobutane (1.7 ml, 14.77 mmol), DMF (20 ml) and $K_2CO_3$ (4.1 g, 29.56 mmol) were reacted together according to general procedure E. Purification by chromatography on silica, eluant ethyl acetate:heptanes (33:66) provided a mixture of bromo and chloro phenoxy ether (1.3 g, 60%) which was used in the next stage. A portion of the mixture (0.5 g, 1.70 mmol) and pyrrolidine (0.42 ml, 5.11 mmol) were refluxed in EtOH (5 ml, 10 vol) overnight. The reaction was concentrated in vacuo and partitioned between 2M NaOH (10 ml) and ethyl acetate (10 ml). The aqueous was extracted with ethyl acetate (3×10 mL). The combined ethyl acetate layers were washed with brine (3×10 ml), dried over $MgSO_4$, filtered, washed with ethyl acetate and concentrated in vacuo. Purification by chromatography on silica, eluant DCM:MeOH:$NH_3$ (95:4:1) increasing gradually to DCM:MeOH:$NH_3$ (93:6:1), gave the title compound as a pale yellow solid (350 mg, 63%). $^1$H NMR (400 MHz, DMSO-$d_6$) δ 7.38 (d, 2H), 6.92 (d, 2H), 4.11-4.03 (m, 2H), 3.99 (t, 2H), 3.89 (td, 2H), 2.58-2.43 (m, 6H), 2.15-1.99 (m, 4H), 1.89-1.64 (m, 8H).

Intermediate 35: 1-[4-(3-bromo-propoxy)-phenyl]-cyclohexanecarbonitrile 1-(4-Hydroxyphenyl)cyclohexanecarbonitrile (2.0 g, 10 mmol) was taken in acetone (150 mL) and then $Cs_2CO_3$ (8.1 g, 25 mmol) was added followed by dropwise addition of 1,3 dibromopropane (5.1 mL, 50 mmol). The mixture was heated for 3 h at 70° C. After cooling and filtration, the mixture was concentrated and the residue was purified by flash chromatography (50 g silica gel, DCM) to provide the title compound (2.8 g, 87%). Note: presence of allyl derivative as impurity.

General procedure G:

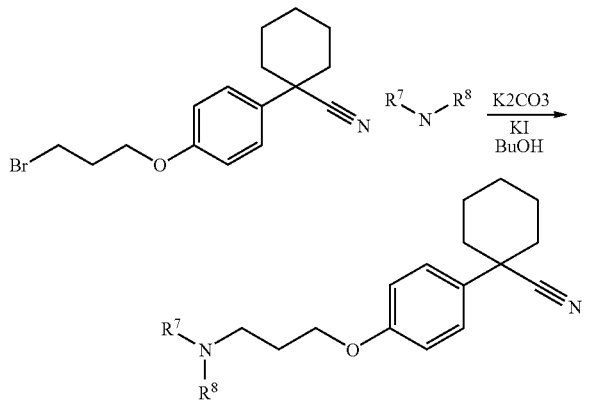

A mixture of 1-[4-(3-bromo-propoxy)-phenyl]-cyclohexanecarbonitrile (0.660 g, 2.0 mmol), amine ($NR^7R^8$) (0.260 g, 3.0 mmol), sodium carbonate (0.320 g, 3 mmol), potassium iodide (20 mg) and 20 mL of butanol was heated for 4 h at 100° C. After cooling, water was added to quench the reaction and the mixture was extracted with DCM. The organics extracts were washed with a saturated aqueous solution of $NaHCO_3$, water and dried over $Na_2SO_4$ filtered and concentrated. The residue was purified by flash chromatography (DCM and DCM/MeOH (10% $NH_3$) to provide (0.440 g, 67%).

Example 104

1-[4-(3-piperidin-1-yl-propoxy)-phenyl]-cyclohexane-carbonitrile

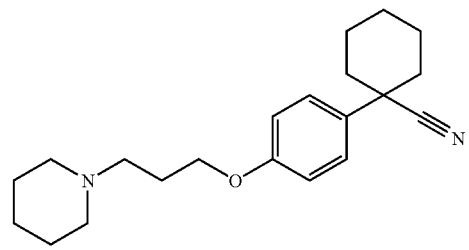

A mixture of 1-[4-(3-bromo-propoxy)-phenyl]-cyclohexanecarbonitrile (0.660 g, 2.0 mmol), piperidine (0.260 g, 3.0 mmol), sodium carbonate (0.320 g, 3 mmol), potassium iodide (20 mg) and 20 mL of butanol was heated for 4 h at 100° C. according to general procedure G. After cooling, water was added to quench the reaction and the mixture was extracted with DCM. The organics extracts were washed with a saturated aqueous solution of $NaHCO_3$, water and dried over $Na_2SO_4$, filtered and concentrated. The residue was purified by flash chromatography (DCM and DCM/MeOH (10% $NH_3$) to provide the title compound (0.440 g, 67%). $^1$H NMR (400 MHz, CDCl$_3$) δ7.37 (d, 2H), 6.90 (d, 2H), 4.00 (t, 2H), 2.49-2.36 (m, 6H), 2.17-2.09 (m, 2H), 1.97 (qt, 2H), 1.88-1.67 (m, 7H), 1.62-1.55 (m, 4H), 1.47-1.40 (m, 2H), 1.32-1.20 (m, 1H).

General procedure H:

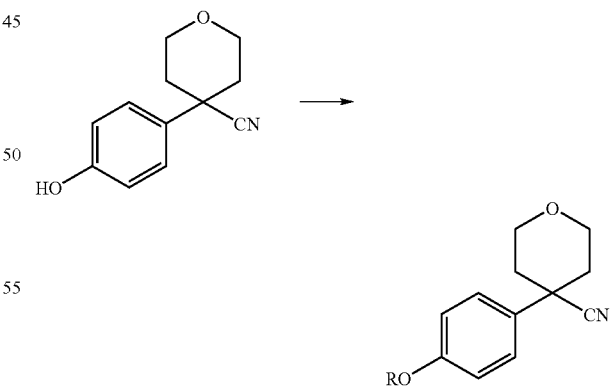

4-(4-Hydroxy-phenyl)-tetrahydro-pyran-4-carbonitrile (1 eq.), alcohol (R—OH) (0.8 eq.) and PPh$_3$ (1 eq.) were mixed together in THF (10 vol) and cooled to 0° C. under $N_2$. DIAD (1 eq.) in THF (10 vol) was added slowly to the reaction and allowed to warm to room temperature overnight. The reaction was quenched with 2M HCl solution (10 vol) and extracted with ethyl acetate (3×10 vol). The aqueous was basified to pH

Example 105

4-[4-(2,2-Dimethyl-3-pyrrolidin-1-ylpropoxy)phenyl]tetrahydro-pyran-4-carbonitrile

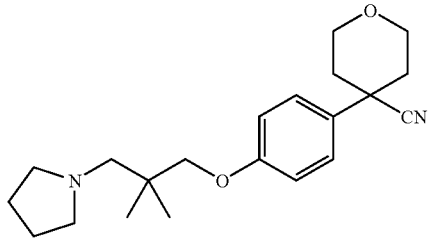

4-(4-Hydroxy-phenyl)-tetrahydro-pyran-4-carbonitrile (1.29 g, 6.4 mmol), 2,2-dimethyl-3-pyrrolidin-1-yl-propan-1-ol (0.8 g, 5.1 mmol), PPh$_3$ (1.67 g, 6.4 mmol), THF (16 ml) and DIAD (1.25 ml, 6.4 mmol) were reacted together according to general procedure H. The crude material was subjected to chromatography on silica eluting with DCM:MeOH (98:2). The resulting solid was slurried in TBME:heptanes (1:2, 1 ml) to provide the title compound (120 mg, 5%) as a white solid. $^1$H NMR (400 MHz, CDCl$_3$), δ 7.37 (d, 2H), 6.94 (d, 2H), 4.12-4.03 (m, 2H), 3.89 (td, 2H), 3.71 (s, 2H), 2.57 (br s, 4H), 2.47 (s, 2H), 2.15-1.99 (m, 4H), 1.70 (brs, 4H), 1.00 (s, 6H).

Example 106

4-[4-(3-Pyrrolidin-1-ylpropoxy)phenyl]tetrahydro-2H-pyran-4-carboxylic acid amide

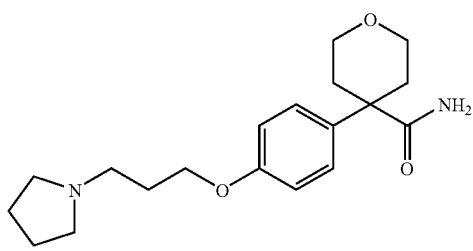

4-[4-(3-Pyrrolidin-1-yl-propoxy)-phenyl]-tetrahydro-pyran-4-carbonitrile (400 mg, 1.27 mmol) was treated with polyphosphoric acid at 80° C. overnight. After allowing the mixture to cool to room temperature, ethyl acetate and water were added. The organic layer was separated. The aqueous layer was basified to pH 10 with concentrated NaOH and extracted with DCM. The combined organic extracts were dried over Na$_2$SO$_4$, filtered, concentrated in vacuo and purified by column chromatography on silica gel eluting to give the title compound (88 mg, 26%). $^1$H NMR (400 MHz, CDCl$_3$) δ7.29 (d, 2H), 6.91 (d, 2H), 5.64-5.30 (d, 2H), 4.02 (t, 2H), 3.76 (t, 4H), 2.62 (t, 2H), 2.52 (m, 4H), 2.37-2.30 (m, 2H), 2.08-1.96 (m, 4H), 1.81-1.75 (m, 4H).

Example 107

4-[4-(3-Pyrrolidin-1-ylpropoxy)phenyl]tetrahydro-2H-pyran-4-carboxylic acid

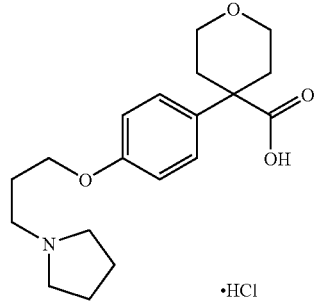

A solution of 4-[4-(3-pyrrolidin-1-ylpropoxy)phenyl]tetrahydro-2H-pyran-4-carbonitrile (20 g, 0.0636 mol) in concentrated hydrochloric acid (200 ml, 10 vol) was heated and stirred at reflux for 16 h after which time LC/LCMS analysis showed the reaction had stalled at 85-90% conversion. The solution was evaporated to dryness in vacuo, azeotroped with methanol (200 ml, 20 vol) and toluene (2×200 ml, 2×20 vol) to yield title compound as a beige solid which was used directly. $^1$H NMR (400 MHz, CDCl$_3$) δ 7.18 (d, 2H), 6.96 (d, 2H), 4.12 (t, 2H), 3.94-3.84 (m, 2H), 3.74-3.66 (m, 2H), 3.60 (dt, 2H), 3.42 (t, 2H), 2.50-2.44 (m, 2H), 2.26-2.00 (m, 8H), 2.96-2.84 (m, 2H); HRMS (ESI$^+$) 334.2013 (M+H)$^+$.

Intermediate 36: Methyl 4-[4-(3-pyrrolidin-1-ylpropoxy)phenyl]tetrahydro-2H-pyran-4-carboxylate A suspension of 4-[4-(3-pyrrolidin-1-ylpropoxy)phenyl]tetrahydro-2H-pyran-4-carboxylic acid (23.5 g, 0.0636 mol) in methanol (235 ml, 10 vol) was stirred and cooled to 0 to −5° C. under nitrogen. Thionyl chloride (9.3 ml, 0.1272 mol, 0.40 vol) was charged dropwise over 20 minutes, maintaining the temperature −5 to +5° C. The resulting slurry was then heated and stirred at reflux under nitrogen for 16 h after which time LC analysis showed 1.4% by area of acid remaining. The solution was evaporated to dryness in vacuo at 40° C. to give a brown sludge. The sludge was dissolved in ethyl acetate (118 ml, 5 vol) and water (235 ml, 10 vol) and the layers separated. The aqueous layer was washed with ethyl acetate (118 ml, 5 vol) and basified to pH 11 with saturated aqueous potassium carbonate (118 ml, 5 vol). The product was extracted into dichloromethane (3×118 ml, 3×5 vol) and the combined extracts dried over magnesium sulfate (23 g, 1 wt) and concentrated in vacuo at 40° C. to yield title compound (21.7 g, 98% from the nitrile) as a cream solid.

Example 108

{4-[4-(3-Pyrrolidin-1-ylpropoxy)phenyl]tetrahydro-2H-pyran-4-yl}methanol

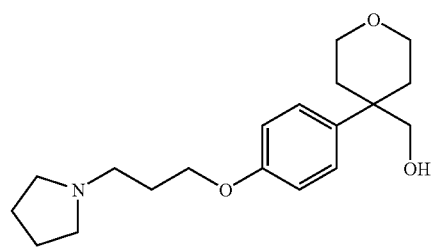

Anhydrous tetrahydrofuran (141 ml, 10 vol) was charged rapidly onto stirred and cooled (0-5° C.) lithium aluminium hydride (6.2 g, 0.1634 mol, 0.44 wt) under nitrogen (Note: very exothermic). The resulting slurry was cooled to 0-5° C. and then a solution of methyl 4-[4-(3-pyrrolidin-1-ylpropoxy)phenyl]tetrahydro-2H-pyran-4-carboxylate (14.1 g, 0.04058 mol) in tetrahydrofuran (99 ml, 7 vol) was added dropwise over 30 minutes maintaining 0-5° C. On complete addition the reaction was allowed to warm to room temperature over 30 minutes and stirred at 18-25° C. for 30 minutes, LC analysis showed the reaction to be complete. The mixture was cooled to 0 to 5° C., a 1:1 mixture of tetrahydrofuran and water (18.6 ml, 1.32 vol) was added very slowly (Note: very exothermic, gas evolution, temperature maintained below 16° C., toward the end of the quench the reaction mixture sets and then becomes freer with continued stirring.). The mixture was further quenched with 20% w/v sodium hydroxide solution (6.2 ml, 0.44 vol) and water (18.6 ml, 1.32 vol) and the resulting white suspension stirred vigorously for 30 minutes at 18-25° C. The slats were removed by filtration and rinsed with tetrahydrofuran (3×150 ml). The combined filtrates were evaporated to dryness at 40° C. to yield title compound (12.1 g, 94%) as a white solid. $^1$H NMR (400 MHz, CDCl$_3$) δ 7.25 (d, 2H), 6.90 (d, 2H), 4.05 (t, 2H), 3.80 (dt, 2H), 3.55 (td, 2H), 2.60 (t, 2H), 2.62-2.41 (m, 4H), 2.10 (dt, 2H), 2.00 (p, 2H), 2.00-1.85 (m, 2H), 1.95-1.72 (m, 4H).

Example 109

1-[4-(3-pyrrolidin-1-ylpropoxy)phenyl]cyclo-pentane-carbonitrile

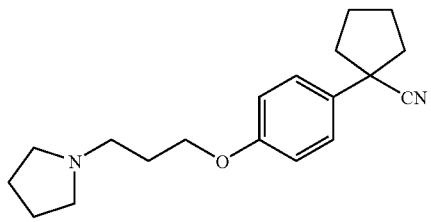

To a suspension of NaH (60%, 0.574 g, 14.35 mmol) in DMF (8 mL) at 0° C. was added dropwise [4-(3-pyrrolidin-1-ylpropoxy)phenyl]acetonitrile (1 g, 4.10 mmol) in DMF (3 mL). The reaction mixture was stirred at 0° C. for 5 min than at room temperature for 30 min. After cooling to 0° C., 1,4-dibromobutane (0.980 mL, 8.2 mmol) in DMF (2 mL) was added dropwise. The reaction mixture was allowed to warm up to room temperature then heated to 50° C. overnight. It was poured into ice-cold water and extracted with DCM. The combined organic extracts were washed with brine, dried over Na$_2$SO$_4$, filtered and concentrated in vacuo. The crude mixture was purified by column chromatography, eluting with a gradient of DCM:MeOH:NH$_3$ (from 99:0:1 to 90:10:1) to give the title compound (0.443 g, 36%). $^1$H NMR (400 MHz, DMSO-d$_6$) δ7.29 (d, 2H), 6.79 (d, 2H), 4.02 (m, 2H), 3.18 (m, 2H), 2.47-2.28 (m, 4H), 2.19-1.75 (m, 11H), 1.19 (m, 3H).

Example 110

4-oxo-1-[4-(3-pyrrolidin-1-ylpropoxy)-phenyl]-cyclohexane-carbonitrile

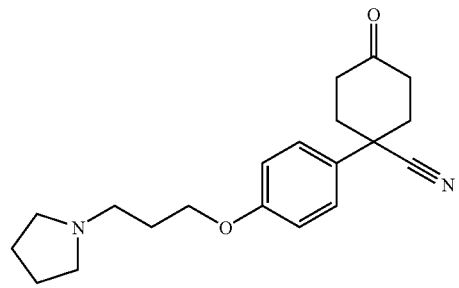

Step 1: A three neck reaction vessel was charged with [4-(3-pyrrolidin-1-ylpropoxy)phenyl]acetonitrile (7 g, 28.6 mmol), benzyltrimethylammonium hydroxide (40% in methanol, 1.3 mL) in acetonitrile (185 mL). The solution was heated to reflux and methyl acrylate (25 mL, 286 mmol) was added dropwise. After refluxing for 5 hr, the mixture was concentrated to half, diethyl ether was added and the organics were washed with HCl 1N and brine, dried over Na$_2$SO$_4$, filtered and concentrated. The residue was purified by flash-chromatography to provide 4-cyano-4-[4-(3-pyrrolidin-1-ylpropoxy)-phenyl]-heptanedioic acid dimethyl ester (8.8 g, 74%). $^1$H NMR (400 MHz, CDCl$_3$) δ7.28 (d, 2H); 6.95 (d, 2H); 4.08-4.0 (m, 2H); 3.6 (s, 6H); 2.68-2.60 (m, 2H); 2.58-2.45 (m, 6H); 2.40-2.20 (m, 4H); 2.20-2.12 (m, 2H); 2.08-2.0 (m, 2H); 1.80-1.75 (m, 4H).

Step 2: To a solution of 4-cyano-4-[4-(3-pyrrolidin-1-ylpropoxy)-phenyl]-heptanedioic acid dimethyl ester (8.8 g, 21.1 mmol) in 1,2-dimethoxyethane (176 mL) was charged portions of NaH (60% dispersion, 2.55 g, 63.4 mmol). The reaction mixture was heated to reflux. After 4.5 hr, the ¾ of solvent were evaporated and the mixture cooled to 20° C. with an ice bath and quenched with water (100 mL), HCl 1N (100 mL). The aqueous layer was extracted with ether (100 mL). After basification with NaOH the aqueous phases were extracted with dichloromethane. The combined organics were washed with water, dried over Na$_2$SO$_4$, filtrered and concentrated to provide 5-cyano-2-oxo-5-[4-(3-pyrrolidin-1-ylpropoxy)-phenyl]-cyclohexane-carboxylic acid methyl ester (6.6 g, 81%) as an oil. $^1$H NMR (400 MHz, CDCl$_3$) δ12.2 (bs, 1H); 7.33 (d, 2H); 6.95 (d, 2H); 4.08-4.00 (m, 2H); 3.75 (s, 3H); 2.95 (d, 1H); 2.80-2.70 (m, 1H); 2.65-2.60 (m, 2H); 2.50-2.42 (m, 6H); 2.30-2.15 (m, 2H); 2.05-1.95 (m, 2H); 1.90-1.85 (m, 4H).

Step 3: To a solution of 5-cyano-2-oxo-5-[4-(3-pyrrolidin-1-ylpropoxy)-phenyl]-cyclohexanecarboxylic acid methyl ester (6.6 g, 17 mmol) and dimethylsulfoxide (128 mL) was added water (8.0 mL) and sodium chloride (6.4 g, 109 mmol). The reaction mixture was heated to 142-146° C. After 5 hr, the mixture was concentrated and the residue was dissolved in DCM (120 mL), washed with water (100 mL), and brine, dried over Na$_2$SO$_4$, filtered and concentrated. The residue was purified by flash chromatography (70 g silica gel, eluant: gradient of DCM/MeOH 95/5 to 90/10) providing 4-oxo-1-[4-(3-pyrrolidin-1-ylpropoxy)-phenyl]-cyclohexanecarbonitrile as a crystallizing oil (2.2 g, 45.5%). After crystallization in ether, 0.2 g of analytical sample were obtained. $^1$H NMR (400 MHz, CDCl$_3$) δ7.32 (d, 2H), 6.88 (d, 2H), 4.1 (t, 2H), 2.95-2.8 (m, 2H), 2.65-2.38 (m, 10H), 2.3-2.15 (m, 2H), 2.0-1.9 (m, 2H), 1.8-1.7 (m, 4H).

Example 111

4-hydroxy-1-[4-(3-pyrrolidin-1-ylpropoxy)-phenyl]cyclo-hexanecarbonitrile

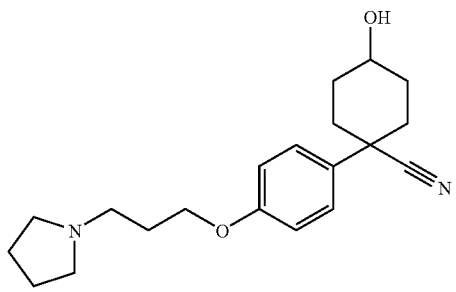

To a stirred suspension of LiAlH$_4$ (0.070 g, 1.85 mmol, 5 eq) in diethyl ether (1.9 mL) was added dropwise at 0° C. a solution of 4-oxo-1-[4-(3-pyrrolidin-1-ylpropoxy)-phenyl]-cyclohexanecarbonitrile (0.12 g, 0.37 mmol) in diethyl ether (5.5 mL). The reaction mixture was stirred at ambient temperature for 4 h. The reaction mixture was cooled to 0° C. and, successively, a solution of water, sodium hydroxide (15% w/v, 0.08 mL) and water again were carefully dropped. After being stirred for 15 min at room temperature, the mixture was filtered over diatomaceous earth and concentrated. The residue was purified by flash chromatography (10 g silica gel, DCM/MeOH (10% NH$_3$) to provide 0.050 g of title compound. $^1$H NMR (400 MHz, DMSO-D6) δ10.6 (bs, 1H), 7.42 (d, 2H), 7 (d, 2H), 4.1-3.95 (m, 2H), 3.6-3.2 (m, 5H), 3.03-2.87 (m, 2H), 2.15-1.8 (m, 10H), 1.65-1.5 (m, 2H).

Intermediate 37: (R)-2-Methylpyrrolidine

Pure enantiomers of 2-methylpyrrolidine can be obtained by resolution with +/− tartaric acid as described in *Acta. Pharm. Suecica* 15, 255-263; 1978.

Intermediate 38: 3-[(2R)-2-Methylpyrrolidin-1-yl]propan-1-ol

3-Bromopropan-1-ol (5.28 mL, 58.4 mmol) was added to a solution of (R)-2-methylpyrrolidine (7.1 g, 58.4 mmol) in water (200 mL). KOH (7.53 g, 134 mmol) was then added and the mixture stirred at ambient temperature for 48 hours. The reaction mixture was then extracted with dichloromethane (5×80 mL) and ethyl acetate (5×80 mL). The combined organic extracts were dried using MgSO$_4$, filtered and concentrated in vacuo. The compound was purified by column chromatography on Biotage® silica gel, eluting with dichloromethane:methanol:ammonia, (90:10:1) to give the title compound as a pale brown oil (5.44, 65%). LCMS (APCI$^+$) 144 (M+H)$^+$.

Intermediate 39: tert-Butyl (3S)-3-methoxypyrrolidine-1-carboxylate

Sodium hydride (80% dispersion in mineral oil, 940 mg, 0.024 mmol) was added in two portions at 0° C. to a solution of tert-butyl (3S)-3-hydroxypyrrolidine-1-carboxylate (4.00 g, 0.02 mmol). The reaction mixture was allowed to warm to room temperature and stirred for 1 h before being cooled once more to 0° C. Methyl iodide (2.00 mL, 0.032 mmol) was added slowly and the reaction mixture warmed to room temperature overnight. The mixture was poured slowly onto 200 mL of ice and stirred until the ice was fully thawed. The product was extracted using dichloromethane (2×250 mL), dried (Na$_2$SO4) and concentrated in vacuo. The compound was purified by column chromatography on Biotage® silica gel, eluting with dichloromethane to give the product as a colourless oil (2.88 g, 67%).

Intermediate 40: (3S)-3-Methoxypyrrolidine

A solution of trifluoroacetic acid (2.5 ml) in dichloromethane (5 mL) was added slowly at 0° C. to a solution of tert-Butyl (3S)-3-methoxypyrrolidine-1-carboxylate (2.88 g, mmol) and the reaction allowed to warm to room temperature and stirred for 2.5 h. The reaction mixture was quenched with saturated sodium carbonate solution (100 mL) and extracted with dichloromethane (2×200 mL). The organics were combined, dried over magnesium sulphate and concentrated in vacuo. The residue was taken up in dichloromethane (30 mL) and cooled to 0° C. in an ice bath. Hydrogen chloride gas was bubbled through the suspension for 1 hour and the reaction mixture allowed to stir at room temperature for 48 hours. The reaction mixture was basified with saturated sodium hydrogencarbonate solution (100 mL) and extracted with dichloromethane (2×200 mL) and ethyl acetate (3×150 mL). The aqueous was concentrated in vacuo and then extracted with warm methanol to yield the title product, 2.00 g.

Intermediate 41: (3R)-1-Benzyl-3-methoxypyrrolidine (3R)-1-Benzyl-3-methoxypyrrolidine was prepared as described in the following patent WO 91/08206 and taken on to the next step as the crude mixture.

Intermediate 42: (3R)-3-Methoxypyrrolidine

A solution of (3R)-1-Benzyl-3-methoxypyrrolidine (2.35 g, 12.3 mmol) in methanol (50 mL) containing concentrated HCl (1 mL) was hydrogenated at ambient temperature at 50 psi in the presence of a catalytic amount of 10% Pd(OH)$_2$ on carbon (250 mg, 10% w/w). The reaction mixture was filtered over celite and rinsed with dichloromethane (60 mL) and methanol (60 mL) to remove the catalyst. The organic layer was basified with NaOH (2.0M, 10 mL) and extracted with diethylether (3×30 mL). The aqueous layer was further acidified to pH3 using concentrated HCl, concentrated in vacuo and azeotroped with toluene to give the product as a yellow solid which was further used without purification.

Intermediate 43: 2,2-Dimethylpyrrolidine

Step 1:1-Benzyl-2,2-dimethylpyrrolidine was prepared according to the procedure described in the following reference. S. M. Denton and A. Wood, *Synlett*, 1999, 55.

Step 2: A solution of 1-Benzyl-2,2-dimethylpyrrolidine (1.02 g, 5.40 mmol) in ethanol (80 mL) and concentrated HCl (0.5 mL) was hydrogenated over 20% Pd(OH)$_2$ (100 mg, 10% w/w) at 60 psi at ambient temperature for 4 hours. The reaction mixture was filtered over arbocel to remove the catalyst and a further 2 mL of concentrated HCl was added to the crude product. The reaction mixture was then concentrated in vacuo and azeotropically dried using toluene to give the product as a brown solid, which appeared to be slightly hygroscopic (732 mg, 100%).

Intermediate 44: (2R,5S)-2,5-Dimethylpyrrolidine

The free base of cis-2,5-dimethylpyrrolidine was prepared as described by C. G. Overberger, L. C. Palmer, B. S. Marks and N. R. Byrd, *J. Am. Chem. Soc.*, 1955, 77, 4100: This was then acidified using HCl (2.0M solution in diethylether) which, upon filtration and subsequent recrystallisation from acetonitrile and i-propylalcohol gave the title compound as a white crystalline solid (5.29 g, 22%) in a ratio of approximately 10:1 ratio of cis:trans.

Intermediates 45 and 46: 1-[4-(3-bromo-propoxy)phenyl]cyclohexane-carbonitrile and 1-[4-(3-chloro-propoxy)-phenyl]-cyclohexane-carbonitrile K₂CO₃ (3.02 g, 21.9 mmol) was added to a solution of 1-(4-hydroxyphenyl)cyclohexanecarbonitrile (4.0 g, 19.9 mmol) in DMF (50 mL). 1-bromo-3-chloroproprane (1.97 ml, 19.9 mmol) was then added dropwise and the reaction heated at 60° C. overnight. The reaction mixture was concentrated, quenched by adding water (50 mL), extracted with dichloromethane (2×50 mL) and the organic extracts were dried over Na₂SO₄, filtered and concentrated in vacuo. The compound was purified by column chromatography on Biotage® silica gel, eluting with diethylether:dichloromethane, 50:50 to 0:100. Yield: 5.32 g (96% of a 3:1 mixture of chloro and bromo compound).

Example 112

1-(4-{3-[(2R)-2-(methoxymethyl)pyrrolidin-1-yl]propoxy}-phenyl)cyclohexanecarbonitrile

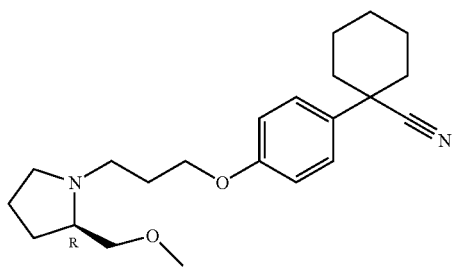

A (1:3) mixture of 1-[4-(3-bromo-propoxy)-phenyl]-cyclohexanecarbonitrile and 1-[4-(3-chloro-propoxy)-phenyl]-cyclohexanecarbonitrile (2.00 g, 7.20 mmol), Cs₂CO₃ (2.58 g, 7.20 mmol), potassium iodide (0.20 g, 1.20 mmol) and (R)-(−)-2-(methoxymethyl)pyrrolidine (1.07 mL, 8.60 mmol) in NMP (20 mL) was heated to 75° C. overnight. The reaction mixture was cooled to ambient temperature, concentrated in vacuo, and quenched by adding water (30 mL). The crude product was extracted with ethyl acetate (30×mL) and the organic extracts were dried over Na₂SO₄, filtered and concentrated in vacuo. The compound was purified by column chromatography on Biotage® silica gel, eluting with dichloromethane:methanol:ammonia, 100:0:0 to 90:10:1 to give the title compound as a brown oil (1.39 g, 54%). ¹H NMR (400 MHz, CDCl₃) δ 7.38 (d, 2H), 6.70 (d, 2H), 4.02 (t, 2H), 3.46-3.38 (m, 1H), 3.36-3.28 (m, 3H), 3.24-3.16 (m, 1H), 3.12-3.04 (m, 1H), 2.72-2.58 (m, 1H), 2.52-2.44 (m, 1H), 2.30-2.20 (m, 1H), 2.18-2.06 (m, 2H), 1.98 (pentet, 2H), 1.92-1.60 (m, 12H), 1.36-1.18 (m, 1H); HRMS (ESI⁺) 357.2537 (M+H)⁺.

Example 113

1-(4-{3-[(3S)-3-methoxypyrrolidin-1-yl]propoxy}phenyl)cyclo-hexanecarbonitrile

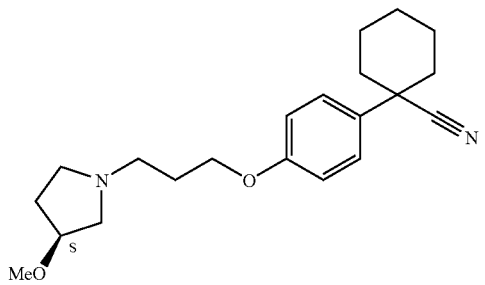

A (1:3) mixture of 1-[4-(3-bromo-propoxy)-phenyl]-cyclohexanecarbonitrile and 1-[4-(3-chloro-propoxy)-phenyl]-cyclohexanecarbonitrile (200 mg, 0.72 mmol), N,N-diisopropylethylamine (251 µL, 1.44 mmol) and (S)-3-methoxypyrrolidine (198 mg, 1.96 mmol) in NMP (0.5 mL) was heated at 160° C. in the microwave (Smith Personal Synthesiser) for 400 seconds. The reaction mixture was quenched with water (10 mL) and extracted with dichloromethane (2×10 mL), dried over Na₂SO₄, filtered and concentrated in vacuo. The compound was purified by column chromatography on Biotage® silica gel, eluting with dichloromethane:methanol:ammonia, 97:3:0.3 to 95:5:0.5. to give the product as a clear oil (102 mg, 41%). ¹H NMR (400 MHz, CDCl₃) δ7.36 (d, 2H), 6.90 (d, 2H), 4.02 (t, 2H), 3.96-3.88 (m, 1H), 3.28 (s, 3H), 2.86-2.52 (m, 6H), 2.18-1.96 (m, 5H), 1.88-1.66 (m, 8H), 1.38-1.16 (m, 1H); LCMS (APCI⁺) 343 (M+H)⁺.

Example 114

1-(4-{3-[(3R)-3-methoxypyrrolidin-1-yl]propoxy}phenyl)-cyclohexanecarbonitrile

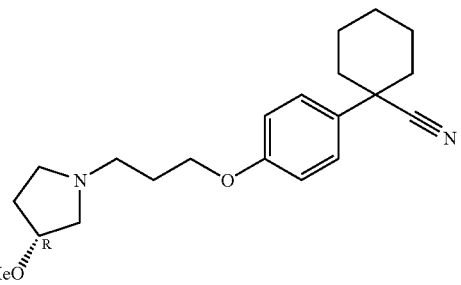

A (1:3) mixture of 1-[4-(3-bromo-propoxy)-phenyl]-cyclohexanecarbonitrile and 1-[4-(3-chloro-propoxy)-phenyl]-cyclohexanecarbonitrile (200 mg, 0.72 mmol), N,N-diisopropylethylamine (251 µL, 1.44 mmol) and (R)-3-methoxypyrrolidine (198 mg, 1.44 mmol) in NMP (0.5 mL) was heated at 160° C. in the microwave (Smith Personal Synthesiser) for 600 seconds. The reaction mixture was quenched with water (30 mL) and extracted with ethylacetate (2×30 mL), dried over Na₂SO₄ filtered and concentrated in vacuo. The compound was purified by column chromatography on Biotage® silica gel, eluting with dichloromethane:methanol:ammonia, 98:2:0.2 to 95:5:0.5 to give a brown oil (37 mg, 11%). ¹H NMR (400 MHz, CDCl₃) δ7.38 (d, 2H), 6.90 (d, 2H), 4.02 (t, 2H), 3.94-3.88 (m, 1H), 3.28 (s, 3H), 2.74-2.66 (m, 2H), 2.64-2.56 (m, 2H), 2.46 (quintet, 2H), 2.17-1.94 (m, 5H) 1.88-1.66 (m, 8H) 1.32-1.18 (m, 1H); HRMS (ESI⁺) 343.2380 (M+H)⁺.

Example 115

4-(4-{3-[(2R,5S)-2,5-dimethylpyrrolidin-1-yl]propoxy}-phenyl)-tetrahydro-2H-pyran-4-carbonitrile

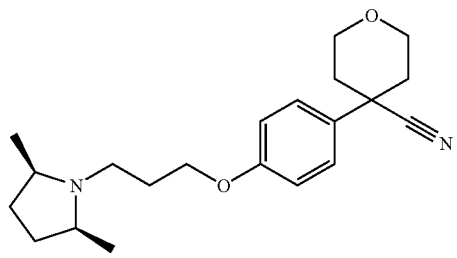

A (1:3) mixture of 1-[4-(3-bromo-propoxy)-phenyl]-cyclohexanecarbonitrile and 1-[4-(3-chloro-propoxy)-phenyl]- cyclohexanecarbonitrile (150 mg, 0.54 mmol), N,N-diisopropylethylamine (187 µL, 1.07 mmol) and (2R,5S)-2,5-dimethylpyrrolidine (145 mg, 1.07 mmol) in NMP (0.5 mL) was heated at 160° C. in the microwave (Smith Personal Synthesiser) for 400 seconds then 170° C. for 600 seconds. The reaction mixture was quenched with NaHCO$_3$ (15 mL) and extracted with ethyl acetate (2×15 mL), dried over Na$_2$SO$_4$, filtered and concentrated in vacuo. The compound was purified by column chromatography on Biotage® silica gel, eluting with dichloromethane:methanol:ammonia, 97:3: 0.3 to 90:10:1. Yield=28% $^1$H NMR (400 MHz, CDCl$_3$) δ7.36 (d, 2H), 6.92 (d, 2H), 4.10-4.04 (m, 2H), 4.00 (t, 2H), 3.88 (dt, 2H), 2.72 (t, 2H), 2.64-2.52 (m, 2H), 2.14-1.98 (m, 4H), 1.94 (pentet, 2H), 1.86-1.78 (m, 2H), 1.42-1.28 (m, 2H), 1.10 (d, 6H); HRMS (ESI$^+$) 343.2380 (M+H)$^+$.

Example 116

1-{4-[3-(2,2-dimethylpyrrolidin-1-yl)propoxy]phenyl}cyclo-hexanecarbonitrile

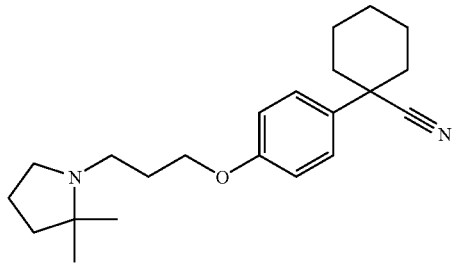

A (1:3) mixture of 1-[4-(3-bromo-propoxy)-phenyl]-cyclohexanecarbonitrile and 1-[4-(3-chloro-propoxy)-phenyl]-cyclohexanecarbonitrile (150 mg, 0.54 mmol), N,N-diisopropylethylamine (188 µL, 1.08 mmol) and 2,2-dimethylpyrrolidine (131 mg, 1.08 mmol) in NMP (0.5 mL) was heated at 180° C. in the microwave (Smith Personal Synthesiser) for 600 seconds. The reaction mixture was quenched with water (15 mL) and extracted with ethyl acetate (2×15 mL), dried over Na$_2$SO$_4$, filtered and concentrated in vacuo. The compound was purified by column chromatography on Biotage® silica gel, eluting with dichloromethane:methanol: ammonia, 98:2:0.2 to 95:5:0.5 to give the title compound as a brown oil (31 mg, 17%). $^1$H NMR (400 MHz, CDCl$_3$) δ7.38 (d, 2H), 6.90 (d, 2H), 4.04 (t, 2H), 2.78 (t, 2H), 2.54 (t, 2H), 2.16-2.12 (m, 2H), 1.94 (pentet, 2H), 1.90-1.64 (m, 11H), 1.20-1.34 (m, 1H), 0.98 (s, 6H); HRMS (ESI$^+$) 341.2588 (M+H)$^+$.

Example 117

1-[1-(4-{3-[(2R)-2-(methoxymethyl)pyrrolidin-1-yl]propoxy}-25 phenyl)cyclohexyl]methanamine

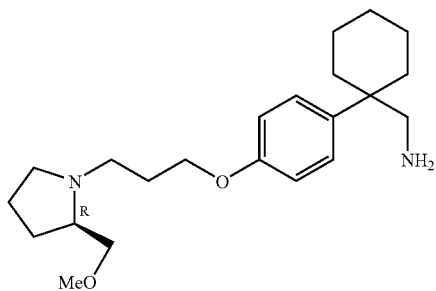

To a stirred suspension of LiAlH$_4$ (1.0M in diethyl ether, 13.7 ml, 13.7 mmol) at 0° C. under an atmosphere of nitrogen was added 1-(4-{3-[(2R)-2-(methoxymethyl)pyrrolidin-1-yl]propoxy}phenyl)cyclohexanecarbonitrile (0.980 g, 2.7 mmol) in Et$_2$O (15 mL) over 15 minutes maintaining the temperature at 5 to 10° C. The reaction mixture was allowed to warm up to ambient temperature for 20 minutes then refluxed for 30 minutes until complete. The reaction mixture was cooled to 0° C., water (0.5 mL) was added followed by NaOH (2.0M, 1.5 mL) and water (0.5 mL). Ethyl acetate (5 mL) was added and the mixture filtered through a short pad of celite, eluting with ethyl acetate (2×15 mL). The organic washings were dried over Na$_2$SO$_4$ and concentrated in vacuo. The compound was purified by column chromatography on Biotage® silica gel, eluting with dichloromethane:methanol: ammonia, 98:2:0.2 to 95:5:0.5 to give the title compound as a clear oil (309 mg, 32%). $^1$H NMR (400 MHz, CDCl$_3$) δ7.22 (d, 2H), 6.88 (d, 2H), 4.04-3.96 (m, 2H), 3.32 (m, 3H), 3.26-3.20 (m, 1H), 3.14-3.04 (m, 1H), 2.74-2.62 (m, 1H), 2.60 (s, 2H), 2.56-2.46 (m, 1H), 2.28 (quartet, 1H), 2.12-1.98 (m, 4H), 1.96-1.90 (m, 1H), 1.82-1.70 (m, 2H), 1.68-1.46 (m, 8H), 1.36-1.30 (m, 3H); HRMS (ESI$^+$) 361.2850 (M+H)$^+$.

Example 118

{[1-(4-{3-[(3S)-3-methoxypyrrolidin-1-yl]propoxy}-phenyl)-cyclohexyl]methyl}amine

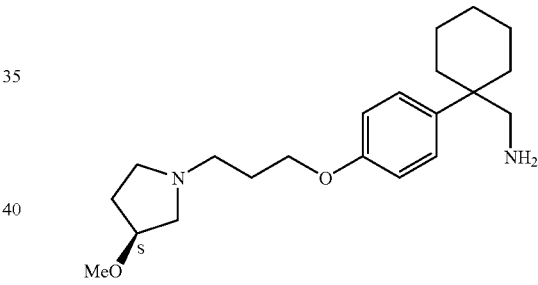

To a stirred suspension of LiAlH$_4$ (1.0M in diethyl ether, 1.46 ml, 1.46 mmol) at 0° C. under an atmosphere of nitrogen was added a solution of 1-(4-{3-[(3S)-3-methoxypyrrolidin-1-yl]propoxy}phenyl)cyclohexanecarbonitrile (0.10 g, 0.29 mmol) in Et$_2$O (2 mL) over 15 minutes maintaining the temperature at 5 to 10° C. The reaction mixture was allowed to warm up to ambient temperature for 20 minutes then refluxed for 30 minutes until complete. The reaction mixture was cooled to 0° C., water (0.5 ml) was added dropwise followed by sodium hydroxide (2.0M, 1.5 ml) and water (0.5 ml). Ethyl acetate (5 mL) was added and the mixture filtered through a short pad of celite, eluting with ethyl acetate (2×15 mL). The organic washings were dried over Na$_2$SO$_4$ and concentrated in vacuo. The compound was purified by column chromatography on Biotage® silica gel, eluting with dichloromethane: methanol:ammonia, 97:3:0.3 to 90:10:1 to give the title compound as a clear oil (75 mg, 75%). $^1$H NMR (400 MHz, CDCl$_3$) δ7.20 (d, 2H), 6.86 (d, 2H), 4.02 (t, 2H), 3.94-3.88 (m, 1H), 3.28 (s, 3H), 2.76-2.68 (m, 2H), 2.58-2.66 (m, 3H), 2.45-2.52 (m, 1H), 2.12-2.04 (m, 3H), 1.98 (pentet, 2H), 1.84-1.74 (m, 1H), 1.56-1.44 (m, 5H), 1.38-1.30 (m, 3H), 1.16-1.25 (m, 2H); HRMS (ESI$^+$) 347.2693 (M+H)$^+$.

Example 119

N-methyl-1-{1-[4-(3-pyrrolidin-1-ylpropoxy)phenyl]cyclo-hexyl}methanamine

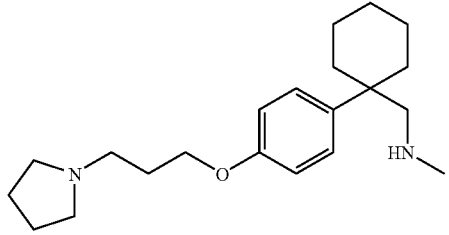

To a stirred solution of ({1-[4-(3-pyrrolidin-1-ylpropoxy)phenyl]cyclo-hexyl}methyl)amine (0.60 g, 1.90 mmol) and N,N-diisopropylethylamine (330 μL, 1.90 mmol) in dry dichloromethane (6 mL) at 0° C. was added dropwise a solution of di-tert-butyldicarbonate (455 mg, 2.09 mmol) in dry dichloromethane (4 mL). The reaction was allowed to warm to ambient temperature and stirred for a further 2 hours. The reaction mixture was concentrated in vacuo, partitioned between NaHCO$_3$ (20 mL) and dichloromethane (20 mL) and extracted with a further 20 mL of dichloromethane. The organic layers were combined, dried over Na$_2$SO$_4$ and concentrated under reduced pressure to provide the crude product. The compound was purified by column chromatography on silica gel, eluting with DCM/MeOH/NH$_3$ (95:5:0.5) to give tert-butyl ({1-[4-(3-pyrrolidin-1-ylpropoxy)phenyl]cyclohexyl}methyl)-carbamate as a clear oil (642 mg, 81%). $^1$H NMR complicated by the presence of rotamers. $^1$H NMR (400 MHz, CDCl$_3$) δ 7.24 (d, 2H), 6.90 (d, 2H), 4.12 (brs, 1H), 4.02 (t, 2H), 3.24-3.06 (m, 2H), 2.66 (t, 2H) 2.56-2.46 (m, 4H), 2.08-1.94 (m, 4H), 1.84-1.72 (m, 4H), 1.62-1.54 (m, 4H), 1.48-1.28 (m, 13H) LCMS (ESI$^+$) 417 (M+H)$^+$ 439 (M+Na)$^+$.

Step 2: A solution of tert-butyl ({1-[4-(3-pyrrolidin-1-ylpropoxy)phenyl]cyclohexyl}methyl)-carbamate (600 mg, 1.44 mmol) in Et$_2$O (5 mL) was added dropwise to a stirred solution of LiAlH$_4$ (1.0M solution in Et$_2$O, 4.32 mL, 4.32 mmol) at 0° C. THF (5 mL) was added and the reaction mixture heated at reflux overnight. Reaction mixture was cooled to 0° C. quenched with water (0.5 mL), aqueous NaOH (2.0M, 0.5 mL) and water (0.5 mL). Dichloromethane and ethyl acetate were added and the mixture filtered over a short pad of celite, and concentrated in vacuo. The compound was purified by column chromatography on Biotage® silica gel, eluting with dichloromethane:methanol:ammonia, 96:4:0.4 to 90:10:1 to give the title compound as a clear oil (230 mg, 48%). $^1$H NMR (400 MHz, CDCl$_3$) δ 7.16 (d, 2H), 6.88 (d, 2H), 4.02 (t, 2H), 2.64 (t, 2H) 2.54 (s, 2H), 2.50-2.58 (m, 4H), 2.26 (s, 3H), 2.14-2.08 (m, 2H), 1.98 (pentet, 2H), 1.84-1.76 (m, 4H), 1.68-1.56 (m, 2H), 1.52-1.32 (m, 6H); HRMS (ESI$^+$) 331.2744 (M+H)$^+$.

Example 120

[(1-{4-[3-(2,2-dimethylpyrrolidin-1-yl)propoxy]phenyl}-cyclo-hexyl)methyl]amine

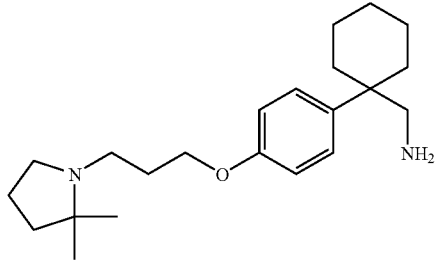

To a stirred suspension of LiAlH$_4$ (1.0M in diethyl ether, 0.4 ml, 0.40 mmol) at 0° C. under an atmosphere of nitrogen was added 1-{4-[3-(2,2-dimethylpyrrolidin-1-yl)propoxy]phenyl}cyclohexanecarbonitrile (27 mg, 0.079 mmol) in Et$_2$O (15 mL) over 15 minutes maintaining the temperature at 5 to 10° C. The reaction mixture was allowed to warm up to ambient temperature for 20 minutes then refluxed for 30 minutes until complete. The reaction mixture was cooled to 0° C., water (0.5 mL) was added followed by NaOH (2.0M, 1.5 mL) and water (0.5 mL). Ethyl acetate (5 mL) was added and the mixture filtered through a short pad of celite, eluting with ethyl acetate (2×15 mL) and concentrated in vacuo. The compound was purified by column chromatography on Biotage® silica gel, eluting with dichloromethane:methanol:ammonia, 97:3:0.3 to give the title compound as a clear oil (10 mg, 37%). $^1$H NMR (400 MHz, CDCl$_3$) δ 7.22 (d, 2H), 6.84 (d, 2H), 4.02 (t, 2H), 2.86-2.76 (m, 2H), 2.66 (s, 2H), 2.58-2.50 (m, 2H), 2.16-2.06 (m, 2H), 2.00-2.90 (m, 2H), 1.84-1.72 (m, 2H), 1.70-1.64 (m, 2H), 1.56-1.46 (m, 4H), 1.40-1.32 (m, 4H), 1.02 (s, 6H). HRMS (ESI$^+$) 345.2901 (M+H)$^+$.

Example 121

N-ethyl-N-({4-[4-(3-pyrrolidin-1-ylpropoxy)phenyl]tetrahydro-2H-pyran-4-yl}methyl)ethanamine

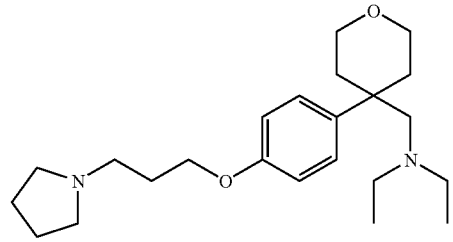

A solution of N-ethyl-N-({4-[4-(3-pyrrolidin-1-ylpropoxy)phenyl]tetrahydro-2H-pyran-4-yl}methyl)acetamide (119 mg, 0.307 mmol) in tetrahydrofuran (1 mL) was added dropwise at 0° C. to a solution of LiAlH$_4$ (1.0M in diethyl-ether, 0.614 mL, 0.614 mmol) under an atmosphere of nitrogen. The reaction mixture was allowed to warm to ambient temperature overnight. The reaction mixture was cooled to 0° C., water (0.5 mL) was then added dropwise followed by sodium hydroxide (2.0M, 0.5 mL) and water (0.5 mL) again. The resulting solid was filtered over a small pad of celite, washed with DCM (100 mL) and concentrated in vacuo. The compound was purified by column chromatography on Biotage® silica gel, eluting with dichloromethane:methanol:ammonia, 94.5:5.5:0.55 to 91:9:0.9 to give the title compound as a pale yellow oil (61 mg, 53%). $^1$H NMR (400 MHz, CDCl$_3$) δ 7.18 (d, 2H), 6.86 (d, 2H), 4.02 (t, 2H), 3.70-3.78 (m, 2H), 3.48 (dt, 2H), 2.64 (t, 2H), 2.58-2.46 (m, 4H), 2.38 (s, 2H), 2.20 (quartet, 4H), 2.13-1.96 (m, 4H), 1.92-1.86 (m, 2H), 1.82-1.78 (m, 4H), 0.82 (t, 6H); HRMS (ESI$^+$) 375.3006 (M+H)$^+$.

Example 122

N-ethyl-N-({4-[4-(3-pyrrolidin-1-ylpropoxy)phenyl]tetrahydro-2H-pyran-4-yl}methyl)acetamide

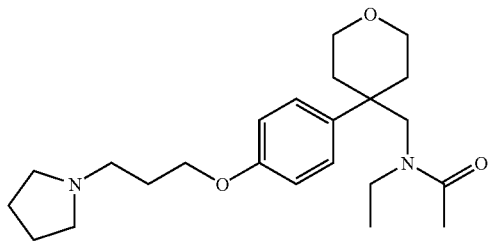

Acetyl chloride (14 μL, 0.20 mmol) was added dropwise to a solution of N-({4-[4-(3-pyrrolidin-1-ylpropoxy)phenyl]tetrahydro-2H-pyran-4-yl}methyl)ethanamine (70 mg, 0.20 mmol) and triethylamine (28 μL, 0.20 mmol) in THF (0.50 mL) at 0° C. and the reaction stirred for 2 hours. The reaction was quenched using NaHCO$_3$ (10 mL), extracted with dichloromethane (3×10 mL) and the organic extracts dried over Na$_2$SO$_4$, filtered and concentrated in vacuo. The compound was purified by column chromatography on silica, eluting with DCM/MeOH/NH$_3$ (95:5:0.5) to provide the title compound as a clear oil (33 mg, 42%). $^1$H NMR complicated by the presence of rotamers. $^1$H NMR (400 MHz, CDCl$_3$) δ 7.20-7.12 (m, 2H), 6.92-6.86 (m, 2H), 4.06-4.00 (m, 2H), 3.88-3.76 (m, 2H), 2.56-2.48 (m, 2H), 3.42 (s, 2H), 2.66 (t, 2H), 2.58-2.52 (m, 4H), 2.48 (quartet, 2H), 2.08 (s, 3H), 2.06-1.92 (m, 6H), 1.84-1.76 (m, 4H), 0.98 (t, 0.6H) 0.86 (t, 2.4H). HRMS (ESI$^+$) 389.2799 (M+H)$^+$.

Example 123

N-methyl-N-({4-[4-(3-pyrrolidin-1-ylpropoxy)phenyl]-tetrahydro-2H-pyran-4-yl}methyl)ethanesulfonamide

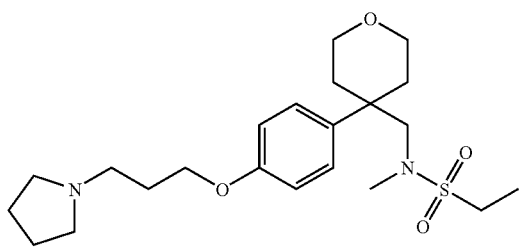

Ethanesulfonyl chloride (43 μL, 0.456 mmol) was added dropwise to a solution of triethylamine (58 μL, 0.418 mmol) and N-methyl-1-{1-[4-(3-pyrrolidin-1-ylpropoxy)phenyl]cyclohexyl}methanamine (125 mg, 0.38 mmol) in dichloromethane (1 mL) at 0° C. and the reaction stirred for 30 minutes. The reaction was quenched with NaHCO$_3$ (20 mL), extracted using dichloromethane (3×10 mL), dried using Na$_2$SO$_4$ and concentrated in vacuo. The compound was purified by column chromatography on Biotage® silica gel, eluting with dichloromethane:methanol:ammonia, 98:2:0.2 to 96:4:0.4 to give the title compound as a pale brown oil (152 mg, 94%). $^1$H NMR (400 MHz, CDCl$_3$) δ 7.24 (d, 2H), 6.90 (d, 2H), 4.04 (t, 2H), 3.84-3.76 (m, 2H), 2.56-2.50 (m, 2H), 3.26 (s, 2H), 2.88 (quartet, 2H), 2.68 (t, 2H), 2.60-2.52 (m, 4H), 2.22 (s, 3H), 2.30-2.12 (m, 2H), 2.02 (pentet, 2H), 1.98-1.90 (m, 2H), 1.86-1.78 (m, 4H) 1.34 (t, 3H); HRMS (ESI$^+$) 425.2469 (M+H)$^+$.

Example 124

N-methyl-N-({4-[4-(3-pyrrolidin-1-ylpropoxy)phenyl]-tetrahydro-2H-pyran-4-yl}methyl)propane-1-sulfonamide

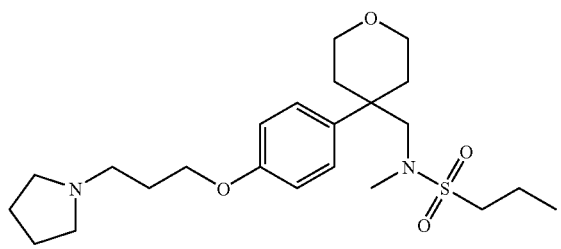

n-Propylsulfonyl chloride (33 μL, 0.289 mmol) was added dropwise to a solution of triethylamine (37 μL, 0.265 mmol) and N-methyl-1-{1-[4-(3-pyrrolidin-1-ylpropoxy)phenyl]cyclohexyl}methanamine (80 mg, 0.24 mmol) in dichloromethane (1 mL) at 0° C. and the reaction stirred for 1 hour. The reaction was quenched with NaHCO$_3$ (20 mL), extracted using dichloromethane (3×15 mL), dried using Na$_2$SO$_4$ and concentrated in vacuo. The compound was purified by column chromatography on Biotage® silica gel, eluting with dichloromethane:methanol:ammonia, 98:2:0.2 to 92:8:0.8 to give the title compound as a pale brown oil (62 mg, 59%). $^1$H NMR (400 MHz, CDCl$_3$) δ 7.22 (d, 2H), 6.90 (d, 2H), 4.02 (t, 2H), 3.82-3.74 (m, 2H), 3.50 (dt, 2H), 3.20 (s, 2H), 2.74 (dt, 2H), 2.64 (t, 2H), 2.56-2.48 (m, 4H), 2.20 (s, 3H), 2.18-2.12 (m, 2H), 2.02 (pentet, 2H), 1.98-1.84 (m, 2H), 1.82-1.68 (m, 6H) 1.00 (t, 3H); HRMS (ESI$^+$) 439.2625 (M+H)$^+$.

Example 125

N-ethyl-N-({4-[4-(3-pyrrolidin-1-ylpropoxy)phenyl]tetrahydro-2H-pyran-4-yl}methyl)methanesulfonamide

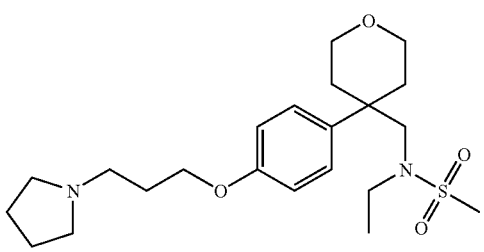

Methanesulfonyl chloride (19 μL, 0.24 mmol) was added dropwise to a solution of triethylamine (31 μL, 0.22 mmol) and N-({4-[4-(3-pyrrolidin-1-ylpropoxy)phenyl]tetrahydro-2H-pyran-4-yl}methyl)ethanamine (70 mg, 0.20 mmol) in dichloromethane (0.5 mL) at 0° C. then was allowed to warm to ambient temperature and stirred overnight. The reaction was quenched with NaHCO$_3$ (10 mL), extracted using dichloromethane (3×15 mL), dried using Na$_2$SO$_4$ and concentrated in vacuo. The compound was purified by column chromatography on Biotage® silica gel, eluting with dichloromethane:methanol:ammonia, 96.5:3.5:0.35 to 95:5:0.5 to give the title compound as a pale brown oil (60 mg, 71%). $^1$H NMR (400 MHz, CDCl$_3$) δ 7.24 (d, 2H), 6.90 (d, 2H), 4.02 (t, 2H), 3.84-3.72 (m, 2H), 3.50 (dt, 2H), 3.28 (s, 2H), 2.72-2.60 (m, 7H), 2.58-2.52 (m, 4H), 2.16 (m, 2H), 2.04 (pentet, 2H), 1.96-1.90 (m, 2H), 1.84-1.76 (m, 4H), 0.90 (t, 3H); HRMS (ESI$^+$) 425.2469 (M+H)$^+$.

Example 126

N-ethyl-N-({4-[4-(3-pyrrolidin-1-ylpropoxy)phenyl]tetrahydro-2H-pyran-4-yl}methyl)ethanesulfonamide

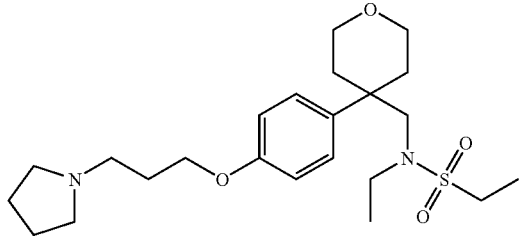

Ethanesulfonyl chloride (26 μL, 0.28 mmol) was added dropwise to a solution of triethylamine (35 μL, 0.25 mmol) and N-({4-[4-(3-pyrrolidin-1-ylpropoxy)phenyl]tetrahydro-2H-pyran-4-yl}methyl)ethanamine (78 mg, 0.23 mmol) in dichloromethane (0.5 mL) at 0° C. allowed to warm to ambient temperature and stirred overnight. The reaction was quenched with NaHCO$_3$ (10 mL), extracted using dichloromethane (3×10 mL), dried using Na$_2$SO$_4$ and concentrated in vacuo. The compound was purified by column chromatography on Biotage® silica gel, eluting with dichloromethane:methanol:ammonia, 96.5:3.5:0.35 to 95:5:0.5 to give the title compound as a pale brown oil (55 mg, 54%). $^1$H NMR (400 MHz, CDCl$_3$) δ 7.24 (d, 2H), 6.90 (d, 2H), 4.02 (t, 2H), 3.84-3.72 (m, 2H), 3.48 (t, 2H), 3.32 (s, 2H), 2.76 (quartet, 2H), 2.72-2.60 (m, 4H), 2.60-2.48 (m, 4H), 2.20-2.08 (m, 2H), 2.04 (pentet, 2H), 1.98-1.90 (m, 2H), 1.86-1.76 (m, 4H), 1.30 (t, 3H), 0.88 (t, 3H). HRMS (ESI$^+$) 439.2625 (M+H)$^+$.

Example 127

N-({4-[4-(3-pyrrolidin-1-ylpropoxy)phenyl]tetrahydro-2H-pyran-4-yl}methyl)ethanamine

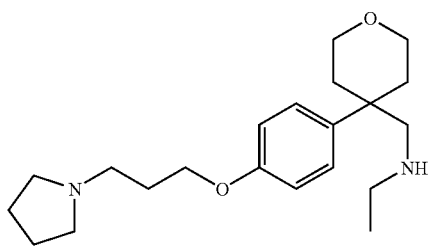

LiAlH$_4$ (1.0M in diethylether, 4.72 mL, 4.72 mmol) was added dropwise at 0° C. to a solution of (N-{4-[4-(3-pyrrolidin-1-yl-propoxy)-phenyl]-tetrahydro-pyran-4-ylmethyl}-acetamide (848 mg, 2.36 mmol) in tetrahydrofuran (2 mL) under an atmosphere of nitrogen. The reaction mixture was allowed to warm to ambient temperature for 2 hours then heated to 50° C. for 10 hours. The reaction mixture was cooled to 0° C., water (3 mL) was added dropwise followed by sodium hydroxide (2.0M, 6 mL) and water (3 mL). The resulting solid was filtered over a small pad of celite, washed with Et$_2$O/DCM (1:1 6×50 mL) and concentrated in vacuo to give the title compound as a pale yellow solid (635 mg, 78%). $^1$H NMR (400 MHz, CDCl$_3$) δ 7.20 (d, 2H), 6.88 (d, 2H), 4.02 (t, 2H), 3.80-3.68 (m, 2H), 3.55 (dt, 2H), 2.68 (s, 2H), 2.60 (t, 2H), 2.58-2.42 (m, 6H), 2.18-2.08 (m, 2H), 2.00 (pentet, 2H) 1.94-1.86 (m, 2H), 1.84-1.76 (m, 4H), 1.92 (t, 3H). HRMS (ESI$^+$) 347.2693 (M+H)$^+$.

Example 128

N-methyl-N-({4-[4-(3-pyrrolidin-1-ylpropoxy)phenyl]tetra-hydro-2H-pyran-4-yl}methyl)ethanamine

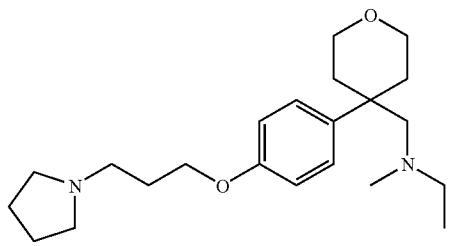

A solution of LiAlH$_4$ (1.0M in diethylether, 1.20 mL, 0.60 mmol) was added dropwise at 0° C. to a solution of N-methyl-N-{4-[4-(3-pyrrolidin-1-yl-propoxy)-phenyl]-tetrahydro-pyran-4-ylmethyl}-acetamide (220 mg, 0.60 mmol) in tetrahydrofuran (1 mL) under an atmosphere of nitrogen. The reaction mixture was allowed to warm to ambient temperature overnight. The reaction mixture was cooled to 0° C., water (1 mL) was added dropwise followed by sodium hydroxide (2.0M, 3 mL) and water (1 mL). The resulting solid was filtered over a small pad of celite, washed with DCM (150 mL) and concentrated in vacuo. The compound was purified by column chromatography on Biotage® silica gel, eluting with dichloromethane:methanol:ammonia, 97.5:2.5:0.25 to 95.5:4.5:0.45 to give the title compound as a pale yellow oil (114 mg, 88%). $^1$H NMR (400 MHz, CDCl$_3$) δ 7.18 (d, 2H), 6.86 (d, 2H), 4.04 (t, 2H), 3.78-3.70 (m, 2H), 3.52 (dt, 2H), 2.66 (t, 2H), 2.52-2.66 (m, 4H), 2.38 (s, 2H), 2.18 (quartet, 2H), 2.00-2.12 (m, 4H), 1.92-1.86 (m, 5H), 1.82-1.76 (m, 4H), 0.86 (t, 3H); HRMS (ESI$^+$) 361.2850 (M+H)$^+$.

Intermediate 47: 4-(4-{3-[(2S)-2-methylpyrrolidinyl]propoxy}phenyl)-tetrahydro-2H-pyran-4-carbonitrile A solution of 4-(4-hydroxy-phenyl)-tetrahydro-pyran-4-carbonitrile (203 mg, 1.0 mmol) and tri-n-butylphosphine (299 μL, 1.20 mmol) in toluene (6 mL) were added to a solution of 3-[(2R)-2-methylpyrrolidin-1-yl]propan-1-ol (172 mg, 1.20 mmol) in toluene (6 mL) and tetrahydrofuran (2 mL) at ambient temperature. 1'1-azobis(N,N-dimethylformamide) (206 mg, 1.20 mmol) was added and the reaction heated to 85° C. overnight. The reaction mixture was concentrated in vacuo followed by addition on dichloromethane (30 mL). The organic solution was then washed with NaOH (2.0M, 2×20 mL), dried with Na$_2$SO$_4$ and concentrated in vacuo. The compound was purified by column chromatography on Biotage® silica gel, eluting with dichloromethane:

methanol:ammonia, 98:2:0.2 to 96:4:0.4 to give the title compound as a pale yellow oil (70 mg, 21%). HRMS (ESI⁺) 329.2224 (M+H)⁺.

Example 129

4-(4-{3-[(2R)-2-methylpyrrolidin-1-yl]propoxy}phenyl)-tetra-hydro-2H-pyran-4-carboxylic acid

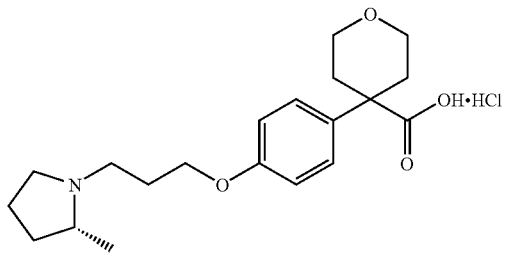

A solution of 4-(4-{3-[(2S)-2-methylpyrrolidinyl]propoxy}phenyl)tetrahydro-2H-pyran-4-carbonitrile (70 mg, 0.21 mmol) in concentrated hydrochloric acid (1 mL) was heated at reflux for 3 days. A further 2 mL of concentrated hydrochloric acid was added and the reaction heated at reflux for a further 2 days. The solution was evaporated to dryness in vacuo, triturated using acetone and azeotroped with toluene to give a pale brown solid (51 mg, 73%). $^1$H NMR (400 MHz, CDCl₃) δ 7.36 (d, 2H), 6.94 (d, 2H), 4.12 (t, 2H), 3.92-3.84 (m, 2H), 3.76-3.46 (m, 6H), 2.54-2.44 (m, 2H), 2.20-2.02 (m, 1H), (m, 8H), (m, 3H); HRMS (ESI⁺) 348.2170 (M+H)⁺.

Intermediate 48: tert-butyl 4-[4-(4-cyanotetrahydro-2H-pyran-4-yl)phenoxy]-1-piperidinecarboxylate tert-Butyl 4-[(methylsulfonyl)oxy]-1-piperidinecarboxylate (1.35 g, 4.93 mmol), 4-(4-hydroxyphenyl)tetrahydro-2H-pyran-4-carbonitrile (1.00 g, 4.93 mmol) and potassium carbonate (1.36 g, 9.85 mmol) were stirred in 10 ml DMF at 56° C. for 28 hours. The reaction mixture was partitioned between ethyl acetate (50 ml) and water (50 ml). The ethyl acetate was dried over Na₂SO₄ and concentrated under reduced pressure. The crude product was then purified by column chromatography on silica gel eluting with 2% diethylamine in ethylacetate. This only gave a poor separation, so the impure material was triturated with diisopropylether (20 ml) to give a white powder (1.5 g). This solid was dissolved in diethylether (100 ml) and washed with 2M NaOH (50 ml) then with water (50 ml). The diethylether was dried over Na₂SO₄ and evaporated to give tert-butyl 4-[4-(4-cyanotetrahydro-2H-pyran-4-yl)phenoxy]-1-piperidinecarboxylate as white crystals (740 mg, 39%).

Intermediate 49: 4-[4-(4-piperidinyloxy)phenyl]tetrahydro-2H-pyran-4-carbonitrile tert-Butyl 4-[4-(4-cyanotetrahydro-2H-pyran-4-yl)phenoxy]-1-piperidinecarboxylate (720 mg) was dissolved in dichloromethane (50 ml) at 0° C. TFA (10 ml) was added and the mixture stirred whilst warming to room temperature over 2 hours. The reaction mixture was then concentrated in vacuo, and partitioned between dichloromethane (80 ml) and 0.5M NaOH (50 ml). The dichlorormethane solution was dried over Na₂SO₄ and evaporated to give 4-[4-(4-piperidinyloxy)phenyl]tetrahydro-2H-pyran-4-carbonitrile as a colorless oil which crystallized on standing (500 mg, 94%).

Example 130

4-{4-[(1-cyclobutyl-4-piperidinyl)oxy]phenyl}tetrahydro-2H-pyran-4-carbonitrile

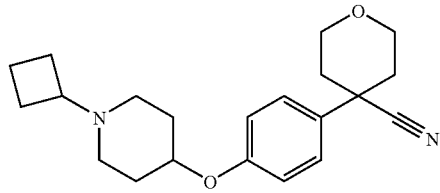

4-[4-(4-Piperidinyloxy)phenyl]tetrahydro-2H-pyran-4-carbonitrile (130 mg, 0.45 mmol) and cyclobutanone (140 μl, 1.9 mmol) were stirred in THF (2 ml) and acetic acid (26 μl, 0.45 mmol) at ambient temperature for 15 min. Sodium triacetoxyborohydride (340 mg, 1.6 mmol) was added and the mixture stirred for 18 hrs. The reaction was quenched by adding 10% aqueous Na₂CO₃ (5 ml) and then partitioned between ethyl acetate (50 ml) and water (30 ml). The organics were dried over Na₂SO₄ and evaporated to give a solid which was purified by column chromatography on silica gel eluting with dichloromethane:methanol:ammonia, 98:2:0.2 to 94:6:0.6 to give the product which was then crystallized from diisopropylether (5 ml) to give 4-{4-[(1-cyclobutyl-4-piperidinyl)oxy]phenyl}tetrahydro-2H-pyran-4-carbonitrile as a white powder (50 mg, 33%). $^1$H NMR (400 MHz, CDCl₃) δ7.38 (d, 2H), 6.93 (d, 2H), 4.33 (m, 1H), 4.08 (m, 2H), 3.89 (m, 2H), 2.75 (pentet, 1H), 2.62 (m, 2H), 2.20-1.58 (m, 16H)

Example 131

4-{4-[(1-isopropylpiperidin-4-yl)oxy]phenyl}tetrahydro-2H-pyran-4-carboxamide

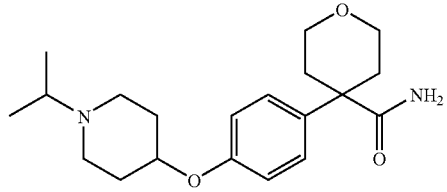

4-[4-(1-Isopropylpiperidin-4-yloxy)phenyl]tetrahydropyran-4-carbonitrile (50 mg, 0.152 mmol) was combined with boron trifluoride-acetic acid complex (500 μL, 3.6 mmol) and stirred at ambient temperature for 18 hours, followed by 65° C. for 3 hours. The reaction mixture was allowed to cool and then basified with saturated NaHCO₃ solution (15 mL). The product was extracted with dichloromethane (2×35 mL). The combined organic extracts were dried using Na₂SO₄ filtered and concentrated in vacuo. The compound was purified by column chromatography on silica gel (15 g), eluting with dichloromethane:methanol:ammonia, (96:4:0.4) to dichloromethane:methanol:ammonia, (90:10:1) to give the title compound as a white solid (22 mg, 42%). $^1$H NMR (400 MHz, CD₃OD) δ7.3 (d, 2H), 6.9 (d, 2H), 4.4 (m, 1H), 3.8 (m, 2H), 3.65 (m, 2H), 2.78-2.85 (m, 3H), 2.5 (m, 2H), 2.4 (d, 2H), 1.95-2.08 (m, 4H), 1.8 (m, 2H), 1.1 (d, 6H)

Example 132

4-{4-[(1-isopropylpiperidin-4-yl)oxy]phenyl}tetrahydro-2H-pyran-4-carboxylic acid

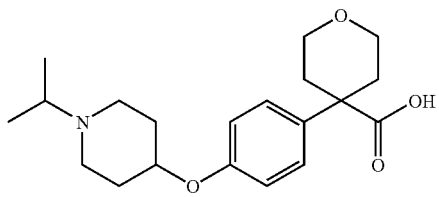

4-[4-(1-Isopropylpiperidin-4-yloxy)phenyl]tetrahydropyran-4-carbonitrile (1 g, 3 mmol) and concentrated hydrochloric acid (10 mL) were combined and heated at reflux for 44 hours. Reaction mixture was concentrated in vacuo the resulting grey solid was triturated with acetone (20 mL) to give a cream coloured solid. The compound was purified using an SCX isolelute column flushed with methanol (60 mL) and then flushed with 2M $NH_3$ in methanol (150 mL). The title compound was isolated as a cream coloured solid (550 mg, 52%). $^1$H NMR (400 MHz, $CD_3OD$) δ7.4 (d, 2H), 6.9 (d, 2H), 4.4 (m, 1H), 3.85 (m, 2H), 3.65 (m, 2H), 3.4 (m, 1H), 3.2 (m, 2h), 3.03 (m, 2H), 2.5 (m, 2H), 2.0-1.8 (m, 6H), 1.3 (d, 6H)

Example 133

4-{4-[(1-isopropylpiperidin-4-yl)oxy]phenyl}-N,N-dimethyltetrahydro-2H-pyran-4-carboxamide

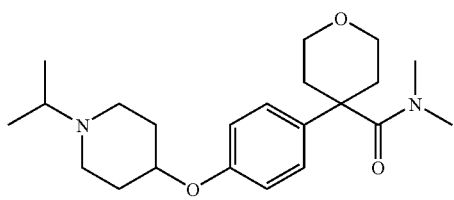

4-{4-[(1-Isopropylpiperidin-4-yl)oxy]phenyl}tetrahydro-2H-pyran-4-carboxylic acid (150 mg, 3.9 mmol), O-(1H-benzotriazol-1-yl)-N,N,N',N'-tetramethyluronium hexafluorophosphate (222 mg, 5.8 mmol), dimethylamine hydrochloride (96 mg, 1.1 mmol), pyridine (126 uL, 1.56 mmol) were combined and dissolved in dimethylformamide (2 mL). The reaction mixture was stirred at ambient temperature for 18 hours. Further O-(1H-benzotriazol-1-yl)-N,N,N',N'-tetramethyluronium hexafluorophosphate (222 mg, 5.8 mmol) and dimethylamine in ethanol (33%) (500 μL) was added and the reaction mixture was stirred at ambient temperature for 18 hours. The reaction mixture was diluted with water (20 mL) and was then extracted with ethyl acetate (2×40 mL). The combined organic extracts were dried using $Na_2SO_4$, filtered and concentrated in vacuo. The compound was purified by column chromatography on silica gel, eluting with dichloromethane:methanol:ammonia (97:3:0.3) to dichloromethane:methanol:ammonia (90:10:1) to give a compound as a clear colourless oil. This was dissolved in ethyl acetate (70 mL) and washed with saturated $NaHCO_3$ solution (2×10 mL). The organic extract was dried using $Na_2SO_4$, filtered and concentrated in vacuo to give the title compound as a clear crystalline solid (72 mg, 50%). $^1$H NMR (400 MHz, $CD_3OD$) δ7.2 (d, 2H), 6.95 (d, 2H), 4.4 (m, 1H), 3.85 (m, 2H), 3.7 (m, 2H), 2.9-2.5 (m, 11H), 2.28 (m, 2H), 2.0 (m, 4H), 1.8 (m, 2H), 1.1 (d, 6H)

Example 134

4-{4-[(1-isopropylpiperidin-4-yl)oxy]phenyl}-N,N-diethyltetra-hydro-2H-pyran-4-carboxamide

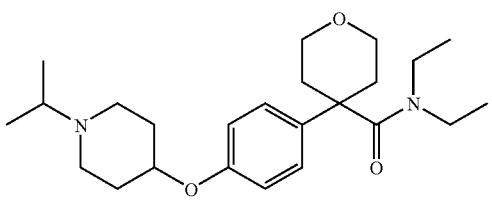

4-{4-[(1-Isopropylpiperidin-4-yl)oxy]phenyl}tetrahydro-2H-pyran-4-carboxylic acid (86 mg, 0.2 mol), diethylamine (27 μL, 0.26 mmol), O-(1H-benzotriazol-1-yl)-N,N,N',N'-tetramethyluronium hexafluorophosphate (108 mg, 0.29 mmol), pyridine (53 uL, 0.66 mmol) were combined and dissolved in dimethylformamide (1.5 mL). The reaction mixture was stirred at 60° C. for 5 hours. Further diethylamine was added (500 μL). The reaction mixture was stirred at ambient temperature for 60 hours. The reaction mixture was diluted with water (25 mL), and extracted with ethyl acetate (2×35 mL). The combined organics were dried using $Na_2SO_4$, filtered and concentrated in vacuo. The compound was purified by column chromatography using 15 g of silica gel, eluting with dichloromethane:methanol:ammonia (96:4:0.4) to dichloromethane:methanol:ammonia (90:10:1) to give the title compound as a clear yellow oil (10 mg, 11%). $^1$H NMR (400 MHz, $CD_3OD$) δ7.2 (d, 2H), 6.95 (d, 2H), 4.4 (m, 1H), 3.85-3.7 (m, 4H), 3.3 (m, 2H), 3.05-2.9 (m, 5H), 2.6 (m, 2H), 2.25 (d, 2H), 2.0 (m, 4H), 1.8 (m, 2H), 1.1 (m, 9H), 0.63 (m, 3H)

Example 135

4-{4-[(1-isopropylpiperidin-4-yl)oxy]phenyl)tetrahydro-2H-pyran-4-yl]carbonyl}pyrrolidine

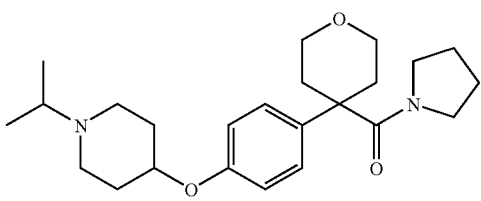

4-{4-[(1-Isopropylpiperidin-4-yl)oxy]phenyl}tetrahydro-2H-pyran-4-carboxylic acid (93 mg, 0.27 mmol) was suspended in dimethylformamide (3 mL), O-(1H-benzotriazol-1-yl)-N,N,N',N'-tetramethyluronium hexafluorophosphate (203 mg, 0.53 mmol), and triethylamine (112 μL, 0.8 mmol) were added. The reaction mixture was stirred at ambient temperature for 1 hour. Pyrrolidine (300 μL) was added and the reaction mixture was stirred at ambient temperature for 2.5 hours. The reaction mixture was concentrated in vacuo, then partitioned between saturated $NaHCO_3$ solution (50 mL)

and dichloromethane (2×75 mL). The combined organics were dried using Na₂SO₄, filtered and concentrated in vacuo. The compound was purified by column chromatography using 209 of silica gel, eluting with dichloromethane:methanol:ammonia (96:4:0.4) to dichloromethane:methanol:ammonia (94:6:0.6) to give the title compound as a clear oil (34 mg, 32%). ¹H NMR (400 MHz, CD₃OD) δ7.2 (d, 2H), 6.9 (d, 2H), 4.4 (m, 1H), 3.85-3.7 (m, 4H), 3.45 (m, 2H), 2.95 (m, 2H), 2.8-2.7 (m, 3H), 2.5 (m, 2H), 2.3 (m, 2H), 2.0 (m, 4H), 1.8-1.7 (m, 4H), 1.6 (m, 2H), 1.1 (d, 6H).

Intermediate 50: 4-[4-(3-pyrrolidin-1-ylpropoxy)phenyl]tetrahydro-2H-pyran-4-carbothioamide 4-[4-(3-Pyrrolidin-1-yl-propoxy)-phenyl]-tetrahydro-pyran-4-carbonitrile (2 g, 6.4 mmol), diethyl dithiophosphate (15 mL, 8.9 mmol), and water (1.5 mL) were combined and stirred at ambient temperature for 5 hours, 55° C. for 2 hours then 70° C. for 2 hours. The reaction mixture was diluted with dichloromethane (100 mL) and basified to pH 8 with a saturated solution of NaHCO₃ in water, and solid NaHCO₃. The layers were separated, and further dichloromethane (100 mL) was used to extract the product. The combined organics were dried using Na₂SO₄, filtered and concentrated in vacuo to leave a yellow oil. The compound was purified with column chromatography on 50 g of silica, eluting with dichloromethane:methanol:ammonia (96:4:0.4) to dichloromethane:methanol:ammonia (90:10:1) to give a clear oil. The clear oil was dissolved in ethyl acetate (150 mL) and washed with 10% Na₂CO₃ solution. The organic layer was dried using Na₂SO₄, filtered and concentrated in vacuo to give the title compound as a white solid (0.61 g, 28%).

Example 136

4-methyl-2-[4-(4-(3-pyrrolidin-1-ylpropoxy)phenyl)tetrahydro-2H-pyran-4-yl]-1,3-thiazole

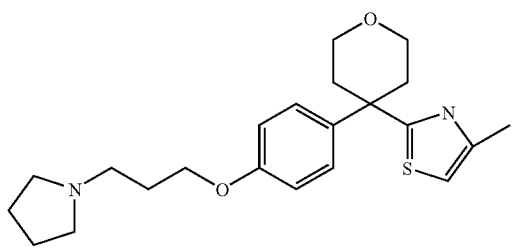

4-[4-(3-Pyrrolidin-1-ylpropoxy)phenyl]tetrahydro-2H-pyran-4-carbothioamide (100 mg, 0.29 mmol), chloroacetone (46 μL, 0.57 mmol) and ethanol (5 mL) were combined and heated at reflux for 18 hours. The reaction mixture was concentrated in vacuo to give a cream coloured solid. This was dissolved in dichloromethane (100 mL) and washed with saturated NaHCO₃ solution (50 mL). The organic extract was dried using Na₂SO₄, filtered and concentrated in vacuo. The compound was purified by column chromatography using 15 g of silica gel, eluting with dichloromethane:methanol:ammonia (97:3:0.3) to dichloromethane:methanol:ammonia (94:6:0.6) to give the title compound as a white solid (68 mg, 61%). ¹H NMR (400 MHz, CDCl₃) δ7.3 (d, 2H), 6.9 (d, 2H), 6.75 (s, 1H), 4.0 (t, 2H), 3.83 (m, 2H), 3.7 (m, 2H), 2.75-2.58 (m, 8H), 2.4 (s, 3H), 2.35 (m, 2H), 2.03 (m, 2H), 1.8 (m, 4H)

Example 137

2-[4-(4-(3-pyrrolidin-1-ylpropoxy)phenyl)tetrahydro-2H-pyran-4-yl]-1,3-thiazole

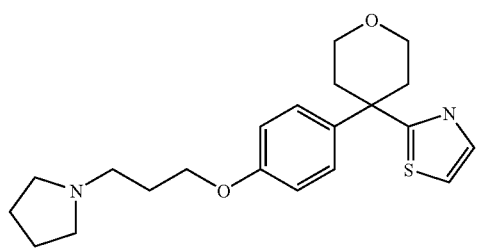

4-[4-(3-Pyrrolidin-1-ylpropoxy)phenyl]tetrahydro-2H-pyran-4-carbothioamide (150 mg, 0.43 mmol), bromoacetaldehyde diethylacetal (67 μL, 0.43 mmol), concentrated hydrochloric acid (5 drops) and ethanol were combined and heated at reflux for 5 hours. The reaction mixture was concentrated in vacuo and partitioned between 10% Na₂CO₃ (20 mL) and dichloromethane (2×35 mL). The combined organics were dried using Na₂SO₄, filtered and concentrated in vacuo. The compound was purified using column chromatography using 15 g of silica gel, eluting with dichloromethane:methanol:ammonia (95:5:0.5) to give a cream coloured solid. This was triturated with 3 mL of diethyl ether to give the title compound as a cream coloured solid (25 mg, 16%). ¹H NMR (400 MHz, CD₃OD) δ7.7 (s, 1H), 7.45 (s, 1H), 7.3 (d, 2H), 6.9 (d, 2H), 4.0 (t, 2H), 3.8 (m, 2H), 3.7 (m, 2H), 2.85-2.75 (m, 6H), 2.6 (m, 2H), 2.4 (m, 2H), 2.03 (m, 2H), 1.9 (m, 4H)

Intermediate 51: (4-{4-[(1-isopropylpiperidin-4-yl)oxy]phenyl}tetrahydro-2H-pyran-4-yl)methylamine To a stirred solution 4-[4-(1-isopropylpiperidin-4-yloxy)phenyl]tetrahydropyran-4-carbonitrile (2.5 g, 7.62 mmol) in dry diethyl ether (15 ml) at 0° C. was added dropwise a solution of LiAlH₄ (1.0M solution in Et₂O, 22.87 ml, 22.9 mmol). Reaction stirred at 0° C. for 30 min, then warmed up to ambient temperature overnight under a nitrogen atmosphere until complete. The reaction was cooled to 0° C., water (0.9 ml) was added dropwise followed by sodium hydroxide (2.0M, 0.9 ml) and water (2.7 ml). Dichloromethane (25 ml) and methanol (1 ml) were added and the mixture filtered through a short pad of arbocel, eluting with 2% methanol in dichloromethane (200 ml). The organic washings were dried over Na₂SO₄ and concentrated in vacuo to give the title compound as an orange oil (2.59 g, 100%).

Intermediate 52: tert-butyl [4-(4-[(1-isopropylpiperidin-4-yl)oxy]phenyl)tetrahydro-2H-pyran-4-yl]methylcarbamate To a stirred solution of (4-{4-[(1-isopropylpiperidin-4-yl)oxy]phenyl}tetrahydro-2H-pyran-4-yl)methylamine (600 mg, 1.81 mmol) and triethylamine (578 μl. 5.42 mmol) in dichloromethane (2.5 ml) at 0° C., was added dropwise a solution of di-tert-butyldicarbonate (540 μl, 2.35 mmol) in dichloromethane (2.5 ml). Solution stirred at 0° C. for 2 hours then allowed to warm up to ambient temperature and stirred until reaction complete. Reaction mixture diluted with dichloromethane (10 ml), washed with water (3×10 ml) then brine (2×10 ml). Organic washings dried over Na₂SO₄ and concentrated in vacuo. The compound was purified by column chromatography on silica gel, eluting with dichloromethane:methanol:ammonia, 100:0:0 to 96:4:0:0.4 to give the title compound as a foam (532 mg, 68%).

Example 138

N-[(4-{4-[(1-isopropylpiperidin-4-yl)oxy]phenyl}tetrahydro-2H-pyran-4-yl)methyl]-N-methylamine

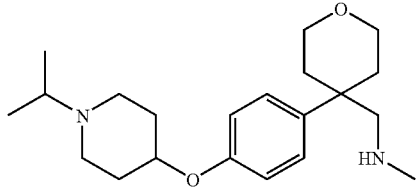

To a stirred solution of tert-butyl [4-(4-[(1-isopropylpiperidin-4-yl)oxy]phenyl)tetrahydro-2H-pyran-4-yl]methylcarbamate (532 mg, 1.23 mmol) in THF (3.5 ml) at 0° C. was added dropwise a solution of LiAlH$_4$ (1.0M solution in Et$_2$O, 3.69 ml, 3.69 mmol). Reaction stirred for 60 hours at ambient temperature before a further dropwise addition of LiAlH$_4$ (1.0M solution in Et$_2$O, 0.6 ml, 0.6 mmol). Heated at 40° C. until reaction complete. The reaction was then cooled to 0° C., water (0.2 ml) was added dropwise followed by sodium hydroxide (2.0M, 0.2 ml) and water (0.6 ml). 1% methanol in dichloromethane (10 ml) was added and the mixture filtered through a short pad of arbocel, eluting with 1% methanol in dichloromethane (25 ml). The organic washings were dried over Na$_2$SO$_4$ and concentrated in vacuo to give the title compound as a solid (399 mg, 94%). $^1$H NMR (400 MHz, CDCl$_3$) δ 7.20 (d, 2H), 7.88 (d, 2H), 4.22-4.34 (m, 1H), 3.70-3.80 (m, 2H), 3.60-4.01 (d, 2H), 2.70-2.88 (m, 3H), 2.64 (s, 2H), 2.32-2.44 (m, 2H) 2.24 (s, 3H), 2.10-2.18 (M, 2H), 1.99-2.08 (m, 2H), 1.79-1.96 (m, 4H), 1.03 (d, 6H).

Example 139

N-{[4-(4-[(1-isopropylpiperidin-4-yl)oxy]phenyl)tetrahydro-2H-pyran-4-yl]methyl}-N-methylacetamide

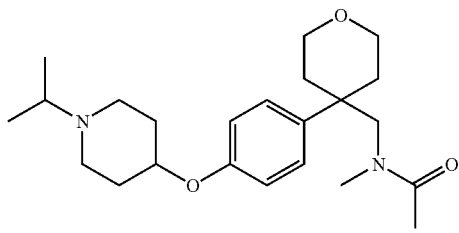

To a stirred solution of N-[(4-{4-[(1-isopropylpiperidin-4-yl)oxy]phenyl}tetrahydro-2H-pyran-4-yl)methyl]-N-methylamine (120 mg, 0.347 mmol) and triethylamine (121 μl, 0.867 mmol) in dichloromethane (1 ml) at 0° C. was added dropwise acetic anhydride (36 μl, 0.382 mmol). The reaction mixture was warmed to ambient temperature until reaction complete. Water (1 ml) and dichloromethane (15 ml) added to the reaction, the extracted with saturated NaHCO$_3$ (2×10 ml). Organic washings were dried over Na$_2$SO$_4$ and concentrated in vacuo to give the title compound as an oil (113 mg, 83%). $^1$H NMR (400 MHz, CDCl$_3$) δ 7.10-7.22 (2 doublets due to rotamers, 2H), 6.80 (d, 2H), 4.24-4.38 (m, 1H), 3.79-3.80 (m, 2H), 3.42-3.60 (m, 2H), 2.70-2.90 (m, 3H), 2.39-2.48 (m, 2H), 3.20-3.35 (singlet and doublet due to rotamers, 3H), 1.75-2.10 (m, 11H), 1.10 (d, 6H).

Example 140

N-{[4-(4-[(1-isopropylpiperidin-4-yl)oxy]phenyl)tetrahydro-2H-pyran-4-yl]methyl}-N-methylpropanamide

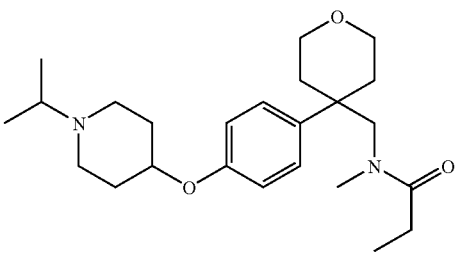

To a stirred solution of N-[(4-{4-[(1-isopropylpiperidin-4-yl)oxy]phenyl}tetrahydro-2H-pyran-4-yl)methyl]-N-methylamine (120 mg, 0.347 mmol) and triethylamine (121 μl, 0.867 mmol) in dichloromethane (1 ml) at 0° C. was added dropwise propionic anhydride (44 μl, 0.382 mmol). Reaction allowed to warm up to ambient temperature until reaction complete. Water (0.5 ml) and dichloromethane (15 ml) added to the reaction. The organic phase was separated and extracted with saturated NaHCO$_3$ (3×10 ml). Organic washings were dried over Na$_2$SO$_4$ and concentrated in vacuo to give the title compound as an oil (153 mg, 82%). $^1$H NMR (400 MHz, CD$_3$OD) δ 7.20-7.32 (2 doublets due to rotamers, 2H), 7.95 (d, 2H), 3.95-4.05 (m, 1H), 3.76-3.85 (m, 2H), 3.40-3.60 (multiple peaks due to rotamers, 4H), 2.70-2.88 (multiple peaks due to rotamers, 4H), 2.42-2.58 (m, 2H), 2.40 (s, 2H), 2.20-2.38 (m, 2H), 1.52-2.58 (several multiplets, 8H), 1.10 (d, 6H), 0.70-1.08 (two triplets due to rotamers, 3H).

Example 141

N-{[4-(4-[(1-isopropylpiperidin-4-yl)oxy]phenyl)tetrahydro-2H-pyran-4-yl]methyl}-acetamide

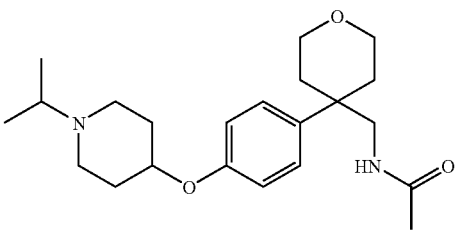

To a stirred solution of (4-{4-[(1-isopropylpiperidin-4-yl)oxy]phenyl}tetrahydro-2H-pyran-4-yl)methylamine (250 mg, 0.753 mmol) and triethylamine (200 μl. 1.88 mmol) in dichloromethane (2 ml) was added dropwise acetic anhydride (78 μl, 0.828 mmol). Reaction left at ambient temperature until reaction complete. Dichloromethane (10 ml) added to the reaction, the organic phase extracted with saturated NaHCO$_3$ (3×10 ml). Organic washings were dried over Na$_2$SO$_4$ and concentrated in vacuo to give the title compound as an oil (203 mg, 72%). ¹H NMR (400 MHz, CDCl₃) δ 7.19 (d, 2H), 6.94 (d, 2H), 4.95-5.02 (broad, 1H), 4.24-4.38 (m, 1H), 3.79-3.88 (m, 2H), 3.52-3.64 (m, 2H), 3.45 (d, 2H), 2.70-2.88 (m, 3H), 2.36-2.45 (m, 2H), 1.98-2.10 (m, 4H), 1.78-1.90 (m, 7H), 1.05 (d, 6H).

Example 142

N-[(4-{4-[(1-isopropylpiperidin-4-yl)oxy]phenyl}-4-tetrahydro-2H-pyran-4-yl)methyl]-N-ethylamine

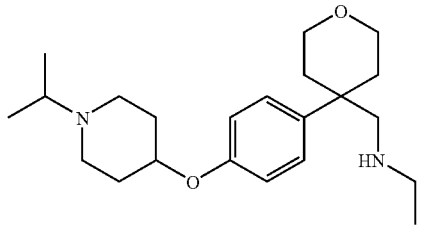

To a stirred solution of N-{[4-(4-[(1-isopropylpiperidin-4-yl)oxy]phenyl)tetrahydro-2H-pyran-4-yl]methyl}-acetamide (192 mg, 0.513 mmol) in THF (1.5 ml) at 0° C. was added dropwise a solution of LiAlH₄ (1.0M solution in Et₂O, 1.54 ml, 1.54 mmol). Reaction heated at 40° C. for 24 hours, then increased to 50° C. A further dropwise addition of LiAlH₄ (1.0M solution in Et₂O, 2 ml, 2 mmol) and further heating at 50° C. for 24 hours was required for reaction to reach completion. The reaction was then cooled to 0° C., water (0.15 ml) was added dropwise followed by sodium hydroxide (2.0M, 0.15 ml) and water (0.45 ml). 1% methanol in dichloromethane (15 ml) was added and the mixture filtered through a short pad of Arbocel®, eluting with 1% methanol in dichloromethane (25 ml). The organic washings were dried over Na₂SO₄ and concentrated in vacuo (185 mg crude, 82%). The compound was purified by column chromatography on silica gel, eluting with dichloromethane:methanol:ammonia, 98:2:0.2, to give the title compound as a white solid (9.9 mg, 4.4%). ¹H NMR (400 MHz, CDCl₃) δ 7.20 (d, 2H), 7.88 (d, 2H), 4.24-4.56 (m, 1H), 3.71-3.82 (m, 2H), 3.52-3.63 (m, 2H), 2.72-2.88 (m, 3H), 2.70 (s, 2H), 2.46-2.52 (quartet, 2H), 2.34-2.42 (m, 2H), 1.78-2.18 (several multiplets, 8H), 1.08 (d, 6H), 0.96 (t, 3H).

Example 143

N-{[4-(4-[(1-isopropylpiperidin-4-yl)oxy]phenyl) tetrahydro-2H-pyran-4-yl]methyl}-N-ethylacetamide

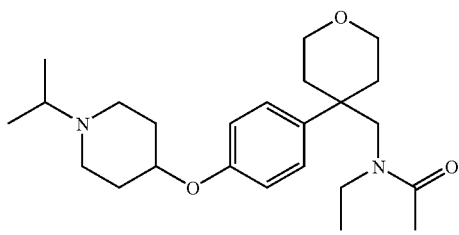

To a stirred solution of N-[(4-{4-[(1-isopropylpiperidin-4-yl)oxy]phenyl}tetrahydro-2H-pyran-4-yl)methyl]-N-ethylamine (102 mg, 0.283 mmol) and triethylamine (99 μl. 0.708 mmol) in dichloromethane (1 ml) was added dropwise acetic anhydride (29 μl, 0.312 mmol). Reaction left at ambient temperature for 4 hours until reaction complete. Water (1 ml) and dichloromethane (10 ml) added to the reaction, the extracted with saturated NaHCO₃ (2×10 ml). Organic washings were dried over Na₂SO₄ and concentrated in vacuo to give the title compound as an oil (107 mg, 94%). ¹H NMR (400 MHz, CD₃OD) δ 7.20-7.31 (multiplet due to rotamers, 2H), 6.92-7.00 (multiplet due to rotamers, 2H), 4.36-4.46 (m, 1H), 3.70-3.88 (m, 2H), 3.20-3.55 (several peaks due to rotamers, 4H), 2.78-2.90 (m, 3H), 2.60, (q, 2H), 2.25-2.52 (multiple peaks due to rotamers, 2H), 1.70-2.10 (multiple peaks, 11H), 1.10 (d, 6H), 0.80-1.00 (two triplets due to rotamers, 3H).

Example 144

1-{[4-(4-[(1-isopropylpiperidin-4-yl)oxy]phenyl) tetrahydro-2H-pyran-4-yl]methyl}pyrrolidin-2-one

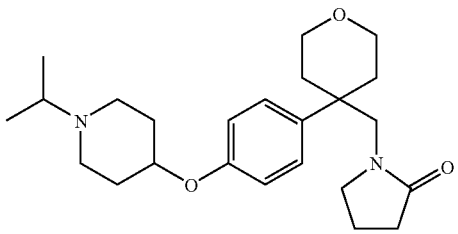

To a solution of (4-{4-[(1-isopropylpiperidin-4-yl)oxy] phenyl}tetrahydro-2H-pyran-4-yl)methylamine (100 mg, 0.301 mmol) in toluene (2 ml) was added ethyl-4-bromobutyrate (43 μl, 0.301 mmol), N,N-diisopropylethylamine (157 μl, 0.904 mmol) and potassium iodide (5 mg, 0.030 mmol). Reaction mixture heated at 80° C. for 48 hours, then increased to reflux. Potassium carbonate (83 mg, 0.602 mmol) was added and reaction left at reflux for a further 24 hours until reaction complete. Reaction mixture was partitioned between ethyl acetate (20 ml) and saturated NaHCO₃ (10 ml). Organic washings were dried over Na₂SO₄ and concentrated in vacuo to give a brown oil (101 mg crude, 84%). The compound was purified by column chromatography on silica gel, eluting with dichloromethane:methanol:ammonia, 100:0:0 to 98:2:0.2, to give the title compound as an oil (7 mg, 6%). ¹H NMR (400 MHz, CDCl₃) δ 7.20 (d, 2H), 7.90 (d, 2H), 4.22-4.36 (m, 1H), 4.80-4.90 (m, 2H), 3.52-3.67 (m, 2H), 3.40 (s, 2H), 2.72-3.88 (several multiplets, 3H), 2.50 (t, 2H), 2.34-2.44 (m, 2H), 2.21-2.30 (t, 2H), 1.60-2.10 (several multiplets, 10H), 1.08 (d, 6H).

Example 145

N-{[4-(4-[(1-isopropylpiperidin-4-yl)oxy]phenyl) tetrahydro-2H-pyran-4-yl]methyl}pyrimidin-2-amine

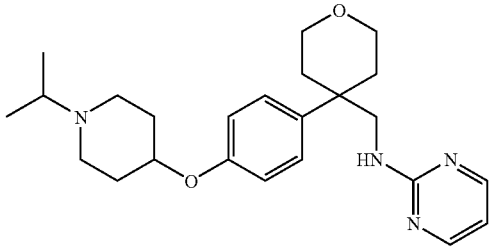

A mixture of (4-{4-[(1-isopropylpiperidin-4-yl)oxy] phenyl}tetrahydro-2H-pyran-4-yl)methylamine (150 mg, 0.422 mmol), 2-chloropyrimidine (52 mg, 0.422 mmol) and N,N-diisopropylethylamine (161 μl, 0.904 mmol) in N-methylpyrrolidinone (0.5 ml) was heated at 150° C. in the microwave (Smith Personal Synthesiser) for 900 seconds. The reaction mixture was partitioned between ethyl acetate (10 ml) and saturated NaHCO₃ (10 ml). The organic washings were dried over Na₂SO₄ and concentrated in vacuo to give an orange oil. The compound was purified by column chromatography on silica gel, eluting with dichloromethane:methanol:ammonia, 100:0:0 to 96:4:0.4, to give the title compound as a solid (87 mg, 47%). $^1$H NMR (400 MHz, CDCl₃) δ 8.20 (d, 2H), 7.21 (d, 2H), 6.90 (d, 2H), 6.48 (t, 2H), 4.71 (m, 1H), 4.20-4.35 (broad, 1H), 3.80-3.90 (m, 2H), 3.55-3.70 (multiple peaks, 4H), 2.70-2.90 (m, 3H), 2.32-2.49 (m, 2H), 1.78-2.19 (several multiplets, 8H), 1.10 (d, 6H).

Example 146

N-{[4-(4-(3-Pyrrolidin-1-ylpropoxy)phenyl)tetrahydro-2H-pyran-4-yl]methyl}pyrimidin-2-amine

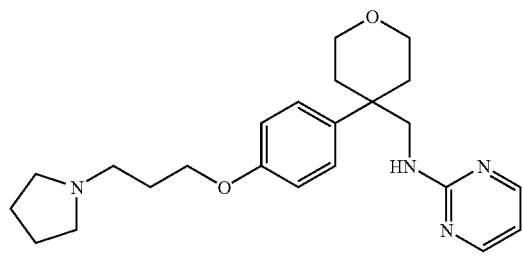

A mixture of {4-[4-(3-pyrrolidin-1-ylpropoxy)phenyl]tetrahydropyran-4-yl}methylamine (100 mg, 0.314 mmol), 2-chloropyrimidine (50 mg, 0.346 mmol) and N,N-diisopropylethylamine (112 μl, 0.629 mmol) in N-methylpyrrolidinone (0.5 ml) was heated at 180° C. in the microwave (Smith Personal Synthesiser) for 600 seconds. The reaction mixture was partitioned between ethyl acetate (10 ml) and saturated NaHCO₃ (10 ml). The organic washings were dried over Na₂SO₄ and concentrated in vacuo to give an oil. The compound was purified by column chromatography on silica gel, eluting with dichloromethane:methanol:ammonia, 100:0:0 to 88:12:1.2. Compound still impure so purified further on the Fraction Lynx automated LC system to give the title compound as a solid (22 mg, 17%) $^1$H NMR (400 MHz, CDCl₃) δ 8.30 (brs, 2H), 7.34 (d, 2H), 6.92 (d, 2H), 6.70 (t, 1H), 4.10 (t, 2H), 3.78-3.84 (m, 2H), 3.62-3.72 (multiple peaks, 4H), 3.44-3.55 (m, 2H), 3.40 (m, 2H), 3.04-3.18 (m, 2H), 1.85-2.25 (multiple peaks, 10H).

Example 147

2-{[4-(4-[(1-isopropylpiperidin-4-yl)oxy]phenyl)tetrahydro-2H-pyran-4-yl]methyl}isothiazolidine 1,1-dioxide

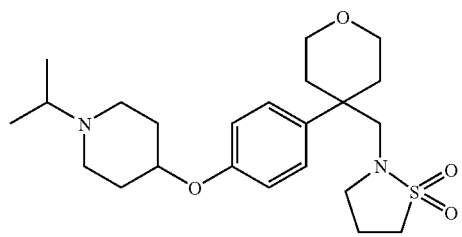

A solution of (4-{4-[(1-isopropylpiperidin-4-yl)oxy]phenyl}tetrahydro-2H-pyran-4-yl)methylamine (100 mg, 0.30 mmol), 3-chloropropanesulphonyl chloride (51 μl, 0.40 mmol) and N,N-diisopropylethylamine (521 μl, 0.30 mmol) in dichloromethane (2 ml) was stirred at room temperature for 18 hrs. The reaction mixture was concentrated in vacuo and then partitioned between dichloromethane (10 ml) and sodium bicarbonate solution (10 ml). The aqueous layer was extracted with a further 10 ml dichloromethane and the combined organics dried over sodium sulphate and concentrated in vacuo to give an oil. This was dissolved in tetrahydrofuran (2 ml). Potassium tert-butoxide (65 mg, 0.60 mmol) was added to the solution and the reaction mixture stirred at 40° C. for 18 hrs. This was then concentrated in vacuo and partitioned between diethyl ether (10 ml) and water (10 ml). The aqueous layer was extracted with a further 10 ml diethyl ether and the combined organics dried over sodium sulphate and concentrated in vacuo to give a pale yellow oil. The compound was purified by column chromatography on Biotage® silica gel, eluting with dichloromethane:methanol:ammonia, 96:4:0.4 to give the title compound as a pale yellow oil (19 mg, 15%). $^1$H NMR (400 MHz, CDCl₃) δ 7.20 (d, 2H), 6.90 (d, 2H), 4.26 (m, 2H), 3.80 (m, 2H), 3.58 (m, 2H), 3.15 (s, 2H), 2.99 (t, 2H), 2.80 (m, 2H), 2.75 (m, 2H), 2.40 (t, 2H), 2.38 (m, 2H), 2.16 (m, 2H), 2.02 (m, 4H), 1.90 (m, 2H) 1.81 (m, 2H), 1.03 (d, 6H); HRMS (ESI⁺) 437.2457 (M+H)⁺.

Intermediate 53: 4-{4-[(1-isopropylpiperidin-4-yl)oxy]phenyl}tetrahydro-2H-pyran-4-carbothioamide The title compound (320 mg, 74%) was prepared from 4-[4-(1-isopropylpiperidin-4-yloxy)phenyl]tetrahydropyran-4-carbonitrile and diethyl dithiophosphate similarly to the procedure used for intermediate 50. LRMS APCI⁺ m/z 363 [MH]⁺.

Example 148

1-isopropyl-4-{4-[4-(1,3-thiazol-2-yl)tetrahydro-2H-pyran-4-yl]phenoxy}piperidine

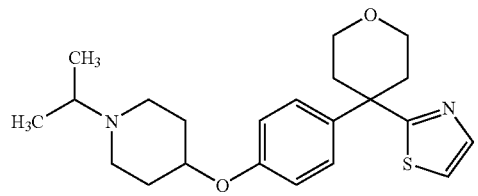

The title compound (320 mg, 74%) was prepared from 4-{4-[(1-isopropylpiperidin-4-yl)oxy]phenyl}tetrahydro-2H-pyran-4-carbothioamide and bromoacetaldehyde diethylacetal similarly to the procedure used for example 137. $^1$H NMR (400 MHz, CD₃OD) δ 1.10 (d, 6H), 1.75-1.80 (m, 2H), 1.98-2.02 (m, 2H), 2.37-2.44 (m, 2H), 2.47-2.51 (m, 2H), 2.61-2.65 (m, 2H), 2.75-2.84 (m, 3H), 3.66-3.70 (m, 2H), 3.78-3.83 (m, 2H), 4.37 (m, 1H), 6.89 (d, 2H), 7.28 (d, 2H), 7.46 (d, 1H), 7.70 (d, 1H). RMS ESI⁺ m/z 387.2090 [MH]⁺. Microanalysis: Found: C, 67.42; H, 7.83; N, 7.08%. C₂₂H₃₀N₂O₂S. 0.2H₂O requires C, 67.73; H, 7.85; N, 7.18%.

Example 149

4-{4-[4-(azetidin-1-ylcarbonyl)tetrahydro-2H-pyran-4-yl]phenoxy}-1-isopropylpiperidine

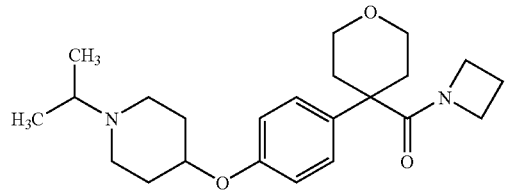

4-{4-[(1-Isopropylpiperidin-4-yl)oxy]phenyl}tetrahydro-2H-pyran-4-carboxylic acid (200 mg, 0.58 mmol), azetidine hydrochloride (81 mg, 0.87 mmol), 1-(3-dimethylaminopropyl)-3-ethylcarbodiimide hydrochloride (121 mg, 0.63 mmol), 1-hydroxybenzotriazole hydrate (97 mg, 0.63 mmol) and triethylamine (210 µL, 1.51 mmol) were stirred in dichloromethane (8 mL) at room temperature for 18 hours. The reaction was diluted with dichloromethane (60 mL) and washed with aqueous sodium bicarbonate. The aqueous were extracted again with dichloromethane. The organics were combined, dried over sodium sulphate, filtered and concentrated under reduced pressure. The crude product was purified by flash chromatography on silica gel eluting with dichloromethane:methanol:ammonia (96:4:0.5, by volume) to provide the title compound (97 mg, 43%) as a white solid. $^1$H NMR (400 MHz, CD$_3$OD) δ 1.11 (d, 6H), 1.77-1.82 (m, 2H), 1.88-1.95 (m, 2H), 2.01-2.08 (m, 4H), 2.26-2.29 (m, 2H), 2.47-2.52 (m, 2H), 2.76-2.86 (m, 3H), 3.66-3.74 (m, 4H), 3.79-3.82 (m, 2H), 3.92-3.96 (m, 2H), 4.40 (m, 1H), 6.95 (d, 2H), 7.22 (d, 2H). HRMS ESI$^+$ m/z 387.2634 [MH]$^+$.

Example 150

N-ethyl-4-{4-[(1-isopropylpiperidin-4-yl)oxy]phenyl}-N-methyltetrahydro-2H-pyran-4-carboxamide

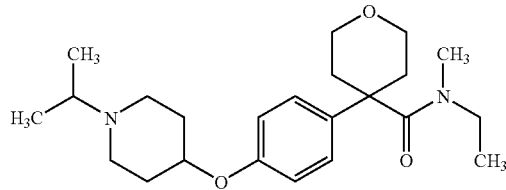

O-(1H-Benzotriazol-1-yl)-N,N,N'N'-tetramethyluronium hexafluorophosphate (286 mg, 0.75 mmol) was added to a solution of 4-{4-[(1-isopropylpiperidin-4-yl)oxy]phenyl}tetrahydro-2H-pyran-4-carboxylic acid (200 mg, 0.58 mmol) in N,N-dimethylformamide (6 mL). Then triethylamine (243 µL, 1.74 mmol) was added. The mixture was stirred at room temperature for 15 minutes. Ethylmethylamine (500 µL, 5.8 mmol) was added and the reaction mixture stirred at room temperature for 18 hours. The reaction was concentrated in vacuo. The residue was partitioned between aqueous sodium bicarbonate solution (30 mL) and ethyl acetate (2×75 mL). The organics were combined, dried over sodium sulphate, filtered and concentrated under reduced pressure. The crude product was purified by flash chromatography on silica gel eluting with dichloromethane:methanol:ammonia (96:4:0.5, by volume) to provide the title compound (80 mg, 35%). $^1$H NMR (400 MHz, CD$_3$OD) δ 1.06-1.25 (m, 9H), 1.90-2.02 (m, 4H), 2.08-2.12 (m, 2H), 2.25-2.28 (m, 2H), 2.58 (m, 2H), 2.87 (m, 3H), 2.95 (m, 2H), 3.09-3.12 (m, 3H), 3.71-3.76 (m, 2H), 3.82-3.86 (m, 2H), 4.53 (m, 1H), 6.98 (d, 2H), 7.20 (d, 2H).

HRMS ESI$^+$ m/z 389.2791 [MH]$^+$.

Example 151

1-[(4-{4-[(1-isopropylpiperidin-4-yl)oxy]phenyl}tetrahydro-2H-pyran-4-yl)carbonyl]-4-methylpiperazine

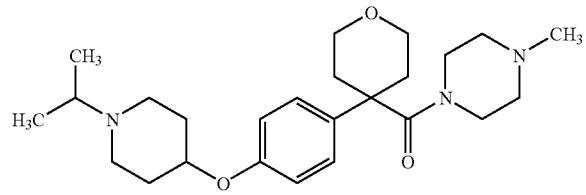

The title compound (60 mg, 48%) was prepared from 4-{4-[(1-isopropylpiperidin-4-yl)oxy]phenyl}tetrahydro-2H-pyran-4-carboxylic acid and N-methyl piperazine similarly to the procedure used for example 150. $^1$H NMR (400 MHz, CDCl$_3$) δ 1.05 (d, 6H), 1.79-1.81 (m, 2H), 2.00-2.03 (m, 7H), 2.15 (s, 3H), 2.18-2.22 (m, 2H), 2.37-2.42 (m, 2H), 2.77-2.79 (m, 3H), 2.99 (m, 1H), 3.27-3.56 (m, 4H), 3.78 (t, 2H), 3.87-3.89 (m, 2H), 4.28 (m, 1H), 6.88 (d, 2H), 7.14 (d, 2H).

HRMS ESI$^+$ m/z 430.3062 [MH]$^+$.

Example 152

N-[(4-{4-[(1-isopropyl piperidin-4-yl)oxy]phenyl}tetrahydro-2H-pyran-4-yl)methyl]pyridin-2-amine

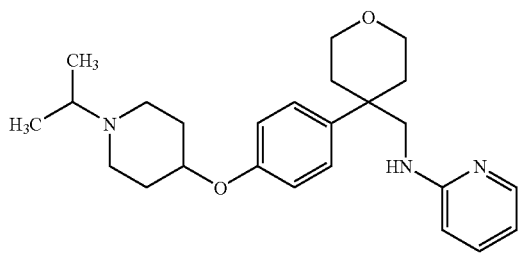

(4-{4-[(1-Isopropylpiperidin-4-yl)oxy]phenyl}tetrahydro-2H-pyran-4-yl)methylamine (300 mg, 0.9 mmol), 2-bromopyridine (50 µL, 0.75 mmol), tris(dibenzylideneacetone)dipalladium(0) (15 mg, 0.018 mmol), 2,2'-bis(diphenylphosphino)-1,1'-binaphthyl (19 mg, 0.036 mmol) and sodium tert-butoxide (100 mg, 1 mmol) were heated at 70° C. in toluene (6 ml) for 24 hours under nitrogen. The reaction was partitioned between aqueous sodium bicarbonate (302 ml) and dichloromethane (2×75 ml). The organics were combined, dried over sodium sulphate, filtered and concentrated under reduced pressure. The crude product was purified by flash chromatography on silica gel eluting with dichloromethane:methanol:ammonia (96:4:0.4, to 94:6:0.6 by volume) to provide the title compound (81 mg, 22%) as a white solid after trituration in diethyl ether. $^1$H NMR (400 MHz, CDCl$_3$) δ 1.11 (d, 6H), 1.86-1.95 (m, 4H), 2.07-2.16 (m, 4H), 2.46-2.51 (m, 2H), 2.82-2.86 (m, 3H), 3.49 (d, 2H), 3.56-3.61 (m, 2H), 3.80-3.85 (m, 2H), 4.03 (m, 1H), 4.33 (m, 1H), 6.22 (d, 1H), 6.51 (t, 1H), 6.91 (d, 2H), 7.24 (d, 2H), 7.32 (t, 1H), 8.01 (d, 1H). HRMS ESI$^+$ m/z 410.2793 [MH]$^+$.

Example 153

N-[(4-}4-[(1-isopropylpiperidin-4-yl)oxy]phenyl}tetrahydro-2H-pyran-4-yl)methyl]pyridin-3-amine

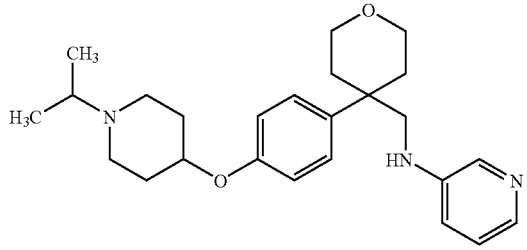

The title compound (20 mg, 5%) was prepared from (4-{4-[(1-isopropylpiperidin-4-yl)oxy]phenyl}tetrahydro-2H-pyran-4-yl)methylamine and 3-iodopyridine similarly to the procedure used for example 152. $^1$H NMR (400 MHz, CDCl$_3$) δ 1.12 (d, 6H), 1.88-1.95 (m, 4H), 2.10-2.21 (m, 4H), 2.51 (m, 2H), 2.83-2.88 (m, 3H), 3.22-3.27 (m, 3H), 3.55-3.59 (m, 2H), 3.77-3.82 (m, 2H), 4.35 (m, 1H), 6.73 (d, 1H), 6.93 (d, 2H), 7.00 (t, 1H), 7.24 (d, 2H), 7.87-7.90 (m, 2H). HRMS ESI$^+$ m/z 410.2791 [MH]$^+$.

Intermediate 54: 1-cyclobutylpiperidin-4-ol

4-Hydroxypiperidine (2.41 g, 23.8 mmol), cyclobutanone (5 g, 71.4 mmol) and acetic acid (1.36 ml, 23.8 mmol) were stirred in tetrahydrofuran (35 ml) at 0° C. for 1.5 hours. Sodium triacetoxyborohydride (10.1 g, 47.7 mmol) was then added at 0° C. and the reaction mixture stirred at 0° C. for 1 hour. The mixture was warmed to room temperature and stirred for 1 hour, then heated to 40° C. for 18 hours. The reaction was concentrated in vacuo. The residue was taken up in water (30 ml). The aqueous layer was basified to pH 9 with ammonia and extracted with diethyl ether (3×50 ml). The organics were combined, dried over magnesium sulphate, filtered and concentrated in vacuo. The crude product was purified by flash chromatography on silica gel eluting with dichloromethane:methanol:ammonia (100:0:0 to 93:7:0.7 by volume) to provide the title compound (2.47 g, 67%) as an oil. LRMS APCI$^+$ m/z 156 [MH]$^+$.

Example 154

1-(4-{4-[(1-cyclobutylpiperidin-4-yl)oxy] phenyl}tetrahydro-2H-pyran-4-yl)-N,N-dimethyl-methanamine

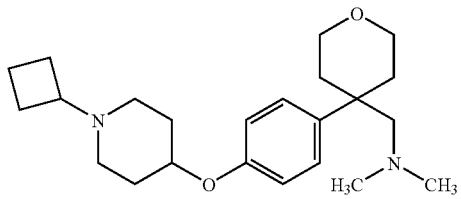

4-(4-Dimethylaminomethyl-tetrahydro-pyran-4-yl)-phenol (0.75 g, 3.19 mmol), 1-cyclobutylpiperidin-4-ol (0.45 g, 2.90 mmol), PPh$_3$ (0.84 g, 3.19 mmol), THF (10 ml) and DIAD (0.66 ml, 3.19 mmol) were reacted together similarly to general procedure C. The crude material was subjected to chromatography on silica gel eluting with dichloromethane: methanol:ammonia (98:2:0.2) to provide the title compound (114 mg, 11%) as an off-white solid. $^1$H NMR (400 MHz, CD$_3$OD) δ 1.71-1.77 (m, 4H), 1.85-1.90 (m, 4H), 1.94 (s, 6H), 1.99-2.06 (m, 4H), 2.12-2.16 (m, 2H), 2.20-2.28 (m, 2H), 2.45 (s, 2H), 2.58-2.70 (m, 2H), 2.79 (m, 1H), 3.46-3.53 (m, 2H), 3.72-3.75 (m, 2H), 4.39 (m, 1H), 6.91 (d, 2H), 7.26 (d, 2H). HRMS ESI$^+$ m/z 373.2846 [MH]$^+$.

Intermediate 55: ethyl {4-[(1-cyclobutylpiperidin-4-yl)oxy] phenyl}acetate

DIAD (9.8 ml, 47.3 mmol) was added dropwise over 10 minutes to a solution of ethyl-4-hydroxy phenylacetate (7.7 g, 42.7 mmol), 1-cyclobutylpiperidin-4-ol (6.58 g, 42.5 mmol) and PPh$_3$ (12.3 g, 47 mmol) in THF (150 ml) at 0° C. The reaction mixture was then stirred at room temperature for 18 hours. The reaction was concentrated in vacuo. The residue was taken up in ethyl acetate (150 ml). The organic layer was washed with water (150 ml) and 2N aqueous hydrochloric acid (50 ml) twice. The acid layers were basified with sodium carbonate and extracted with dichloromethane (2×80 ml). These organics were combined, dried over sodium sulphate, filtered and concentrated in vacuo. The crude product was purified by flash chromatography on silica gel eluting with ethyl acetate:pentane:diethylamine (70:30:2 by volume) to provide the title compound (2.0 g, 15%) as a colourless oil. LRMS APCI$^+$ m/z 318 [MH]$^+$.

Intermediate 56: ethyl 4-{4-[(1-cyclobutylpiperidin-4-yl) oxy]phenyl}tetrahydro-2H-pyran-4-carboxylate NaH (60% dispersion in oil, 800 mg, 20 mmol) was added at 0° C. to a solution of ethyl {4-[(1-cyclobutylpiperidin-4-yl)oxy]phenyl}acetate (2 g, 6.3 mmol) in THF (25 ml) and N-methylpyrrolidinone (2 ml) under nitrogen. The reaction was stirred at 0° C. for 15 minutes. Bis(2-bromoethyl)ether (1.2 ml, 9.54 mmol) and potassium iodide (500 mg, 3 mmol) were added and the mixture stirred at 0° C. for 45 minutes. The reaction was then warmed to room temperature and stirred for 18 hours. The reaction was cooled to 0° C., quenched with ice and solid carbon dioxide. The mixture was diluted with water and extracted with ethyl acetate (100 ml and 20 ml). The combined organic extracts were dried over sodium sulphate, filtered and concentrated in vacuo. The crude product was purified by flash chromatography on silica gel eluting with ethyl acetate:diethylamine (99:1 by volume) to provide the title compound (870 mg, 36%) as a pale yellow oil. LRMS APCI$^+$ m/z 388 [MH]$^+$.

Intermediate 57: 4-{4-[(1-cyclobutylpiperidin-4-yl)oxy] phenyl}tetrahydro-2H-pyran-4-carboxylic acid Sodium hydroxide (200 mg, 5 mmol) was added to a solution of ethyl 4-{4-[(1-cyclobutylpiperidin-4-yl)oxy] phenyl}tetrahydro-2H-pyran-4-carboxylate (870 mg, 2.25 mmol) in dioxane (10 ml) and water (2 ml). The reaction mixture was heated to reflux for 16 hours under nitrogen. The reaction was not complete. More sodium hydroxide (190 mg, 4.75 mmol) in water (4 ml) was added and the reaction heated at reflux for 18 hours. 2N Hydrochloric acid (5 ml, 9.75 mmol) was added and the mixture concentrated in vacuo to a white powder (2.0 g) containing the title compound and sodium chloride. LRMS APCI$^+$ m/z 360 [MH]$^+$.

Examples 155-160

The compounds of the following tabulated Examples of the general formula

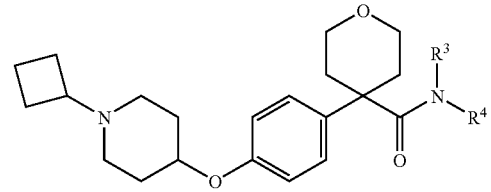

were prepared using 4-{4-[(1-cyclobutylpiperidin-4-yl)oxy] phenyl}tetrahydro-2H-pyran-4-carboxylic acid and the appropriate amines similarly to the procedure used for example 149.

| Ex No | NR$^3$R$^4$ | Analytical Data |
|---|---|---|
| 155 | NMe$_2$ | 4-{4-[(1-cyclobutylpiperidin-4-yl)oxy]phenyl}-N,N-dimethyltetrahydro-2H-pyran-4-carboxamide. $^1$H NMR (400 MHz, CD$_3$OD) δ 1.70-1.79 (m, 4H), 1.89-2.02 (m, 6H), 2.07-2.10 (m, 2H), 2.25 (d, 4H), 2.63-2.87 (m, 9H), 3.73 (t, 2H), 3.82-3.85 (m, 2H), 4.41 (m, 1H), 6.94 (d, 2H), 7.16 (d, 2H). HRMS ESI$^+$ m/z 387.2637 [MH]$^+$. 25% yield |

-continued

| Ex No | NR³R⁴ | Analytical Data |
|---|---|---|
| 156 | NHMe | 4-{4-[(1-cyclobutylpiperidin-4-yl)oxy]phenyl}-N-methyltetrahydro-2H-pyran-4-carboxamide. ¹H NMR (400 MHz, CD₃OD) δ 1.70-1.76 (m, 4H), 1.88-2.08 (m, 8H), 2.22-2.25 (m, 2H), 2.38-2.42 (m, 2H), 2.59-2.63 (m, 2H), 2.66 (s, 3H), 2.80 (m, 1H), 3.61 (t, 2H), 3.75-3.80 (m, 2H), 4.39 (m, 1H), 6.90 (d, 2H), 7.27 (d, 2H). HRMS ESI⁺ m/z 373.2480 [MH]⁺. 10% yield. |
| 157 | 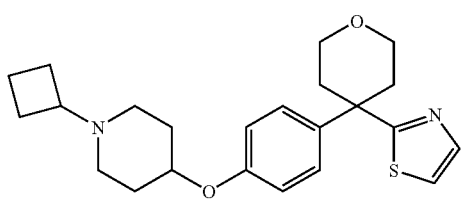 | 4-[(4-{4-[(1-cyclobutylpiperidin-4-yl)oxy]-phenyl}tetrahydro-2H-pyran-4-yl)carbonyl]-morpholine. ¹H NMR (400 MHz, CD₃OD) δ 1.70-1.76 (m, 4H), 1.85-2.09 (m, 8H), 2.20-2.24 (m, 4H), 2.63-2.67 (m, 2H), 2.81 (m, 1H), 3.25-3.31 (m, 6H), 3.33-3.39 (m, 2H), 3.73 (t, 2H), 3.82-3.87 (m, 2H), 4.41 (m, 1H), 6.96 (d, 2H), 7.20 (d, 2H). HRMS ESI⁺ m/z 429.2740 [MH]⁺. 20% yield |
| 158 | NH₂ | 4-{4-[(1-cyclobutylpiperidin-4-yl)oxy]phenyl}-tetrahydro-2H-pyran-4-carboxamide. ¹H NMR (400 MHz, CD₃OD) δ 1.76-1.82 (m, 2H), 1.94-2.00 (m, 4H), 2.06-2.10 (m, 4H), 2.20-2.22 (m, 2H), 2.42 (d, 2H), 2.65-2.79 (m, 2H), 2.89-2.99 (m, 2H), 3.26 (m, 1H), 3.66 (t, 2H), 3.78-3.82 (m, 2H), 4.55 (m, 1H), 6.95 (d, 2H), 7.34 (d, 2H). HRMS ESI⁺ m/z 359.2322 [MH]⁺. 13% yield |
| 159 | NHiPr | 4-{4-[(1-cyclobutylpiperidin-4-yl)oxy]phenyl}-N-isopropyltetrahydro-2H-pyran-4-carboxamide. ¹H NMR (400 MHz, CD₃OD) δ 1.04 (d, 6H), 1.70-1.77 (m, 4H), 1.88-2.00 (m, 6H), 2.05-2.08 (m, 2H), 2.20-2.26 (m, 2H), 2.42 (d, 2H), 2.60-2.68 (m, 2H), 2.81 (m, 1H), 3.62 (t, 2H), 3.77-3.82 (m, 2H), 3.99 (m, 1H), 4.39 (m, 1H), 6.90 (d, 2H), 7.28 (d, 2H). HRMS ESI⁺ m/z 401.2789 [MH]⁺. 13% yield |
| 160 | NHEt | 4-{4-[(1-cyclobutylpiperidin-4-yl)oxy]phenyl}-N-ethyltetrahydro-2H-pyran-4-carboxamide. ¹H NMR (400 MHz, CD₃OD) δ 1.01 (t, 3H), 1.69-1.75 (m, 4H), 1.88-2.01 (m, 6H), 2.04-2.07 (m, 2H), 2.16-2.28 (m, 2H), 2.41 (d, 2H), 2.56-2.68 (m, 2H), 2.79 (m, 1H), 3.15 (q, 2H), 3.62 (t, 2H), 3.76-3.80 (m, 2H), 4.38 (m, 1H), 6.89 (d, 2H), 7.28 (d, 2H). HRMS ESI⁺ m/z 387.2636 [MH]⁺. 22% yield |

Intermediate 58: 4-{4-[(1-cyclobutylpiperidin-4-yl)oxy]phenyl}tetrahydro-2H-pyran-4-carbothioamide The title compound (223 mg, 50%) was prepared from 4-{4-[(1-cyclobutyl-4-piperidinyl)oxy]phenyl}tetrahydro-2H-pyran-4-carbonitrile and diethyl dithiophosphate similarly to the procedure used for intermediate 50. LRMS APCI⁺ m/z 375 [MH]⁺.

Example 161

1-cyclobutyl-4-{4-[4-(1,3-thiazol-2-yl)tetrahydro-2H-pyran-4-yl]phenoxy}piperidine

The title compound (92 mg, 39%) was prepared from 4-{4-[(1-cyclobutylpiperidin-4-yl)oxy]phenyl}tetrahydro-2H-pyran-4-carbothioamide and bromoacetaldehyde diethylacetal similarly to the procedure used for example 137. ¹H NMR (400 MHz, CDCl₃) δ 1.66-1.72 (m, 2H), 1.77-1.89 (m, 5H), 1.95-2.04 (m, 4H), 2.11 (m, 1H), 2.36-2.43 (m, 2H), 2.58-2.72 (m, 5H), 3.71 (t, 2H), 3.84-3.88 (m, 2H), 4.27 (m, 1H), 6.84 (d, 2H), 7.23-7.26 (m, 3H), 7.70 (s, 1H). LRMS APCI⁺ m/z 399 [MH]⁺.

Example 162

1-cyclobutyl-4-{4-[4-(4-methyl-1,3-thiazol-2-yl)tetrahydro-2H-pyran-4-yl]phenoxy}piperidine

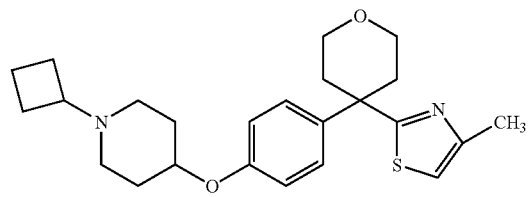

The title compound (155 mg, 83%) was prepared from 4-{4-[(1-cyclobutylpiperidin-4-yl)oxy]phenyl}tetrahydro-2H-pyran-4-carbothioamide and chloroacetone similarly to the procedure used for example 136. ¹H NMR (400 MHz, CDCl₃) δ 1.64-1.71 (m, 2H), 1.78-1.81 (m, 2H), 1.88-2.04 (m, 6H), 2.10-2.20 (m, 2H), 2.31-2.38 (m, 2H), 2.42 (s, 3H), 2.61-2.64 (m, 4H), 2.74 (m, 1H), 3.71 (t, 2H), 3.81-3.85 (m, 2H), 4.28 (m, 1H), 6.75 (s, 1H), 6.83 (d, 2H), 7.23 (d, 2H). HRMS ESI⁺ m/z 413.2257 [MH]⁺.

Intermediate 59: 1-(4-{4-[(1-cyclobutylpiperidin-4-yl)oxy]phenyl}tetrahydro-2H-pyran-4-yl)methanamine The title compound (1.05 g, 100%) was prepared from 4-{4-[(1-cyclobutyl-4-piperidinyl)oxy]phenyl}tetrahydro-2H-pyran-4-carbonitrile and lithium aluminium hydride similarly to the procedure used for intermediate 51. LRMS APCI⁺ m/z 345 [MH]⁺.

Example 163

N-[(4-{4-[(1-cyclobutylpiperidin-4-yl)oxy]phenyl}tetrahydro-2H-pyran-4-yl)methyl]pyrimidin-2-amine

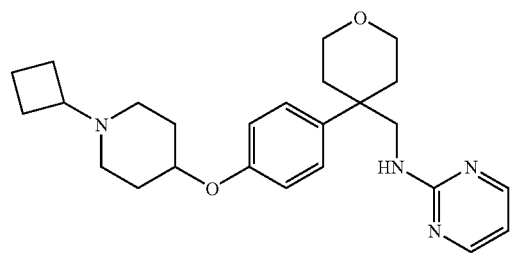

The title compound (31 mg, 25%) was prepared from 1-(4-{4-[(1-cyclobutylpiperidin-4-yl)oxy]phenyl}tetrahydro-2H-pyran-4-yl)methanamine and 2-chloropyrimidine similarly to the procedure used for example 145. ¹H NMR (400 MHz, CDCl₃) δ 1.66-1.73 (m, 2H), 1.83-1.95 (m, 6H), 1.98-2.15 (m, 8H), 2.60-2.66 (m, 2H), 2.75 (m, 1H), 3.57-3.62 (m, 2H), 3.66 (d, 2H), 3.81-3.85 (m, 2H), 4.31 (m, 1H), 4.68 (t, 1H), 6.47 (t, 1H), 6.90 (d, 2H), 7.23 (d, 2H), 8.20 (d, 2H). LRMS APCI⁺ m/z 423 [MH]⁺.

Example 164

N-[(4-{4-[(1-cyclobutylpiperidin-4-yl)oxy]phenyl}tetrahydro-2H-pyran-4-yl)methyl]pyridin-2-amine

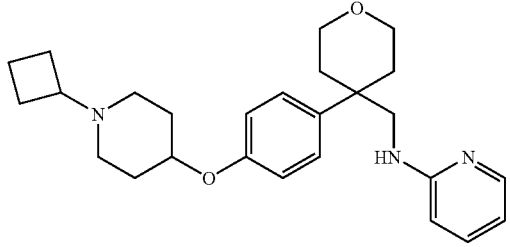

The title compound (25 mg, 31%) was prepared from 1-(4-{4-[(1-cyclobutylpiperidin-4-yl)oxy]phenyl}tetrahydro-2H-pyran-4-yl)methanamine and 2-bromopyridine similarly to the procedure used for example 152. $^1$H NMR (400 MHz, CDCl$_3$) δ 1.68-1.72 (m, 2H), 1.84-1.94 (m, 6H), 2.00-2.16 (m, 8H), 2.63-2.67 (m, 2H), 2.74 (m, 1H), 3.49 (d, 2H), 3.56-3.62 (m, 2H), 3.80-3.85 (m, 2H), 4.02 (m, 1H), 4.31 (m, 1H), 6.22 (d, 1H), 6.51 (t, 1H), 6.91 (d, 2H), 7.24 (d, 2H), 7.32 (t, 1H), 8.01 (d, 1H). HRMS ESI$^+$ m/z 422.2792 [MH]$^+$.

Example 165

N-[(4-{4-[(1-cyclobutylpiperidin-4-yl)oxy]phenyl}tetrahydro-2H-pyran-4-yl)methyl]pyridin-3-amine

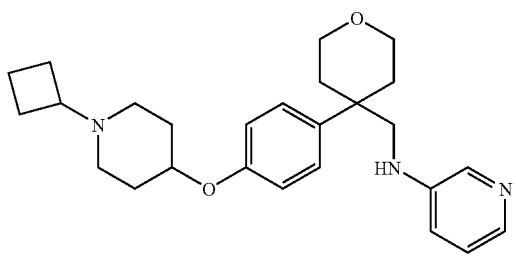

The title compound (28 mg, 18%) was prepared from 1-(4-{4-[(1-cyclobutylpiperidin-4-yl)oxy]phenyl}tetrahydro-2H-pyran-4-yl)methanamine and 3-iodopyridine similarly to the procedure used for example 153. $^1$H NMR (400 MHz, CDCl$_3$) δ 1.66-1.94 (m, 8H), 2.01-2.06 (m, 4H), 2.17-2.20 (m, 4H), 2.60-2.68 (m, 2H), 2.76 (m, 1H), 3.22-3.27 (m, 3H), 3.57 (t, 2H), 3.77-3.81 (m, 2H), 4.32 (m, 1H), 6.73 (d, 1H), 6.92 (d, 2H), 6.99 (m, 1H), 7.23 (d, 2H), 7.88 (m, 2H). HRMS ESI$^+$ m/z 422.2789 [MH]$^+$.

Example 166

1-acetyl-4-({4-[4-(3-pyrrolidin-1-ylpropoxy)phenyl]tetrahydro-2H-pyran-4-yl}methyl)piperazine

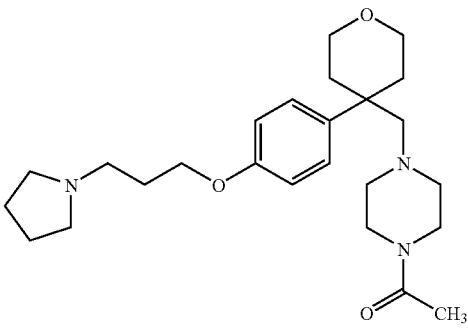

To a stirred solution of 1-{4-[4-(3-pyrrolidin-1-ylpropoxy)phenyl]tetrahydropyran-4-ylmethyl}piperazine (160 mg, 0.41 mmol) and N,N-diisopropylethylamine (180 μl, 1.03 mmol) in dichloromethane (2 ml) at 0° C. was added dropwise acetic anhydride (47 μl, 0.49 mmol). The reaction was allowed to warm up to room temperature and stirred for 18 hours. The reaction mixture was concentrated under reduced pressure and the residue partitioned between dichloromethane (20 ml) and aqueous sodium carbonate solution (20 ml). The layers were separated and the aqueous layer was extracted again with dichloromethane (20 ml). The organics were combined, dried over sodium sulphate, filtered and concentrated in vacuo. The crude product was purified by flash chromatography on silica gel eluting with dichloromethane:methanol:ammonia (96:4:0.4 to 90:10:1 by volume) to provide the title compound (34 mg, 19%) as a clear oil. $^1$H NMR (400 MHz, CDCl$_3$) δ 1.78-1.81 (m, 4H), 1.83-1.89 (m, 2H), 1.99 (s, 3H), 2.01-2.03 (m, 2H), 2.06-2.11 (m, 3H), 2.15-2.18 (m, 3H), 2.40 (s, 2H), 2.51-2.53 (m, 4H), 2.63 (t, 2H), 3.22 (t, 2H), 3.42-3.44 (m, 2H), 3.52 (t, 2H), 3.73-3.76 (m, 2H), 4.02 (t, 2H), 6.86 (d, 2H), 7.21 (d, 2H). HRMS ESI$^+$ m/z 430.3052 [MH]$^+$.

Example 167

1-isopropyl-4-({4-[4-(3-pyrrolidin-1-ylpropoxy)phenyl]tetrahydro-2H-pyran-4-yl}methyl)piperazine

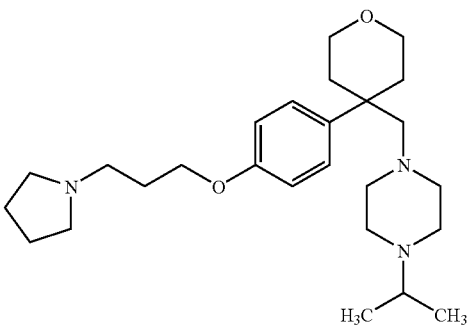

The title compound (78 mg, 44%) was prepared from 1-{4-[4-(3-pyrrolidin-1-ylpropoxy)phenyl]tetrahydropyran-4-ylmethyl}piperazine and acetone similarly to the procedure used for example 54. $^1$H NMR (400 MHz, CDCl$_3$) δ 0.98 (d, 6H), 1.77-1.80 (m, 4H), 1.86-1.93 (m, 2H), 1.98-2.02 (m, 2H), 2.06-2.09 (m, 2H), 2.20-2.22 (m, 4H), 2.34-2.36 (m, 6H), 2.50-2.54 (m, 5H), 2.62 (t, 2H), 3.52 (t, 2H), 3.71-3.75 (m, 2H), 4.02 (t, 2H), 6.85 (d, 2H), 7.21 (d, 2H). HRMS ESI$^+$ m/z 430.3417 [MH]$^+$.

Example 168

1-(cyclopropylmethyl)-4-({4-[4-(3-pyrrolidin-1-yl-propoxy)-phenyl]-tetrahydro-2H-pyran-4-yl}methyl)-piperazine

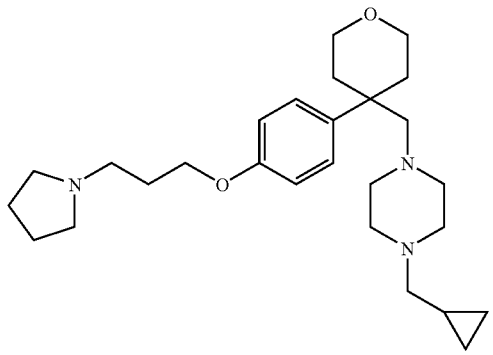

The title compound (26 mg, 14%) was prepared from 1-{4-[4-(3-pyrrolidin-1-ylpropoxy)phenyl]tetrahydropyran-4-ylmethyl}piperazine and cyclopropane carboxaldehyde similarly to the procedure used for example 54. $^1$H NMR (400 MHz, CDCl$_3$) δ 0.02 (q, 2H), 0.43 (q, 2H), 0.76 (m, 1H), 1.74-1.76 (m, 4H), 1.83-1.89 (m, 2H), 1.95-1.99 (m, 2H), 2.03-2.06 (m, 3H), 2.13 (d, 2H), 2.19-2.21 (m, 4H), 2.26-2.40 (m, 5H), 2.47-2.51 (m, 4H), 2.59 (t, 2H), 3.49 (t, 2H), 3.68-3.72 (m, 2H), 3.98 (t, 2H), 6.82 (d, 2H), 7.17 (d, 2H). HRMS ESI$^+$ m/z 442.3412 [MH]$^+$.

Example 169

1-cyclopropyl-N-(cyclopropylmethyl)-N-({4-[4-(3-pyrrolidin-1-ylpropoxy)phenyl]-tetrahydro-2H-pyran-4-yl}methyl)methanamine

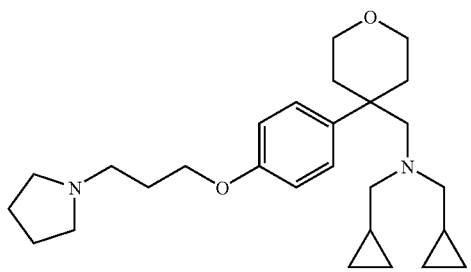

The title compound (169 mg, 51%) was prepared from {4-[4-(3-pyrrolidin-1-ylpropoxy)phenyl]tetrahydropyran-4-yl}methylamine free base and cyclopropane carboxaldehyde similarly to the procedure used for example 54. 3 equivalents of cyclopropane carboxaldehyde were required for the synthesis of this Example. $^1$H NMR (400 MHz, CDCl$_3$) δ −0.04 (q, 4H), 0.39 (q, 4H), 0.71-0.76 (m, 2H), 1.80-1.86 (m, 4H), 1.94-2.12 (m, 6H), 2.16 (d, 4H), 2.55-2.72 (m, 8H), 3.51 (t, 2H), 3.75-3.79 (m, 2H), 4.04 (t, 2H), 6.88 (d, 2H), 7.21 (d, 2H). HRMS ESI$^+$ m/z 427.3306 [MH]$^+$.

Examples 170-178

The compounds of the following tabulated Examples of the general formula

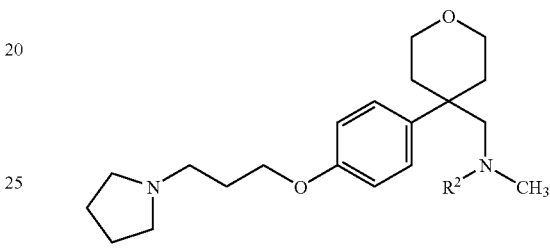

were prepared using methyl-{4-[4-(3-pyrrolidin-1-ylpropoxy)phenyl]-tetrahydropyran-4-ylmethyl}amine and the appropriate aldehydes or ketones similarly to the procedure used for example 54.

| Ex No | R$^2$ | Analytical Data |
|---|---|---|
| 170 | cyclopentyl | N-methyl-N-({4-[4-(3-pyrrolidin-1-ylpropoxy)-phenyl]tetrahydro-2H-pyran-4-yl}methyl)-cyclopentanamine. $^1$H NMR (400 MHz, CDCl$_3$) δ 1.21-1.28 (m, 2H), 1.39-1.43 (m, 2H), 1.53-1.60 (m, 4H), 1.83-1.94 (m, 9H), 2.07-2.12 (m, 4H), 2.41 (s, 2H), 2.61-2.72 (m, 7H), 3.49 (t, 2H), 3.73-3.79 (m, 2H), 4.02 (t, 2H), 6.89 (d, 2H), 7.20 (d, 2H). HRMS ESI$^+$ m/z 401.3162 [MH]$^+$. 53% yield |
| 171 | n-propyl (H$_3$C—) | N-methyl-N-({4-[4-(3-pyrrolidin-1-ylpropoxy)-phenyl]tetrahydro-2H-pyran-4-yl}methyl)-butan-1-amine. $^1$H NMR (400 MHz, CDCl$_3$) δ 0.83 (t, 3H), 1.15-1.20 (m, 2H), 1.23-1.29 (m, 2H), 1.85-1.92 (m, 9H), 2.07-2.15 (m, 6H), 2.40 (s, 2H), 2.69-2.77 (m, 6H), 3.51 (t, 2H), 3.73-3.78 (m, 2H), 4.03 (t, 2H), 6.86 (d, 2H), 7.20 (d, 2H). HRMS ESI$^+$ m/z 389.3153 [MH]$^+$. 57% yield |
| 172 | cyclohexyl | N-methyl-N-({4-[4-(3-pyrrolidin-1-ylpropoxy)-phenyl]tetrahydro-2H-pyran-4-yl}methyl)-cyclohexanamine. $^1$H NMR (400 MHz, CD$_3$OD) δ 1.02-1.14 (m, 6H), 1.53 (m, 1H), 1.60 (d, 2H), 1.69 (d, 2H), 1.81-1.87 (m, 6H), 1.91 (s, 3H), 1.99-2.03 (m, 2H), 2.14 (d, 2H), 2.49 (s, 2H), 2.61 (t, 4H), 2.69 (t, 2H), 3.48 (t, 2H), 3.72-3.76 (m, 2H), 4.03 (t, 2H), 6.89 (d, 2H), 7.24 (d, 2H). HRMS ESI$^+$ m/z 415.3314 [MH]$^+$. 61% yield |

-continued

| Ex No | R² | Analytical Data |
|---|---|---|
| 173 | 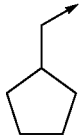 | 1-cyclopentyl-N-methyl-N-({4-[4-(3-pyrrolidin-1-ylpropoxy)phenyl]tetrahydro-2H-pyran-4-yl}methyl)methanamine. ¹H NMR (400 MHz, CD₃OD) δ 1.07-1.12 (m, 2H), 1.46-1.50 (m, 4H), 1.60-1.64 (m, 2H), 1.82-1.85 (m, 5H), 1.87-1.91 (m, 5H), 1.99-2.01 (m, 2H), 2.04 (d, 2H), 2.14 (d, 2H), 2.43 (s, 2H), 2.59-2.62 (m, 4H), 2.69 (t, 2H), 3.49 (t, 2H), 3.71-3.76 (m, 2H), 4.02 (t, 2H), 6.88 (d, 2H), 7.24 (d, 2H). HRMS ESI⁺ m/z 415.3313 [MH]⁺. 44% yield |
| 174 | 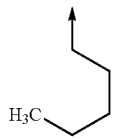 | N-methyl-N-({4-[4-(3-pyrrolidin-1-ylpropoxy)phenyl]tetrahydro-2H-pyran-4-yl}methyl)-pentan-1-amine. ¹H NMR (400 MHz, CD₃OD) δ 0.86 (t, 3H), 1.08-1.13 (m, 2H), 1.20-1.28 (m, 4H), 1.82-1.88 (m, 6H), 1.92 (s, 3H), 1.97-2.01 (m, 2H), 2.08 (t, 2H), 2.14 (d, 2H), 2.44 (s, 2H), 2.60-2.64 (m, 4H), 2.70 (t, 2H), 3.49 (t, 2H), 3.71-3.76 (m, 2H), 4.02 (t, 2H), 6.89 (d, 2H), 7.25 (d, 2H). HRMS ESI⁺ m/z 403.3313 [MH]⁺. 30% yield |
| 175 | 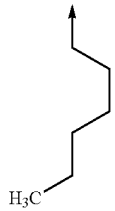 | N-methyl-N-({4-[4-(3-pyrrolidin-1-ylpropoxy)phenyl]tetrahydro-2H-pyran-4-yl}methyl)-hexan-1-amine. ¹H NMR (400 MHz, CDCl₃) δ 0.87 (t, 3H), 1.13-1.20 (m, 4H), 1.23-1.29 (m, 4H), 1.83-1.91 (m, 9H), 2.06-2.13 (m, 6H), 2.40 (s, 2H), 2.58-2.72 (m, 6H), 3.51 (t, 2H), 3.73-3.77 (m, 2H), 4.02 (t, 2H), 6.85 (d, 2H), 7.19 (d, 2H). HRMS ESI⁺ m/z 417.3469 [MH]⁺. 74% yield |
| 176 | 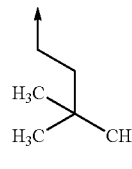 | N,3,3-trimethyl-N-({4-[4-(3-pyrrolidin-1-ylpropoxy)phenyl]tetrahydro-2H-pyran-4-yl}methyl)butan-1-amine. ¹H NMR (400 MHz, CDCl₃) δ 0.77 (s, 9H), 1.17 (t, 2H), 1.84-1.90 (m, 6H), 1.92 (s, 3H), 2.08-2.12 (m, 6H), 2.41 (s, 2H), 2.57-2.70 (m, 6H), 3.52 (t, 2H), 3.73-3.78 (m, 2H), 4.01 (t, 2H), 6.86 (d, 2H), 7.20 (d, 2H). HRMS ESI⁺ m/z 417.3457 [MH]⁺. 59% yield |
| 177 | 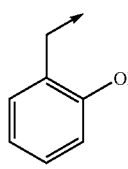 | 2-{[methyl({4-[4-(3-pyrrolidin-1-ylpropoxy)phenyl]tetrahydro-2H-pyran-4-yl}methyl)amino]methyl}phenol. ¹H NMR (400 MHz, CDCl₃) δ 1.78 (s, 3H), 1.79-1.85 (m, 6H), 2.06-2.09 (m, 2H), 2.21 (d, 2H), 2.67-2.75 (m, 8H), 3.48-3.54 (m, 4H), 3.70-3.75 (m, 2H), 4.03 (t, 2H), 6.73 (t, 1H), 6.77 (d, 1H), 6.86 (d, 1H), 6.90 (d, 2H), 7.13 (t, 1H), 7.25 (d, 2H). HRMS ESI⁺ m/z 439.2943 [MH]⁺. 30% yield |
| 178 | 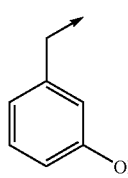 | 3-{[methyl({4-[4-(3-pyrrolidin-1-ylpropoxy)phenyl]tetrahydro-2H-pyran-4-yl}methyl)amino]methyl}phenol. ¹H NMR (400 MHz, CD₃OD) δ 1.83 (brs, 7H), 1.88-1.91 (m, 2H), 1.95-2.01 (m, 2H), 2.11-2.15 (m, 2H), 2.55 (s, 2H), 2.58-2.62 (m, 4H), 2.69 (t, 2H), 3.17 (s, 2H), 3.49 (t, 2H), 3.63-3.67 (m, 2H), 4.02 (t, 2H), 6.62 (d, 1H), 6.67 (d, 1H), 6.72 (s, 1H), 6.89 (d, 2H), 7.05 (t, 1H), 7.29 (d, 2H). HRMS ESI⁺ m/z 439.2941 [MH]⁺. 68% yield |

Examples 179-191

The compounds of the following tabulated Examples of the general formula

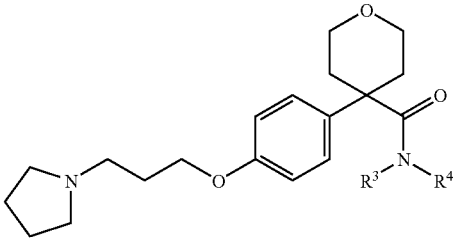

were prepared using 4-[4-(3-pyrrolidin-1-ylpropoxy)phenyl]tetrahydro-2H-pyran-4-carboxylic acid, the appropriate amines and O-(1H-benzotriazol-1-yl)-N,N,N',N'-tetramethyluronium hexafluorophosphate (HBTU), O-(1H-benzotriazol-1-yl)-N,N,N',N'-tetramethyluronium tetrafluoroborate (TBTU) or 1-[3-(Dimethylamino)propyl]-3-ethylcarbodiimide hydrochloride (WSCDI) similarly to the procedure used for example 150.

| Ex No | NR³R⁴ | Analytical Data |
|---|---|---|
| 179 | NEt₂ | N,N-diethyl-4-[4-(3-pyrrolidin-1-ylpropoxy)phenyl]tetrahydro-2H-pyran-4-carboxamide. ¹H NMR (400 MHz, CDCl₃) δ 0.64-0.74 (m, 3H), 1.04-1.12 (m, 3H), 1.79-1.82 (m, 4H), 1.91-2.03 (m, 4H), 2.23 (d, 2H), 2.54-2.58 (m, 4H), 2.65 (t, 2H), 2.86-2.94 (m, 2H), 3.27-3.35 (m, 2H), 3.77-3.89 (m, 4H), 4.01 (t, 2H), 6.86 (d, 2H), 7.15 (d, 2H). HRMS ESI⁺ m/z 389.2789 [MH]⁺. Microanalysis: Found: C, 69.16; H, 9.18; N, 7.05%. C₂₃H₃₆N₂O₃. 0.5H₂O requires C, 69.49; H, 9.38; N, 7.05% 68% yield |
| 180 | 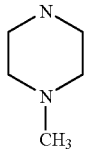 | 1-methyl-4-({4-[4-(3-pyrrolidin-1-ylpropoxy)phenyl]tetrahydro-2H-pyran-4-yl}carbonyl)-piperazine. ¹H NMR (400 MHz, CDCl₃) δ 1.76-1.81 (m, 4H), 1.97-2.03 (m, 8H), 2.15 (s, 3H), 2.19-2.22 (m, 2H), 2.50-2.54 (m, 4H), 2.62 (t, 2H), 3.26-3.44 (m, 4H), 3.78 (t, 2H), 3.87-3.90 (m, 2H), 4.02 (t, 2H), 6.88 (d, 2H), 7.15 (d, 2H). HRMS ESI⁺ m/z 416.2908 [MH]⁺. 9% yield |
| 181 | 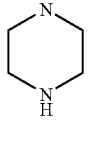 | 1-({4-[4-(3-pyrrolidin-1-ylpropoxy)phenyl]tetrahydro-2H-pyran-4-yl}carbonyl)piperazine. ¹H NMR (400 MHz, CDCl₃) δ 1.77-1.80 (m, 6H), 1.97-2.02 (m, 4H), 2.20 (d, 2H), 2.50-2.54 (m, 6H), 2.61 (t, 2H), 3.24-3.38 (m, 4H), 3.78 (t, 2H), 3.86-3.90 (m, 2H), 4.00 (t, 2H), 6.87 (d, 2H), 7.15 (d, 2H). HRMS ESI⁺ m/z 402.2746 [MH]⁺. 43% yield |
| 182 | 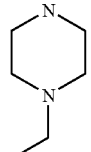 | 1-propyl-4-({4-[4-(3-pyrrolidin-1-ylpropoxy)phenyl]tetrahydro-2H-pyran-4-yl}carbonyl)-piperazine. ¹H NMR (400 MHz, CDCl₃) δ 0.84 (t, 3H), 1.37-1.43 (m, 2H), 1.1.69-1.77 (m, 2H), 1.84-1.88 (m, 4H), 1.98-2.07 (m, 6H), 2.14-2.19 (m, 4H), 2.65-2.69 (m, 4H), 2.74 (t, 2H), 3.26-3.40 (m, 4H), 3.78 (t, 2H), 3.87-3.89 (m, 2H), 4.02 (t, 2H), 6.86 (d, 2H), 7.15 (d, 2H). HRMS ESI⁺ m/z 444.3196 [MH]⁺. 71% yield |
| 183 | 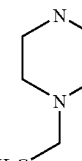 | 1-ethyl-4-({4-[4-(3-pyrrolidin-1-ylpropoxy)phenyl]tetrahydro-2H-pyran-4-yl}carbonyl)-piperazine. ¹H NMR (400 MHz, CDCl₃) δ 0.97 (t, 3H), 1.76-1.83 (m, 4H), 1.98-2.01 (m, 8H), 2.18 (d, 2H), 2.25 (d, 2H), 2.51-2.55 (m, 4H), 2.62 (t, 2H), 3.20-3.40 (m, 4H), 3.77 (t, 2H), 3.85-3.88 (m, 2H), 3.98-4.03 (m, 2H), 6.85 (d, 2H), 7.13 (d, 2H). HRMS ESI⁺ m/z 430.3047 [MH]⁺. 81% yield |

-continued

| Ex No | NR³R⁴ | Analytical Data |
|---|---|---|
| 184 | (1-methyl-1,4-diazepane group, N-CH₃) | 1-methyl-4-({4-[4-(3-pyrrolidin-1-ylpropoxy)-phenyl]tetrahydro-2H-pyran-4-yl}carbonyl)-1,4-diazepane. ¹H NMR (400 MHz, CDCl₃) δ 1.75-1.81 (m, 8H), 1.98-2.03 (m, 4H), 2.14-2.29 (m, 7H), 2.51-2.54 (m, 4H), 2.62 (t, 2H), 3.12-3.24 (m, 2H), 3.54-3.65 (m, 2H), 3.77-3.88 (m, 4H), 4.01 (t, 2H), 6.88 (d, 2H), 7.16 (d, 2H). HRMS ESI⁺ m/z 430.3057 [MH]⁺. 68% yield |
| 185 | (N-ethyl-N'-(2-dimethylaminoethyl) group) | N-[2-(dimethylamino)ethyl]-N-ethyl-4-[4-(3-pyrrolidin-1-ylpropoxy)phenyl]tetrahydro-2H-pyran-4-carboxamide. ¹H NMR (400 MHz, CDCl₃) δ 0.66-0.72 (m, 3H), 1.76-1.81 (m, 4H), 1.98-2.02 (m, 6H), 2.23-2.26 (m, 6H), 2.40-2.45 (m, 2H), 2.50-2.55 (m, 4H), 2.61 (t, 2H), 2.93-3.00 (m, 2H), 3.30-3.39 (m, 2H), 3.80 (t, 2H), 3.86-3.89 (m, 2H), 4.01 (t, 2H), 6.88 (d, 2H), 7.16 (d, 2H). HRMS ESI⁺ m/z 432.3215 [MH]⁺. 62% yield |
| 186 | (N-methyl-N'-(2-dimethylaminoethyl) group) | N-[2-(dimethylamino)ethyl]-N-methyl-4-[4-(3-pyrrolidin-1-ylpropoxy)phenyl]tetrahydro-2H-pyran-4-carboxamide. ¹H NMR (400 MHz, CDCl₃) δ 1.77-1.80 (m, 4H), 1.96-2.01 (m, 6H), 2.18-2.27 (m, 6H), 2.35-2.42 (m, 3H), 2.50-2.53 (m, 4H), 2.62 (t, 2H), 3.03 (s, 2H), 3.35-3.45 (m, 2H), 3.79 (t, 2H), 3.86-3.88 (m, 2H), 4.01 (t, 2H), 6.87 (d, 2H), 7.15 (d, 2H). HRMS ESI⁺ m/z 418.3052 [MH]⁺. 61% yield |
| 187 | (pyrrolidine) | 1-(3-{4-[4-(pyrrolidin-1-ylcarbonyl)tetrahydro-2H-pyran-4-yl]phenoxy}propyl)pyrrolidine. ¹H NMR (400 MHz, CDCl₃) δ 1.40-1.52 (m, 3H), 1.52-1.80 (m, 3H), 1.82-2.10 (m, 6H), 2.10-2.30 (m, 2H), 2.30-2.38 (m, 2H), 2.60-3.05 (m, 6H), 3.40-3.60 (m, 2H), 3.75-3.90 (m, 4H), 4.05 (t, 2H), 6.84 (d, 2H), 7.18 (d, 2H). LRMS APCI⁺ m/z 387 [MH]⁺. HRMS ESI⁺ m/z 387.2634 [MH]⁺. |
| 188 | (piperidine) | 1-({4-[4-(3-pyrrolidin-1-ylpropoxy)phenyl]-tetrahydro-2H-pyran-4-yl}carbonyl)piperidine. ¹H NMR (400 MHz, CDCl₃) δ 1.18-1.38 (m, 2H), 1.40-1.50 (m, 2H), 1.50-1.80 (m, 6H), 1.84-2.05 (m, 2H), 2.10-2.30 (m, 8H), 2.30-2.48 (m, 2H), 3.10-3.40 (m, 4H), 3.75-3.90 (m, 4H), 4.10 (t, 2H), 6.88 (d, 2H), 7.20 (d, 2H). LRMS APCI⁺ m/z 401 [MH]⁺. HRMS ESI m/z 401.2670 [MH]⁺. |
| 189 | (azetidine) | 1-(3-{4-[4-(azetidin-1-ylcarbonyl)tetrahydro-2H-pyran-4-yl]phenoxy}propyl)pyrrolidine. ¹H NMR (400 MHz, CDCl₃) δ 1.80-2.00 (m, 6H), 2.00-2.20 (m, 4H), 2.20-2.30 (m, 2H), 2.60-2.82 (m, 6H), 3.50-3.65 (m, 2H), 3.72-3.90 (m, 4H), 3.90-4.05 (m, 2H), 4.08 (t, 2H), 6.90 (d, 2H), 7.20 (d, 2H). LRMS APCI⁺ m/z 373 [MH]⁺. HRMS ESI⁺ m/z 373.2477 [MH]⁺. |
| 190 | (N-ethyl-N-methyl) | N-ethyl-N-methyl-4-[4-(3-pyrrolidin-1-ylpropoxy)phenyl]tetrahydro-2H-pyran-4-carboxamide. ¹H NMR (400 MHz, CDCl₃) δ 1.00-1.20 (m, 3H), 1.78-1.86 (m, 4H), 1.92-2.08 (m, 4H), 2.18-2.30 (m, 2H), 2.45-2.60 (m, 6H), 2.60-2.70 (t, 3H), 3.22-3.50 (m, 2H), 3.70-3.94 (m, 4H), 4.00 (t, 2H), 6.88 (d, 2H), 7.15 (d, 2H). LRMS APCI⁺ m/z 375 [MH]⁺. HRMS ESI⁺ m/z 375.2634 [MH]⁺. |
| 191 | (N,N-dimethyl) | N,N-dimethyl-4-[4-(3-pyrrolidin-1-ylpropoxy)phenyl]tetrahydro-2H-pyran-4-carboxamide. ¹H NMR (400 MHz, CDCl₃) δ 1.70-1.90 (m, 4H), 1.92-2.10 (m, 4H), 2.20-2.30 (m, 2H), 2.50-2.90 (m, 12H), 3.70-3.82 (m, 2H), 2.82-2.92 (m, 2H), 4.00 (t, 2H), 6.88 (d, 2H), 7.15 (d, 2H). LRMS APCI⁺ m/z 361 [MH]⁺. HRMS ESI⁺ m/z 361.2478 [MH]⁺. |

Intermediate 60: 1-(methoxyacetyl)-4-({4-[4-(3-pyrrolidin-1-ylpropoxy)phenyl]tetrahydro-2H-pyran-4-yl}carbonyl)piperazine Methoxyacetyl chloride (55 μl, 0.6 mmol) was added dropwise at 0° C. to a solution of 1-({4-[4-(3-pyrrolidin-1-ylpropoxy)phenyl]tetrahydro-2H-pyran-4-yl}carbonyl)piperazine of example 181 (200 mg, 0.5 mmol) and N,N-diisopropylethylamine (100 μl, 0.6 mmol) in dichloromethane (3 ml). The reaction mixture was stirred at room temperature for 1 hour. The reaction mixture was diluted with dichloromethane (20 ml) and washed with 2N sodium hydroxide (20 ml). The layers were separated and the aqueous layer was further extracted with dichloromethane (20 ml). The organics were combined, dried over sodium sulphate, filtered and concentrated in vacuo. The crude product was purified by flash chromatography on silica gel eluting with dichloromethane:methanol:ammonia (97:3:0.3 to 90:10:1 by volume) to provide the title compound (160 mg, 67%). HRMS ESI⁺ m/z 474.2952 [MH]⁺.

Examples 192-195

The compounds of the following tabulated Examples of the general formula

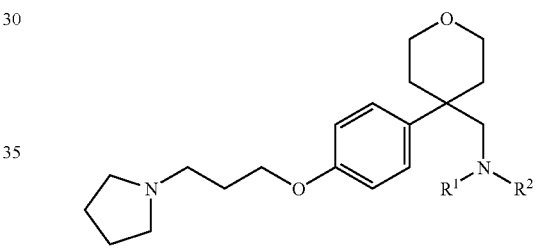

were prepared using lithium aluminium hydride, the amides of examples 182, 183, 184 and intermediate 60 similarly to the procedure used for example 142.

| Ex No | NR¹R² | Analytical Data |
|---|---|---|
| 192 (from Ex 182) | (N-propylpiperazine) | 1-propyl-4-({4-[4-(3-pyrrolidin-1-ylpropoxy)phenyl]tetrahydro-2H-pyran-4-yl}methyl)piperazine. ¹H NMR (400 MHz, CDCl₃) δ 0.85 (t, 3H), 1.40-1.46 (m, 2H), 1.77-1.80 (m, 4H), 1.84-1.91 (m, 2H), 1.98-2.03 (m, 2H), 2.08 (d, 2H), 2.18-2.22 (m, 4H), 2.24-2.28 (m, 4H), 2.36 (s, 2H), 2.51-2.54 (m, 4H), 2.63 (t, 2H), 3.51 (t, 2H), 3.72-3.75 (m, 2H), 4.01 (t, 2H), 6.84 (d, 2H), 7.20 (d, 2H). HRMS ESI⁺ m/z 430.3410 [MH]⁺. 96% yield |
| 193 (from Ex 183) | (N-ethylpiperazine) | 1-ethyl-4-({4-[4-(3-pyrrolidin-1-ylpropoxy)phenyl]tetrahydro-2H-pyran-4-yl}methyl)piperazine. ¹H NMR (400 MHz, CDCl₃) δ 1.02 (t, 3H), 1.77-1.81 (m, 4H), 1.86-1.91 (m, 2H), 1.99-2.02 (m, 2H), 2.08 (d, 2H), 2.19-2.23 (m, 4H), 2.27-2.35 (m, 6H), 2.38 (s, 2H), 2.51-2.54 (m, 4H), 2.63 (t, 2H), 3.52 (t, 2H), 3.73-3.76 (m, 2H), 4.02 (t, 2H), 6.85 (d, 2H), 7.21 (d, 2H). HRMS ESI⁺ m/z 416.3267 [MH]⁺. 54% yield |

-continued

| Ex No | NR¹R² | Analytical Data |
|---|---|---|
| 194 (from Ex 184) | ![structure with N-CH3 diazepane] | 1-methyl-4-({4-[4-(3-pyrrolidin-1-ylpropoxy)-phenyl]tetrahydro-2H-pyran-4-yl}methyl)-1,4-diazepane. ¹H NMR (400 MHz, CDCl₃) δ 1.60 (p, 2H), 1.77-1.80 (m, 4H), 1.86-1.92 (m, 4H), 1.98-2.02 (m, 2H), 2.08 (d, 2H), 2.28 (s, 3H), 2.38-2.40 (m, 2H), 2.47-2.53 (m, 8H), 2.57 (s, 2H), 2.62 (t, 2H), 3.50 (t, 2H), 3.73-3.77 (m, 2H), 4.01 (t, 2H), 6.85 (d, 2H), 7.19 (d, 2H). HRMS ESI⁺ m/z 416.3265 [MH]⁺. 13% yield |
| 195 (from Int 60) | ![piperazine with methoxyethyl] | 1-(2-methoxyethyl)-4-({4-[4-(3-pyrrolidin-1-ylpropoxy)phenyl]tetrahydro-2H-pyran-4-yl}-methyl)piperazine. ¹H NMR (400 MHz, CDCl₃) δ 1.76-1.79 (m, 4H), 1.84-1.89 (m, 2H), 1.97-2.01 (m, 2H), 2.06 (d, 2H), 2.19-2.21 (m, 4H), 2.28-2.33 (m, 4H), 2.35 (s, 2H), 2.47 (t, 2H), 2.50-2.53 (m, 4H), 2.61 (t, 2H), 3.29 (s, 3H), 3.43 (t, 2H), 3.50 (t, 2H), 3.71-3.74 (m, 2H), 4.00 (t, 2H), 6.83 (d, 2H), 7.19 (d, 2H). HRMS ESI⁺ m/z 446.3374 [MH]⁺. 31% yield |

Intermediate 61: 2-nitro-N-({4-[4-(3-pyrrolidin-1-ylpropoxy)phenyl]tetrahydro-2H-Pyran-4-yl}methyl)aniline {4-[4-(3-Pyrrolidin-1-ylpropoxy)phenyl]tetrahydropyran-4-yl}methylamine (300 mg, 0.94 mmol), 2-fluoronitrobenzene (100 μl, 0.95 mmol) and potassium carbonate (150 mg, 1.08 mmol) were stirred together at room temperature in N,N-dimethylformamide (1 ml) for 2 days. The reaction mixture was concentrated in vacuo and the residue partitioned between water (30 ml) and ethyl acetate (100 ml). The layers were separated and the organic phase washed with water (2×20 ml), dried over sodium sulphate, filtered and concentrated in vacuo to give the title compound as a yellow gum (570 mg, 100%). HRMS ESI⁺ m/z 440.2537 [MH]⁺.

Intermediate 62: N-({4-[4-(3-pyrrolidin-1-ylpropoxy)phenyl]tetrahydro-2H-pyran-4-yl}methyl)benzene-1,2-diamine A solution of 2-nitro-N-({4-[4-(3-pyrrolidin-1-ylpropoxy)phenyl]tetrahydro-2H-pyran-4-yl}methyl)aniline (570 mg, 1.3 mmol) in ethanol (40 mL) was hydrogenated for 5 hours at room temperature at 50 psi in the presence of 10% Pd/C (60 mg, 10% w/w). The reaction mixture was filtered over Arbocel® and rinsed with ethanol. The filtrate was concentrated in vacuo to give the title compound as a gum, used without further purification (500 mg, 94%). HRMS ESI⁺ m/z 410.2791 [MH]⁺.

Example 196

2-{4-[4-(3-pyrrolidin-1-ylpropoxy)phenyl]tetrahydro-2H-pyran-4-yl}-1H-benzimidazole

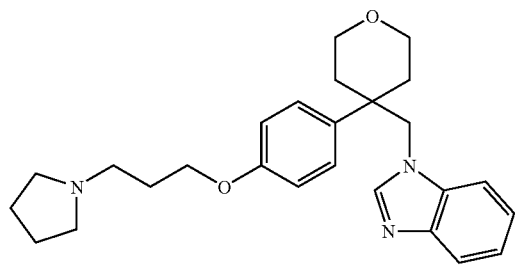

N-({4-[4-(3-Pyrrolidin-1-ylpropoxy)phenyl]tetrahydro-2H-pyran-4-yl}methyl)benzene-1,2-diamine (500 mg, 1.22 mmol), trimethylorthoformate (5 ml) and formic acid (0.5 ml) were stirred at room temperature for 18 hours. The reaction mixture was concentrated in vacuo and the residue partitioned between aqueous sodium carbonate (50 ml) and ethyl acetate (100 ml). The layers were separated and the organic phase washed with water (50 ml), dried over sodium sulphate, filtered and concentrated in vacuo. The crude product was purified by flash chromatography on silica gel eluting with dichloromethane:methanol:ammonia (98:2:0.2 to 92:8:1 by volume). The relevant fractions were evaporated and the residue taken up in diethyl ether (20 ml). The unsoluble material was filtered off and the filtrate concentrated in vacuo to provide the title compound (150 mg, 29%). ¹H NMR (400 MHz, CD₃OD) δ 1.83-1.85 (m, 4H), 1.98-2.06 (m, 4H), 2.23 (d, 2H), 2.62 (s, 4H), 2.69 (t, 2H), 3.42 (t, 2H), 3.82 (d, 2H), 4.00 (t, 2H), 4.33 (s, 2H), 6.84 (d, 2H), 7.06 (d, 2H), 7.14-7.18 (m, 3H), 7.26 (s, 1H), 7.55 (d, 1H). HRMS ESI⁺ m/z 420.2637 [MH]⁺.

Examples 197-200

The compounds of the following tabulated Examples of the general formula

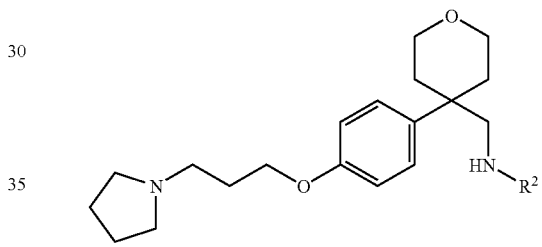

were prepared using {4-[4-(3-pyrrolidin-1-ylpropoxy)phenyl]tetrahydropyran-4-yl}methylamine and the appropriate bromo or iodopyridines similarly to the palladium coupling procedure used for example 152.

| Ex No | R² | Analytical Data |
|---|---|---|
| 197 | ![pyridin-2-yl] | N-({4-[4-(3-pyrrolidin-1-ylpropoxy)phenyl]-tetrahydro-2H-pyran-4-yl}methyl)pyridin-2-amine. ¹H NMR (400 MHz, CDCl₃) δ 1.81-1.86 (m, 4H), 1.90-1.96 (m, 2H), 2.05-2.17 (m, 4H), 2.58-2.75 (m, 6H), 3.50 (d, 2H), 3.59 (t, 2H), 3.81-3.85 (m, 2H), 4.00 (t, 1H), 4.05 (t, 2H), 6.23 (d, 1H), 6.51 (t, 1H), 6.92 (d, 2H), 7.25 (d, 2H), 7.32 (t, 1H), 8.02 (d, 1H). HRMS ESI⁺ m/z 396.2633 [MH]⁺. 14% yield |
| 198 | ![pyridin-3-yl] | N-({4-[4-(3-pyrrolidin-1-ylpropoxy)phenyl]-tetrahydro-2H-pyran-4-yl}methyl)pyridin-3-amine. ¹H NMR (400 MHz, CDCl₃) δ 1.80-1.84 (m, 4H), 1.88-1.94 (m, 2H), 2.03-2.07 (m, 2H), 2.19 (d, 2H), 2.56-2.63 (m, 4H), 2.66-2.70 (m, 2H), 3.24 (s, 3H), 3.57 (t, 2H), 3.77-3.82 (m, 2H), 4.05 (t, 2H), 6.74 (d, 1H), 6.93 (d, 2H), 7.01 (t, 1H), 7.24 (d, 2H), 7.88-7.91 (m, 2H). HRMS ESI⁺ m/z 396.2640 [MH]⁺. 13% yield |

| Ex No | R² | Analytical Data |
|---|---|---|
| 199 | ![pyridine with CH3] | 6-methyl-N-({4-[4-(3-pyrrolidin-1-ylpropoxy)-phenyl]tetrahydro-2H-pyran-4-yl}methyl)-pyridin-3-amine. ¹H NMR (400 MHz, CDCl₃) δ 1.83 (d, 7H), 1.94-2.01 (m, 2H), 2.04 (t, 2H), 2.24 (d, 2H), 2.2.58-2.62 (m, 4H), 2.68 (t, 2H), 2.98 (t, 1H), 3.29 (d, 2H), 3.59 (t, 2H), 3.79-3.83 (m, 2H), 4.04 (t, 2H), 6.85 (d, 1H), 6.94 (d, 2H), 7.27 (d, 2H), 7.86 (d, 1H), 7.92 (s, 1H). HRMS ESI⁺ m/z 410.2793 [MH]⁺. 11% yield |
| 200 | ![pyridine with CH3] | 4-methyl-N-({4-[4-(3-pyrrolidin-1-ylpropoxy)-phenyl]tetrahydro-2H-pyran-4-yl}methyl)-pyridin-3-amine. ¹H NMR (400 MHz, CDCl₃) δ 1.81-1.83 (m, 4H), 1.87-1.94 (m, 2H), 2.05 (t, 2H), 2.18 (d, 2H), 2.38 (s, 3H), 2.58-2.61 (m, 4H), 2.69 (t, 2H), 3.10 (t, 1H), 3.20 (d, 2H), 3.56 (t, 2H), 3.77-3.82 (m, 2H), 4.05 (t, 2H), 6.69 (dd, 1H), 6.87 (d, 1H), 6.93 (d, 2H), 7.24 (d, 2H), 7.78 (s, 1H). HRMS ESI⁺ m/z 410.2793 [MH]⁺. 13% yield |

Example 201

1-methyl-N-({4-[4-(3-pyrrolidin-1-ylpropoxy)phenyl]tetrahydro-2H-pyran-4-yl}methyl)-1H-benzimidazol-2-amine

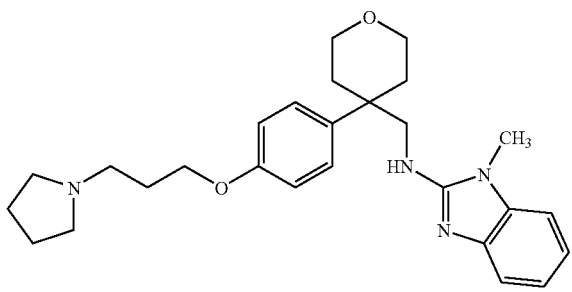

A mixture of {4-[4-(3-pyrrolidin-1-ylpropoxy)phenyl]tetrahydropyran-4-yl}methylamine (150 mg, 0.47 mmol), 1-methylbenzimidazole-2-sulfonic acid (83.4 mg, 0.39 mmol) and N,N-diisopropylethylamine (175 μl, 0.98 mmol) in acetonitrile (1.5 ml) was heated at 155° C. in the Smith Personal Synthesiser for 2400 seconds and then a further 900 seconds. The reaction mixture was partitioned between dichloromethane (10 ml) and saturated aqueous sodium bicarbonate solution (10 ml). The organic layer was dried over sodium sulphate, filtered and concentrated in vacuo. The crude product was purified by flash chromatography on silica gel eluting with dichloromethane:methanol:ammonia (100: 0:0 to 95:5:0.5 by volume) to provide the title compound (29 mg, 14%). ¹H NMR (400 MHz, CD₃OD) δ 1.83-1.86 (m, 4H), 1.96-2.02 (m, 4H), 2.19 (d, 2H), 2.63-2.66 (m, 4H), 2.70 (t, 2H), 3.41 (s, 3H), 3.50 (t, 2H), 3.57 (s, 2H), 3.79-3.82 (m, 2H), 3.97 (t, 2H), 6.91 (d, 2H), 6.97-7.02 (m, 2H), 7.08 (d, 1H), 7.22 (d, 1H), 7.36 (d, 2H). LRMS APCI⁺ m/z 449 [MH]⁺.

Intermediate 63: 6-chloro-N-({4-[4-(3-pyrrolidin-1-ylpropoxy)phenyl]tetrahydro-2H-pyran-4-yl}methyl)pyrimidin-4-amine A mixture of {4-[4-(3-pyrrolidin-1-ylpropoxy)phenyl]tetrahydropyran-4-yl}methylamine (100 mg, 0.31 mmol), 4,6-dichloropryrimidine (46.8 mg, 0.31 mmol) and N,N-diisopropylethylamine (137 μl, 0.78 mmol) in isopropanol (1 ml) was stirred at room temperature for 18 hours. The reaction mixture was partitioned between ethyl acetate (3×10 ml) and saturated aqueous sodium bicarbonate (10 ml). The combined organic layers were dried over sodium sulphate, filtered and concentrated in vacuo. The crude product was purified by flash chromatography on silica gel eluting with dichloromethane:methanol:ammonia (100:0:0 to 92:8:0.8 by volume) to provide the title compound (50 mg, 37%). LRMS APCI⁺ m/z 431 [MH]⁺.

Example 202

N-({4-[4-(3-pyrrolidin-1-ylpropoxy)phenyl]tetrahydro-2H-pyran-4-yl}methyl)pyrimidin-4-amine

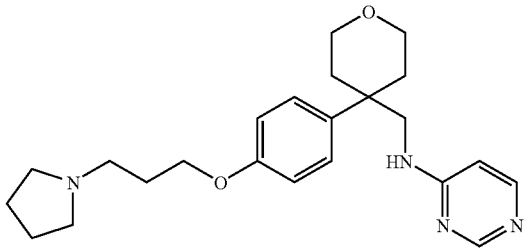

A solution of 6-chloro-N-({4-[4-(3-pyrrolidin-1-ylpropoxy)phenyl]tetrahydro-2H-pyran-4-yl}methyl)pyrimidin-4-amine (50 mg, 0.12 mmol) and triethylamine (48.6 μl, 0.35 mmol) in ethanol (2 mL) was hydrogenated for 16 hours at room temperature at 50 psi in the presence of 10% Pd/C (5 mg, 10% w/w). The reaction mixture was filtered through Arbocel® and rinsed with ethanol and water. The filtrate was concentrated in vacuo. The residue was partitioned between ethyl acetate (20 ml) and saturated aqueous sodium carbonate (20 ml). The organic layer was dried over sodium sulphate, filtered and concentrated in vacuo. The crude product was purified by flash chromatography on silica gel eluting with dichloromethane:methanol:ammonia (100:0:0 to 95:5:0.5 by volume) to provide the title compound (9 mg, 20%).
¹H NMR (400 MHz, CDCl₃) δ 1.78-1.81 (m, 4H), 1.85-1.90 (m, 2H), 2.00-2.05 (m, 2H), 2.09-2.16 (m, 2H), 2.53-2.60 (m, 4H), 2.66 (t, 2H), 3.54-3.58 (m, 4H), 3.79-3.83 (m, 2H), 4.02 (t, 2H), 4.44 (brs, 1H), 6.12 (d, 1H), 6.92 (d, 2H), 7.20 (d, 2H), 8.05 (d, 1H), 8.47 (s, 1H). HRMS ESI⁺ m/z 397.2596 [MH]⁺.

Intermediate 64: 4-chloro-N-({4-[4-(3-pyrrolidin-1-ylpropoxy)phenyl]tetrahydro-2H-pyran-4-yl}methyl)phthalazin-1-amine A mixture of {4-[4-(3-pyrrolidin-1-ylpropoxy)phenyl]tetrahydropyran-4-yl}methylamine (300 mg, 0.94 mmol), 1,4-dichlorophthalazine (188 mg, 0.94 mmol) and N,N-diisopropylethylamine (410 μl, 2.36 mmol) in N,N-dimethylformamide (1 ml) was stirred at room temperature for 18 hours. More 1,4-dichlorophthalazine (188 mg, 0.94 mmol) was added and the reaction stirred at room temperature for 36 hours, then heated at 55° C. for 18 hours. The reaction mixture was partitioned between ethyl acetate (20 ml) and saturated aqueous sodium bicarbonate solution (20 ml). The organic layer was washed with more aqueous sodium bicarbonate, brine, dried over sodium sulphate, filtered and concentrated in vacuo. The crude product was purified by flash chromatography on silica gel eluting with dichloromethane:

Example 203

N-({4-[4-(3-pyrrolidin-1-ylpropoxy)phenyl]tetrahydro-2H-pyran-4-yl}methyl)phthalazine-1-amine

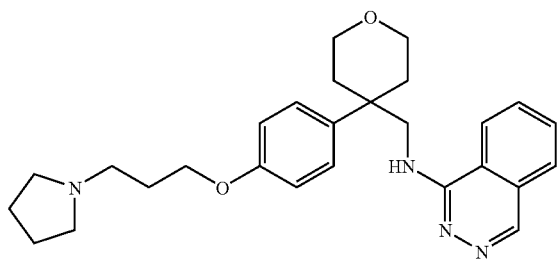

The title compound (86 mg, 51%) was prepared from 4-chloro-N-({4-[4-(3-pyrrolidin-1-ylpropoxy)phenyl]tetrahydro-2H-pyran-4-yl}methyl)phthalazin-1-amine by hydrogenation similarly to the procedure used for example 202. $^1$H NMR (400 MHz, CDCl$_3$) δ 1.80-1.84 (m, 4H), 2.01-2.08 (m, 4H), 2.15-2.20 (m, 2H), 2.55-2.60 (m, 4H), 2.68 (t, 2H), 3.61-3.66 (m, 2H), 3.86-3.92 (m, 2H), 3.98 (d, 2H), 4.07 (t, 2H), 4.62 (t, 1H), 7.00 (d, 2H), 7.32-7.36 (m, 3H), 7.68-7.77 (m, 3H), 8.89 (s, 1H). HRMS ESI$^+$ m/z 447.2746 [MH]$^+$.

Example 204

2-{4-[4-(3-pyrrolidin-1-ylpropoxy)phenyl]tetrahydro-2H-pyran-4-yl}-1H-benzimidazole

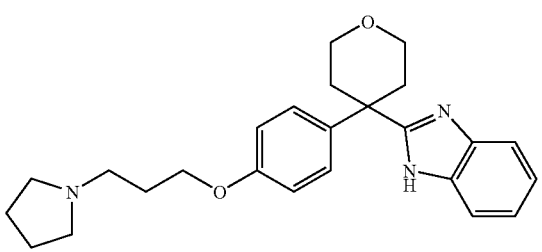

A mixture of 4-[4-(3-pyrrolidin-1-ylpropoxy)phenyl]tetrahydro-2H-pyran-4-carboxylic acid (400 mg, 1.20 mmol), 1,2-diaminobenzene (129 mg, 1.20 mmol) and polyphosphoric acid (2 g) was heated at 130° C. for 2 days. The cooled reaction mixture was partitioned between dichloromethane (20 ml) and aqueous ammonia (20 ml). The aqueous layer was further extracted with dichloromethane (2×50 ml). The organic layers were combined, dried over sodium sulphate, filtered and concentrated in vacuo. The crude product was purified by preparative HPLC on Fraction-Lynx® eluting with water:acetonitrile:TFA (95:5:0.1) to provide the title compound (3.5 mg, 1%). $^1$H NMR (400 MHz, CDCl$_3$) δ 1.92-1.96 (m, 2H), 2.06-2.21 (m, 4H), 2.40-2.46 (m, 2H), 2.96-3.00 (m, 4H), 3.05-3.09 (m, 2H), 3.16-3.20 (m, 2H), 3.57-3.65 (m, 4H), 3.93 (d, 2H), 5.45 (d, 2H), 7.06 (d, 2H), 7.45 (d, 2H), 7.71-7.74 (m, 2H). LCMS ESI$^+$ m/z 406 [MH]$^+$.

Example 205

2-{4-[4-(3-pyrrolidin-1-ylpropoxy)phenyl]tetrahydro-2H-pyran-4-yl}-pyridine

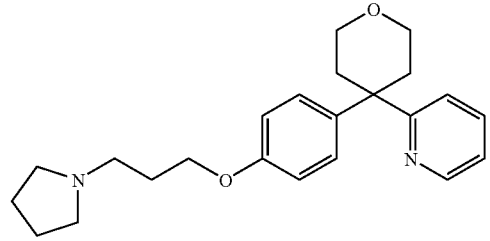

Trimethylsilylacetylene (0.9 ml, 6 mmol) was added at room temperature to a solution of 4-[3-(3-pyrrolidin-1-ylpropoxy)phenyl]tetrahydropyran-4-carbonitrile (200 mg, 0.6 mmol) and dicarbonylcyclopentadienyl cobalt (12 mg, 0.07 mmol) in toluene (3 ml). Tetrabutylammonium fluoride (1.54 g, 6 mmol) was added portionwise over 10 minutes. The reaction mixture was then stirred at room temperature under visible light under nitrogen for 12 days. The reaction mixture was concentrated in vacuo. The residue was partitioned between dichloromethane (50 ml) and aqueous sodium hydroxide solution (50 ml). The aqueous layer was extracted again with dichloromethane (50 ml). The organic layers were combined, dried over sodium sulphate, filtered and concentrated in vacuo. The crude product was purified by preparative HPLC on Fraction-Lynx® eluting with water:acetonitrile:TFA (95:5:0.1) to provide the title compound (4 mg, 2%). $^1$H NMR (400 MHz, CDCl$_3$) δ 1.78-1.81 (m, 4H), 1.95-2.02 (m, 2H), 2.32-2.39 (m, 2H), 2.51-2.56 (m, 4H), 2.61-2.70 (m, 4H), 3.67 (t, 2H), 3.78-3.84 (m, 2H), 3.98 (d, 2H), 6.81 (d, 2H), 7.06 (t, 1H), 7.13 (d, 1H), 7.21 (d, 2H), 7.55 (t, 1H), 8.58 (d, 1H). HRMS ESI$^+$ m/z 367.2375 [MH]$^+$.

Example 206

5-{4-[4-(3-pyrrolidin-1-ylpropoxy)phenyl]tetrahydro-2H-pyran-4-yl}-1,3-oxazole

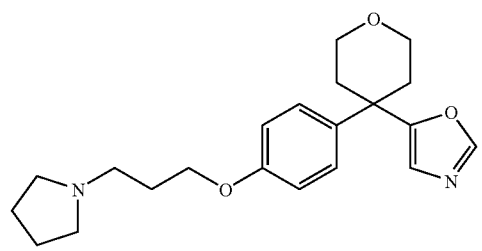

Tosylmethyl isocyanide (370 mg, 1.89 mmol) was added to a solution of 4-[4-(3-pyrrolidin-1-ylpropoxy)phenyl]tetrahydro-2H-pyran-4-carbaldehyde (500 mg, 1.58 mmol) and potassium carbonate (652 mg, 4.73 mmol) in methanol (7 ml). The reaction mixture was heated at reflux for 3 hours. The reaction mixture was partitioned between ethyl acetate (2×75 ml) and water (20 ml). The organic layers were combined, dried over sodium sulphate, filtered and concentrated in vacuo. The crude product was taken up in 2N hydrochloric acid (3 ml) and stirred at room temperature for 1.5 hours. The mixture was then partitioned between aqueous sodium carbonate and dichloromethane (2×75 ml). The combined organic layers were dried over sodium sulphate, filtered and concentrated in vacuo. The crude product was purified by flash chromatography on silica gel eluting with dichloromethane:methanol:ammonia (95:5:0.5 by volume) to provide the title compound (12 mg, 2%). ¹H NMR (400 MHz, CD₃OD) δ 1.81-1.85 (m, 4H), 1.97-2.02 (m, 2H), 2.25-2.31 (m, 2H), 2.38-2.43 (m, 2H), 2.60-2.63 (m, 4H), 2.69 (t, 2H), 3.61 (t, 2H), 3.78-3.83 (m, 2H), 4.01 (t, 2H), 6.87 (d, 2H), 6.98 (s, 1H), 7.22 (d, 2H), 8.09 (s, 1H). LRMS APCI⁺ m/z 357 [MH]⁺.

Example 207

4-({4-[4-(3-pyrrolidin-1-ylpropoxy)phenyl]tetrahydro-2H-pyran-4-yl}methoxy)pyridine

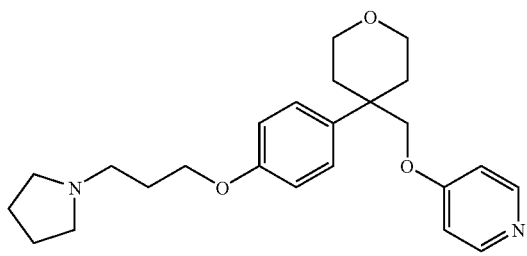

The title compound (75 mg, 60%) was prepared from {4-[4-(3-pyrrolidin-1-ylpropoxy)phenyl]tetrahydro-2H-pyran-4-yl}methanol and 4-bromopyridine similarly to the procedure used for example 152. ¹H NMR (400 MHz, CDCl₃) δ 1.76-1.82 (m, 4H), 1.98-2.04 (m, 2H), 2.12-2.17 (m, 4H), 2.49-2.58 (m, 4H), 2.61-2.66 (m, 2H), 3.54-3.60 (m, 2H), 3.81-3.85 (m, 2H), 3.87 (s, 2H), 4.03 (t, 2H), 6.71 (d, 2H), 6.91 (d, 2H), 7.29 (d, 2H), 8.36 (d, 2H). HRMS ESI⁺ m/z 397.2479 [MH]⁺.

Intermediate 65: 1-{4-[4-(3-chloropropoxy)phenyl]tetrahydro-2H-pyran-4-yl}-N,N-dimethylmethanamine 1-Bromo-3-chloropropane (0.42 ml, 4.25 mmol) was added to a solution of 4-(4-dimethylaminomethyl-tetrahydro-pyran-4-yl)-phenol (1.0 g, 4.25 mmol) and potassium carbonate (1.5 g, 10.8 mmol) in N,N-dimethylformamide (10 ml). The reaction mixture was stirred at 45° C. for 18 hours. The reaction mixture was concentrated in vacuo. The residue was partitioned between ethyl acetate (100 ml) and water (50 ml). The organic layer was separated, dried over sodium sulphate, filtered and concentrated in vacuo to provide the title compound (800 mg, 60%). LRMS APCI⁺ m/z 412 [MH]⁺.

Example 208

N,N-dimethyl-1-(4-{4-[3-(4-methylpiperazin-1-yl)propoxy]phenyl}tetrahydro-2H-pyran-4-yl)methanamine

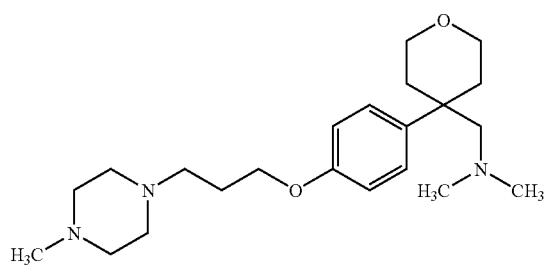

A mixture of 1-{4-[4-(3-chloropropoxy)phenyl]tetrahydro-2H-pyran-4-yl}-N,N-dimethylmethanamine (200 mg, 0.7 mmol), N-methyl piperazine (87 µl, 0.79 mmol), solid sodium bicarbonate (66 mg, 0.79 mmol) and a catalytic amount of potassium iodide was heated at 50° C. in N,N-dimethylformamide (2 ml) for 18 hours. The reaction mixture was concentrated in vacuo. The residue was partitioned between ethyl acetate (2×75 ml) and water (20 ml). The organic layers were combined, dried over sodium sulphate, filtered and concentrated in vacuo. The crude product was purified by flash chromatography on silica gel eluting with dichloromethane:methanol:ammonia (96:4:0.4 by volume) to provide the title compound (102 mg, 39%). ¹H NMR (400 MHz, CDCl₃) δ 1.84-1.91 (m, 2H), 1.95-1.99 (m, 8H), 2.07-2.11 (m, 2H), 2.30 (s, 3H), 2.40 (s, 2H), 2.42-2.59 (m, 10H), 3.54 (t, 2H), 3.72-3.78 (m, 2H), 4.00 (t, 2H), 6.86 (d, 2H), 7.20 (d, 2H). HRMS ESI⁺ m/z 376.2951 [MH]⁺.

Intermediate 66: N,N-dimethylazetidin-3-amine ditrifluoroacetate

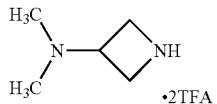

This amine was described in patent WO 2004096810 (prep 170, p240).

Examples 209-211

The compounds of the following tabulated examples of the general formula

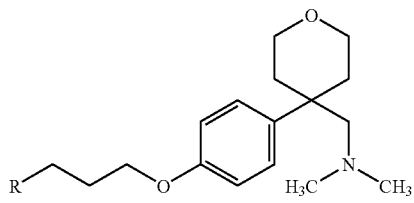

were prepared using 1-{4-[4-(3-chloropropoxy)phenyl]tetrahydro-2H-pyran-4-yl}-N,N-dimethylmethanamine and the appropriate amines similarly to the procedure used for example 208.

| Ex No | R | Analytical Data |
|---|---|---|
| 209 | ![N-methyl-diazepane] | N,N-dimethyl-1-(4-{4-[3-(4-methyl-1,4-diazepan-1-yl)propoxy]phenyl}tetrahydro-2H-pyran-4-yl)methanamine. ¹H NMR (400 MHz, CDCl₃) δ 1.77-1.91 (m, 6H), 1.94 (s, 6H), 2.04-2.08 (m, 2H), 2.33 (s, 3H), 2.38 (s, 2H), 2.57-2.65 (m, 6H), 2.70-2.73 (m, 4H), 3.52 (t, 2H), 3.70-3.75 (m, 2H), 3.98 (t, 2H), 6.84 (d, 2H), 7.18 (d, 2H). LRMS APCI⁺ m/z 390 [MH]⁺. 30% yield |
| 210 | ![azetidine-dimethylamine] | 1-[3-(4-{4-[(dimethylamino)methyl]tetrahydro-2H-pyran-4-yl}phenoxy)propyl]-N,N-dimethylazetidin-3-amine. ¹H NMR (400 MHz, CDCl₃) δ 1.62-1.90 (m, 6H), 1.96 (s, 6H), 2.11 (s, 6H), 2.40 (s, 2H), 2.63 (t, 3H), 2.80-2.86 (m, 3H), 3.52-3.56 (m, 4H), 3.72-3.76 (m, 2H), 3.96-3.99 (m, 2H), 6.85 (d, 2H), 7.20 (d, 2H). HRMS ESI⁺ m/z 376.2959 [MH]⁺. 53% yield |

-continued

| Ex No | R | Analytical Data |
|---|---|---|
| 211 |  | Dimethyl-{4-[4-(3-[1,4]oxazepan-4-yl-propoxy)-phenyl]-tetrahydro-pyran-4-ylmethyl}-amine. $^1$H NMR (400 MHz, CDCl$_3$) δ 1.85-2.04 (m, 12H), 2.11 (M, 2H), 2.42 (s, 2H), 2.7-2.8 (m, 6H), 3.55 (t, 2H), 3.72-3.82 (m, 6H), 4.02 (t, 2H), 6.87 (d, 2H), 7.22 (d, 2H). HRMS ESI$^+$ m/z 377.2792 [MH]$^+$ 35% yield |

Intermediate 67: 1-benzhydryl-3-chloromethyl-azetidine hydrochloride (1-Benzhydryl-azetidin-3-yl)-methanol (3.07 g, 12.1 mmol) was dissolved in dichloromethane (60 ml). The reaction was cooled to 0-5° C. and thionyl chloride (1.07 ml, 14.6 mmol) was added slowly. The reaction was allowed to warm to room temperature and stirred for 18 hours. The reaction was concentrated in vacuo and azeotroped with toluene (3×20 ml) to give the title compound (3.8 g, 100%) as a pale brown solid.

Example 212

1-(4-{4-[(1-cyclopentylazetidin-3-yl)methoxy]phenyl}tetrahydro-2H-Pyran-4-yl)-N,N-dimethyl-methanamine

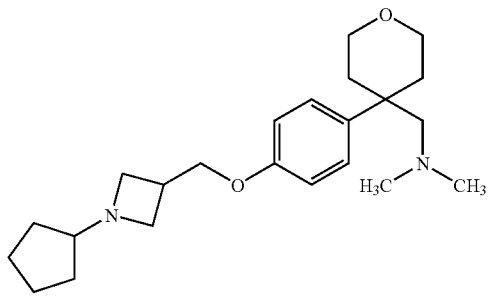

Step 1: 4-(4-Dimethylaminomethyl-tetrahydro-pyran-4-yl)-phenol (1.15 g, 5.65 mmol), 1-benzhydryl-3-chloromethyl-azetidine hydrochloride (1.58 g, 5.13 mmol), N,N-dimethylformamide (32 ml) and potassium carbonate (2.84 g, 20.52 mmol) were reacted together according to general procedure B. The reaction mixture was diluted with ethyl acetate. The organic layer was washed with 2M sodium hydroxide (3×50 ml), brine (3×50 ml), dried over magnesium sulphate, filtered and concentrated in vacuo to provide 1-[4-(4-{[1-benzhydrylazetidin-3-yl]methoxy}phenyl)tetrahydro-2H-pyran-4-yl]-N,N-dimethylmethanamine (1.82 g, 81%) as an off-white solid.

Step 2: This intermediate was hydrogenated in ethanol (20 ml) for 4 hours at 60° C. at atmospheric pressure in the presence of 10% Pd/C (300 mg). The reaction mixture was filtered through Arbocel® and rinsed with ethanol and water. The filtrate was concentrated in vacuo. The residue was taken up in 2N hydrochloric acid (50 ml) and extracted with tert-butylmethyl ether (3×50 ml). The aqueous layer was then basified to pH14 with 2M sodium hydroxide and extracted with dichloromethane (3×50 ml). These organic layers were combined, dried over magnesium sulphate, filtered and concentrated in vacuo to provide 1-{4-[4-(azetidin-3-ylmethoxy)phenyl]tetrahydro-2H-pyran-4-yl]-N,N-dimethylmethanamine (850 mg, 85%) as an off-white solid.

Step 3: Cyclopentyl bromide (0.17 ml, 1.54 mmol) and 5M aqueous sodium hydroxide (0.34 ml, 1.68 mmol) were added to a solution of 1-{4-[4-(azetidin-3-ylmethoxy)phenyl]tetrahydro-2H-pyran-4-yl]-N,N-dimethylmethanamine (425 mg, 1.4 mmol) in acetone (9 ml). The reaction mixture was stirred at room temperature for 18 hours. The reaction mixture was concentrated in vacuo. The residue was taken up in 2N hydrochloric acid to reach pH 1 and extracted with tert-butylmethyl ether (2×15 ml). The aqueous layer was then basified to pH14 with 4M sodium hydroxide (ca 40 ml) and extracted with dichloromethane (3×30 ml). These organic layers were combined, dried over magnesium sulphate, filtered and concentrated in vacuo. The crude product was purified by flash chromatography on silica gel eluting with dichloromethane:methanol:ammonia (95:4:1 by volume) to provide the title compound (55 mg, 11%) as a yellow solid. $^1$H NMR (400 MHz, CDCl$_3$) δ 1.28-1.73 (m, 8H), 1.83-1.93 (m, 2H), 1.96 (s, 6H), 2.05-2.13 (m, 2H), 2.40 (s, 2H), 2.71 (m, 1H), 2.90 (m, 1H), 3.00 (t, 2H), 3.39-3.58 (m, 4H), 3.72-3.78 (m, 2H), 4.05 (d, 2H), 6.87 (d, 2H), 7.21 (d, 2H). LRMS ESI$^+$ m/z 373 [MH]$^+$.

Example 213

N,N-dimethyl-1-{4-[4-(3-morpholin-4-ylpropoxy)phenyl]tetrahydro-2H-pyran-4-yl}methanamine

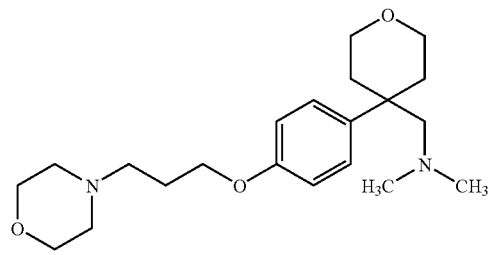

A mixture of 1-{4-[4-(3-chloropropoxy)phenyl]tetrahydro-2H-pyran-4-yl}-N,N-dimethylmethanamine (100 mg, 0.32 mmol), morpholine (100 mg, 1.1 mmol) and potassium carbonate (100 mg, 0.72 mmol) was heated at reflux in acetonitrile (5 ml) for 8 hours. Further morpholine (100 mg, 1.1 mmol) and potassium carbonate (100 mg, 0.72 mmol) were added and the reaction mixture heated at reflux for 6 hours. The reaction mixture was concentrated in vacuo. The residue was purified by flash chromatography on silica gel eluting with dichloromethane:methanol:ammonia (90:10:1 by volume) to provide the title compound (61 mg, 52%). $^1$H NMR (400 MHz, CD$_3$OD) δ 0.81-0.87 (m, 2H), 1.04-2.01 (m, 8H), 2.13-2.18 (m, 2H), 2.48-2.50 (m, 6H), 2.56 (t, 2H), 3.50 (t, 2H), 3.68-3.77 (m, 6H), 4.03 (t, 2H), 6.90 (d, 2H), 7.27 (d, 2H). HRMS ESI$^+$ m/z 363.2635 [MH]$^+$.

Example 214

4-(4-{3-[(2S)-2-hydroxymethyl)pyrrolidin-1-yl]propoxy}phenyl)tetrahydro-2H-pyran-4-carbonitrile

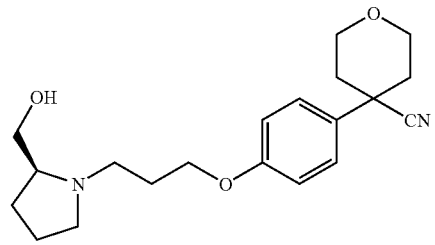

The title compound (30 mg, 12%) was prepared using 4-[4-(3-chloro-propoxy)-phenyl]-tetrahydropyran-4-carbonitrile and (S)-(+)-2-pyrrolidine methanol similarly to the procedure used for example 208.

$^1$H NMR (400 MHz, CDCl$_3$) δ 1.79-1.85 (m, 3H), 1.94 (m, 1H), 2.01-2.12 (m, 7H), 2.41 (m, 1H), 2.58 (m, 1H), 2.78 (m, 1H), 3.08 (m, 1H), 3.33 (m, 1H), 3.49 (m, 1H), 3.71 (d, 1H), 3.88 (t, 2H), 4.04-4.09 (m, 4H), 6.92 (d, 2H), 7.38 (d, 2H). HRMS ESI$^+$ m/z 345.2167 [MH]$^+$.

Intermediate 68: 1-{4-[4-(3-thiomorpholin-4-ylpropoxy) phenyl]tetrahydro-2H-pyran-4-yl}methanamine The title compound (1.58 g, 92%) was prepared using 4-[4-(3-thiomorpholin-4-ylpropoxy)phenyl]tetrahydro-2H-pyran-4-carbonitrile and lithium aluminium hydride similarly to the procedure used for intermediate 51. LRMS APCI$^+$ m/z 351 [MH]$^+$.

Example 215

N-({4-[4-(3-thiomorpholin-4-ylpropoxy)phenyl] tetrahydro-2H-pyran-4-yl}methyl)acetamide

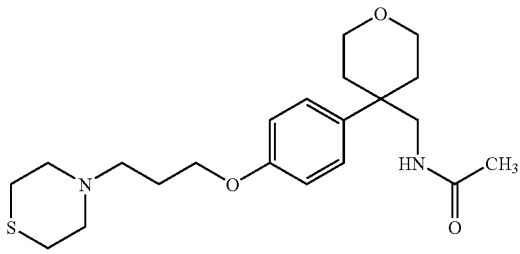

The title compound (1.16 g, 100%) was prepared using 1-{4-[4-(3-thiomorpholin-4-ylpropoxy)phenyl]tetrahydro-2H-pyran-4-yl}methanamine and acetic anhydride similarly to the procedure used for example 140. $^1$H NMR (400 MHz, CDCl$_3$) δ 1.82-1.86 (m, 2H), 1.87 (s, 3H), 2.00-2.04 (m, 4H), 2.58-2.85 (m, 10H), 3.45 (d, 2H), 3.56-3.61 (m, 2H), 3.79-3.84 (m, 2H), 4.02 (t, 2H), 4.97 (brs, 1H), 6.91 (d, 2H), 7.19 (d, 2H). LRMS APCI$^+$ m/z 393 [MH]$^+$.

Example 216

N-({4-[4-(3-thiomorpholin-4-ylpropoxy)phenyl] tetrahydro-2H-pyran-4-yl}methyl)ethanamine

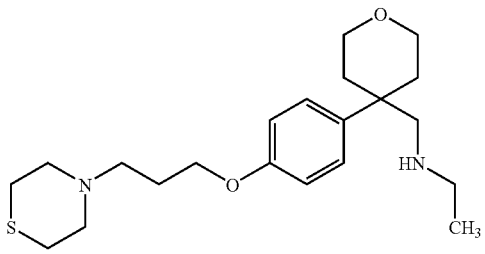

The title compound (492 mg, 44%) was prepared using N-({4-[4-(3-thiomorpholin-4-ylpropoxy)phenyl]tetrahydro-2H-pyran-4-yl}methyl)acetamide and lithium aluminium hydride similarly to the procedure used for example 142. $^1$H NMR (400 MHz, CDCl$_3$) δ 0.96 (t, 3H), 1.88-1.98 (m, 4H), 2.11-2.15 (m, 2H), 2.49 (q, 2H), 2.55 (t, 2H), 2.68-2.74 (m, 10H), 3.55 (t, 2H), 3.74-3.79 (m, 2H), 4.00 (t, 2H), 6.89 (d, 2H), 7.22 (d, 2H). LRMS APCI$^+$ m/z 379 [MH]$^+$.

Intermediate 69: 4-(4-methoxyphenyl)tetrahydro-2H-pyran-4-carboxylic acid 4-(4-Methoxyphenyl)-tetrahydro-2H-pyran-4-carbonitrile (10 g, 46 mmol) was heated at reflux for 18 hours in concentrated hydrochloric acid (100 mL). The reaction mixture was extracted with dichloromethane (2×100 mL). The combined organic layers were dried over sodium sulphate, filtered and concentrated in vacuo to a gummy solid. This was partitioned between 2M sodium hydroxide (300 ml) and ethyl acetate (300 ml). The aqueous layer was then acidified with concentrated hydrochloric acid (a white precipitate formed which was dissolved by adding dichloromethane (250 ml)). The layers were separated and the aqueous layer was further extracted with dichloromethane (250 ml). These dichloromethane organic layers were combined, dried over sodium sulphate, filtered and concentrated in vacuo to provide the title compound (3.4 g, 31%) as a white solid. LRMS APCI$^-$ m/z 235 [M–H]$^-$.

Intermediate 70: 1-{[4-(4-methoxyphenyl)tetrahydro-2H-pyran-4-yl]carbonyl}-4-methylpiperazine The title compound (515 mg, 77%) was prepared using 4-(4-methoxyphenyl)tetrahydro-2H-pyran-4-carboxylic acid, N-methyl-piperazine and O-(1H-benzotriazol-1-yl)-N, N,N',N'-tetramethyluronium tetrafluoroborate (TBTU) similarly to the procedure used for example 166. HRMS ESI$^+$ m/z 319.2009 [MH]$^+$.

Intermediate 71: 1-{[4-(4-methoxyphenyl)tetrahydro-2H-pyran-4-yl]methyl}-4-methylpiperazine The title compound (428 mg, 93%) was prepared using 1-{[4-(4-methoxyphenyl)tetrahydro-2H-pyran-4-yl]carbonyl}-4-methylpiperazine and lithium aluminium hydride similarly to the procedure used for example 142. HRMS ESI$^+$ m/z 305.2220 [MH]$^+$.

Intermediate 72: 4-{4-[(4-methylpiperazin-1-yl)methyl]tetrahydro-2H-pyran-4-yl}phenol To a suspension of sodium thiomethoxide (660 mg, 9.4 mmol) in N,N-dimethylformamide (2 ml) was added 1-{[4-(4-methoxyphenyl)tetrahydro-2H-pyran-4-yl]methyl}4-methylpiperazine (410 mg, 1.3 mmol) in N,N-dimethylformamide (3 ml). The reaction mixture was heated to 130° C. under nitrogen for 18 hours. The mixture was then allowed to cool down to room temperature and saturated aqueous ammonium chloride was added. The mixture was extracted with ethyl acetate (2×30 ml). The combined organic extracts were dried over sodium sulphate, filtered and concentrated in vacuo to provide a pale brown oil. This was azeotroped with toluene and dried under high vacuum to provide the title compound (390 mg, 100%) as an off-white solid. HRMS ESI$^+$ m/z 291.2062 [MH]$^+$.

Example 217

1-[(4-{4-[(1-isopropylpiperidin-4-yl)oxy] phenyl}tetrahydro-2H-pyran-4-yl)methyl]-4-methylpiperazine

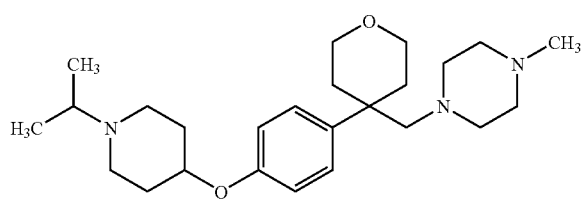

The title compound (72 mg, 14%) was prepared using 4-{4-[(4-methylpiperazin-1-yl)methyl]tetrahydro-2H-pyran-4-yl}phenol, 1-isopropyl-4-hydroxypiperidine (step 1 of intermediate 21), PPh₃ and DIAD similarly to the procedure used for intermediate 55. ¹H NMR (400 MHz, CDCl₃) δ 1.04 (d, 6H), 1.76-1.90 (m, 4H), 1.96-2.08 (m, 4H), 2.17-2.26 (m, 11H), 2.33-2.38 (m, 4H), 2.69-2.80 (m, 3H), 3.51 (t, 2H), 3.69-3.74 (m, 2H), 4.24 (m, 1H), 6.84 (d, 2H), 7.18 (d, 2H). HRMS ESI⁺ m/z 416.3268 [MH]⁺.

Intermediate 73: 4-{[4-(4-methoxyphenyl)tetrahydro-2H-pyran-4-yl]carbonyl}morpholine The title compound (3.1 g, 87%) was prepared using 4-(4-methoxyphenyl)tetrahydro-2H-pyran-4-carboxylic acid, morpholine and O-(1H-benzotriazol-1-yl)-N,N,N',N'-tetramethyluronium tetrafluoroborate (TBTU) similarly to the procedure used for example 166. HRMS ESI⁺ m/z 306.1696 [MH]⁺.

Intermediate 74: 4-{[4-(4-methoxyphenyl)tetrahydro-2H-pyran-4-yl]methyl}-morpholine The title compound (2.48 g, 87%) was prepared using 4-{[4-(4-methoxyphenyl)tetrahydro-2H-pyran-4-yl]carbonyl}morpholine and lithium aluminium hydride similarly to the procedure used for example 142. HRMS ESI⁺ m/z 292.1897 [MH]⁺.

Intermediate 75: 4-[4-(morpholin-4-ylmethyl)tetrahydro-2H-pyran-4-yl]phenol

The title compound (1.70 g, 75%) was prepared using 4-{[4-(4-methoxyphenyl)tetrahydro-2H-pyran-4-yl]methyl}-morpholine and sodium thiomethoxide similarly to the procedure used for intermediate 72. HRMS ESI⁺ m/z 278.1740 [MH]⁺.

Example 218

4-[(4-{4-[(1-isopropylpiperidin-4-yl)oxy]phenyl}tetrahydro-2H-pyran-4-yl)methyl]-morpholine

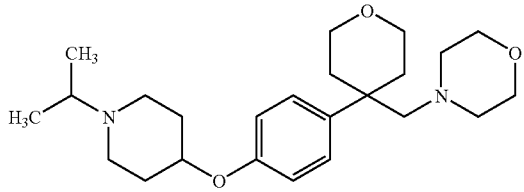

The title compound (52 mg, 12%) was prepared using 4-[4-(morpholin-4-ylmethyl)tetrahydro-2H-pyran-4-yl]phenol, 1-isopropyl-4-hydroxypiperidine (step 1 of intermediate 21), PPh₃ and DIAD similarly to the procedure used for intermediate 55. ¹H NMR (400 MHz, CD₃OD) δ 1.09 (d, 6H), 1.74-1.80 (m, 2H), 1.83-1.90 (m, 2H), 1.98-2.04 (m, 2H), 2.12-2.18 (m, 6H), 2.40 (s, 2H), 2.47 (t, 2H), 2.75 (m, 1H), 2.80-2.85 (m, 2H), 3.47-3.54 (m, 6H), 3.71-3.77 (m, 2H), 4.36 (m, 1H), 6.90 (d, 2H), 7.28 (d, 2H). HRMS ESI⁺ m/z 403.2951 [MH]⁺.

Intermediate 76: 4-{[4-{[1-(benzhydryl)azetidin-3-yl]methoxy}phenyl) tetrahydro-2H-pyran-4-yl]methyl}-morpholine The title compound (1.09 g, 66%) was prepared using 4-[4-(morpholin-4-ylmethyl)tetrahydro-2H-pyran-4-yl]phenol, (1-benzhydryl-azetidin-3-yl)-methanol, PPh₃ and DIAD similarly to the procedure used for intermediate 55. HRMS ESI⁺ m/z 513.3103 [MH]⁺.

Intermediate 77: 4-({4-[4-(azetidin-3-ylmethoxy)phenyl]tetrahydro-2H-pyran-4-yl}methyl)-morpholine A solution of 4-{[4-(4-{[1-(benzhydryl)azetidin-3-yl]methoxy}phenyl)tetrahydro-2H-pyran-4-yl]methyl}-morpholine (1.0 g, 1.95 mmol) in ethanol (10 mL) was hydrogenated for 16 hours at room temperature at 60 psi in the presence of Pd(OH)₂/C (150 mg, 15% w/w). 2N Hydrochloric acid (few drops) was added and the reaction mixture hydrogenated for 16 hours at 60° C. at 60 psi. The reaction mixture was basified with aqueous sodium carbonate and the mixture filtered over Arbocel® and rinsed with ethanol. The filtrate was concentrated in vacuo. The residue was purified by flash chromatography on silica gel eluting with dichloromethane:methanol:ammonia (96:4:0.4 to 90:10:1 by volume) to provide the title compound (210 mg, 31%). HRMS ESI⁺ m/z 347.2323 [MH]⁺.

Examples 219-221

The compounds of the following tabulated examples of the general formula

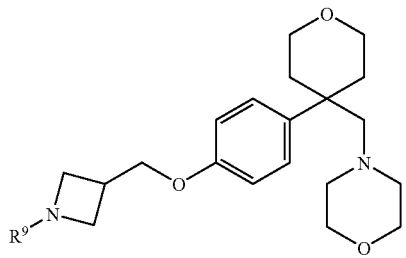

were prepared using 4-({4-[4-(azetidin-3-ylmethoxy)phenyl]tetrahydro-2H-pyran-4-yl}methyl)-morpholine, the appropriate ketones and sodium triacetoxyborohydride similarly to the procedure used for example 54.

| Ex No | R⁹ | Analytical Data |
|---|---|---|
| 219 | cyclopentyl | 4-[(4-{4-[(1-cyclopentylazetidin-3-yl)methoxy]phenyl}tetrahydro-2H-pyran-4-yl)methyl]morpholine. ¹H NMR(400MHz, CDCl₃) δ 1.32-1.37(m, 2H), 1.49-1.53(m, 2H), 1.58-1.69(m, 4H), 1.83-1.89(m, 2H), 2.08-2.15(m, 6H), 2.38(s, 2H), 2.74(m, 1H), 2.91(m, 1H), 3.03(t, 2H), 3.45(t, 2H), 3.49-3.54(m, 6H), 3.72-3.76(m, 2H), 4.04(d, 2H), 6.84(d, 2H), 7.22(d, 2H). HRMS ESI⁺ m/z 415.2946 [MH]⁺. 92% yield |
| 220 | isopropyl | 4-[(4-{4-[(1-isopropylazetidin-3-yl)methoxy]phenyl}tetrahydro-2H-pyran-4-yl)methyl]morpholine. ¹H NMR(400MHz, CDCl₃) δ 0.92(d, 6H), 1.83-1.90(m, 2H), 2.09-2.14(m, 6H), 2.31(m, 1H), 2.38 (s, 2H), 2.85(m, 1H), 3.03(t, 2H), 3.41(t, 2H), 3.49-3.54(m, 6H), 3.72-3.76(m, 2H), 4.06(d, 2H), 6.85(d, 2H), 7.22(d, 2H). HRMS ESI⁺ m/z 389.2791 [MH]⁺. 61% yield |
| 221 | cyclobutyl | 4-[(4-{4-[(1-cyclobutylazetidin-3-yl)methoxy]phenyl}tetrahydro-2H-pyran-4-yl)methyl]morpholine. ¹H NMR(400MHz, CDCl₃) δ 1.62-1.75(m, 2H), 1.82-1.90(m, 4H), 1.93-1.99(m, 2H), 2.09-2.15(m, 6H), 2.38(s, 2H), 2.88(m, 1H), 3.07(t, 2H), 3.14(m, 1H), 3.40(t, 2H), 3.49-3.55(m, 6H), 3.72-3.77(m, 2H), 4.07(d, 2H), 6.85(d, 2H), 7.22(d, 2H). HRMS ESI⁺ m/z 401.2791 [MH]⁺. 50% yield |

Intermediate 78: 4-[4-(methylthio)phenyl]tetrahydro-2H-pyran-4-carbonitrile

The title compound (5.5 g, 77%, solid after trituration in pentane) was prepared using 4-(methylthio)phenylacetonitrile, bis(2-bromoethyl)ether, sodium hydride and potassium iodide similarly to the procedure used for intermediate 56. Microanalysis: Found: C, 66.62; H, 6.46; N, 5.97%. $C_{13}H_{15}NOS$ requires C, 66.92; H, 6.48; N, 6.00%.

Intermediate 79: 4-[4-(methylsulfinyl)phenyl]tetrahydro-2H-pyran-4-carbonitrile A solution of meta-chloroperbenzoic acid (5.08 g, 22.66 mmol) in dichloromethane (30 ml) was added dropwise over 15 minutes at 0° C. to a solution of 4-[4-(methylthio)phenyl]tetrahydro-2H-pyran-4-carbonitrile (4.8 g, 20.6 mmol) in dichloromethane (40 ml). The reaction mixture was warmed to room temperature over 4 hours. The mixture was then diluted with dichloromethane (180 ml), washed with sodium sulphite solution and 10% aqueous sodium carbonate. The organic layer was separated, dried over sodium sulphate and concentrated in vacuo. The crude product was purified by flash chromatography on silica gel eluting with dichloromethane:methanol:ammonia (100:0:0 to 95:5:0.5 by volume) to provide the title compound (4.55 g, 89%) as an off-white solid. LRMS APCI$^+$ m/z 250 [MH]$^+$.

Example 222

4-{4-[(3-pyrrolidin-1-ylpropyl)thio]phenyl}tetrahydro-2H-pyran-4-carbonitrile

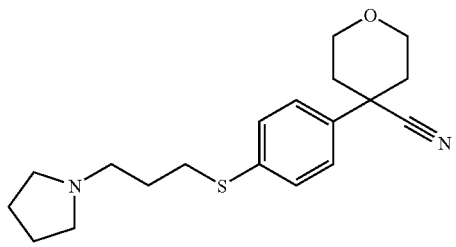

2,6-Lutidine (3.33 ml, 28.6 mmol) was added to a solution of 4-[4-(methylsulfinyl)phenyl]tetrahydro-2H-pyran-4-carbonitrile (2.3 g, 9.23 mmol) in acetonitrile (70 ml). The mixture was cooled in an ice-acetone bath and trifluoroacetic anhydride (3.87 ml, 27.69 mmol) added slowly. The solution was stirred at this temperature under nitrogen for 3 hours. The reaction mixture was then concentrated in vacuo and the residue taken up in methanol (7 ml). Triethylamine (7 ml) was added at 0° C. and the mixture stirred at 0° C. for 30 minutes. N,N-Dimethylformamide (10 ml) was added at 0° C., followed by potassium carbonate (2.8 g, 20.31 mmol) and 1-(3-chloro-propyl)-pyrrolidine (2.72 g, 18.46 mmol) in N,N-dimethylformamide (10 ml). The mixture was then warmed to room temperature and stirred for 18 hours. The reaction mixture was concentrated in vacuo. The residue was taken up in water (50 ml) and extracted with ethyl acetate (2×150 ml). The organic layers were combined, dried over sodium sulphate, filtered and concentrated in vacuo. The crude product was purified by flash chromatography on silica gel eluting with dichloromethane:methanol:ammonia (97:3:0.3 to 95:5:0.5 by volume) to provide the title compound (2.62 g, 86%) as a solid. $^1$H NMR (400 MHz, CDCl$_3$) δ 1.77-1.80 (m, 4H), 1.84-1.91 (m, 2H), 2.01-2.14 (m, 4H), 2.48-2.52 (m, 4H), 2.58 (t, 2H), 2.99 (t, 2H), 3.89 (t, 2H), 4.06-4.10 (m, 2H), 7.34-7.39 (m, 4H). LRMS APCI$^+$ m/z 331 [MH]$^+$.

Intermediate 80: 1-(4-{4-[(3-pyrrolidin-1-ylpropyl)thio]phenyl}tetrahydro-2H-pyran-4-yl)methanamine The title compound (2.42 g, 91%) was prepared using 4-{4-[(3-pyrrolidin-1-ylpropyl)thio]phenyl}tetrahydro-2H-pyran-4-carbonitrile and lithium aluminium hydride similarly to the procedure used for intermediate 51. LRMS APCI$^+$ m/z 335 [MH]$^+$. Microanalysis: Found: C, 64.08; H, 8.79; N, 7.447%. $C_{19}H_{30}N_2OS.0.33DCM$ requires C, 64.04; H, 8.52; N, 7.73%.

Example 223

N,N-dimethyl-1-(4-{4-[(3-pyrrolidin-1-ylpropyl)thio]phenyl}tetrahydro-2H-pyran-4-yl)methanamine

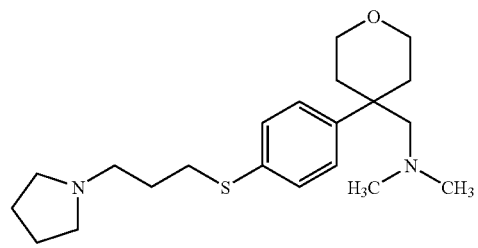

Formaldehyde (37% w/w solution in water, 650 μl, 7.58 mmol) was added to a solution of 1-(4-{4-[(3-pyrrolidin-1-ylpropyl)thio]phenyl}tetrahydro-2H-pyran-4-yl)methanamine (1.0 g, 3.03 mmol) in tetrahydrofuran (10 ml). Acetic acid (173 μl, 3.03 mmol) was then added and the mixture stirred at room temperature for 10 minutes. The mixture was cooled to 0° C. and sodium triacetoxyborohydride (1.6 g, 7.57 mmol) was added in 2 portions. The mixture was then warmed to room temperature and stirred for 18 hours. The reaction was quenched with water and concentrated in vacuo. The residue was taken up in sodium bicarbonate until the aqueous layer pH reached 8. The aqueous layer was then extracted with dichloromethane (2×100 ml). The organic extracts were combined, dried over sodium sulphate, filtered and concentrated in vacuo. The crude product was purified by flash chromatography on silica gel eluting with dichloromethane:methanol:ammonia (97:3:0.3 to 90:10:1 by volume) to provide the title compound (139 mg, 13%) as an oil which crystallised on standing. $^1$H NMR (400 MHz, CD$_3$OD) δ 1.77-1.91 (m, 8H), 1.95 (s, 6H), 2.13-2.18 (m, 2H), 2.49 (s, 2H), 2.51-2.54 (m, 4H), 2.60 (t, 2H), 2.96 (t, 2H), 3.50 (t, 2H), 3.73-3.78 (m, 2H), 7.31-7.36 (m, 4H). HRMS ESI$^+$ m/z 363.2462 [MH]$^+$.

Example 224

N,N-dimethyl-1-(4-{4-[(3-pyrrolidin-1-ylpropyl)sulphonyl]phenyl}tetrahydro-2H-pyran-4-yl)methanamine

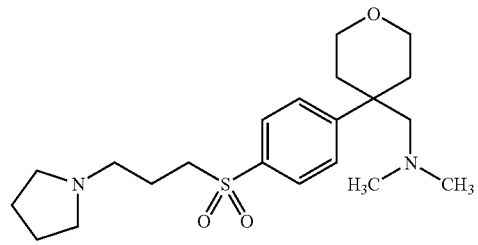

N,N-Dimethyl-1-(4-{4-[(3-pyrrolidin-1-ylpropyl)thio]phenyl}tetrahydro-2H-pyran-4-yl)methanamine (70 mg, 0.19 mmol) was dissolved in acetone (2 ml) and water (0.5 ml). The mixture was cooled to 0° C. and a solution of Oxone® (131 mg, 0.21 mmol) in water (0.5 ml) added dropwise. The reaction mixture was stirred at room temperature for 18 hours. The mixture was then diluted with more water, basified with 10% aqueous sodium carbonate and extracted with dichloromethane (2×20 ml). The organic layers were combined, dried over sodium sulphate, filtered and concentrated in vacuo. The crude product was purified by flash chromatography on silica gel eluting with dichloromethane: methanol:ammonia (96:4:0.4 by volume) to provide the title compound (23 mg, 30%) as an oil. $^1$H NMR (400 MHz, CDCl$_3$) δ 1.72-1.75 (m, 4H), 1.90-1.99 (m, 10H), 2.10-2.14 (m, 2H), 2.40-2.44 (m, 4H), 2.48-2.52 (m, 4H), 3.20 (t, 2H), 3.52 (t, 2H), 3.75-3.80 (m, 2H), 7.52 (d, 2H), 7.86 (d, 2H). HRMS ESI$^+$ m/z 395.2363 [MH]$^+$.

Intermediate 81: 4-{4-[(3-pyrrolidin-1-ylpropyl)thio] phenyl}tetrahydro-2H-pyran-4-carboxylic acid 4-{4-[(3-Pyrrolidin-1-ylpropyl)thio]phenyl}tetrahydro-2H-pyran-4-carbonitrile (1 g, 3.03 mmol) was heated at reflux in concentrated hydrochloric acid (10 ml) for 18 hours. More hydrochloric acid (11 ml) was added and the mixture heated at reflux for a further 18 hours. The reaction mixture was then concentrated in vacuo to a solid. This was taken up in dichloromethane and triethylamine (4 ml) added. The reaction mixture was then concentrated in vacuo. This was repeated twice to provide the title compound (2.03 g) as a solid containing triethylamine hydrochloride. LRMS APCI$^+$ m/z 350 [MH]$^+$.

Intermediate 82: 1-[3-({4-[4-(pyrrolidin-1-ylcarbonyl)tetrahydro-2H-pyran-4-yl]phenyl}thio)propyl]pyrrolidine The title compound (228 mg, 40%) was prepared using 4-{4-[(3-pyrrolidin-1-ylpropyl)thio]phenyl}tetrahydro-2H-pyran-4-carboxylic acid and pyrrolidine similarly to the procedure used for example 149.

HRMS ESI$^+$ m/z 403.2403 [MH]$^+$.

Example 225

1-[3-({4-[4-(pyrrolidin-1-ylmethyl)tetrahydro-2H-pyran-4-yl]phenyl}thio)propyl]pyrrolidine

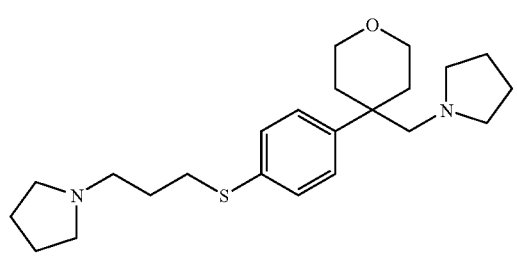

The title compound (58 mg, 27%) was prepared using 1-[3-({4-[4-(pyrrolidin-1-ylcarbonyl)tetrahydro-2H-pyran-4-yl]phenyl}thio)propyl]pyrrolidine and lithium aluminium hydride similarly to the procedure used for example 142. $^1$H NMR (400 MHz, CDCl$_3$) δ 1.54-1.57 (m, 4H), 1.75-1.79 (m, 4H), 1.84-1.94 (m, 4H), 2.06-2.10 (m, 2H), 2.18-2.22 (m, 4H), 2.47-2.50 (m, 4H), 2.57 (t, 2H), 2.63 (s, 2H), 2.96 (t, 2H), 3.54 (t, 2H), 3.73-3.78 (m, 2H), 7.22 (d, 2H), 7.29 (d, 2H). HRMS ESI$^+$ m/z 389.2615 [MH]$^+$.

Intermediate 83: 1-[4-(3-pyrrolidin-1-ylpropoxy)phenyl]cyclohexanecarboxylic acid The title compound (contaminated with ammonium chloride) was prepared using 1-[4-(3-pyrrolidin-1-ylpropoxy) phenyl]cyclohexanecarbonitrile and concentrated hydrochloric acid similarly to the procedure used for intermediate 80. LRMS ESI$^+$ m/z 332 [MH]$^+$.

Intermediate 84: 1-({1-[4-(3-pyrrolidin-1-ylpropoxy)phenyl]cyclohexyl}carbonyl)piperidin-4-ol The title compound (200 mg, 16%) was prepared using 1-[4-(3-pyrrolidin-1-ylpropoxy)phenyl]cyclohexanecarboxylic acid and 4-hydroxypiperidine similarly to the procedure used for example 149. HRMS ESI$^+$ m/z 415.2943 [MH]$^+$.

Example 226

1-({1-[4-(3-pyrrolidin-1-ylpropoxy)phenyl] cyclohexyl}methyl) piperidin-4-ol

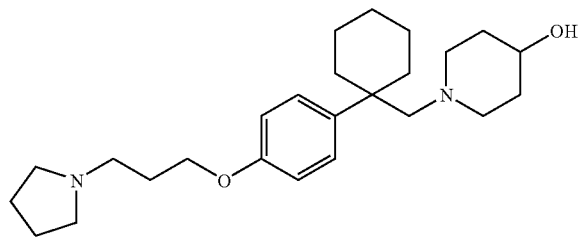

The title compound (90 mg, 46%) was prepared using 1-({1-[4-(3-pyrrolidin-1-ylpropoxy)phenyl] cyclohexyl}carbonyl)piperidin-4-ol and lithium aluminium hydride similarly to the procedure used for example 142. $^1$H NMR (400 MHz, CDCl$_3$) δ 1.29-1.55 (m, 10H), 1.64-1.69 (m, 2H), 1.77-1.81 (m, 4H), 1.90-2.06 (m, 4H), 2.10-2.13 (m, 2H), 2.23 (s, 2H), 2.26-2.30 (m, 2H), 2.51-2.54 (m, 4H), 2.62 (t, 2H), 3.51 (m, 1H), 4.01 (t, 2H), 6.83 (d, 2H), 7.25 (d, 2H). HRMS ESI$^+$ m/z 401.3154 [MH]$^+$.

Example 227

1-methyl-4-({1-[4-(3-pyrrolidin-1-ylpropoxy)phenyl]cyclohexyl}carbonyl)piperazine

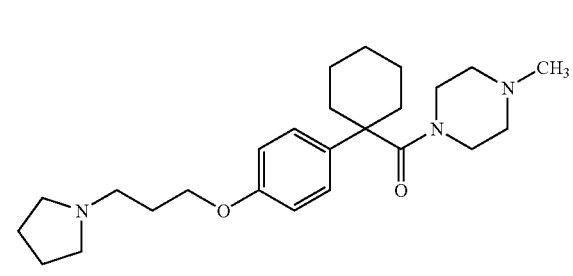

The title compound (10 mg, 8%) was prepared using 1-[4-(3-pyrrolidin-1-ylpropoxy)phenyl]cyclohexanecarboxylic acid and 1-methylpiperazine similarly to the procedure used for example 149. $^1$H NMR (400 MHz, CD$_3$OD) δ 1.32 (m, 1H), 1.64-1.69 (m, 7H), 1.81-1.85 (m, 4H), 1.98-2.03 (m, 2H), 2.05-2.13 (m, 4H), 2.15 (s, 3H), 2.25-2.28 (m, 2H), 2.59-2.62 (m, 4H), 2.69 (t, 2H), 3.33-3.42 (m, 4H), 4.01 (t, 2H), 6.90 (d, 2H), 7.16 (d, 2H). HRMS ESI⁺ m/z 414.3107 [MH]⁺.

Intermediate 85: 1-({1-[4-(3-pyrrolidin-1-ylpropoxy)phenyl]cyclohexyl}carbonyl)piperazine The title compound (351 mg, 19%) was prepared using 1-[4-(3-pyrrolidin-1-ylpropoxy)phenyl]cyclohexanecarboxylic acid and piperazine similarly to the procedure used for example 149. LRMS APCI⁺ m/z 400 [MH]⁺.

Example 228

1-({1-[4-(3-pyrrolidin-1-ylpropoxy)phenyl]cyclohexyl}methyl) piperazine

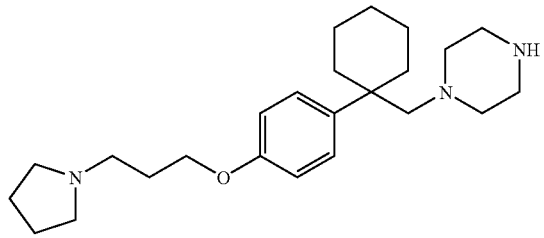

The title compound (187 mg, 59%) was prepared using 1-({1-[4-(3-pyrrolidin-1-ylpropoxy)phenyl]cyclohexyl}carbonyl)piperazine and lithium aluminium hydride similarly to the procedure used for example 142. ¹H NMR (400 MHz, CDCl₃) δ 1.30-1.33 (m, 3H), 1.46-1.54 (m, 4H), 1.78-1.81 (m, 4H), 1.98-2.05 (m, 4H), 2.09-2.12 (m, 6H), 2.23 (s, 2H), 2.53-2.57 (m, 4H), 2.62-2.71 (m, 6H), 4.01 (t, 2H), 6.83 (d, 2H), 7.26 (d, 2H). LRMS APCI⁺ m/z 386 [MH]⁺.

Example 229

1-acetyl-4-({1-[4-(3-pyrrolidin-1-ylpropoxy)phenyl]cyclohexyl}methyl)piperazine

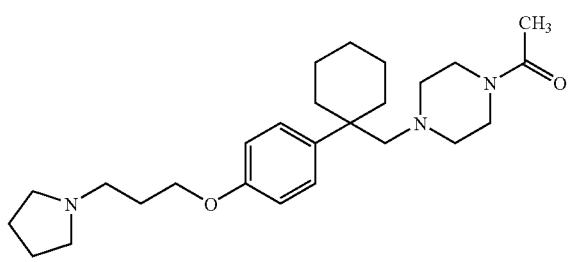

The title compound (73 mg, 73%) was prepared using 1-({1-[4-(3-pyrrolidin-1-ylpropoxy)phenyl]cyclohexyl}methyl) piperazine and acetic anhydride similarly to the procedure used for example 166. ¹H NMR (400 MHz, CDCl₃) δ 1.31-1.34 (m, 3H), 1.48-1.53 (m, 5H), 1.82-1.85 (m, 4H), 1.99 (s, 3H), 2.02-2.07 (m, 4H), 2.13-2.17 (m, 4H), 2.28 (s, 2H), 2.58-2.64 (m, 4H), 2.70 (t, 2H), 3.20 (t, 2H), 3.41-3.43 (m, 2H), 4.01 (t, 2H), 6.83 (d, 2H), 7.25 (d, 2H). HRMS ESI⁺ m/z 428.3264 [MH]⁺.

Example 230

1-(methylsulfonyl)-4-({1-[4-(3-pyrrolidin-1-ylpropoxy)phenyl]cyclohexyl}methyl)piperazine

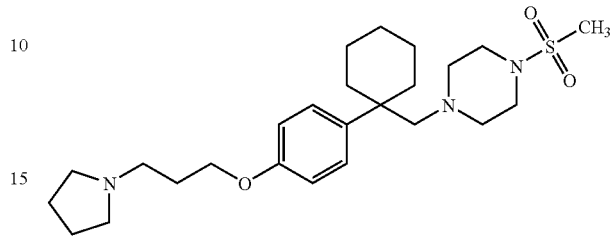

Methanesulphonic acid anhydride (49 mg, 0.28 mmol) was added at 0° C. to a solution of 1-({1-[4-(3-pyrrolidin-1-ylpropoxy)phenyl]cyclohexyl}methyl) piperazine (90 mg, 0.23 mmol) and pyridine (47 μl, 0.58 mmol) in dichloromethane (1 ml). The reaction was stirred at 0° C. for 10 minutes, then allowed to warm up to room temperature and stirred for 18 hours. The reaction mixture was concentrated under reduced pressure and partitioned between dichloromethane (20 ml) and aqueous sodium carbonate (20 ml). The layers were separated. The organic layer was dried over sodium sulphate, filtered and concentrated in vacuo. The crude product was purified by flash chromatography on silica gel eluting with dichloromethane:methanol:ammonia (96:4:0.4 by volume) to provide the title compound (61 mg, 56%). ¹H NMR (400 MHz, CDCl₃) δ 1.29-1.36 (m, 3H), 1.45-1.52 (m, 5H), 1.85-1.90 (m, 4H), 2.08-2.15 (m, 4H), 2.22 (t, 4H), 2.32 (s, 2H), 2.67-2.79 (m, 9H), 3.00-3.03 (m, 4H), 4.02 (t, 2H), 6.83 (d, 2H), 7.24 (d, 2H). HRMS ESI⁺ m/z 464.2931 [MH]⁺.

Intermediate 86: tert-butyl bis(2-chloroethyl)carbamate

Bis-(2-chloroethyl)amine hydrochloride (10 g, 56 mmol) was stirred vigorously in a mixture of dichloromethane (150 ml) and aqueous 10% sodium hydroxide (50 ml). Di-tert-butyldicarbonate (12.2 g, 56 mmol) as a solution in dichloromethane (75 ml) was then added dropwise. The reaction mixture was stirred at room temperature for 5 hours. TLC showed the reaction was not complete so more di-tert-butyldicarbonate (4 g, 18.3 mmol) was added. The mixture was stirred vigorously for 18 hours at room temperature. The layers were then separated and the aqueous layer extracted with more dichloromethane (2×50 ml). The combined organic layers were dried over Na₂SO₄, filtered and concentrated under reduced pressure. The crude product was purified by flash chromatography on silica gel eluting with pentane:ethyl acetate (99:1 to 80:20 by volume) to provide the title compound (7.9 g, 58%).

Intermediate 87: tert-butyl 4-cyano-4-[4-(3-pyrrolidin-1-ylpropoxy)phenyl]piperidine-1-carboxylate The title compound (1.8 g, 53%) was prepared using [4-(3-pyrrolidin-1-ylpropoxy)phenyl]acetonitrile, tert-butyl bis(2-chloroethyl)carbamate, sodium hydride and potassium iodide similarly to the procedure used for intermediate 56. LRMS APCI⁺ m/z 414 [MH]⁺ and m/z 245 [SMH]⁺.

Example 231

4-[4-(3-pyrrolidin-1-ylpropoxy)phenyl]piperidine-4-carbonitrile

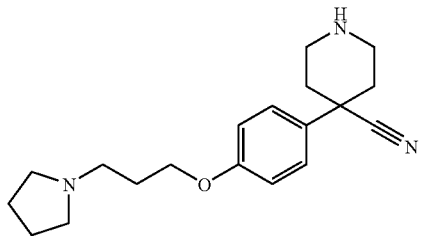

tert-Butyl 4-cyano-4-[4-(3-pyrrolidin-1-ylpropoxy)phenyl]piperidine-1-carboxylate (500 mg, 1.24 mmol) was stirred for 1 hour in trifluoroacetic acid (1.91 ml, 24.8 mmol) and dichloromethane (30 ml). More trifluoroacetic acid (3 ml) was added and the reaction stirred at room temperature for another hour. The reaction mixture was quenched with saturated aqueous sodium carbonate solution (15 ml) and the layers separated. The organic layer was dried over sodium sulphate and concentrated in vacuo. The crude product was purified by flash chromatography on silica gel eluting with dichloromethane:methanol:ammonia (95:5:0.5 to 90:10:1 by volume) to provide the title compound (450 mg, 18% over 2 steps). $^1$H NMR (400 MHz, CD$_3$OD) δ 1.81-1.85 (m, 4H), 1.91-2.09 (m, 6H), 2.59-2.62 (m, 4H), 2.69 (t, 2H), 2.99 (t, 2H), 3.12-3.15 (m, 2H), 4.04 (t, 2H), 6.96 (d, 2H), 7.42 (d, 2H). HRMS ESI$^+$ m/z 314.2227 [MH]$^+$.

Example 232

1-acetyl-4-[4-(3-pyrrolidin-1-ylpropoxy)phenyl]piperidine-4-carbonitrile

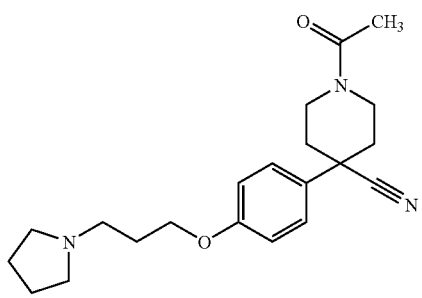

Acetyl chloride (27 µl, 0.37 mmol) was added dropwise to a solution of 4-[4-(3-pyrrolidin-1-ylpropoxy)phenyl]piperidine-4-carbonitrile (90 mg, 0.28 mmol) and triethylamine (78 µl, 0.56 mmol) in dichloromethane (3 ml). The reaction mixture was stirred at room temperature for 1 hour. The reaction mixture was diluted with dichloromethane (15 ml) and washed with water (15 ml). The layers were separated and the aqueous layer was further extracted with dichloromethane (2×10 ml). The organics were combined, washed with brine, dried over sodium sulphate, filtered and concentrated in vacuo. The crude product was purified by flash chromatography on silica gel eluting with ethyl acetate:methanol:ammonia (95:5:0.5 by volume) to provide the title compound (28 mg, 28%). $^1$H NMR (400 MHz, CD$_3$OD) δ 1.82-1.85 (m, 4H), 1.89-2.18 (m, 9H), 2.60-2.63 (m, 4H), 2.69 (t, 2H), 3.00 (t, 1H), 3.50 (t, 1H), 4.03-4.12 (m, 3H), 4.70 (d, 1H), 6.97 (d, 2H), 7.44 (d, 2H). HRMS ESI$^+$ m/z 356.2329 [MH]$^+$.

Example 233

1-methyl-4-[4-(3-pyrrolidin-1-ylpropoxy)phenyl]piperidine-4-carbonitrile

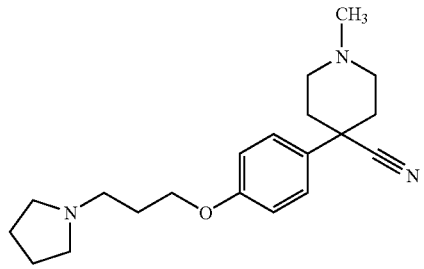

The title compound (80 mg, 76%) was prepared from 4-[4-(3-pyrrolidin-1-ylpropoxy)phenyl]piperidine-4-carbonitrile, formaldehyde and sodium triacetoxyborohydride similarly to the procedure used for example 54. $^1$H NMR (400 MHz, CD$_3$OD) δ 1.81-1.85 (m, 4H), 1.97-2.15 (m, 6H), 2.37 (s, 3H), 2.45 (t, 2H), 2.58-2.62 (m, 4H), 2.68 (t, 2H), 2.99 (d, 2H), 4.04 (t, 2H), 6.96 (d, 2H), 7.42 (d, 2H). LRMS APCI$^+$ m/z 328 [MH]$^+$. Microanalysis: Found: C, 73.01; H, 8.94; N, 12.81%. C$_{20}$H$_{29}$N$_3$O requires C, 73.36; H, 8.93; N, 12.83%.

Example 234

1-isopropyl-4-[4-(3-pyrrolidin-1-ylpropoxy)phenyl]piperidine-4-carbonitrile

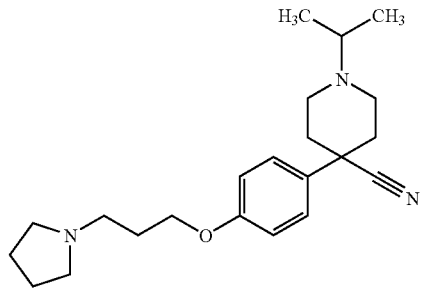

The title compound (45 mg, 58%) was prepared from 4-[4-(3-pyrrolidin-1-ylpropoxy)phenyl]piperidine-4-carbonitrile, acetone and sodium triacetoxyborohydride similarly to the procedure used for example 54. $^1$H NMR (400 MHz, CD$_3$OD) δ 1.12 (d, 6H), 1.81-1.84 (m, 4H), 1.99-2.14 (m, 6H), 2.58-2.69 (m, 8H), 2.82 (m, 1H), 3.02 (d, 2H), 4.04 (t, 2H), 6.96 (d, 2H), 7.42 (d, 2H). HRMS ESI$^+$ m/z 356.2691 [MH]$^+$.

Example 235

1-(2-methoxyethyl)-4-[4-(3-pyrrolidin-1-ylpropoxy)phenyl]piperidine-4-carbonitrile

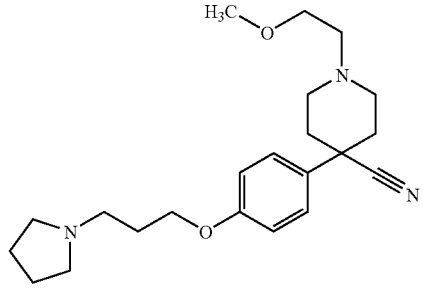

A mixture of 4-[4-(3-pyrrolidin-1-ylpropoxy)phenyl]piperidine-4-carbonitrile (68 mg, 0.22 mmol), 2-bromoethylmethylether (21 μl, 0.22 mmol), solid sodium bicarbonate (84 mg, 1.0 mmol) and potassium iodide (5 mg, catalytic) was heated at 50° C. in acetonitrile (1 ml) for 18 hours. The reaction mixture was concentrated in vacuo. The residue was partitioned between dichloromethane (2×50 ml) and 10% aqueous sodium carbonate (20 ml). The organic layers were combined, dried over sodium sulphate, filtered and concentrated in vacuo. The crude product was purified by flash chromatography on silica gel eluting with dichloromethane: methanol:ammonia (97:3:0.3 to 95:5:0.5 by volume) to provide the title compound (46 mg, 61%). $^1$H NMR (400 MHz, CD$_3$OD) 61.83-1.87 (m, 4H), 2.01-2.10 (m, 6H), 2.45-2.52 (m, 2H), 2.65-2.69 (m, 6H), 2.75 (t, 2H), 3.09 (d, 2H), 3.35 (s, 3H), 3.56 (t, 2H), 4.04 (t, 2H), 6.96 (d, 2H), 7.42 (d, 2H). HRMS ESI$^+$ m/z 372.2639 [MH]$^+$.

Example 236

2-[methyl({4-[4-(3-pyrrolidin-1-ylpropoxy)phenyl] tetrahydro-2H-pyran-4-yl}methyl)amino]ethanol

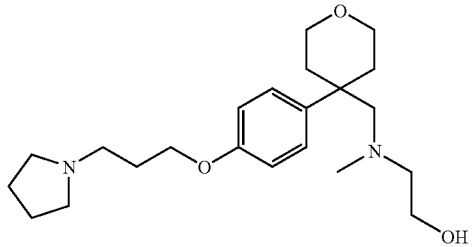

A solution of methyl-{4-[4-(3-pyrrolidin-1-ylpropoxy) phenyl]-tetrahydropyran-4-ylmethyl}amine (350 mg, 1.05 mmol), glycolaldehyde dimer (130 mg, 1.05 mmol) and AcOH (0.15 ml, 2.1 mmol) in DCM (5 ml) was stirred at room temperature for 18 hours. Saturated aqueous sodium carbonate (10 ml) and DCM (10 ml) were added and the mixture was shaken and partitioned. The aqueous phase was extracted with DCM (2×10 ml) and the combined organics dried (K$_2$CO$_3$), filtered and concentrated in vacuo. The crude product was purified by flash chromatography on silica gel eluting with dichloromethane:methanol:ammonia (92:8:1) to provide the title compound as a clear colourless oil (223 mg, 0.59 mmol, 56%). $^1$H NMR (400 MHz, CDCl$_3$) δ 1.70-1.90 (m, 6H), 1.96 (s, 3H), 2.00 (quintet, 2H), 2.14 (m, 2H), 2.37 (t, 2H), 2.40-2.60 (m, 6H), 2.65 (t, 2H), 3.35 (t, 2H), 3.50 (m, 2H), 3.76 (m, 2H), 4.01 (t, 2H), 6.89 (d, 2H), 7.19 (d, 2H). HRMS ESI$^+$ m/z 377.2796 [MH]$^+$.

Example 237

N-methyl-N-({4-[4-(3-pyrrolidin-1-ylpropoxy)phenyl]tetrahydro-2H-Pyran-4-yl}methyl)cyclopropanamine

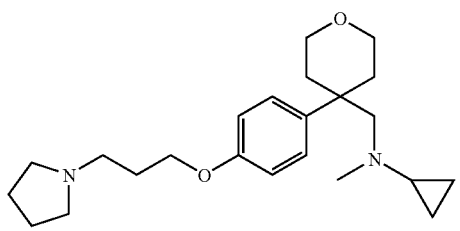

A mixture of methyl-{4-[4-(3-pyrrolidin-1-ylpropoxy) phenyl]-tetrahydropyran-4-ylmethyl}amine (115 mg, 0.35 mmol), (1-Ethoxy-cyclopropoxy)-trimethylsilane (360 mg, 2.0 mmol), AcOH (0.2 ml, 3.5 mmol), NaCNBH$_3$ (110 mg, 1.75 mmol) and 4 Å molecular sieves (100 mg) in MeOH (5 ml) was heated to reflux for 18 hours. The mixture was cooled, concentrated in vacuo and partitioned between 2M NaOH (10 ml) and DCM (10 ml). The organic phase was separated and the aqueous phase extracted with DCM (2×10 ml). The combined organic phases were concentrated in vacuo and purified by flash chromatography on silica gel eluting with dichloromethane:methanol:ammonia (92:8:1) to provide the title compound as a clear colourless oil (20 mg, 0.054 mmol, 15%). $^1$H NMR (400 MHz, CDCl$_3$) δ 0.15 (m, 2H), 0.29 (m, 2H), 1.68 (m, 1H), 1.70-1.90 (m, 6H), 1.85 (s, 3H), 2.00-2.10 (m, 4H), 2.60 (m, 4H), 2.65 (s, 2H), 2.68 (m, 2H), 3.50 (t, 2H), 3.76 (m, 2H), 4.01 (t, 2H), 6.85 (d, 2H), 7.16 (d, 2H). HRMS ESI$^+$ m/z 373.2844 [MH]$^+$.

Example 238

1-(3-{4-[4-(aziridin-1-ylmethyl)tetrahydro-2H-pyran-4-yl]phenoxy}propyl)pyrrolidine

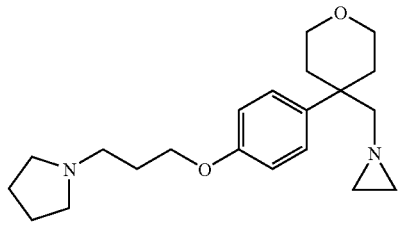

A mixture of {4-[4-(3-Pyrrolidin-1-ylpropoxy)phenyl]tetrahydropyran-4-yl}methylamine (482 mg, 1.50 mmol), 1,2-dibromoethane (0.13 ml, 1.50 mmol) and K$_2$CO$_3$ (420 mg, 3.0 mmol) in acetonitrile (50 ml) was heated to 70° C. for 3 days. The mixture was concentrated in vacuo and purified by flash chromatography on silica gel eluting with dichloromethane:methanol:ammonia (93:7:1 to 91:9:1) to provide the title compound as a clear colourless oil (51 mg, 0.15 mmol, 10%). $^1$H NMR (400 MHz, CDCl$_3$) δ 0.71 (m, 2H), 1.48 (m, 2H), 1.78 (m, 4H), 2.00 (m, 4H), 2.19 (m, 2H), 2.30 (s, 2H), 2.54 (m, 4H), 2.63 (t, 2H), 3.54 (m, 2H), 3.78 (m, 2H), 4.01 (t, 2H), 6.86 (d, 2H), 7.21 (d, 2H). HRMS ESI$^+$ m/z 345.2534 [MH]$^+$.

Example 239

2-(methylthio)-1-({4-[4-(3-pyrrolidin-1-ylpropoxy) phenyl]tetrahydro-2H-pyran-4-yl}methyl)-1H-imidazole

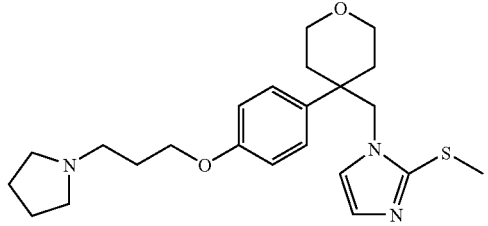

A solution of {4-[4-(3-Pyrrolidin-1-ylpropoxy)phenyl]tetrahydropyran-4-yl}methylamine (159 mg, 0.50 mmol) and dimethyl 2,2-diethoxyethyldithioimido-carbonate (120 mg, 0.50 mmol, ARKIVOC 2001, viii, 34-39) in AcOH (5 ml) was heated at reflux for 8 h. The mixture was concentrated in vacuo and partitioned between saturated aqueous sodium bicarbonate (10 ml) and DCM (10 ml). The aqueous phase was extracted with DCM (2×10 ml) and the combined organics dried ($K_2CO_3$), filtered and concentrated in vacuo. The crude product was purified by flash chromatography on silica gel eluting with dichloromethane:methanol:ammonia (90:10:1) to provide the title compound as a clear colourless gum (90 mg, 0.22 mmol, 43%). $^1$H NMR (400 MHz, $CDCl_3$) δ 1.80-2.00 (m, 6H), 2.12 (m, 2H), 2.21 (quintet, 2H), 2.48 (s, 3H), 2.80-3.00 (m, 6H), 3.45 (m, 2H), 3.83 (m, 2H), 3.98 (s, 2H), 4.06 (t, 2H), 6.10 (s, 1H), 6.85 (d, 2H), 6.87 (s, 1H), 7.01 (d, 2H). LRMS APCI$^+$ m/z 416 [MH]$^+$.

Example 240

1-{4-[4-(3-Pyrrolidin-1-yl-propoxy)-phenyl]-tetrahydro-pyran-4-ylmethyl}-1H-imidazole

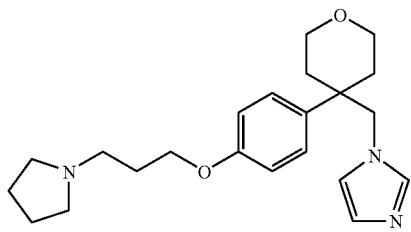

To a solution of 2-(methylthio)-1-({4-[4-(3-pyrrolidin-1-ylpropoxy)phenyl]tetrahydro-2H-pyran-4-yl}methyl)-1H-imidazole (90 mg, 0.22 mmol) in EtOH (4 ml) and water (1 ml) was added Raney Nickel (50% slurry in water) in 200 mg aliquots every 30 min. After 3 h all starting material had been consumed. The mixture was filtered through Arbocel® with EtOH (200 ml) and concentrated in vacuo. The crude product was purified by flash chromatography on silica gel eluting with dichloromethane:methanol:ammonia (90:10:1) to provide the title compound as a yellow oil (29 mg, 0.078 mmol, 36%). $^1$H NMR (400 MHz, $CDCl_3$) δ 1.80-2.00 (m, 6H), 2.10 (m, 4H), 2.70-2.90 (m, 6H), 3.50 (t, 2H), 3.81 (m, 2H), 3.97 (s, 2H), 4.04 (t, 2H), 6.32 (s, 1H), 6.80-6.90 (m, 4H), 6.98 (d, 2H). HRMS ESI$^+$ m/z 370.2485 [MH]$^+$.

Intermediate 88: 4-(4-{[tert-butyl(dimethyl)silyl]oxy}phenyl)tetrahydro-2H-pyran-4-carbonitrile A solution of 4-(4-hydroxy-phenyl)-tetrahydro-pyran-4-carbonitrile (5 g, 25 mmol), t-butyldimethylsilyl chloride (4.46 g, 29 mmol) and imidazole (2.34 g, 34 mmol) were stirred in DMF (15 ml) at room temperature. After 30 minutes, a yellow suspension was observed. The reaction was partitioned between ether (75 ml) and water (100 ml). The ether was then washed further with water (4×50 ml), dried over sodium sulphate, filtered and concentrated in vacuo. The title compound was isolated as a pale orange waxy solid (7 g, 90%).

Intermediate 89: 1-[4-(4-{[tert-butyl(dimethyl)silyl]oxy}phenyl)tetrahydro-2H-pyran-4-yl]methanamine To a stirred solution of 4-(4-{[tert-butyl(dimethyl)silyl]oxy}phenyl)tetrahydro-2H-pyran-4-carbonitrile (3.5 g, 11 mmol) in THF (35 ml) at 0° C. was added dropwise lithium aluminium hydride (1M solution in ether, 44 ml, 44 mmol). The reaction was allowed to warm up to room temperature and stirred for 4 hours until complete. The reaction mixture was cooled to 0° C., water (1.66 mL) was added followed by NaOH (2.0M, 1.66 mL) and water (4.97 mL). The mixture was filtered through a short pad of celite, eluting with dichloromethane:methanol (97:3, 150 ml) and concentrated in vacuo. Solid obtained was partitioned between ethyl acetate (50 ml) and sodium bicarbonate (50 ml). The organic layer was then dried over sodium sulphate, filtered and concentrated in vacuo to give the title compound (2.04 g, 58%). LRMS APCI$^+$ m/z 322 [MH]$^+$.

Intermediate 90: N-{[4-(4-{[tert-butyl(dimethyl)silyl]oxy}phenyl)tetrahydro-2H-pyran-4-yl]methyl}pyridin-2-amine 1-[4-(4-{[tert-butyl(dimethyl)silyl]oxy}phenyl)tetrahydro-2H-pyran-4-yl]methanamine (3.65 g, 11.4 mmol), 2-bromopyridine (910 μl, 9.48 mmol), tris(dibenzylideneacetone)dipalladium(0) (471 mg, 0.455 mmol), 2,2'-bis(diphenylphosphino)1,1'-binaphyl (567 mg, 0.910 mmol) and sodium tert-butoxide (1.29 g, 13.0 mmol) were stirred in toluene (50 ml) at 70° C. under nitrogen for 24 hours. The toluene was removed in vacuo and the residue partitioned between dichloromethane (50 ml) and saturated sodium bicarbonate solution (50 ml). The organic layer was separated and dried over sodium sulphate, filtered and concentrated in vacuo. The crude product was purified by flash chromatography on silica gel eluting with ether:pentane (80:20 by volume) to provide the title compound (2.10 g, 46%) as a yellow solid. LRMS APCI$^+$ m/z 399 [MH]$^+$.

Intermediate 90: N-{[4-(4-{[tert-butyl(dimethyl)silyl]oxy}phenyl)tetrahydro-2H-pyran-4-yl]methyl}pyridin-2-amine 1-[4-(4-{[tert-butyl(dimethyl)silyl]oxy}phenyl)tetrahydro-2H-pyran-4-yl]methanamine (3.65 g, 11.4 mmol), 2-bromopyridine (910 μl, 9.48 mmol), tris(dibenzylideneacetone)dipalladium(0) (471 mg, 0.455 mmol), 2,2'-bis(diphenylphosphino)1,1'-binaphyl (567 mg, 0.910 mmol) and sodium tert-butoxide (1.29 g, 13.0 mmol) were stirred in toluene (50 ml) at 70° C. under nitrogen for 24 hours. The toluene was removed in vacuo and the residue partitioned between dichloromethane (50 ml) and saturated sodium bicarbonate solution (50 ml). The organic layer was separated and dried over sodium sulphate, filtered and concentrated in vacuo. The crude product was purified by flash chromatography on silica gel eluting with ether:pentane (80:20 by volume) to provide the title compound (2.10 g, 46%) as a yellow solid. LRMS APCI$^+$ m/z 399 [MH]$^+$.

Intermediate 91: 4-{4-[(pyridin-2-ylamino)methyl]tetrahydro-2H-pyran-4-yl}phenol N-{[4-(4-{[tert-butyl(dimethyl)silyl]oxy}phenyl)tetrahydro-2H-pyran-4-yl]methyl}pyridin-2-amine (2.099 g, 5.27 mmol) and tetrabutylammonium fluoride (1M solution in THF, 5.80 ml, 5.80 mmol) were stirred in THF (20 ml) at room temperature for 24 hours until complete. THF was removed in vacuo and the residue partitioned between dichloromethane (75 ml) and sodium bicarbonate (50 ml). The organic layer was washed further with sodium bicarbonate (2×50 ml), then separated and dried over sodium sulphate, filtered and concentrated in vacuo. The crude product was purified by column chromatography on Biotage® silica gel eluting with dichloromethane:methanol:ammonia (100:0:0 to 90:10:1 by volume) to give the title compound (862 mg, 58%) as a solid. LRMS APCI$^+$ m/z 285 [MH]$^+$.

Intermediate 92: N-({4-[4-(4-chlorobutoxy)phenyl]tetrahydro-2H-pyran-4-yl}methyl)pyridin-2-amine 4-{4-[(pyridin-2-ylamino)methyl]tetrahydro-2H-pyran-4-yl}phenol (220 mg, 0.775 mmol), 1-bromo-4-chlorobutane (146 mg, 0.852 mmol) and potassium carbonate (118 mg, 0.852 mmol) were stirred in DMF (1 ml) at 60° C. for 24 hours until complete. Reaction was partitioned between ethyl acetate (50 ml) and water (75 ml). The organic layer was separated and washed further with water (2×30 ml), then dried over sodium sulphate, filtered and concentrated in vacuo. The crude compound was purified by flash chromatography on silica gel eluting with dichloromethane:methanol:ammonia (100:0:0 to 98:2:0.2 by volume) to give the title compound (184 mg, 63%) as a yellow solid. LRMS APCI+ m/z 375 [MH]+.

Example 241

N-({4-[4-(4-pyrrolidin-1-ylbutoxy)phenyl]tetrahydro-2H-pyran-4-yl}methyl)pyridin-2-amine

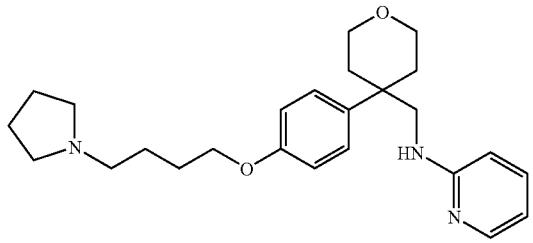

A mixture of N-({4-[4-(4-chlorobutoxy)phenyl]tetrahydro-2H-pyran-4-yl}methyl)pyridin-2-amine (180 mg, 0.481 mmol), pyrrolidine (80 μl, 0.963 mmol), sodium carbonate (102 mg, 0.963 mmol) and sodium iodide (4 mg, 0.024 mmol) were stirred in butanol (5 ml) at 100° C. for 24 hours until complete. Butanol was removed in vacuo and the residue partitioned between ethyl acetate (40 ml) and water (40 ml). Organic layer was dried over sodium sulphate, filtered and concentrated in vacuo to give a brown solid. Solid was purified by flash chromatography on silica gel eluting with dichloromethane:methanol:ammonia (98:2:02 to 96:4:0.4 by volume), followed by recrystallisation from ether (1.5 ml) to give the title compound (56.6 mg, 29%). $^1$H NMR (400 MHz, CDCl$_3$) δ 1.78-2.00 (m, 12H), 2.08-2.20 (m, 2H), 2.54-2.90 (m, 4H), 3.50 (d, 2H), 2.54-2.63 (m, 2H), 3.79-3.88 (m, 2H), 3.96-4.08 (m, 2H), 6.23 (d, 1H), 6.50 (t, 1H), 6.90 (d, 2H), 7.25 (d, 2H), 7.32 (t, 1H), 8.01 (d, 1H). LRMS APCI+ m/z 410 [MH]+.

Example 242

N-({4-[4-(3-piperidin-1-ylpropoxy)phenyl]tetrahydro-2H-pyran-4-yl}methyl)pyridin-2-amine

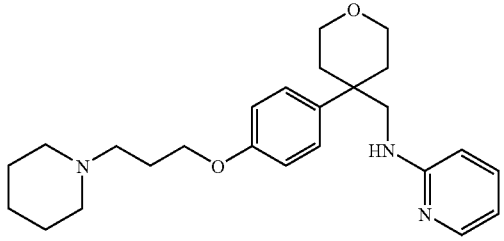

4-{4-[(pyridin-2-ylamino)methyl]tetrahydro-2H-pyran-4-yl}phenol (200 mg, 0.704 mmol), 3-chloropropylpiperidine hydrochloride (152 mg, 0.775 mmol) and potassium carbonate (204 mg, 1.48 mmol) were stirred in DMF (1 ml) at 45° C. for 24 hours until complete. The reaction was then partitioned between ethyl acetate (40 ml) and water (40 ml). The organic layer was separated, dried over sodium sulphate and concentrated in vacuo to give a solid. The solid was purified by preparative HPLC to give the title compound (220 mg, 76%) as a white solid. $^1$H NMR (400 MHz, CDCl$_3$) δ 1.44-1.55 (m, 2H), 1.64-1.78 (m, 4H), 1.85-2.00 (m, 2H), 2.08-2.18 (m, 4H), 2.52-2.70 (m, 6H), 3.48 (d, 2H), 3.52-3.62 (m, 2H), 3.78-3.85 (m, 2H), 4.02 (t, 2H), 6.21 (d, 1H), 6.50 (t, 1H), 6.90 (d, 2H), 7.24 (d, 2H), 7.34 (t, 1H), 8.01 (d, 1H). LRMS APCI+ m/z 410 [MH]+.

Example 243

N-[(4-{4-[(1-ethylpiperidin-4-yl)oxy]phenyl}tetrahydro-2H-pyran-4-yl)methyl]pyridin-2-amine

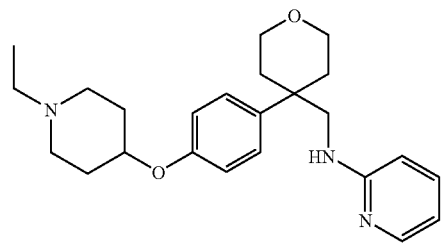

To a solution of 4-{4-[(pyridin-2-ylamino)methyl]tetrahydro-2H-pyran-4-yl}phenol (250 mg, 0.881 mmol), 1-ethylpiperidin-4-ol (103 mg, 0.8 mmol) and triphenylphosphine (231 mg, 0.881 mmol) in THF (5 ml) at 0° C. under nitrogen was added dropwise diisopropyl azodicarboxylate (95% solution, 183 μl, 0.881 mmol). Reaction was stirred for 10 minutes then warmed to room temperature for 72 hours until complete. THF was removed in vacuo and the residue partitioned between ethyl acetate (50 ml) and saturated sodium bicarbonate solution (50 ml). The organic layer was separated, dried over sodium sulphate, filtered and concentrated in vacuo. Crude product was purified by flash chromatography eluting with dichloromethane:methanol:ammonia (100:0:0 to 96:4:0.4 by volume) to give the title compound (8.2 mg, 23%) as a yellow oil. $^1$H NMR (400 MHz, CDCl$_3$) δ 1.05 (t, 3H), 1.80-1.98 (m, 4H), 2.00-2.18 (m, 4H), 2.28-2.42 (m, 2H), 2.44-2.54 (q, 2H), 2.72-2.86 (m, 2H), 3.50 (d, 2H), 3.55-3.62 (m, 2H), 3.78-3.88 (m, 2H), 4.00-4.08 (m, 1H), 4.30-4.39 (m, 1H), 6.22 (d, 1H), 6.50 (t, 1H), 6.90 (d, 2H), 7.23 (d, 2H), 7.30 (t, 1H), 8.01 (d, 1H). LRMS APCI+ m/z 396 [MH]+. HRMS ESI+ m/z 396.2641 [MH]+.

Intermediate 93: N-(3-chloropropyl)-N-methylcyclobutanamine

To a solution of N-methylcyclobutanamine (1 g, 3.89 mmol) and potassium carbonate (1.18 g, 8.56 mmol) in acetonitrile (20 ml) at 0° C. was added 1-bromo-3-chloropropane (383 μl, 3.89 mmol). Reaction was warmed to room temperature and stirred for 24 hours. Solid removed by filtration and filtrate concentrated in vacuo to give the title compound (241 mg, 38%) as an oil. No purification was performed. LRMS APCI+ m/z 162 [MH]+.

Example 244

N-{[4-(4-{3-[cyclobutyl(methyl)amino]
propoxy}phenyl)tetrahydro-2H-pyran-4-yl]
methyl}pyridin-2-amine

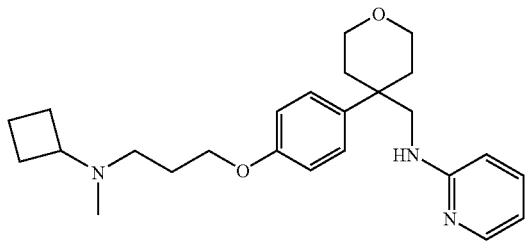

4-{4-[(pyridin-2-ylamino)methyl]tetrahydro-2H-pyran-4-yl}phenol (386 mg, 1.36 mmol), N-(3-chloropropyl)-N-methylcyclobutanamine (241 mg, 1.496 mmol) and potassium carbonate (280 mg, 2.03 mmol) were stirred in DMF (2 ml) at 45° C. for 24 hours until complete. Reaction was partitioned between ethyl acetate (40 ml) and saturated sodium bicarbonate solution (50 ml), then the organic layer washed with water (50 ml). Organic layer separated and dried over sodium sulphate, filtered and concentrated in vacuo. Crude product purified by flash chromatography on silica gel eluting with dichloromethane:methanol:ammonia (100:0:0 to 90:10:1 by volume) to give the title compound (165 mg, 30%). $^1$H NMR (400 MHz, CDCl$_3$) δ 1.55-1.72 (m, 2H), 1.80-1.99 (m, 6H), 2.00-2.09 (m, 2H), 2.10-2.20 (m, 4H), 2.40 (t, 2H), 2.80 (quintet, 1H), 3.50 (d, 2H), 3.54-3.62 (m, 2H), 3.78-3.88 (m, 2H), 4.00 (m, 3H), 6.20 (d, 1H), 6.50 (t, 1H), 6.92 (d, 2H), 7.22 (d, 2H), 7.32 (t, 1H), 8.00 (d, 1H). LRMS APCI$^+$ m/z 410 [MH]$^+$. HRMS ESI$^+$ m/z 410.2794[MH]$^+$.

Intermediate 94: 4-{4-[(1-isopropylpiperidin-4-yl)oxy]phenyl}tetrahydro-2H-pyran-4-carbaldehyde To a cooled solution of 4-{4-[(1-isopropylpiperidin-4-yl)oxy]phenyl}tetrahydro-2H-pyran-4-carbonitrile (1.16 g, 3.53 mmol) in dichloromethane (12 ml) at −78° C. under nitrogen, was added dropwise diisobutylaluminium hydride (1M solution in dichloromethane, 12.38 ml, 12 mmol) keeping the temperature below −60° C. Reaction stirred at −78° C. for 40 minutes, then at −20° C. for 1 hour before allowing to warm to room temperature. After 1 hour, reaction cooled and quenched with 2M HCl (13.2 ml) and basified with sodium carbonate to pH 8, and filtered though a short pad of celite eluting with dichloromethane:methanol (99:1 by volume). Reaction then partitioned between dichloromethane (50 ml) and water (50 ml), and organic layer washed with a further portion of water (50 ml) before being separated, dried over sodium sulphate, filtered and concentrated in vacuo. Purified by flash chromatography eluting with dichloromethane:methanol (99:1 to 92:8 by volume) to give the title compound (318 mg, 27%). LRMS APCI$^+$ m/z 332 [MH]$^+$.

Example 245

4-{4-[4-(4,5-dimethyl-1H-imidazol-2-yl)tetrahydro-2H-pyran-4-yl]phenoxy}-1-isopropylpiperidine

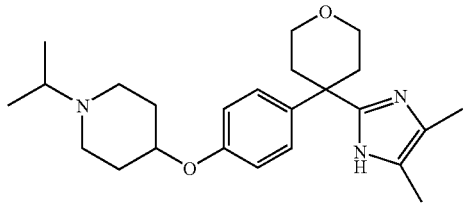

4-{4-[(1-isopropylpiperidin-4-yl)oxy]phenyl}tetrahydro-2H-pyran-4-carbaldehyde (50 mg, 0.151 mmol), ammonium acetate (116 mg, 1.51 mmol) and 2,3-butanedione (13 mg, 0.151 mmol) in acetic acid (1 ml) heated in a Smith Personal Synthesiser microwave for 900 seconds at 180° C. Acetic acid removed in vacuo and residue partitioned between ethyl acetate (20 ml) and saturated sodium bicarbonate solution (20 ml). Organic layer was separated, dried over sodium sulphate and concentrated in vacuo. Purified by flash chromatography eluting with dichloromethane:methanol:ammonia (100:0:0 to 95:5:0.5 by volume) to give the title compound (25.5 mg, 43%) as a brown oil. $^1$H NMR (400 MHz, CDCl$_3$) δ 1.08 (d, 6H), 1.76-1.88 (m, 2H), 1.96-2.07 (m, 2H), 2.10 (s, 6H), 2.19-2.28 (m, 2H), 2.39-2.50 (m, 4H), 2.72-2.87 (m, 3H), 3.67-3.84 (m, 4H), 4.20-4.34 (m, 1H), 6.83 (d, 2H), 7.14 (d, 2H). LRMS APCI$^+$ m/z 398 [MH]$^+$.

Intermediate 95: (3-Nitro-pyridin-4-yl)-{4-[4-(3-pyrrolidin-1-yl-propoxy)-phenyl]-tetrahydro-pyran-4-ylmethyl}-amine To a stirred solution of {4-[4-(3-Pyrrolidin-1-ylpropoxy)phenyl]tetrahydropyran-4-yl}methylamine (390 mg, 1.2 mmol) in acetonitrile (~5 mL), was added Hunig's base (230 µL, 1.35 mmol, 1.1 eq.) and 4-ethoxy-3-nitropyridine hydrogen chloride (250 mg, 1.2 mmol, 1 eq.) and the mixture stirred at reflux for 72 hours. To this a further portion of 4-ethoxy-3-nitropyridine hydrogen chloride (50 mg, 0.24 mmol, 0.2 eq.) was added and the mixture stirred at reflux for a further 24 hours. The reaction mixture was then concentrated in vacuo to give a dark yellow oily residue. This was partitioned between 2M NaOH (30 mL) and DCM (2×30 mL). The organics were combined, dried over sodium sulphate, filtered and concentrated in vacuo to give a dark yellow oil. The crude product was purified by flash chromatography on silica gel eluting with dichloromethane:methanol:ammonia (98:2:0.2 to 90:10:1, by volume) to provide the title compound (205 mg, 38%). HRMS ESI$^+$ m/z 441.2486 [MH]$^+$.

Intermediate 96: (3-Nitro-pyridin-2-yl)-{4-[4-(3-pyrrolidin-1-yl-propoxy)-phenyl]-tetrahydro-pyran-4-ylmethyl}-amine To a stirred solution of {4-[4-(3-Pyrrolidin-1-ylpropoxy)phenyl]tetrahydropyran-4-yl}methylamine (320 mg, 1.0 mmol) in acetonitrile (~5 mL), was added Hunig's base (190 µL, 1.1 mmol, 1.1 eq.) and 2-chloro-3-nitropyridine (175 mg, 1.1 mmol, 1.1 eq.) and the mixture stirred at reflux for 4 hours. The reaction mixture was then concentrated in vacuo and partitioned between saturated NaHCO$_3$ solution (20 mL) and DCM (2×20 mL). The organics were combined, dried over sodium sulphate, filtered and concentrated in vacuo to give the title compound (475 mg, 100%) as a yellow oil. LRMS APCI$^+$ m/z 441 [MH]$^+$.

Intermediate 97: N*4*-{4-[4-(3-Pyrrolidin-1-yl-propoxy)-phenyl]-tetrahydro-pyran-4-ylmethyl}-pyridine-3,4-diamine A solution of (3-Nitro-pyridin-4-yl)-{4-[4-(3-pyrrolidin-1-yl-propoxy)-phenyl]-tetrahydro-pyran-4-ylmethyl}-amine (200 mg, 0.45 mmol) in ethanol (~5 mL) was hydrogenated for 4 hours at room temperature at 40 psi in the presence of 10% Pd/C (20 mg, 10% w/w). The reaction mixture was filtered over Arbocel® and rinsed with ethanol. The filtrate was concentrated in vacuo to give a brown oily residue. The crude product was purified by flash chromatography on silica gel eluting with dichloromethane:methanol:ammonia (94:6:0.6, by volume) to provide the title compound (68 mg, 36%). HRMS ESI$^+$ m/z 411.2750 [MH]$^+$.

Example 246

2-Methyl-1-{4-[4-(3-pyrrolidin-1-yl-propoxy)-phenyl]-tetrahydro-pyran-4-ylmethyl}-1H-imidazo[4,5-c]pyridine

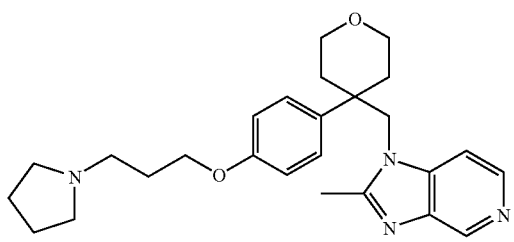

N*4*-{4-[4-(3-Pyrrolidin-1-yl-propoxy)-phenyl]-tetrahydro-pyran-4-ylmethyl}-pyridine-3,4-diamine (60 mg, 0.15 mmol) and acetic anhydride (~1 mL) were stirred at reflux for 18 hours. The reaction mixture was quenched with ~1 mL water, then basified with dilute sodium carbonate solution then extracted with DCM (2×20 mL). The organics were combined, dried over sodium sulphate, filtered and concentrated in vacuo to give a brown oil. The crude product was purified by flash chromatography on silica gel eluting with dichloromethane:methanol:ammonia (95:5:0.5 to 90:10:1 by volume) to provide the title compound as a brown oil (19 mg, 30%). $^1$H NMR (400 MHz, CDCl$_3$) δ 1.78-1.82 (m, 6H), 1.97-2.10 (m, 5H), 2.23 (m, 2H), 2.54 (m, 4H), 2.62 (t, 2H), 3.40 (m, 2H), 3.82 (m, 2H), 4.00 (t, 2H), 4.07 (s, 2H), 6.80-6.88 (m, 4H), 7.00 (d, 1H), 8.30 (d, 1H), 8.92 (s, 1H). LRMS ESI$^+$ m/z 435 [MH]$^+$.

Intermediate 98: N*2*-{4-[4-(3-Pyrrolidin-1-yl-propoxy)-phenyl]-tetrahydro-pyran-4-ylmethyl}-pyridine-2,3-diamine A solution of (3-Nitro-pyridin-2-yl)-{4-[4-(3-pyrrolidin-1-yl-propoxy)-phenyl]-tetrahydro-pyran-4-ylmethyl}-amine (465 mg, 1.06 mmol) in ethanol (~10 mL) was hydrogenated for 4 hours at room temperature at 40 psi in the presence of 10% Pd/C (45 mg, 10% w/w). The reaction mixture was filtered over Arbocel® and rinsed with ethanol (30 mL), 2M HCl (20 mL) and EtOH (30 mL). The filtrate was concentrated in vacuo to give the title compound (365 mg, 84%). HRMS ESI$^+$ m/z 411.2750 [MH]$^+$.

Example 247

1-({4-[4-(3-pyrrolidin-1-ylpropoxy)phenyl]tetrahydro-2H-pyran-4-yl}methyl)-1H-imidazo[4,5-c]pyridine

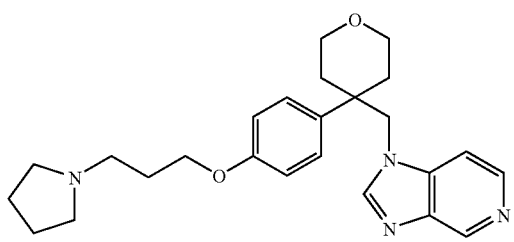

N*4*-{4-[4-(3-Pyrrolidin-1-yl-propoxy)-phenyl]-tetrahydro-pyran-4-ylmethyl}-pyridine-3,4-diamine (280 mg, 0.68 mmol), trimethylorthoformate (5 mL) and formic acid (0.5 mL) were stirred at 40° C. for 18 hours then at 60° C. for 24 hours, then at 80° C. for 24 hours. The reaction mixture was concentrated in vacuo and the residue partitioned between 2M NaOH (30 mL) and DCM (2×30 mL). The organics were combined, dried over sodium sulphate, filtered and concentrated in vacuo to give a brown oil. The crude product was purified by flash chromatography on silica gel eluting with dichloromethane:methanol:ammonia (95:5:0.5 to 90:10:1 by volume) to provide the title compound as a clear viscous oil (185 mg, 65%). $^1$H NMR (400 MHz, CDCl$_3$) δ 1.78-1.82 (m, 4H), 1.91-2.03 (m, 4H), 2.15-2.20 (m, 2H), 2.52 (m, 4H), 2.61 (t, 2H), 3.44 (m, 2H), 3.82 (m, 2H), 4.00 (t, 2H), 4.19 (s, 2H), 6.82 (d, 2H), 6.86-6.93 (m, 3H), 7.08 (s, 1H), 8.30 (d, 1H), 9.01 (s, 1H). HRMS ESI$^+$ m/z 421.2590 [MH]$^+$.

Example 248

3-({4-[4-(3-pyrrolidin-1-ylpropoxy)phenyl]tetrahydro-2H-pyran-4-yl}methyl)-3H-imidazo[4,5-b]pyridine

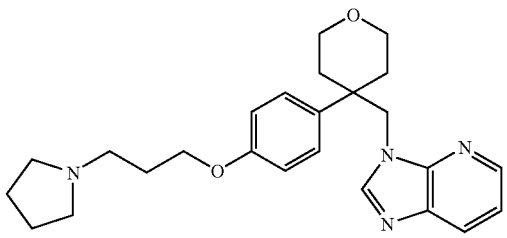

N*2*-{4-[4-(3-Pyrrolidin-1-yl-propoxy)-phenyl]-tetrahydro-pyran-4-ylmethyl}-pyridine-2,3-diamine (350 mg, 0.85 mmol), trimethylorthoformate (5 mL) and formic acid (0.5 mL) were stirred at 40° C. for 3 hours. The reaction mixture was concentrated in vacuo and the residue partitioned between saturated NaHCO$_3$ solution (40 mL) and DCM (2×40 mL). The organics were combined, dried over sodium sulphate, filtered and concentrated in vacuo to give a brown oil. The crude product was purified by flash chromatography on silica gel eluting with dichloromethane:methanol:ammonia (97:3:0.3 to 93:7:0.7 by volume) to provide the title compound as a brown oil (255 mg, 71%). $^1$H NMR (400 MHz, CDCl$_3$) δ 1.78-1.82 (m, 4H), 1.99-2.10 (m, 6H), 2.57 (m, 4H), 2.64 (t, 2H), 3.56 (m, 2H), 3.92 (m, 2H), 4.03 (t, 2H), 4.40 (s, 2H), 6.82 (s, 1H), 6.90 (d, 2H), 7.02 (d, 2H), 7.20 (m, 1H), 7.99 (d, 1H), 8.38 (d, 1H). HRMS ESI$^+$ m/z 421.2586 [MH]$^+$.

Example 249

1-({4-[4-(3-pyrrolidin-1-ylpropoxy)phenyl]tetrahydro-2H-pyran-4-yl}methyl)-1H-imidazo[4,5-b]pyridine

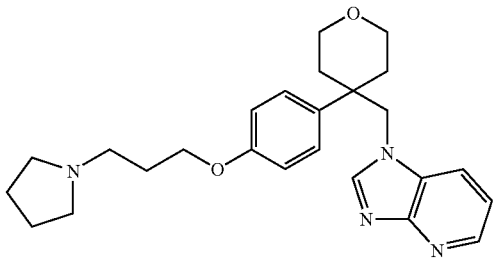

Step 1: Trifluoro-methanesulfonic acid 2-nitro-pyridin-3-yl ester (1.1 g, 4.1 mmo), {4-[4-(3-Pyrrolidin-1-ylpropoxy)

phenyl]tetrahydropyran-4-yl}methylamine (1.3 g, 4.1 mmol) and Hunig's base (1.7 mL, 9.8 mmol) were stirred at 60° C. for 72 hours. The mixture was diluted with DCM (30 mL) and washed with water (10 mL). The DCM layer was dried over sodium sulphate, filtered and concentrated in vacuo to give a dark brown oil. The crude product was purified by flash chromatography on silica gel eluting with dichloromethane:methanol:ammonia (98:2:0.2 to 90:10:1, by volume) to give a green oily residue after concentration in vacuo.

Step 2: To a solution of this residue in methanol (10 mL) was added methyl viologen dichloride hydrate (5 mg, 0.02 mmol) and a solution of sodium dithionite (1.07 g, 6.13 mmol) and NaHCO$_3$ (940 mg, 11.2 mmol) in water (10 mL). The mixture was stirred at room temperature for 10 minutes and then extracted with DCM (2×30 mL). The organics were dried over sodium sulphate, filtered and concentrated in vacuo to give a dark green oil. The crude product was purified by flash chromatography on silica gel eluting with dichloromethane:methanol:ammonia (94:6:0.6 to 90:10:1, by volume) to give a dark green solid after concentration in vacuo.

Step 3: This green solid, trimethylorthoformate (5 mL) and formic acid (0.5 mL) were stirred at room temperature for 18 hours. The reaction mixture was concentrated in vacuo and the residue partitioned between saturated 2M NaOH solution (20 mL) and DCM (2×20 mL). The organics were combined, dried over sodium sulphate, filtered and concentrated in vacuo to give an orange oil. The crude product was purified by flash chromatography on silica gel eluting with dichloromethane:methanol:ammonia (96:4:0.4 to 90:10:1 by volume) to provide the title compound as a pale yellow oil (95 mg, 6%). $^1$H NMR (400 MHz, CDCl$_3$) δ 1.80 (m, 4H), 1.90-2.02 (m, 4H), 2.17 (m, 2H), 2.52 (m, 4H), 2.61 (t, 2H), 3.41 (t, 2H), 3.80 (m, 2H), 3.98 (t, 2H), 4.16 (s, 2H), 6.78 (d, 2H), 6.90 (d, 2H), 7.02 (m, 1H), 7:17 (d, 1H), 7.31 (s, 1H), 8.43 (m, 1H). LRMS APCI$^+$ m/z 421 [MH]$^+$.

Example 250

N-({4-[4-(3-pyrrolidin-1-ylpropoxy)phenyl]tetrahydro-2H-pyran-4-yl}methyl)pyridazin-4-amine

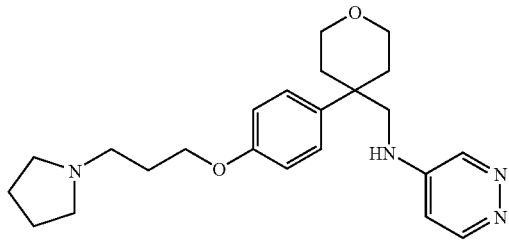

Step 1: A mixture of {4-[4-(3-Pyrrolidin-1-ylpropoxy)phenyl]tetrahydropyran-4-yl}methylamine (500 mg, 1.57 mmol), 3,4,5-Trichloro-pyridazine (403 mg, 2.20 mmol) and potassium carbonate (240 mg, 1.73 mmol) in acetonitrile (5 mL) were stirred at room temperature for 72 hours. The mixture was concentrated in vacuo and partitioned between water (30 mL) and DCM (2×30 mL). The combined organics were dried over sodium sulphate, filtered and concentrated in vacuo to give a deep red oil. The crude product was purified by flash chromatography on silica gel eluting with dichloromethane:methanol:ammonia (96:4:0.4 to 93:70:7, by volume) to give a deep red oil after concentration in vacuo.

Step 2: A solution of this oil and sodium hydroxide (110 mg, 2.7 mmol) in ethanol (~5 mL) was hydrogenated for 18 hours at room temperature at 50 psi in the presence of 10% Pd/C (60 mg, 10% w/w). The reaction mixture was filtered over Arbocel® and rinsed with ethanol. The filtrate was concentrated in vacuo to give an oily residue. The crude product was purified by flash chromatography on silica gel eluting with dichloromethane:methanol:ammonia (94:6:0.6 to 90:10:1, by volume) to provide the title compound (230 mg, 37%). $^1$H NMR (400 MHz, CDCl$_3$) δ 1.80 (m, 4H), 1.86 (m, 2H), 2.01 (m, 2H), 2.20 (m, 2H), 2.55 (m, 4H), 2.63 (t, 2H), 3.25 (d, 2H), 3.55 (m, 2H), 3.80 (m, 2H), 3.90 (t, 1H), 4.02 (t, 2H), 6.33 (m, 1H), 6.96 (d, 2H), 7.20 (d, 2H), 8.40 (d, 1H), 8.57 (d, 1H). HRMS ESI$^+$ m/z 397.2591 [MH]$^+$.

Intermediate 99: 4-[4-(3-Morpholin-4-yl-propoxy)-phenyl]-tetrahydro-pyran-4-carboxylic acid hydrochloride A solution of 4-[4-(3-morpholino-4-ylpropoxy)phenyl]tetrahydropyran-4-carbonitrile (2.0 g, 6.05 mmol) in concentrated hydrochloric acid (30 mL, 10 vol) was heated at reflux for 16 h. The solution was cooled to room temperature affording a precipitate. This was filtered, washed with water (~5 mL) and diethyl ether (~10 mL) and then dried to give the title compound (1.34 g, 57%) as a pale orange solid. LRMS (APCI$^-$) 348 (M–H+)$^-$. Microanalysis: Found: C, 58.16; H, 7.30; N, 3.45%. C$_{19}$H$_{28}$NO$_5$Cl.0.3H$_2$O requires C, 58.32; H, 7.37; N, 3.58%.

Example 251

N-methyl-4-[4-(3-morpholin-4-ylpropoxy)phenyl]tetrahydro-2H-pyran-4-carboxamide

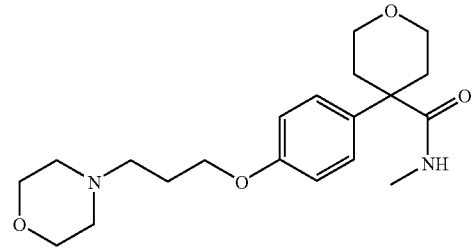

O-(1H-Benzotriazol-1-yl)-N,N,N',N'-tetramethyluronium hexafluorophosphate (640 mg, 1.7 mmol) was added to a solution of 4-[4-(3-Morpholin-4-yl-propoxy)-phenyl]-tetrahydro-pyran-4-carboxylic acid hydrochloride (500 mg, 1.3 mmol), methylamine hydrogen chloride (130 mg, 1.9 mmol) and Hunig's base (790 µL, 4.5 mmol) in N,N-dimethylformamide (5 mL). The mixture was stirred at room temperature for 2 hours and then concentrated in vacuo. The residue was partitioned between 2M NaOH solution (20 mL) and DCM (2×20 mL). The organics were combined, dried over sodium sulphate, filtered and concentrated under reduced pressure. The crude product was purified by flash chromatography on silica gel eluting with dichloromethane:methanol:ammonia (95:5:0.5 to 90:10:1, by volume) to provide the title compound (355 mg, 76%) as an off-white solid. $^1$H NMR (400 MHz, CDCl$_3$) δ 1.93-2.00 (m, 2H), 2.01-2.08 (m, 2H), 2.37-2.40 (m, 2H), 2.48 (m, 4H), 2.50 (t, 2H), 2.70 (d, 3H), 3.67-3.80 (m, 8H), 4.02 (t, 2H), 6.88 (d, 2H), 7.22 (d, 2H). LRMS APCI$^+$ m/z 363 [MH]$^+$.

Example 252

4-(3-{4-[4-(morpholin-4-ylcarbonyl)tetrahydro-2H-pyran-4-yl]phenoxy}propyl)morpholine

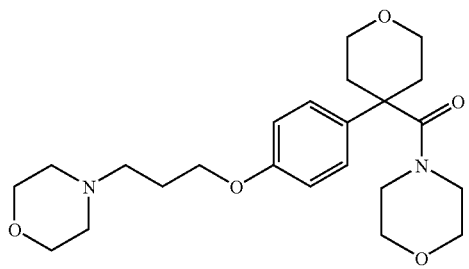

O-(1H-Benzotriazol-1-yl)-N,N,N',N'-tetramethyluronium hexafluorophosphate (200 mg, 0.5 mmol) was added to a solution of 4-[4-(3-Morpholin-4-yl-propoxy)-phenyl]-tetrahydro-pyran-4-carboxylic acid hydrochloride (160 mg, 0.4 mmol), morpholine (54 μL, 0.6 mmol) and Hunig's base (180 μL, 1 mmol) in N,N-dimethylformamide (2 mL). The mixture was stirred at room temperature for 3 hours and then concentrated in vacuo. The residue was partitioned between 2M NaOH solution (20 mL) and DCM (2×20 mL). The organics were combined, dried over sodium sulphate, filtered and concentrated under reduced pressure. The crude product was purified by flash chromatography on silica gel eluting with dichloromethane:methanol:ammonia (95:5:0.5 to 90:10:1, by volume) to provide the title compound (182 mg, 100%) as a pale brown solid. $^1$H NMR (400 MHz, CDCl$_3$) δ 1.93-2.04 (m, 4H), 2.20 (m, 2H), 2.42-2.55 (m, 6H), 3.22-3.43 (br m, 8H), 3.72 (t, 4H), 3.79 (m, 2H), 3.90 (m, 2H), 4.00 (t, 2H), 6.88 (d, 2H), 7.17 (d, 2H). LRMS APCI$^+$ m/z 419 [MH]$^+$.

Example 253

4-(3-{4-[4-(morpholin-4-ylmethyl)tetrahydro-2H-pyran-4-yl]phenoxy}propyl)morpholine

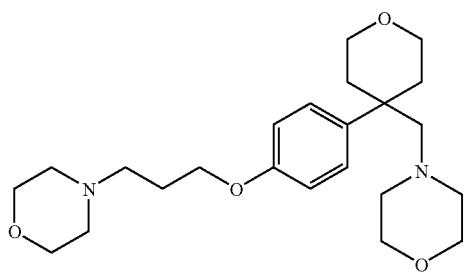

To a stirred solution of 4-(3-{4-[4-(morpholin-4-ylcarbonyl)tetrahydro-2H-pyran-4-yl]phenoxy}propyl)morpholine (160 mg, 0.38 mmol) in THF (4 mL) at 0° C. was added dropwise a solution of LiAlH$_4$ (1.0M solution in Et$_2$O, 1.15 mL, 1.15 mmol). The reaction mixture was stirred at 0° C. for 20 mins then heated at reflux for 1.5 hours. The reaction was then cooled to 0° C., water (0.10 ml) was added dropwise followed by sodium hydroxide (2.0M, 0.10 ml) and water (0.30 ml). The mixture was filtered through a short pad of celite, eluting with 1% methanol in dichloromethane (15 ml) and the organic washings concentrated in vacuo. The crude compound was purified by column chromatography on silica gel, eluting with dichloromethane:methanol:ammonia, 97:3: 0.3 to 92:8:0.8, to give the title compound as a clear oil (125 mg, 81%). $^1$H NMR (400 MHz, CDCl$_3$) δ 1.83 (m, 2H), 1.95 (m, 2H), 2.07-2.16 (m, 6H), 2.40 (s, 2H), 2.43-2.50 (m, 4H), 2.52 (t, 2H), 3.51 (m, 6H), 3.76 (m, 6H), 4.01 (t, 2H), 6.82 (d, 2H), 7.21 (d, 2H). HRMS ESI$^+$ m/z 405.2742 [MH]$^+$.

Example 254

N-methyl-1-{4-[4-(3-morpholin-4-ylpropoxy)phenyl]tetrahydro-2H-pyran-4-yl}methanamine

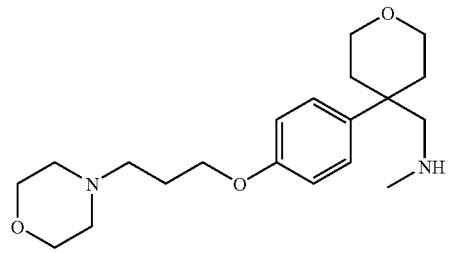

The title compound (252 mg, 77%) was prepared from N-methyl-4-[4-(3-morpholin-4-ylpropoxy)phenyl]tetrahydro-2H-pyran-4-carboxamide and a solution of LiAlH$_4$ (10M solution in Et$_2$O) similarly to the procedure used for 4-(3-{4-[4-(morpholin-4-ylmethyl)tetrahydro-2H-pyran-4-yl]phenoxy}propyl)morpholine. $^1$H NMR (400 MHz, CD$_3$OD) δ 1.85-2.00 (m, 6H), 2.12 (m, 2H), 2.24 (s, 3H), 2.45 (m, 4H), 2.53 (t, 2H), 2.63 (s, 2H), 3.57 (m, 2H), 3.70-3.80 (m, 6H), 4.01 (t, 1H), 6.88 (d, 2H), 7.20 (d, 2H). HRMS ESI$^+$ m/z 349.2477 [MH]$^+$.

Example 255

N-methyl-2-(methylsulfonyl)-N-({4-[4-(3-morpholin-4-ylpropoxy)phenyl]tetrahydro-2H-pyran-4-yl}methyl)ethanamine

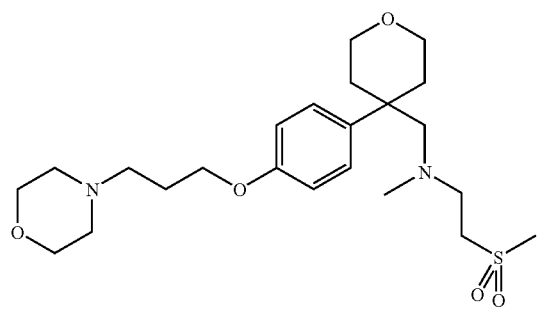

To a stirred solution of N-methyl-1-{4-[4-(3-morpholin-4-ylpropoxy)phenyl]tetrahydro-2H-pyran-4-yl}methanamine (230 mg, 0.66 mmol) in methanol (2 mL) was added methanesulfonyl-ethene (64 μL, 0.72 mmol) and the mixture stirred at room temperature for 18 hours. The mixture was concentrated in vacuo and triturated with diethyl ether to give the title compound as a white solid (274 mg, 91%). $^1$H NMR (400 MHz, CDCl$_3$) δ 1.81 (m, 2H), 1.97 (m, 2H), 2.04 (s, 3H), 2.13 (m, 2H), 2.42-2.58 (m, 8H), 2.62 (t, 2H), 2.74 (s, 3H), 2.81 (t, 2H), 3.50 (m, 2H), 3.70-3.80 (m, 6H), 4.00 (t, 2H), 6.86 (d, 2H), 7.20 (d, 2H). HRMS ESI$^+$ m/z 455.2570 [MH]$^+$. Microanalysis: Found: C, 60.61; H, 8.47; N, 6.09%. $C_{23}H_{38}N_2O_5S$ requires C, 60.76; H, 8.42; N, 6.16%.

Example 256

6-{4-[4-(3-pyrrolidin-1-ylpropoxy)phenyl]tetrahydro-2H-pyran-4-yl}-5H-pyrrolo[2,3-b]pyrazine

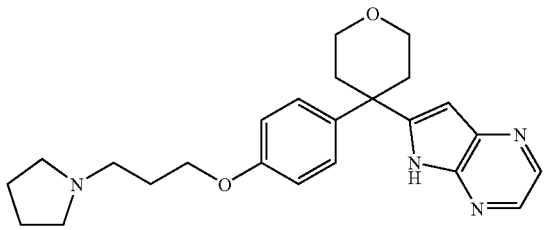

A solution of 2-methyl-pyrazine (580 μL, 6.4 mmol) in THF (4 mL) was added to 4.7 mL of 1.5M lithium diisopropylamide:THF complex in hexanes at −40° C. and the resulting deep red solution stirred at −40° C. for 0.5 hours. A solution of 4-[4-(3-Pyrrolidin-1-yl-propoxy)-phenyl]-tetrahydro-pyran-4-carbonitrile (1.00 g, 3.2 mmol) in THF (5 mL) was added at −40° C. and the reaction mixture stirred at this temperature for 0.5 hours, then at room temperature for 18 hours. A further 1 equivalent of lithium diisopropylamide complex was then added and the reaction mixture stirred at reflux for 24 hours. The mixture was cooled to room temperature, water (10 mL) added and the mixture concentrated in vacuo. The residue was partitioned between water (60 mL) and DCM (2×60 mL). The organics were combined, dried over sodium sulphate, filtered and concentrated under reduced pressure. The crude product was purified by flash chromatography on silica gel eluting with dichloromethane:methanol:ammonia (95:5:0.5 to 90:10:1, by volume) to provide the title compound (65 mg, 6%) as a brown oil. $^1$H NMR (400 MHz, CDCl$_3$) δ 1.74-1.80 (m, 6H), 2.00 (m, 2H), 2.42-2.55 (m, 6H), 2.60 (t, 2H), 3.80 (m, 4H), 4.00 (t, 2H), 6.60 (s, 1H), 6.86 (d, 2H), 7.21 (d, 2H), 8.05 (d, 1H), 8.39 (d, 1H). HRMS ESI$^+$ m/z 407.2437 [MH]$^+$.

Example 257

4-[4-(3-azetidin-1-ylpropoxy)phenyl]tetrahydro-2H-pyran-4-carbonitrile

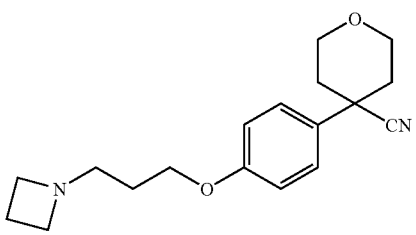

A mixture of 4-[4-(3-chloro-propoxy)-phenyl]-tetrahydro-pyran-4-carbonitrile and 4-[4-(3-bromo-propoxy)-phenyl]-tetrahydropyran-4-carbonitrile (7.5 g, 27 mmol), K$_2$CO$_3$ (9.6 g, 70 mmol) and azetidine hydrochloride (4.0 g, 43 mmol) in acetonitrile (80 mL) was heated at 40° C. for 18 hours. The mixture was concentrated in vacuo then partitioned between water (150 mL) and ethyl acetate (150 mL). The organic layer was extracted with 2M HCl solution (2×100 mL) and the combined acid layers basified with 40% potassium hydroxide solution, then extracted with DCM (2×150 mL). The DCM layers were combined, dried over sodium sulphate, filtered and concentrated under reduced pressure to give the title compound (1.1 g, 57%) as a clear, viscous oil. $^1$H NMR (400 MHz, DMSO) δ 1.80 (quintet, 2H), 2.00-2.14 (m, 6H), 2.58 (t, 2H), 3.20 (t, 4H), 3.88 (m, 2H), 4.00-4.11 (m, 4H), 6.90 (d, 2H), 7.38 (d, 2H). LRMS (APCI$^+$) m/z 301 (MH)$^+$.

Example 258

4-({4-[4-(3-azetidin-1-ylpropoxy)phenyl]tetrahydro-2H-pyran-4-yl}carbonyl)morpholine

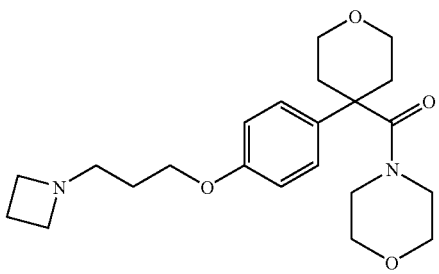

Step 1: A solution of 4-[4-(3-azetidin-1-ylpropoxy)phenyl]tetrahydro-2H-pyran-4-carbonitrile (1.1 g, 3.7 mmol) in concentrated hydrochloric acid (15 mL, 10 vol) was heated and stirred at reflux for 24 hours. The solution was cooled to room temperature and then concentrated in vacuo affording a brown oily solid. Hunig's base (6 mL) was added and the mixture concentrated in vacuo to give a brown oily residue.

Step 2: O-(1H-Benzotriazol-1-yl)-N,N,N',N'-tetramethyluronium hexafluorophosphate (1.7 g, 4.5 mmol) was added to a solution of this residue, morpholine (600 μL, 6.9 mmol) and Hunig's base (780 μL, 4.5 mmol) in N,N-dimethylformamide (5 mL). The mixture was stirred at room temperature for 72 hours and then concentrated in vacuo. The residue was partitioned between water (50 mL) and DCM (2×50 mL). The organics were combined, dried over sodium sulphate, filtered and concentrated under reduced pressure. The crude product was purified by flash chromatography on silica gel eluting with dichloromethane:methanol:ammonia (95:5:0.5 to 90:10:1, by volume) to provide the title compound (128 mg, 9%) as a pale pink foam after trituration with diethyl ether. $^1$H NMR (400 MHz, CDCl$_3$) δ 1.93-2.04 (m, 4H), 2.20 (m, 2H), 2.51-2.60 (m, 2H), 3.22-3.45 (br m, 10H), 3.78 (m, 2H), 3.86 (m, 2H), 4.02 (t, 2H), 4.13 (t, 4H), 6.88 (d, 2H), 7.18 (d, 2H). HRMS ESI$^+$ m/z 389.2426 [MH]$^+$.

Example 259

4-({4-[4-(3-azetidin-1-ylpropoxy)phenyl]tetrahydro-2H-pyran-4-yl}methyl)morpholine

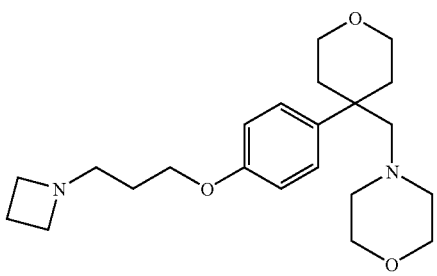

To a stirred solution of 4-({4-[4-(3-azetidin-1-ylpropoxy)phenyl]tetrahydro-2H-pyran-4-yl}carbonyl)morpholine (120 mg, 0.31 mmol) in THF (1 mL) at 0° C. was added dropwise a solution of LiAlH₄ (1.0M solution in Et₂O, 1.00 mL, 1.00 mmol). The reaction mixture was stirred at 0° C. for 20 mins then heated at reflux for 3 hours. The reaction was then cooled to 0° C., water (0.10 ml) was added dropwise followed by sodium hydroxide (2.0M, 0.10 ml) and water (0.30 ml). The mixture was filtered through a short pad of celite, eluting with 1% methanol in dichloromethane (15 ml) and the organic washings concentrated in vacuo. The crude compound was purified by column chromatography on silica gel, eluting with dichloromethane:methanol:ammonia, 97:3: 0.3 to 94:6:0.6, to give the title compound as a clear oil (25 mg, 22%). ¹H NMR (400 MHz, CDCl₃) δ 1.78-1.90 (m, 8H), 2.08 (m, 2H), 2.13 (m, 4H), 2.38 (s, 2H), 2.59 (t, 2H), 3.20 (t, 2H), 3.51 (m, 6H), 3.76 (m, 2H), 4.00 (t, 2H), 6.82 (d, 2H), 7.21 (d, 2H). LRMS APCI⁺ m/z 375 [MH]⁺.

Intermediate 100: 4-(4-{[1-(diphenylmethyl)azetidin-3-yl]methoxy}phenyl)tetrahydro-2H-pyran-4-carbonitrile 4-(4-Hydroxy-phenyl)-tetrahydro-pyran-4-carbonitrile (6.18 g, 30.4 mmol), (1-benzhydryl-azetidin-3-yl)-methanol (7 g, 28 mmol), PPh₃ (8 g, 30.4 mmol), and DIAD (69 mL, 30.4 mmol), were reacted together similarly to general procedure C. The crude material was purified by flash chromatography on silica gel eluting with pentane:ethyl acetate:diethylamine (50:45:5 to 0:95:5) to provide the title compound (5.03 g, 41%) as a yellow solid. LRMS APCI⁺ m/z 439 [MH]⁺.

Intermediate 101: 4-[4-(azetidin-3-ylmethoxy)phenyl]tetrahydro-2H-pyran-4-carbonitrile 4-(4-{[1-(diphenylmethyl)azetidin-3-yl]methoxy}phenyl)tetrahydro-2H-pyran-4-carbonitrile (0.605 g, 1.38 mmol), palladium hydroxide (0.08 g), concentrated hydrochloric acid (0.115 mL, 1.38 mmol), and ethanol (8 mL) were combined and hydrogenated for 18 hours at 40° C. at 40 psi. The mixture was filtered through Arbocel® and rinsed with ethanol. The filtrate was concentrated in vacuo. The residue was dissolved in DCM (50 mL) and washed with 10% aqueous sodium carbonate (20 mL). The organics were dried over sodium sulphate, filtered and concentrated in vacuo to provide a green oil. This was purified by flash chromatography on silica gel eluting with dichloromethane:methanol:ammonia (95:5:0.5 to 90:10:1) to provide the title compound (0.145 g, 39%) as a yellow oil. LRMS APCI⁺ m/z 273 [MH]⁺.

Example 260

4-{4-[(1-cyclobutylazetidin-3-yl)methoxy]phenyl}tetrahydro-2H-pyran-4-carbonitrile

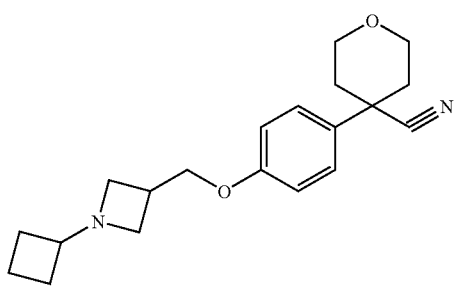

4-[4-(azetidin-3-ylmethoxy)phenyl]tetrahydro-2H-pyran-4-carbonitrile (0.29, 0.73 mmol) was dissolved in THF (2 mL). Cyclobutanone (0.06 mL, 0.80 mmol) and acetic acid (0.042 mL, 0.73 mmol) were added. The mixture was stirred at room temperature for 30 minutes. Sodium triacetoxyborohydride (0.311 g, 1.47 mmol) was added. The mixture was stirred at room temperature for 18 hours. The reaction mixture was diluted with 10% aqueous sodium carbonate (5 mL) then extracted with DCM (2×50 mL). The organics were combined, dried over sodium sulphate, filtered and concentrated in vacuo to provide a clear oil. This was purified by flash chromatography on silica gel eluting with dichloromethane:methanol:ammonia (96:4:0.4 to 95:5:0.5) to provide the title compound (0.194 g, 81%) as a clear oil. ¹H NMR (400 MHz, CDCl₃) δ 1.60-1.70 (m, 2H), 1.70-1.80 (m, 2H), 1.80-1.90 (m, 2H), 1.95-2.00 (m, 2H), 2.0-2.15 (m, 2H), 2.9 (m, 1H), 3.1 (t, 2H), 3.16 (m, 1H), 3.4 (t, 2H), 3.9 (m, 2H), 4.10 (m, 4H), 6.90 (d, 2H), 7.40 (d, 2H). HRMS ESI⁺ m/z 327.2059 [MH]⁺.

Example 261

1-(4-{4-[(1-cyclobutylazetidin-3-yl)methoxy]phenyl}tetrahydro-2H-pyran-4-yl)methanamine

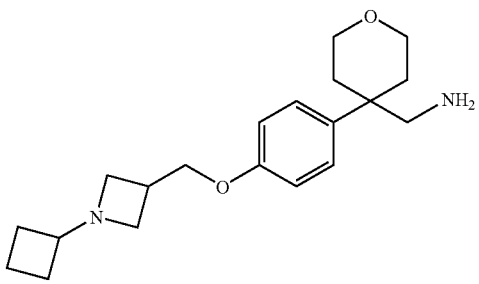

4-{4-[(1-cyclobutylazetidin-3-yl)methoxy]phenyl}tetrahydro-2H-pyran-4-carbonitrile (0.29 g, 0.89 mmol), was dissolved in THF (5 mL). The solution was cooled to 0° C. under nitrogen. Lithium aluminiumhydride (2.7 mL, 1.0M solution in diethyl ether) was added dropwise. The reaction was stirred at 0° C. for 30 minutes, then warmed up to ambient temperature for 4 hours under a nitrogen atmosphere until complete. The reaction was cooled to 0° C., water (0.1 mL) was added dropwise followed by sodium hydroxide (2.0M, 0.1 mL) and water (0.3 mL). The mixture was filtered (using dichloromethane:methanol (90:10)) through celite. The organics were dried over sodium sulphate, filtered and concentrated in vacuo to provide a clear oil. This was purified by flash chromatography on silica gel eluting with dichloromethane:methanol:ammonia (96:4:0.4 to 90:10:1) to provide the title compound (0.175 g, 59%) as a clear colourless oil. ¹H NMR (400 MHz, CDCl₃) δ 1.60-1.70 (m, 2H), 1.70-1.85 (m, 2H), 1.85-1.95 (m, 2H), 1.95-2.06 (m, 2H), 2.1-2.18 (m, 2H), 2.79 (s, 2H), 2.9 (m, 1H), 3.1 (t, 2H), 3.2 (m, 1H), 3.48 (m, 2H), 3.54 (m, 2H), 3.8 (m, 2H), 4.10 (d, 2H), 6.9 (d, 2H), 7.2 (d, 2H). HRMS ESI⁺ m/z 331.2374 [MH]⁺.

Example 262

N-[(4-{4-[(1-cyclobutylazetidin-3-yl)methoxy]phenyl}tetrahydro-2H-pyran-4-yl)methyl]pyridin-2-amine

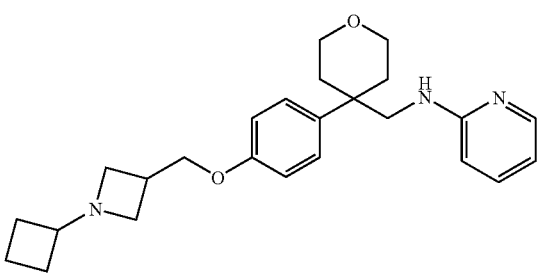

1-(4-{4-[(1-cyclobutylazetidin-3-yl)methoxy]phenyl}tetrahydro-2H-pyran-4-yl)methanamine (0.175 g, 0.53 mmol) was dissolved in toluene (5 mL), 2-bromopyridine (0.051 mL, 0.53 mmol), 2,2'-bis(diphenylphosphino)-1,1'binapthyl (0.013 g, 0.02 mmol) and sodium tert-butoxide (0.076 g, 0.79 mmol) were added. The reaction mixture was purged with nitrogen, tris(dibenzylideneacetone)dipalladium (0) (0.011 g, 0.01 mmol) was added. The mixture was heated under nitrogen at 70° C. for 18 hours. The reaction mixture was diluted with water (20 mL) and extracted with DCM (2×30 mL). The combined organics were dried over sodium sulphate, filtered and concentrated in vacuo to provide a yellow oil. This was purified by HPLC eluting with methanol: 10 nM ammonium formate (aq) (1:1), fractions were combined and concentrated in vacuo to leave a clear oil. This was dissolved in DCM (50 mL) and washed with saturated sodium hydrogen carbonate solution in water (10 mL). The organic was dried over sodium sulphate, filtered and concentrated in vacuo to provide the title compound (0.016 g, 7%) as a clear colourless oil. $^1$H NMR (400 MHz, CDCl$_3$) δ 1.60-1.70 (m, 2H), 1.70-1.80 (m, 2H), 1.80-1.92 (m, 2H), 1.92-2.0 (m, 2H), 2.18 (m, 2H), 2.90 (m, 1H), 3.10 (t, 2H), 3.15 (m, 1H), 3.40 (t, 2H), 3.50 (d, 2H), 3.60 (m, 2H), 3.80 (m, 2H), 4.0 (m, 1H), 4.10 (d, 2H), 6.22 (d, 1H), 6.50 (d, 1H), 6.90 (d, 2H), 7.28 (d, 2H), 7.32 (t, 1H), 8.0 (d, 1H). HRMS ESI$^+$ m/z 408.2641 [MH]$^+$.

Intermediate 102: N-[(dimethylamino)methylene]-4-[4-(3-pyrrolidin-1-ylpropoxy)phenyl]tetrahydro-2H-pyran-4-carboxamide 4-[4-(3-Pyrrolidin-1-ylpropoxy)phenyl]tetrahydro-2H-pyran-4-carboxylic acid amide (0.561 g, 1.69 mmol) and N,N-dimethylformamide dimethyl acetal (5 mL) were combined and heated at reflux for 4 hours. The reaction mixture was concentrated in vacuo and azeotroped with toluene (2×10 mL) to provide the title compound (0.655 g, 100%) as a brown solid. $^1$H NMR (400 MHz, CDCl$_3$) δ 1.80-1.85 (m, 4H), 1.85-1.95 (m, 2H), 2.0-2.10 (m, 2H), 2.6-2.78 (m, 8H), 3.0 (s, 3H), 3.05 (s, 3H), 3.60 (m, 2H), 3.90 (m, 2H), 4.0 (t, 2H), 6.80 (d, 2H), 7.35 (d, 2H), 8.30 (s, 1H). LRMS APCI$^+$ m/z 388 [MH]$^+$.

Example 263

3-{4-[4-(3-pyrrolidin-1-ylpropoxy)phenyl]tetrahydro-2H-pyran-4-yl}-1H-1,2,4-triazole

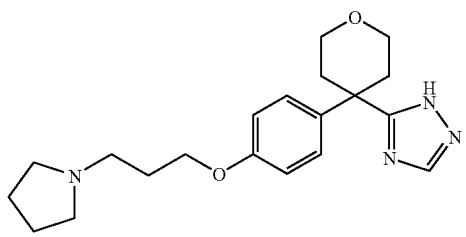

N-[(dimethylamino)methylene]-4-[4-(3-pyrrolidin-1-ylpropoxy)phenyl]tetrahydro-2H-pyran-4-carboxamide (0.15 g, 0.39 mmol), hydrazine hydrate (0.048 mL, 0.98 mmol) and acetic acid (1 mL) were combined and heated at 100° C. for 1.5 hours. The reaction mixture was concentrated in vacuo. The residue was dissolved in dichloromethane (100 mL) and washed with 10% aqueous sodium carbonate (20 mL). The organic was dried over sodium sulphate and evaporated to provide a clear oil. This was purified by flash chromatography on silica gel eluting with dichloromethane:methanol:ammonia (92:8:0.8 to 90:10:1) to produce a clear oil which was triturated with diethyl ether (3 mL), a white solid was isolated as the title compound (0.034 g, 24%). $^1$H NMR (400 MHz, CDCl$_3$) δ 1.82-1.95 (m, 4H), 2.0-2.10 (m, 2H), 2.30 (m, 2H), 2.60-2.70 (m, 2H), 2.70-2.80 (m, 6H), 3.62 (t, 2H), 3.89 (m, 2H), 3.95 (t, 2H), 6.80 (d, 2H), 7.20 (d, 2H), 7.95 (d, 1H). HRMS ESI$^+$ m/z 357.2279 [MH]$^+$.

Example 264

1-methyl-5-{4-[4-(3-pyrrolidin-1-ylpropoxy)phenyl]tetrahydro-2H-pyran-4-yl}-1H-1,2,4-triazole

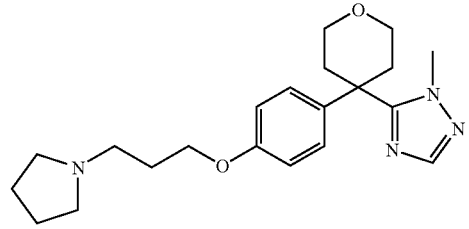

N-[(dimethylamino)methylene]-4-[4-(3-pyrrolidin-1-ylpropoxy)phenyl]tetrahydro-2H-pyran-4-carboxamide (0.34 g, 0.88 mmol), methyl hydrazine (0.116 mL, 2.19 mmol) and acetic acid (1 mL) were combined and heated at 100° C. for 2 hours. The reaction mixture was diluted with water (10 mL), solid sodium carbonate was added until the mixture was pH9. Dichloromethane (2×50 mL) was used to extract. The combined organics were dried over sodium sulphate, filtered and concentrated in vacuo to provide a yellow oil. This was purified by flash chromatography on silica gel eluting with dichloromethane:methanol:ammonia (96:4:0.4 to 90:10:1) to produce the title compound (0.065 g, 20%) as a white solid. $^1$H NMR (400 MHz, CDCl$_3$) δ 1.83-1.93 (m, 4H), 2.05-2.16 (m, 2H), 2.30 (m, 2H), 2.48 (m, 2H), 2.60-2.85 (m, 6H), 3.37 (s, 3H), 3.80 (m, 2H), 3.90 (m, 2H), 4.0 (t, 2H), 6.85 (d, 2H), 7.07 (d, 2H), 7.88 (s, 1H). HRMS ESI$^+$ m/z 371.2434 [MH]$^+$.

Intermediate 103: N'-formyl-4-[4-(3-pyrrolidin-1-ylpropoxy)phenyl]tetrahydro-2H-pyran-4-carbohydrazide 4-[4-(3-Pyrrolidin-1-ylpropoxy)phenyl]tetrahydro-2H-pyran-4-carboxylic acid (0.75 g, 0.225 mmol), formic hydrazide (0.162 g, 0.27 mmol), 1-hydroxybenzotriazole (0.304 g, 0.225 mmol), diisopropylethylamine (1.18 mL, 0.68 mmol), 1-(3-dimethylaminopropyl)-3-ethylcarbodiimide hydrochloride (0.431 g, 0.225 mmol) in dichloromethane (10 mL) was stirred at room temperature for 18 hours. The reaction mixture was diluted with dichloromethane (100 mL) and washed with water (2×20 mL) The organics were dried over sodium sulphate, filtered and concentrated in vacuo to provide a cream solid. This was purified by flash chromatography on silica gel eluting with dichloromethane:methanol:ammonia (95:5:0.5 to 90:10:1) to provide the title compound (0.145 g, 17%) as a clear oil. LRMS ESI$^+$ m/z 376 [MH]$^+$, ESI$^-$ m/z 374 [M−H$^+$]$^-$.

Example 265

2-{4-[4-(3-pyrrolidin-1-ylpropoxy)phenyl]tetrahydro-2H-pyran-4-yl}-1,3,4-oxadiazole

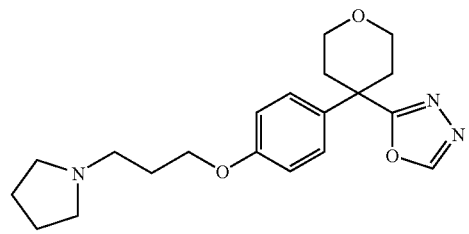

Triphenylphosphine (0.203 g, 0.78 mmol), iodine (0.198 g, 0.78 mmol) and triethylamine (0.217 mL, 1.56 mmol) were dissolved in dichloromethane (5 mL). The mixture was stirred at room temperature for 10 minutes. N'-formyl-4-[4-(3-pyrrolidin-1-ylpropoxy)phenyl]tetrahydro-2H-pyran-4-carbohydrazide (0.145 g, 0.39 mmol) in dichloromethane (5 mL) was added. The mixture was stirred at room temperature for 18 hours. The reaction mixture was diluted with dichloromethane (100 mL) and washed with water (25 mL). The organic was dried over sodium sulphate, filtered and concentrated in vacuo to provide a yellow oil. This was purified using preparative HPLC on Fraction-Lynx® eluting with water:acetonitrile:trifluoroacetic acid (95:5:0.1) to provide the title compound (0.028 g, 20%) as a clear oil. $^1$H NMR (400 MHz, CDCl$_3$) δ1.78-1.85 (m, 4H), 2.05 (m, 2H), 2.30 (m, 2H), 2.56-2.60 (m, 4H), 2.60-2.70 (m, 4H), 3.59 (m, 2H), 3.90-4.05 (m, 4H), 6.90 (d, 2H), 7.20 (d, 2H), 8.30 (s, 1H). HRMS ESI$^+$ m/z 358.2117 [MH]$^+$.

Intermediate 104: 2-{4-[4-(3-pyrrolidin-1-ylpropoxy)phenyl]tetrahydro-2H-pyran-4-yl}-4,5-dihydro-1H-imidazole 4-[4-(3-Pyrrolidin-1-yl-propoxy)-phenyl]-tetrahydro-pyran-4-carbonitrile (0.5 g, 3.1 mmol), ethylenediamine (1.5 mL, 22 mmol), copper (II) acetate (0.07 g, 0.3 mmol) and N-methylpyrrolidinone (1.5 mL) were combined and subjected to microwave (Smith Personal Synthesiser) irradiation at 220° C. for 1 hour. The reaction mixture was concentrated in vacuo to provide a brown oil. This was columned by flash chromatography on silica gel eluting with dichlromethane:methanol:ammonia (94:6:0.6 to 85:15:1.5) to provide the title compound (0.157 g, 31%) as a yellow oil. LRMS ESI$^+$ m/z 358 [MH]$^+$.

Example 266

2-{4-[4-(3-pyrrolidin-1-ylpropoxy)phenyl]tetrahydro-2H-pyran-4-yl}-1H-imidazole

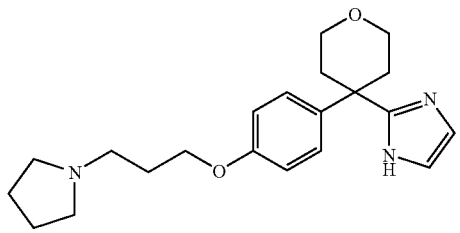

Dimethylsulphoxide (0.156 mL, 2.19 mmol) and dichloromethane (15 mL) were combined and cooled to −78° C. under nitrogen, oxalyl chloride (0.191 mL, 2.19 mmol) was added and the reaction mixture was stirred at −78° C. under nitrogen for 1 hour. A solution of 2-{4-[4-(3-pyrrolidin-1-ylpropoxy)phenyl]tetrahydro-2H-pyran-4-yl}4,5-dihydro-1H-imidazole (0.314 g, 0.88 mol) in dichloromethane (15 mL) was added slowly. The reaction was stirred at −78° C. for 1 hour. Triethylamine (0.611 mL, 4.4 mmol) was then added and the reaction was stirred for a further hour. The reaction mixture allowed to warm to room temperature for 1 hour. The reaction mixture was diluted with dichloromethane (100 mL) and washed with an aqueous ammonia solution (20 mL). The organic was dried over sodium sulphate, filtered and concentrated in vacuo to provide a yellow oil. This was purified by flash chromatography on silica gel eluting with dichloromethane:methanol:ammonia (96:4:0.4 to 90:10:1) to provide a yellow oil, which was triturated with diethyl ether. A cream solid was filtered to provide the title compound (0.07 g, 22%). $^1$H NMR (400 MHz, CDCl$_3$) δ 1.80 (m, 4H), 2.05 (m, 2H), 2.30 (m, 2H), 2.50 (m, 2H), 2.60-2.78 (m, 6H), 3.73 (m, 2H), 3.83 (m, 2H) (4.0 (t, 2H), 6.85 (d, 2H), 6.95 (s, 2H), 7.15 (d, 2H). HRMS ESI$^+$ m/z 356.2327 [MH]$^+$.

Example 267

N-[(4-{4-[(1-isopropylpiperidin-4-yl)oxy]phenyl}tetrahydro-2H-pyran-4-yl)methyl]pyridazin-4-amine

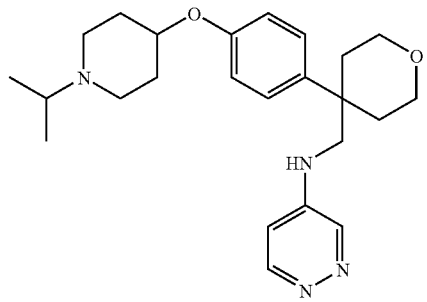

Step 1: (4-{4-[(1-isopropylpiperidin-4-yl)oxy]phenyl}tetrahydro-2H-pyran-4-yl)methylamine (0.5 g, 1.5 mmol), 3,4,5-trichloropyridazine (0.275 g, 1.5 mmol), potassium carbonate (0.690 g, 5 mmol) and acetonitrile (5 mL) were combined and stirred at room temperature for 20 hours. The reaction mixture was partitioned between water (20 mL) and dichloromethane (2×50 mL). The combined organics were dried over sodium sulphate, filtered and concentrated in vacuo to provide an orange oil. This was purified by flash chromatography eluting with dichloromethane:methanol:ammonia (100:0:0 to 90:10:1) to provide a brown oil.

Step 2: The product from step 1 (0.162 g, 0.34 mmol) and sodium hydroxide (0.033 g, 0.82 mmol) were dissolved in ethanol (3 mL). 10% Palladium on charcoal (0.02 g) was added. The mixture was hydrogenated for 18 hours at room temperature at 50 psi. The reaction mixture was filtered through Arbocel®, the filtrate was concentrated in vacuo to provide a yellow oil. This was purified by flash chromatography on silica gel eluting with dichloromethane:methanol:ammonia (94:6:0.6 to 90:10:1) to provide the title compound (0.08 g, 60%) as a yellow oil. $^1$H NMR (400 MHz, CDCl$_3$) δ 1.08 (d, 6H), 1.78-1.90 (m, 4H), 2.05 (m, 2H), 2.20 (m, 2H), 2.43 (m, 2H), 2.72-2.82 (m, 3H), 3.28 (d, 2H), 3.55 (m, 2H), 3.78 (m, 2H), 4.30 (m, 1H), 4.35 (m, 1H), 6.25 (d, 1H), 6.90 (d, 2H), 7.20 (d, 2H), 8.40 (s, 1H), 8.48 (d, 1H). HRMS ESI$^+$ m/z 411.2749 [MH]$^+$.

Intermediate 105: 4-[4-(3-[1,4]Oxazepan-4-yl-propoxy)-phenyl]-tetrahydro-pyran-4-carbonitrile 4-[4-(3-Chloro-propoxy)-phenyl]-tetrahydro-pyran-4-carbonitrile (5.3 g, 19 mmol) was taken in acetonitrile (30 ml), to which was added Hunig's base (6 g, 47 mmol) and homo-morpholine hydrogen chloride (2.8 g, 20 mmol). This solution was heated at reflux for 18 hours. The solvent was removed in vacuo and the residue purified by silica gel column chromatography, eluting with a gradient of DCM:MeOH:NH$_3$ (from 98:2:0.2 to 94:6:0.6) to afford the title compound as a yellow oil (3.35 g, 51%). HRMS ESI$^+$ m/z 345.2166 [MH]$^+$.

Intermediate 106: C-{4-[4-(3-[1,4]Oxazepan-4-yl-propoxy)-phenyl]-tetrahydro-pyran-4-yl}-methylamine 4-[4-(3-[1,4]Oxazepan-4-yl-propoxy)-phenyl]-tetrahydro-pyran-4-carbonitrile (900 mg, 26 mmol) was dissolved in THF (5 ml) and cooled to 0° C. under nitrogen. Lithium aluminium hydride (1M in EtO₂, 7.8 ml, 78 mmol) was added dropwise and left to stir for 10 minutes before heating to reflux for 18 hours. The solution was cooled to 0° C. before quenching with water (0.78 ml), followed by sodium hydroxide (2M, 0.78 ml) and finally water (2.4 ml). The resulting slurry was filtered through Arbocel®, washing through with DCM (2×10 ml). The filtrate was concentrated in vacuo to afford the title compound as a colourless oil (650 mg, 72%). HRMS ESI⁺ m/z 349.2480 [MH]⁺.

Example 268

4-(3-{4-[4-(morpholin-4-ylmethyl)tetrahydro-2H-pyran-4-yl]phenoxy}propyl)-1,4-oxazepane

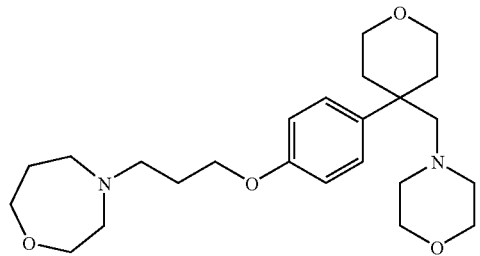

C-{4-[4-(3-[1,4]Oxazepan-4-yl-propoxy)-phenyl]-tetrahydro-pyran-4-yl}-methylamine (150 mg, 0.43 mmol) and 1-Bromo-2-(2-bromo-ethoxy)-ethane (110 mg, 0.47 mmol) were dissolved in acetonitrile (10 ml) and K₂CO₃ (130 mg, 0.95 mmol) was added. The solution was heated at 60° C. for 18 hours before filtering the solution to remove to the solid K₂CO₃. The filtrate was concentrated in vacuo before purifying using column chromatography, eluting with a gradient of DCM:MeOH:NH₃ (from 99:1:0.1 to 90:10:1) to afford the title compound as a colourless oil (75 mg, 42%). ¹H NMR (400 MHz, CD₃OD) δ 1.80-2.00 (m, 6H), 2.11-2.20 (m, 6H), 2.41 (s, 2H), 2.69-2.79 (m, 6H), 3.48 (m, 6H), 3.72-3.80 (m, 6H), 4.02 (t, 2H), 6.87 (d, 2H), 7.15 (d, 2H). HRMS ESI⁺ m/z 419.2896 [MH]⁺.

Example 269

N-[(4-{4-[3-(1,4-oxazepan-4-yl)propoxy]phenyl}tetrahydro-2H-pyran-4-yl)methyl]pyridin-2-amine

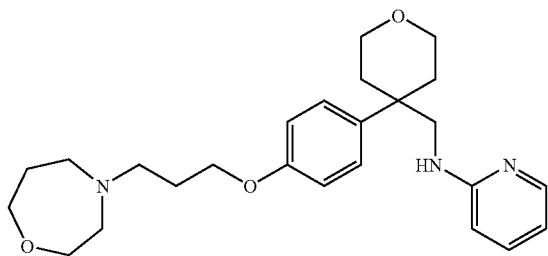

C-{4-[4-(3-[1,4]Oxazepan-4-yl-propoxy)-phenyl]-tetrahydro-pyran-4-yl}-methylamine (210 mg, 0.48 mmol) was added to a solution of 2-bromopyridine (70 mg, 0.42 mmol), Pd₂(dba)₃ (91 mg, 0.1 mmol), BINAP (126 mg, 2 mmol) and sodium tert-butoxide (56 mg, 5.7 mmol) in toluene (3 ml). This solution was heated in the microwave (Smith Personal Synthesiser) at 110° C. for 15 minutes. The solution was filtered through Celite and the filtrate was concentrated in vacuo. The residue was purified by column chromatography, eluting with a gradient of DCM:MeOH:NH₃ (from 99:1:0.1 to 95:5:0.5) to afford the title compound as a yellow oil (120 mg, 59%). ¹H NMR (400 MHz, CD₃OD) δ 1.88-2.00 (m, 6H), 2.17 (m, 2H), 2.68-2.79 (m, 6H), 3.43 (s, 2H), 3.50 (m, 2H), 3.76 (m, 2H), 3.80 (m, 4H), 4.03 (t, 2H), 6.39 (d, 1H), 6.44 (t, 1H), 6.91 (d, 2H), 7.33 (m, 3H), 7.81 (d, 1H). HRMS ESI⁺ m/z 426.2741 [MH]⁺.

Example 270

4-(3-{4-[4-(piperazin-1-ylcarbonyl)tetrahydro-2H-pyran-4-yl]phenoxy}propyl)-1,4-oxazepane

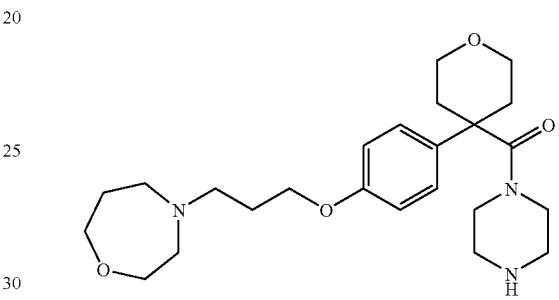

Step 1: 4-[4-(3-[1,4]Oxazepan-4-yl-propoxy)-phenyl]-tetrahydro-pyran-4-carbonitrile (1 g, 29 mmol) was dissolved in concentrated hydrochloric acid (15 ml) and heated at 90° C. for 24 hours, and the solvent was then removed in vacuo. 2-tert butyl 1,1,2,2 tetramethyl guanidine (2 ml) and water (1 ml) was then added to the residue and concentrated in vacuo and azeotroped with toluene (2×4 ml) to afford crude 4-[4-(3-[1,4]Oxazepan-4-yl-propoxy)-phenyl]-tetrahydro-pyran-4-carboxylic acid guanidine salt (3 g) an orange oil.

Step 2: 4-[4-(3-[1,4]Oxazepan-4-yl-propoxy)-phenyl]-tetrahydro-pyran-4-carboxylic acid guanidine (1.2 g, 0.88 mmol of free acid) was dissolved in DMF (5 ml), to which was added N-BOC piperidine (200 mg, 1.06 mmol), HBTU (400 mg, 1.06 mmol) and Hunig's base (129 mg, 1.06 mmol). The reaction was stirred at room temperature for 3 hours before adding saturated sodium bicarbonate solution (15 ml) and extracting the product into EtOAc (15 ml). The organic layer was washed with brine (15 ml), dried over Na₂SO₄ and concentrated in vacuo before purifying the residue by column chromatography, eluting with a gradient of DCM:MeOH:NH₃ (from 99:1:0.1 to 92:8:0.8). This afforded 4-{4-[4-(3-[1,4]Oxazepan-4-yl-propoxy)-phenyl]-tetrahydro-pyran-4-carbonyl}-piperazine-1-carboxylic acid tert-butyl ester as a colourless oil that became a white solid (260 mg, 55%) on standing overnight.

Step 3: 4-{4-[4-(3-[1,4]Oxazepan-4-yl-propoxy)-phenyl]-tetrahydro-pyran-4-carbonyl}-piperazine-1-carboxylic acid tert-butyl ester (260 mg, 0.48 mmol) was dissolved in a solution of hydrogen chloride in dioxane (4M, 5 ml) and was stirred at room temperature for 2 hours. The solvent was removed in vacuo and the residue dissolved in DCM (10 ml) and washed with saturated sodium bicarbonate solution (15 ml). The organic layer was dried over Na₂SO₄ and concentrated in vacuo before purifying the residue using column chromatography, eluting with a gradient of DCM:MeOH:

NH₃ (from 99:1:0.1 to 92:8:0.8) to afford the title compound as a white solid (80 mg, 37%). ¹H NMR (400 MHz, d₆-DMSO) δ 1.70-1.88 (m, 6H), 2.08 (m, 2H), 2.52-2.63 (m, 6H), 3.04-3.35 (m, 8H), 3.58 (m, 4H), 3.64 (m, 2H), 3.72 (m, 2H), 3.98 (t, 2H), 6.92 (d, 2H), 7.12 (d, 2H). LRMS ESI⁺ m/z 432 [MH]⁺.

Example 271

4-[3-{4-[4-[(4-methylpiperazin-1-yl)carbonyl]tetrahydro-2H-pyran-4-yl}phenoxy)propyl]-1,4-oxazepane

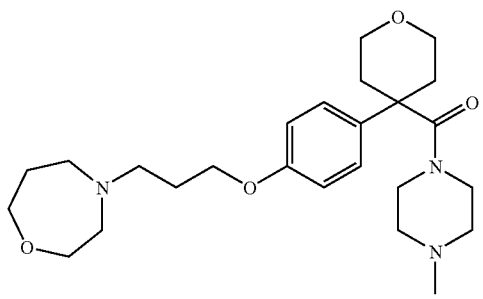

4-(3-{4-[4-(piperazin-1-ylcarbonyl)tetrahydro-2H-pyran-4-yl]phenoxy}propyl)-1,4-oxazepane (45 mg, 0.1 mmol) was dissolved in DCM (3 ml), to which was added formaldehyde (37% w/w in H₂O, 12 mg, 0.12 mmol) and acetic acid (8 mg, 0.12 mmol) and was stirred at room temperature for 30 minutes before adding STAB (25 mg, 0.12 mmol). The solution was allowed to stir for a further 45 minutes before washing the solution with saturated sodium bicarbonate (10 ml), followed by brine (10 ml). The organic layer was dried over Na₂SO₄ and concentrated in vacuo to afford the title compound as a white solid (25 mg, 56%). ¹H NMR (400 MHz, d₆-DMSO) δ 1.76-2.13 (m, 11H), 2.55-2.78 (m, 6H), 3.16-3.39 (m, 8H), 3.50-3.62 (m, 4H), 3.63 (m, 2H), 3.72 (M, 2H), 3.99 (t, 2H), 6.92 (d, 2H), 7.12 (d, 2H). LRMS ESI⁺ m/z 446 [MH]⁺.

Example 272

4-({4-[4-(3-pyrrolidin-1-ylpropoxy)phenyl]tetrahydro-2H-pyran-4-yl}methyl)-4H-1,2,4-triazole

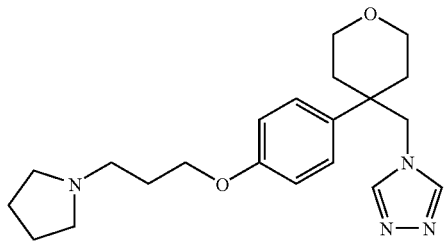

A mixture of {4-[4-(3-pyrrolidin-1-ylpropoxy)phenyl]tetrahydropyran-4-yl}methylamine (200 mg, 0.63 mmol), N'-[(1E)-(dimethylamino)methylene]-N,N-dimethylhydrazonoformamide (300 mg, 2.11 mmol) and p-toluenesulphonic acid monohydrate (10 mg, 0.05 mmol), was heated at reflux in toluene (2 ml) for 24 hours. The reaction mixture was concentrated in vacuo. The crude product was purified by flash chromatography on silica gel eluting with dichloromethane:methanol:ammonia (95:5:0.5 to 80:20:2 by volume) to provide 160 mg of beige gum. This gum was triturated with diethyl ether (3 ml) to give the title compound as a white powder (120 mg, 51%). ¹H NMR (400 MHz, CDCl₃) δ 7.46 (s, 2H), 6.97 (d, 2H), 6.89 (d, 2H), 4.02 (m, 4H), 3.82 (m, 2H), 3.43-3.52 (m, 2H), 2.62 (t, 2H), 2.51 (m, 4H), 2.12 (m, 2H), 2.02 (m, 2H), 1.84 (m, 2H), 1.80 (m, 4H). LRMS ESI⁺ m/z 371 [M+H]⁺. HRMS ESI⁺ m/z 371.2433 [M+H]⁺.

Intermediate 107: (1-isopropylazetidin-3-yl)methanol hydrochloride

A mixture of (1-benzhydrylazetidin-3-yl)methanol (4.0 g, 15.8 mmol), acetone (20 ml), 2-propanol (80 ml), c.HCl (1.5 ml) and Pd(OH)₂ was hydrogenated at 50 psi/50° for 18 hours. The reaction mixture was filtered through Arbocel® and concentrated in vacuo, the residue was triturated with diisopropyl ether (50 ml) to give the title compound as a pale green hygroscopic powder (2.6 g, 99%). LRMS ESI+m/z 130 [M+H]⁺.

Intermediate 108: 3-(chloromethyl)-1-isopropylazetidine hydrochloride (1-isopropylazetidin-3-yl)methanol hydrochloride (2.6 g, 15.7 mmol) was dissolved in dichloromethane (50 ml) and cooled to 0° C. Thionyl chloride (1.4 ml, 19.2 mmol) was added dropwise over 5 min. The reaction mixture was then stirred whilst warming to ambient temperature. Stirred at ambient temperature for 48 hours. The reaction mixture was concentrated in vacuo and azeotroped with toluene (40 ml) to give the title compound as a beige hygroscopic powder (2.8 g, 99%). LRMS ESI⁺ m/z 148/150 [M+H]⁺ (Cl isotopes).

Example 273

4-{4-[(1-isopropylazetidin-3-yl)methoxy]phenyl}tetrahydro-2H-pyran-4-carbonitrile

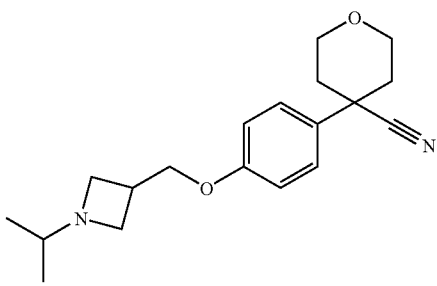

3-(chloromethyl)-1-isopropylazetidine hydrochloride (2.8 g, 15.2 mmol), 4-(4-hydroxyphenyl)tetrahydropyran-4-carbonitrile (3.1 g, 15.2 mmol) and potassium carbonate (8.5 g, 61.6 mmol) were combined in DMF (40 ml) and stirred at 500 for 2 hours. Potassium iodide (0.5 g 3.0 mmol) was added and the mixture was stirred at 50° for 18 hours then at 90-95° for a further 5 hours. The reaction mixture was concentrated in vacuo then partitioned between ethyl acetate (80 ml) and water (50 ml). The ethyl acetate was washed with saturated NaCl (50 ml) then dried over Na₂SO₄ and concentrated in vacuo to give a brown semi-crystalline material which was triturated with diisopropyl ether (25 ml) to give the title compound as a beige powder (2.9 g, 60%). ¹H NMR (400 MHz, CDCl₃) δ7.38 (d, 2H), 6.91 (d, 2H), 4.08 (m, 4H), 3.89 (m, 2H), 3.41 (t, 2H), 3.02 (t, 2H), 2.87 (m, 1H), 2.31 (m, 1H), 2.15-2.00 (m, 4H), 0.94 (d, 6H).

Example 274

1-(4-{4-[(1-isopropylazetidin-3-yl)methoxy]phenyl}tetrahydro-2H-pyran-4-yl)methanamine

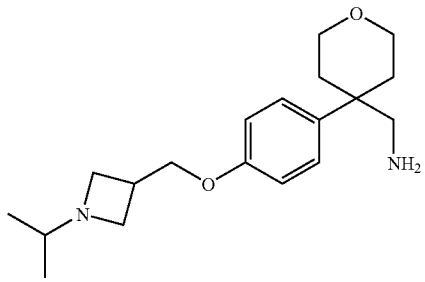

A solution of 4-{4-[(1-isopropylazetidin-3-yl)methoxy]phenyl}tetrahydro-2H-pyran-4-carbonitrile (1.8 g, 5.73 mmol) in THF (80 ml) was cooled to 0° C. under an atmosphere of nitrogen. A solution of lithium aluminium hydride (1.0M solution in Et$_2$O, 17 ml, 17 mmol) was added dropwise over 5 min. The mixture was stirred whilst warming to ambient temperature over 18 hours. The reaction was cooled to 0° C. and quenched with water (0.5 ml) then 2M NaOH (0.5 ml) and then water (1.5 ml). Celite® (3 g) was added and the mixture stirred at ambient temperature for 0.5 hour. Diluted with ethyl acetate (50 ml), filtered and concentrated in vacuo to give a colourless oil (1.8 g). The crude product was purified by flash chromatography on silica gel eluting with dichloromethane:methanol:ammonia (97:3:0.3 to 88:12:1.2 by volume) to give the title compound as a white crystalline solid (1.55 g, 85%). $^1$H NMR (400 MHz, CDCl$_3$) δ 7.18 (d, 2H), 6.89 (d, 2H), 4.18 (d, 2H), 3.77 (m, 2H), 3.54 (m, 2H), 3.41 (t, 2H), 3.02 (t, 2H), 2.88 (m, 1H), 2.75 (s, 2H), 2.31 (quintet, 1H), 2.11 (m, 2H), 1.80 (m, 2H), 0.95 (d, 6H). LRMS ESI$^+$ m/z 319 [M+H]$^+$. HRMS ESI$^+$ m/z 319.2375 [MH]$^+$.

Example 275

N-[(4-{4-[(1-isopropylazetidin-3-yl)methoxy]phenyl}tetrahydro-2H-pyran-4-yl)methyl]pyridin-2-amine

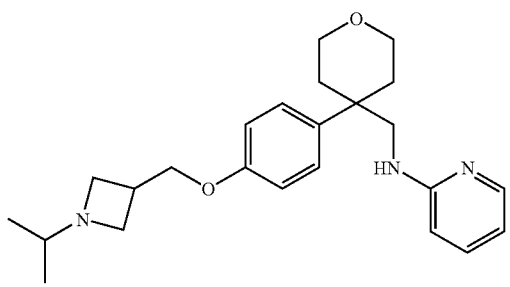

1-(4-{4-[(1-isopropylazetidin-3-yl)methoxy]phenyl}tetrahydro-2H-pyran-4-yl)methanamine was stirred with 2-bromopyridine (60 μl, 0.63 mmol), tris(dibenzylideneacetone)dipalladium(0) (15 mg, 0.018 mmol), 2,2'-bis(diphenylphosphino)-1,1'-binaphthyl (19 mg, 0.036 mmol) and sodium tert-butoxide (90 mg, 0.94 mmol) and heated at 80° C. in toluene (5 ml) for 3 hours under nitrogen. The reaction mixture was partitioned between aqueous sodium hydroxide (50 ml) and ethyl acetate (80 ml). The organics were dried over Na$_2$SO$_4$, filtered and concentrated in vacuo. The crude product was purified by flash chromatography on silica gel eluting with dichloromethane:methanol:ammonia (97:3:0.3 to 90:10:1 by volume) to give the product which required further purification by flash chromatography on silica gel eluting with dichloromethane:methanol:ammonia (96:4:0.4 to 94:6:0.6 by volume) to give a pale yellow oil which crystallized on standing, this was triturated with diethyl ether (2 ml) to give the title compound as a pale yellow powder (65 mg, 26%). $^1$H NMR (400 MHz, CDCl$_3$) δ 8.02 (d, 1H), 7.31 (t, 1H), 7.25 (d, 2H), 6.91 (d, 2H), 6.50 (t, 1H), 6.20 (d, 1H), 4.09 (d, 2H), 3.99 (t, 1H), 3.82 (m, 2H), 3.59 (m, 2H), 3.48 (d, 2H), 3.45 (m, 2H), 3.03 (m, 2H), 2.88 (m, 1H), 2.33 (m, 1H), 2.13 (m, 2H), 1.92 (m, 2H), 0.93 (d, 6H). LRMS ESI$^+$ m/z 396 [M+H]$^+$. HRMS ESI$^+$ m/z 396.2639 [M+H]$^+$.

Intermediate 109: 1-{4-[4-(3-pyrrolidin-1-ylpropoxy)phenyl]tetrahydro-2H-pyran-4-yl}ethanone To a solution of 4-[4-(3-Pyrrolidin-1-ylpropoxy)-phenyl]tetrahydropyran-4-carbonitrile (2.0 g, 6.37 mmol) in diethyl ether (30 ml) and THF (5 ml) was added methyl lithium/lithium bromide complex (1.5M solution in diethyl ether, 4.5 ml, 6.75 mmol), the reaction mixture was stirred at ambient temperature for 18 hours. The reaction mixture was quenched by adding water (5 ml) and concentrated in vacuo. The residue was partitioned between DCM (100 ml) and water (30 ml), the organics were dried over Na$_2$SO$_4$, filtered and concentrated in vacuo to give a crude product which was purified by flash chromatography on silica gel eluting with dichloromethane:methanol:ammonia (98:2:0.2 to 92:8:0.8 by volume) to provide a colourless gum (500 mg, 24%). LRMS ESI$^+$ m/z 332 [M+H]$^+$.

Example 276

4-{4-[4-(3-pyrrolidin-1-ylpropoxy)phenyl]tetrahydro-2H-pyran-4-yl}pyrimidine

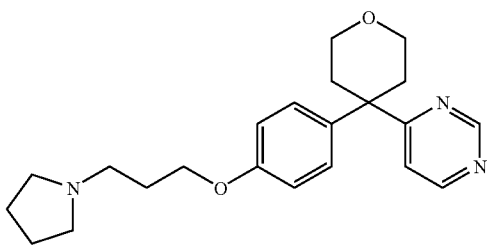

Step 1. 1-{4-[4-(3-pyrrolidin-1-ylpropoxy)phenyl]tetrahydro-2H-pyran-4-yl}ethanone_(500 mg, 1.51 mmol) was dissolved in dimethylformamide dimethylacetal (3 ml) and heated in a sealed tube microwave reactor (Smiths Personal Synthesizer) at 150° C. for 1800 seconds then at 170° C. for 2400 seconds. The reaction mixture concentrated in vacuo to give a crude product (3-Dimethylamino-1-{4-[4-(3-pyrrolidin-1-ylpropoxy)phenyl]tetrahydropyran-4-yl}propenone, 500 mg) which was used without purification in the next step.

Step 2. The crude intermediate was dissolved in ethanol (10 ml), formamidine acetate (320 mg, 3.07 mmol) and sodium ethoxide (21% w/v solution in ethanol, 1.0 ml, 3.09 mmol)

were added and the mixture stirred at ambient temperature for 1.5 hours then heated at 70° C. for 2 hours. Formamidine acetate (500 mg, 4.80 mmol) was added and stirred at 70° C. for 18 hours. Formamidine acetate (500 mg, 4.80 mmol) and potassium carbonate (2.0 g, 14.5 mmol) were added and stirred at reflux for 5 hours. Formamidine acetate (500 mg, 4.80 mmol) was added and stirred at reflux for 18 hours. The reaction mixture was partitioned between DCM (80 ml) and 10% Na$_2$CO$_3$ (50 ml), the organics were dried over Na$_2$SO$_4$, filtered and concentrated in vacuo to give a black solid. The crude product was purified by flash chromatography on silica gel eluting with dichloromethane:methanol:ammonia (100:0:0 to 94:6:0.6 by volume) to give the title compound as a brown oil (45 mg, 8%). $^1$H NMR (400 MHz, CDCl$_3$) δ 9.16 (s, 1H), 8.53 (d, 1H), 7.20 (d, 2H), 7.08 (d, 1H), 6.83 (d, 2H), 3.96 (t, 2H), 3.78 (m, 2H), 3.66 (m, 2H), 2.68-2.55 (m, 2H), 2.50 (m, 4H), 2.33 (m, 2H), 1.96 (m, 4H), 1.76 (m, 4H). LRMS ESI$^+$ m/z 368 [M+H]$^+$.

Intermediate 110: 4-methyl-1-({4-[4-(3-pyrrolidin-1-ylpropoxy)phenyl]tetrahydro-2H-Pyran-4-yl}methyl)-1H-imidazole-2-thiol 2-Aminopropionaldehyde dimethyl acetal (0.2 g, 1.7 mmol), thiocarbonyldiimidazole (0.36 g, 2.0 mmol) and triethylamine (0.23 ml, 1.7 mmol) were stirred in DMF (2.0 ml) at ambient temperature for 30 minutes before heating to 50° C. for 18 hours. {4-[4-(3-pyrrolidin-1-ylpropoxy)phenyl]tetrahydropyran-4-yl}methylamine (540 mg, 1.7 mmol) was added and stirred at ambient temperature for 4 hours. 2M HCl (6 ml) was added, stirred at 70° C. for 18 hours, then c.HCl (1.0 ml) was added and the mixture stirred at 110° C. for 18 hours. The reaction mixture was cooled and partitioned between ethyl acetate (100 ml) and dilute aqueous sodium carbonate (50 ml). The organics were dried over Na$_2$SO$_4$ and concentrated in vacuo to give the title compound as a grey solid (600 mg, 84%). LRMS ESI$^+$ m/z 416 [M+H]$^+$.

Example 277

4-methyl-1-({4-[4-(3-pyrrolidin-1-ylpropoxy)phenyl]tetrahydro-2H-pyran-4-yl}methyl)-1H-imidazole

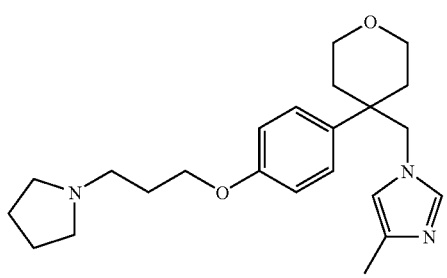

4-methyl-1-({4-[4-(3-pyrrolidin-1-ylpropoxy)phenyl]tetrahydro-2H-pyran-4-yl}methyl)-1H-imidazole-2-thiol (0.6 g, 1.44 mmol) was dissolved in ethanol (20 mL), water (5 mL) was added, and the mixture was cooled in ice. Raney nickel (4 g) was added, the reaction mixture was warmed to room temperature and stirred for 2 hours. The reaction mixture was filtered though Arbocel® and concentrated in vacuo to provide a brown oil. This was purified by flash chromatography on silica gel eluting with ethyl acetate:diethylamine (95:5) to provide the title compound (0.086, 16%) as a clear oil. $^1$H NMR (400 MHz CDCl$_3$) δ 1.80-1.90 (m, 6H), 2.08-2.18 (m, 7H), 2.65-2.80 (m, 6H), 3.50 (t, 2H), 3.80 (m, 2H), 3.90 (s, 2H), 4.05 (t, 2H), 6.10 (s, 1H), 6.70 (s, 1H), 6.89 (d, 2H), 7.0 (d, 2H). LRMS ESI$^+$ m/z 384 [MH]$^+$.

Example 278

4-{4-[4-(3-pyrrolidin-1-ylpropoxy)phenyl]tetrahydro-2H-pyran-4-yl}-1H-imidazole

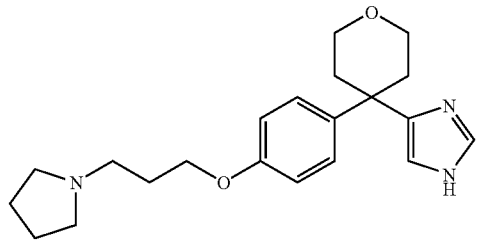

Step 1: 4-[4-(3-pyrrolidin-1-ylpropoxy)phenyl]tetrahydro-2H-pyran-4-carbaldehyde (500 mg, 1.6 mmol) and TosMIC (340 mg, 1.7 mmol) were dissolved in EtOH (20 ml), to which NaCN (12 mg, 0.25 mmol) was added. The solution immediately turned pale yellow and was allowed to stir for 2 hours at room temperature. The solvent was removed in vacuo and the residue was taken up in DCM (10 ml) and washed with saturated sodium bicarbonate solution (15 ml), followed by brine (15 ml). The organic layer was dried over Na$_2$SO$_4$ and concentrated in vacuo to afford 5-{4-[4-(3-Pyrrolidin-1-yl-propoxy)-phenyl]-tetrahydro-pyran-4-yl}-4-(toluene-4-sulfonyl)-4,5-dihydro-oxazole as a pale brown foam (500 mg). LRMS ESI$^+$ m/z 513 [MH]$^+$ Step 2: The 5-{4-[4-(3-Pyrrolidin-1-yl-propoxy)-phenyl]-tetrahydro-pyran-4-yl}-4-(toluene-4-sulfonyl)-4,5-dihydro-oxazole (500 mg) was dissolved in EtOH saturated with ammonia (7 ml) before heating in a bomb at 110° C. for 18 hours. The solvent was removed in vacuo and the residue was taken up in DCM (10 ml) and washed with saturated sodium bicarbonate solution (15 ml), followed by brine (15 ml). The organic layer was dried over Na$_2$SO$_4$ and concentrated in vacuo, before purifying by column chromatography, eluting with a gradient of DCM:MeOH:NH$_3$ (from 99:1:0.1 to 90:10:1), but this failed to separate the product from a close running impurity. The residue was therefore purified using column chromatography a second time, eluting with an isocratic solution of cyclohexane:DCM:Et$_2$O:MeOH:NH$_3$ (10:5:3:2:0.2) to afford the title compound as a colourless solid (70 mg, 12%). $^1$H NMR (400 MHz, CDCl$_3$) δ 1.8 (m, 4H), 1.93-2.05 (m, 2H), 2.24-2.39 (m, 4H), 2.57 (m, 4H), 2.63 (t, 2H), 3.67 (m, 2H), 3.79 (m, 2H), 4.00 (t, 2H), 6.77 (s, 1H), 6.81 (d, 2H), 7.18 (d, 2H), 7.38 (s, 1H). LRMS ESI$^+$ m/z 356 [MH]$^+$, 354 [M−H$^+$]$^-$.

Example 279

4-[4-(4-{3-[ethyl(methyl)amino]propoxy}phenyl)tetrahydro-2H-pyran-4-ylmethyl]-morpholine

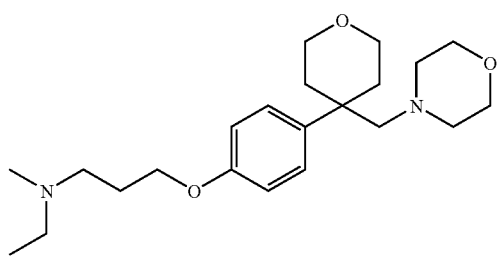

Step 1: A mixture of 4-[4-(3-chloro-propoxy)-phenyl]-tetrahydropyran-4-carbonitrile (3.0 g, 10.7 mmol), potassium iodide (100 mg, 0.60 mmol) and ethylmethylamine (5.0 ml, 58.3 mmol) in acetonitrile (30 mL) was heated to 60° C. overnight. The mixture was cooled, concentrated in vacuo and partitioned between dilute $Na_2CO_3$ solution (40 ml) and ethyl acetate (80 ml). The organic phase was dried ($Na_2SO_4$), filtered and concentrated in vacuo. Purification of the crude material was carried out with flash chromatography (silica gel, ethyl acetate/methanol/aqueous ammonia 98:2:0.2 to 85:15:1.5) to afford 4-(4-{3-[ethyl(methyl)amino] propoxy}phenyl)tetrahydro-2H-pyran-4-carbonitrile as a pale yellow oil (2.0 g, 6.6 mmol, 62%). $^1$H NMR (400 MHz $CDCl_3$) δ 1.06 (t, 3H), 1.91-2.00 (m, 2H), 2.00-2.14 (m, 4H), 2.25 (s, 3H), 2.40-2.50 (m, 2H), 2.53 (t, 2H), 3.89 (m, 2H), 4.00-4.11 (m, 4H), 6.91 (d, 2H), 7.38 (d, 2H).

LRMS $ESI^+$ m/z 303 $[MH]^+$.

Step 2: Lithium aluminium hydride (9.93 ml of a 1M solution in tetrahydrofuran, 9.93 mmol) was added to a solution of 4-(4-{3-[ethyl(methyl)amino]propoxy}phenyl)tetrahydro-2H-pyran-4-carbonitrile (2.0 g, 6.6 mmol) in tetrahydrofuran (10 ml) at 0° C. under $N_2$. The reaction mixture was warmed to room temperature over 18 h and then quenched by the sequential addition of water (0.4 ml), 2M NaOH solution (0.4 ml) and water (0.4 ml). The mixture was filtered through arbocel and concentrated in vacuo to yield 3-{4-[4-(aminomethyl)tetrahydro-2H-pyran-4-yl]phenoxy}-N-ethyl-N-methylpropan-1-amine as a pale yellow oil (1.93 g, 6.3 mmol, 95%). $^1$H NMR (400 MHz $CDCl_3$) δ 1.02-1.08 (t, 3H), 1.73-1.83 (m, 2H), 1.90-2.00 (m, 2H), 2.06-2.16 (m, 2H), 2.23 (s, 3H), 2.40-2.48 (q, 2H), 2.50-2.58 (t, 2H), 2.75 (s, 2H), 3.48-3.58 (m, 2H), 3.70-3.80 (m, 2H), 3.98-4.04 (t, 2H), 6.89 (d, 2H), 7.19 (d, 2H). LRMS $APCI^+$ m/z 307 $[MH]^+$.

Step 3: To a stirred solution of 3-{4-[4-(aminomethyl) tetrahydro-2H-pyran-4-yl]phenoxy}-N-ethyl-N-methylpropan-1-amine (500 mg, 1.6 mmol) and bis(2-bromoethyl)ether (345 mg, 1.5 mmol) in anhydrous acetonitrile (50 mL) was added potassium carbonate (450 mg, 3.3 mmol). The mixture was heated to 60° C. overnight then concentrated in vacuo. The crude product was partitioned between dichloromethane (50 ml) and water (50 ml), the aqueous phase was extracted with dichloromethane (25 ml) and the combined organics were dried ($Na_2SO_4$), filtered and concentrated in vacuo. Purification of the crude material was carried out with flash chromatography (silica gel, dichloromethane/methanol/ aqueous ammonia 100:0:0 to 96:4:0.4) to afford the title compound as a clear colourless oil (315 mg, 0.84 mmol, 52%). $^1$H NMR (400 MHz $CDCl_3$) δ 1.05 (t, 3H), 1.82-1.93 (m, 2H), 1.92-2.00 (m, 2H), 2.08-2.20 (m, 6H), 2.25 (s, 3H), 2.39 (s, 2H), 2.40-2.50 (q, 2H), 2.50-2.59 (m, 2H), 3.48-3.60 (m, 6H), 3.70-3.80 (m, 2H), 4.00 (t, 2H), 6.86 (d, 2H), 7.20 (d, 2H). LRMS $APCI^+$ m/z 377 $[MH]^+$. HRMS $ESI^+$ m/z 377.2792 $[MH]^+$.$^-$ $H_3$Cell Based Functional Assay Compounds were evaluated using a cell based functional assay measuring cAMP through β-lactamase reporter gene activity. A stable cell line was generated from HEK-293 cells expressing a CRE β-lactamase reporter gene and transfected with human histamine $H_3$ receptor cDNA. Cells were seeded at a density of 500,000 cells/ml, and grown overnight in MEM (Invitrogen) supplemented with 1% dialysed FBS (Sigma), 2 mM glutamine (Sigma), 1 mM sodium pyruvate (Sigma), 0.1 mM non essential amino acids (Invitrogen) and 25 mM HEPES (Sigma) in poly D lysine coated 384 well plates (BD Biosciences). $H_3$ receptor agonist imetit (Tocris) dose dependently inhibited 10 μM forskolin (Calbiochem) stimulated synthesis of cAMP measured after 4.5 hours by β-lactamase cleavage of CCF4-AM dye (Invitrogen). For $IC_{50}$ determination, test compounds were prepared in PBS (Sigma) and DMSO (Sigma) at a dose response of $5\times10^{-10}$ to $5\times10^{-5}$ M with a final DMSO concentration in the assay of 0.5%. Cells were incubated for 15 minutes plus/minus compound and their ability to permit 10 μM forskolin-stimulated cAMP synthesis in the presence of 1 nM imetit was measured as described above. Functional $K_i$ values were calculated from the $IC_{50}$ of compound tested as antagonists based on an experimentally determined imetit $EC_{50}$ (represented in the equation $K_d$) of 350 pM, and an imetit concentration [L] of 1 nM, according to the Cheng-Prussoff equation where $K_i= (IC_{50})/(1+([L]/K_d))$.

All the examples were tested in the assay described above and found to have a $K_i$ value of less than 5 μM. Most of the examples have a $K_i$ value of less than 100 nM.

The data for some of said preferred compounds are given below by way of example:

| Example Number | $K_i$ (H3 cell based assay - nM) |
|---|---|
| 29 | 0.4 |
| 133 | 12.4 |
| 136 | 3.9 |
| 155 | 1.0 |
| 156 | 2.0 |
| 160 | 1.5 |
| 187 | 7.3 |
| 188 | 6.8 |
| 189 | 14.3 |
| 190 | 2.4 |
| 191 | 10.3 |
| 196 | 0.6 |
| 205 | 5.8 |
| 206 | 12.9 |
| 213 | 2.6 |
| 220 | 2.2 |
| 247 | 3.9 |
| 248 | 0.3 |
| 249 | 9.7 |
| 250 | 4.6 |
| 254 | 1.3 |
| 266 | 9.7 |
| 267 | 5.8 |
| 268 | 6.5 |
| 276 | 6.2 |
| 272 | 10.8 |

The invention claimed is:
1. A compound of the formula (I):

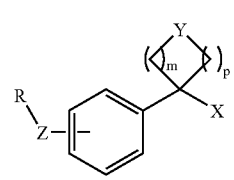

a stereoisomer thereof, or a pharmaceutically acceptable salt of said compound or stereoisomer, wherein:
-Z-R is in the meta or para position of the phenyl group;
X is —CN, —$CH_2OH$, —$CH_2$—O—($C_1$-$C_4$)alkyl, —C(O)OH, —C(O)O($C_1$-$C_4$)alkyl, —$CH_2$—$NR^1R^2$, —C(O)$NR^3R^4$, —$CH_2$—O-$het^2$, —$CH_2$-$het^1$ or $het^1$, wherein the group $het^1$ in both —$CH_2$-$het^1$ and $het^1$ is optionally and independently substituted with one to two halo, cyano, $(C_1-C_4)$alkyl, —S—$(C_1-C_4)$alkyl or $(C_1-C_4)$alkoxy;

$R^1$ is hydrogen or $(C_1-C_4)$alkyl optionally substituted with $(C_3-C_6)$cycloalkyl;

$R^2$ is: (i) hydrogen; (ii) $(C_1-C_6)$alkyl optionally and independently substituted with one to two $(C_3-C_6)$cycloalkyl, hydroxy, —S—$(C_1-C_4)$alkyl, —O—$(C_1-C_4)$alkyl, —SO$_2$—$(C_1-C_4)$alkyl, —SO—$(C_1-C_4)$alkyl, halo, het$^1$, amino, $(C_1-C_4)$alkylamino, [$(C_1-C_4)$alkyl]$_2$amino or phenyl, wherein said phenyl is optionally and independently substituted with one to two halo, hydroxy, cyano, $(C_1-C_4)$alkyl or $(C_1-C_4)$alkoxy; (iii) $(C_3-C_6)$cycloalkyl; (iv) het$^2$, optionally and independently substituted with one to two halo, cyano, $(C_1-C_4)$alkyl, NH$_2$ or $(C_1-C_4)$alkoxy; (v) —SO$_2$—R$^5$ wherein $R^5$ is $(C_1-C_4)$alkyl, amino, $(C_1-C_4)$alkylamino, [$(C_1-C_4)$alkyl]$_2$amino, phenyl or —$(C_1-C_4)$alkyl-phenyl, wherein said phenyl and phenyl of the group —$(C_1-C_4)$alkyl-phenyl is optionally and independently substituted with one to two halo, cyano, $(C_1-C_4)$alkyl or $(C_1-C_4)$alkoxy; or (vi) —C(O)—R$^6$ wherein R$^6$ is $(C_1-C_4)$alkyl, amino, $(C_1-C_4)$alkylamino, [$(C_1-C_4)$alkyl]$_2$amino, phenyl or —$(C_1-C_4)$alkyl-phenyl, wherein said phenyl and phenyl of the group —$(C_1-C_4)$alkyl-phenyl is optionally and independently substituted with one to two halo, cyano, $(C_1-C_4)$alkyl or $(C_1-C_4)$alkoxy; or $R^1$ and $R^2$ are taken together with the N atom to which they are attached to form a 3-, 4-, 5-, 6- or 7-membered saturated heterocycle wherein one C atom is optionally replaced with N, O, S, SO or SO$_2$ and wherein said saturated heterocycle is optionally and independently substituted with one to two hydroxy, halo, oxo, $(C_1-C_4)$alkyl, —$(C_1-C_4)$alkyl($C_3-C_6$)cycloalkyl, $(C_1-C_4)$alkoxy, hydroxy$(C_1-C_4)$alkyl, $(C_1-C_4)$alkoxy$(C_1-C_4)$alkyl, —SO$_2$$(C_1-C_4)$alkyl, —C(O)$(C_1-C_4)$alkyl, [$(C_1-C_4)$alkyl]$_2$amino, amino, $(C_1-C_4)$alkylamino, —C(O)NH$_2$, C(O)O$(C_1-C_4)$alkyl or pyrrolidinone;

$R^3$ and $R^4$ are taken separately and are independently hydrogen, $(C_3-C_6)$cycloalkyl, or $(C_1-C_4)$alkyl, said $(C_3-C_6)$cycloalkyl and $(C_1-C_4)$alkyl are optionally and independently substituted with amino, $(C_1-C_4)$alkylamino, [$(C_1-C_4)$alkyl]$_2$amino or $(C_3-C_6)$cycloalkyl; or $R^3$ and $R^4$ are taken together with the N atom to which they are attached to form a 4-, 5-, 6- or 7-membered saturated heterocycle wherein one C atom may be replaced by N or O and wherein said saturated heterocycle is optionally substituted with $(C_1-C_4)$alkyl, [$(C_1-C_4)$alkyl]$_2$amino, amino, $(C_1-C_4)$alkylamino, or —C(O)$(C_1-C_4)$alkyl optionally substituted with methoxy or ethoxy;

Y is O;

Z is O, S, SO or SO$_2$;

m and p are independently 1, 2 or 3, provided that m+p is equal to 2, 3 or 4 so that the ring formed by:

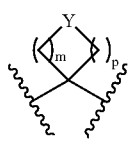

is a 4-, 5- or 6-membered ring;

R is a group of formula:

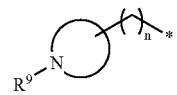

wherein * represents the attachment point to Z, the N-containing ring is a 4- to 7-membered saturated heterocycle, n is an integer equal to 0, 1 or 2, and R$^9$ is hydrogen, $(C_1-C_4)$alkyl, hydroxy$(C_1-C_6$ alkyl) or $(C_3-C_6)$cycloalkyl; and het$^1$ is a monocyclic or bicyclic heteroaromatic group comprising a 5- to 10-membered ring containing 1, 2, 3 or 4 heteroatom selected from N, O, and S; and het$^2$ is a monocyclic or bicyclic heteroaromatic group comprising a 5- to 10-membered ring containing 1, 2, 3 or 4 heteroatom selected from N, O and S.

2. A compound of claim 1, wherein X is —CH$_2$—NR$^1$R$^2$, —C(O)NR$^3$R$^4$, —CH$_2$-het$^1$ or het$^1$, wherein het$^1$ is optionally and independently substituted with one to two $(C_1-C_4)$alkyl.

3. A compound of claim 2, wherein X is —CH$_2$-het$^1$ or het$^1$, and het$^1$ is a 5- or 6-membered monocyclic heteroaromatic group or a 9-membered bicyclic heteroaromatic group, wherein each of said heteroaromatic groups contain 1 to 3 N, or 1 to 2 N and 1 O, or 1 N and 1 S, and each heteroaromatic group is optionally and independently substituted with one to two $(C_1-C_4)$alkyl.

4. A compound of claim 3, wherein X is thiazolyl, benzimidazolylmethyl-, pyridinyl, oxazolyl, imidazopyridinylmethyl-, pyrimidinyl, imidazolyl, imidazolylmethyl- or triazolylmethyl-, said thiazolyl, benzimidazolylmethyl-, pyridinyl, oxazolyl, imidazopyridinylmethyl-, pyrimidinyl, imidazolyl, imidazolylmethyl- or triazolylmethyl-, and wherein X is further optionally substituted with a methyl group.

5. A compound of claim 1, wherein R$^1$ is hydrogen, methyl or ethyl.

6. A compound of claim 1, wherein R$^2$ is (i) hydrogen; (ii) $(C_1-C_6)$alkyl optionally and independently substituted with one to two —S—$(C_1-C_4)$alkyl, —O—$(C_1-C_4)$alkyl, —SO$_2$—$(C_1-C_4)$alkyl, or phenyl, said phenyl optionally and independently substituted with one to two halo, hydroxy, cyano, $(C_1-C_4)$alkyl or $(C_1-C_4)$alkoxy; (iii) $(C_3-C_6)$cycloalkyl; (iv) het$^2$ optionally and independently substituted with one to two halo, cyano, $(C_1-C_4)$alkyl or $(C_1-C_4)$alkoxy; (v) —SO$_2$—R$^5$ wherein R$^5$ is $(C_1-C_4)$alkyl, [$(C_1-C_4)$alkyl]$_2$amino, phenyl, or —$(C_1-C_4)$alkyl-phenyl, wherein said phenyl and phenyl of the group —$(C_1-C_4)$alkyl-phenyl is optionally and independently substituted with one halo or cyano; and (vi) —C(O)—R$^6$, wherein R$^6$ is $(C_1-C_4)$alkyl, ($(C_1-C_4)$alkyl]$_2$amino, amino, or —$(C_1-C_4)$alkyl-phenyl, said phenyl and phenyl of the group —$(C_1-C_4)$alkyl-phenyl is optionally and independently substituted with one to two halo, cyano, $(C_1-C_4)$alkyl or $(C_1-C_4)$alkoxy.

7. A compound of claim 6, wherein R$^2$ is $(C_1-C_3)$alkyl optionally substituted with —O—$(C_1-C_3)$alkyl; $(C_3-C_5)$cycloalkyl; het$^2$ wherein het$^2$ is a 5- or 6-membered monocyclic heteroaromatic group containing one to two nitrogen, or one nitrogen and one oxygen, or one nitrogen and one sulphur, and said het$^2$ is optionally substituted with $(C_1-C_4)$alkyl; SO$_2$—R$^5$ wherein R$^5$ is $(C_1-C_4)$alkyl; or C(O)—R$^6$ wherein R$^6$ is $(C_1-C_4)$alkyl.

8. A compound of claim 7, wherein R$^2$ is $(C_1-C_3)$alkyl optionally substituted by methoxy.

9. A compound of claim 7, wherein $R^2$ is $het^2$, and $het^2$ is a 5 or 6 membered monocyclic heteroaromatic group containing one or two nitrogen.

10. A compound of claim 9, wherein $R^2$ is pyridazinyl.

11. A compound of claim 1, wherein $R^1$ and $R^2$ are taken together with the N atom to which they are attached to form a 4-, 5-, 6- or 7-membered saturated heterocycle wherein one C atom is optionally replaced by N, O, S, SO or $SO_2$, and wherein said saturated heterocycle is optionally and independently substituted with one to two hydroxy, halo, oxo, $(C_1$-$C_4)$alkyl, —$(C_1$-$C_4)$alkyl$(C_3$-$C_6)$cycloalkyl, $(C_1$-$C_4)$alkoxy, hydroxy$(C_1$-$C_4)$alkyl, $(C_1$-$C_4)$alkoxy$(C_1$-$C_4)$alkyl, —$SO_2$$(C_1$-$C_4)$alkyl, —C(O)$(C_1$-$C_4)$alkyl, $[(C_1$-$C_4)$alkyl$]_2$amino, —C(O)$NH_2$, C(O)O$(C_1$-$C_4)$alkyl or pyrrolidinone.

12. A compound of claim 11, wherein $R^1$ and $R^2$ are taken together with the N atom to which they are attached to form a morpholinyl group.

13. A compound of claim 1, wherein $R^3$ and $R^4$ are taken separately and are independently hydrogen or $(C_1$-$C_4)$alkyl; or $R^3$ and $R^4$ are taken together with the N atom to which they are attached to form a 4-, 5- or 6-membered saturated heterocycle wherein one C atom is optionally replaced by N or O, and wherein said saturated heterocycle is optionally substituted with $(C_1$-$C_4)$alkyl.

14. A compound of claim 13, wherein $R^3$ and $R^4$ are taken separately and are independently hydrogen, methyl or ethyl; or $R^3$ and $R^4$ are taken together with the N atom to which they are attached to form a pyrrolidinyl, piperidinyl, piperazinyl or azetidinyl ring, wherein said pyrrolidinyl, piperidinyl, piperazinyl and azetidinyl ring are optionally substituted with methyl.

15. A compound of claim 1, wherein Z is O.

16. A compound of claim 1, wherein m and p are both 2.

17. A compound of claim 1, wherein R is a group of formula:

and wherein * represents the attachment point to Z; the N-containing ring is a 4- or 6-membered saturated heterocycle; n is an integer equal to 0 or 1; and $R^9$ is hydrogen, $(C_1$-$C_4)$alkyl or $(C_3$-$C_6)$cycloalkyl.

18. A compound of claim 17, wherein $R^9$ is isopropyl or cyclobutyl.

19. A pharmaceutical composition comprising a compound of claim 1, a stereoisomer thereof, or a pharmaceutically acceptable salt of said compound or stereoisomer, and pharmaceutically acceptable vehicle, excipient or diluent.

20. A pharmaceutical composition comprising:
  a) a compound of claim 1, a stereoisomer thereof, or a pharmaceutically acceptable salt of said compound or stereoisomer;
  b) a histamine $H_1$ receptor antagonist; and
  c) a pharmaceutically acceptable vehicle, excipient or diluent.

21. A compound selected from:
{4-[4-(1-isopropylpiperidin-4-yloxy)phenyl]tetrahydro-pyran-4-ylmethyl}dimethyl-amine;
4-[4-(1-isopropylpiperidin-4-yloxy)phenyl]tetrahydropyran-4-carbonitrile;
4-{4-[(1-cyclobutyl-4-piperidinyl)oxy]phenyl}tetrahydro-2h-pyran-4-carbonitrile;
4-{4-[(1-isopropylpiperidin-4-yl)oxy]phenyl}tetrahydro-2h-pyran-4-carboxamide;
4-{4-[(1-isopropylpiperidin-4-yl)oxy]phenyl]-n,n-dimethyltetrahydro-2h-pyran-4-carboxamide;
4-{4-[(1-isopropylpiperidin-4-yl)oxy]phenyl]-n,n-diethyltetra-hydro-2h-pyran-4-carboxamide;
4-{4-[(1-isopropylpiperidin-4-yl)oxy]phenyl}tetrahydro-2h-pyran-4-yl]carbonyl}pyrrolidine;
n-[(4-{4-[(1-isopropylpiperidin-4-yl)oxy]phenyl}tetrahydro-2h-pyran-4-yl)methyl]-n-methylamine;
n-[(4-{4-[(1-isopropylpiperidin-4-yl)oxy]phenyl}tetrahydro-2h-pyran-4-yl)methyl]-n-ethylamine;
n-{[4-(4-[(1-isopropylpiperidin-4-yl)oxy]phenyl)tetrahydro-2h-pyran-4-yl]methyl}pyrimidin-2-amine;
1-(4-{4-[(1-cyclopentylazetidin-3-yl)methoxy]phenyl}tetrahydro-2h-pyran-4-yl)-n,n-dimethylmethanamine;
1-(4-{4-[(1-cyclobutylpiperidin-4-yl)oxy]phenyl}tetrahydro-2h-pyran-4-yl)-n,n-dimethylmethanamine;
4-{4-[(1-cyclobutylpiperidin-4-yl)oxy]phenyl}tetrahydro-2h-pyran-4-carboxamide;
4-{4-[4-(4,5-dimethyl-1h-imidazol-2-yl)tetrahydro-2h-pyran-4-yl]phenoxy}-1-isopropylpiperidine;
4-[(4-{4-[(1-cyclopentylazetidin-3-yl)methoxy]phenyl}tetrahydro-2h-pyran-4-yl)methyl]morpholine;
4-{4-[(1-cyclobutylpiperidin-4-yl)oxy]phenyl}-n,n-dimethyltetrahydro-2h-pyran-4-carboxamide;
4-{4-[(1-cyclobutylpiperidin-4-yl)oxy]phenyl}-n-isopropyltetrahydro-2h-pyran-4-carboxamide;
1-cyclobutyl-4-{4-[4-(1,3-thiazol-2-yl)tetrahydro-2h-pyran-4-yl]phenoxy}piperidine;
n-[(4-{4-[(1-cyclobutylpiperidin-4-yl)oxy]phenyl}tetrahydro-2h-pyran-4-yl)methyl]pyridin-2-amine;
1-[(4-{4-[(1-isopropylpiperidin-4-yl)oxy]phenyl}tetrahydro-2h-pyran-4-yl)carbonyl]-4-methylpiperazine;
4-{4-[(1-cyclobutylpiperidin-4-yl)oxy]phenyl}-n-ethyltetrahydro-2h-pyran-4-carboxamide;
n-[(4-{4-[(1-cyclobutylpiperidin-4-yl)oxy]phenyl}tetrahydro-2h-pyran-4-yl)methyl]pyrimidin-2-amine;
n,n-diethyl-4-[4-(3-pyrrolidin-1-ylpropoxy)phenyl]tetrahydro-2h-pyran-4-carboxamide;
4-[(4-{4-[(1-cyclobutylazetidin-3-yl)methoxy]phenyl}tetrahydro-2h-pyran-4-yl)methyl]morpholine;
4-{4-[(1-cyclobutylpiperidin-4-yl)oxy]phenyl}-n-methyltetrahydro-2h-pyran-4-carboxamide;
1-cyclobutyl-4-{4-[4-(4-methyl-1,3-thiazol-2-yl)tetrahydro-2h-pyran-4-yl]phenoxy}piperidine;
4-[(4-{4-[(1-isopropylazetidin-3-yl)methoxy]phenyl}tetrahydro-2h-pyran-4-yl)methyl]morpholine;
1-isopropyl-4-{4-[4-(1,3-thiazol-2-yl)tetrahydro-2h-pyran-4-yl]phenoxy}piperidine;
1-(4-{4-[(1-cyclobutylazetidin-3-yl)methoxy]phenyl}tetrahydro-2h-pyran-4-yl)methanamine;
1-(4-{4-[(1-isopropylazetidin-3-yl)methoxy]phenyl}tetrahydro-2h-pyran-4-yl)methanamine;
1-[(4-{4-[(1-isopropylpiperidin-4-yl)oxy]phenyl}tetrahydro-2h-pyran-4-yl)methyl]4-methylpiperazine;
4-[(4-{4-[(1-cyclobutylpiperidin-4-yl)oxy]phenyl}tetrahydro-2h-pyran-4-yl)carbonyl]morpholine;

n-[(4-{4-[(1-cyclobutylpiperidin-4-yl)oxy]
phenyl}tetrahydro-2h-pyran-4-yl)methyl]pyridin-3-
amine;
n-[(4-{4-[(1-isopropylpiperidin-4-yl)oxy]
phenyl}tetrahydro-2h-pyran-4-yl)methyl]pyridin-2-
amine;
n-ethyl-4-{4-[(1-isopropylpiperidin-4-yl)oxy]phenyl}-n-
methyltetrahydro-2h-pyran-4-carboxamide;
4-{4-[4-(azetidin-1-ylcarbonyl)tetrahydro-2h-pyran-4-yl]
phenoxy}-1-isopropylpiperidine;
n-[(4-{4-[(1-isopropylpiperidin-4-yl)oxy]
phenyl}tetrahydro-2h-pyran-4-yl)methyl]pyridazin-4-
amine;
n-[(4-{4-[(1-isopropylazetidin-3-yl)methoxy]
phenyl}tetrahydro-2h-pyran-4-yl)methyl]pyridin-2-
amine;
4-[(4-{4-[(1-isopropylpiperidin-4-yl)oxy]
phenyl}tetrahydro-2h-pyran-4-yl)methyl]morpholine;
n-[(4-{4-[(1-isopropylpiperidin-4-yl)oxy]
phenyl}tetrahydro-2h-pyran-4-yl)methyl]pyridin-3-
amine;
n-[(4-{4-[(1-ethylpiperidin-4-yl)oxy]phenyl}tetrahydro-
2h-pyran-4-yl)methyl]pyridin-2-amine;
n-[(4-{4-[(1-cyclobutylazetidin-3-yl)methoxy]
phenyl}tetrahydro-2h-pyran-4-yl)methyl]pyridin-2-
amine;
dimethyl-{4-[4-(3-pyrrolidin-1-ylpropoxy)phenyl]-tet-
rahydropyran-4-ylmethyl]amine;
4-{4-[(1-cyclobutylpiperidin-4-yl)oxy]phenyl}-N-eth-
yltetrahydro-2H-pyran-4-carboxamide;
{4-[4-(1-cyclopentylpiperidin-4-yloxy)phenyl]tetrahy-
dropyran-4-ylmethyl}dimethylamine;
Dimethyl-(4-{4-[2-(1-methylpyrrolidin-2-yl)ethoxy]phe-
nyl}-tetrahydropyran-4-ylmethyl)amine;
4-{4-[2-(1-Methylpyrrolidin-2-yl)ethoxy]
phenyl}tetrahydro-pyran-4-carbonitrile;
4-[4-(1-Cyclopentylpiperidin-4-yloxy)phenyl]tetrahydro-
pyran-4-carbonitrile;
4-{4-[(1-isopropylpiperidin-4-yl)oxy]phenyl}tetrahydro-
2H-pyran-4-carboxylic acid;
N-{[4-(4-[(1-isopropylpiperidin-4-yl)oxy]phenyl)tetrahy-
dro-2H-pyran-4-yl]methyl}-N-methylacetamide;
N-{[4-(4-[(1-isopropylpiperidin-4-yl)oxy]phenyl)tetrahy-
dro-2H-pyran-4-yl]methyl}-N-methylpropanamide;
N-{[4-(4-[(1-isopropylpiperidin-4-yl)oxy]phenyl)tetrahy-
dro-2H-pyran-4-yl]methyl}-acetamide;
N-{[4-(4-[(1-isopropylpiperidin-4-yl)oxy]phenyl)tetrahy-
dro-2H-pyran-4-yl]methyl}-N-ethylacetamide;
1-{[4-(4-[(1-isopropylpiperidine-4-yl)oxy]phenyl)tet-
rahydro-2H-pyran-4-yl]methyl}pyrrolidin-2-one;
N-{[4-(4-[(1-isopropylpiperidine-4-yl)oxy]phenyl)tet-
rahydro-2H-pyran-4-yl]methyl}pyrimidin-2-amide;
2-{[4-(4-[(1-isopropylpiperidin-4-yl)oxy]phenyl)tetrahy-
dro-2H-pyran-4-yl]methyl}isothiazolidine1,1-dioxide;
4-{4-[(1-cyclobutylazetidin-3-yl)methoxy]
phenyl}tetrahydro-2H-pyran-4-carbonitrile;
4-{4-[(1-cyclobutylpiperidine-4-yl)oxy]phenyl}-N-meth-
yltetrahydro-2H-pyran-4-carboxamide; and
4-{4-[(1-isopropylazetidin-3-yl)methoxy]
phenyl}tetrahydro-2H-pyran-4-carbonitrile; or
a stereoisomer thereof, or a pharmaceutically acceptable salt
of said compound or stereoisomer.

22. The compound of claim 21, wherein said compound is
4-{4-[(1-isopropylpiperidin-4-yl)oxy]phenyl]-N,N-dimeth-
yltetrahydro-2H-pyran-4-carboxamide; or a stereoisomer
thereof, or a pharmaceutically acceptable salt of said com-
pound or stereoisomer.

23. The compound of claim 21, wherein said compound is
4-{4-[(1-cyclobutylpiperidin-4-yl)oxy]phenyl}-N-ethyltet-
rahydro-2H-pyran-4-carboxamide; or a stereoisomer thereof,
or a pharmaceutically acceptable salt of said compound or
stereoisomer.

* * * * *